US012064478B2

United States Patent
Weaver

(10) Patent No.: US 12,064,478 B2
(45) Date of Patent: Aug. 20, 2024

(54) METHODS OF MAKING AND USING UNIVERSAL CENTRALIZED INFLUENZA VACCINE GENES

(71) Applicant: NUtech Ventures, Lincoln, NE (US)

(72) Inventor: Eric Anthony Weaver, Lincoln, NE (US)

(73) Assignee: NUtech Ventures, Lincoln, NE (US)

( * ) Notice: Subject to any disclaimer, the term of this patent is extended or adjusted under 35 U.S.C. 154(b) by 632 days.

(21) Appl. No.: 17/277,426

(22) PCT Filed: Sep. 20, 2019

(86) PCT No.: PCT/US2019/052137
§ 371 (c)(1),
(2) Date: Mar. 18, 2021

(87) PCT Pub. No.: WO2020/061443
PCT Pub. Date: Mar. 26, 2020

(65) Prior Publication Data
US 2021/0353738 A1 Nov. 18, 2021

Related U.S. Application Data

(60) Provisional application No. 62/734,791, filed on Sep. 21, 2018.

(51) Int. Cl.
*A61K 39/145* (2006.01)
*A61K 39/00* (2006.01)
*C12N 7/00* (2006.01)

(52) U.S. Cl.
CPC ............ *A61K 39/145* (2013.01); *C12N 7/00* (2013.01); *A61K 2039/55555* (2013.01); *C12N 2710/10034* (2013.01); *C12N 2740/10034* (2013.01); *C12N 2750/14134* (2013.01); *C12N 2760/18034* (2013.01); *C12N 2760/20034* (2013.01); *C12N 2770/36134* (2013.01)

(58) Field of Classification Search
CPC ........ A61K 39/145; A61K 2039/55555; A61K 39/12; C12N 7/00; C12N 2710/10034; C12N 2740/10034; C12N 2750/14134; C12N 2760/18034; C12N 2760/20034; C12N 2770/36134; C12N 2760/16134
See application file for complete search history.

(56) References Cited

U.S. PATENT DOCUMENTS

| | | | |
|---|---|---|---|
| 2011/0159031 A1 | 6/2011 | Falkner et al. | |
| 2012/0064116 A9 * | 3/2012 | Weiner | A61P 31/16 536/23.1 |
| 2013/0115235 A1 * | 5/2013 | Jin | C07K 14/005 435/235.1 |

FOREIGN PATENT DOCUMENTS

| | | | |
|---|---|---|---|
| CN | 103328629 | 9/2013 | |
| CN | 104059941 | 9/2014 | |
| CN | 107074912 | 8/2017 | |
| CN | 108290932 | 7/2018 | |
| WO | WO 2012036993 | 3/2012 | |
| WO | WO 2012089833 | 7/2012 | |
| WO | WO-2016137929 A1 * | 9/2016 | ............ A61K 39/12 |
| WO | WO 2018037246 | 3/2018 | |
| WO | WO-2023018817 A1 * | 2/2023 | |

OTHER PUBLICATIONS

Kowitdamrong E, et. al. Hemagglutinin, partial [Influenza A virus (A/Thailand/CU-MV8/2010(H1N1))]. GenBank: ADK26546.1. Dep. Jul. 25, 2016. (Year: 2016).*
Herlocher et al., "Ferrets as a Transmission Model for Influenza: Sequence Changes in HA1 of Type A (H3N2) Virus," J. Infect. Dis., Sep. 1, 2001, 184(5):542-546.
International Preliminary Report on Patentability in International Appln. No. PCT/US2019/052137, dated Apr. 1, 2021, 7 pages.
International Search Report and Written Opinion in International Appln. No. PCT/US2019/052137, dated Jan. 17, 2020, 10 pages.
Invitation to Pay Additional Fees in International Appln. No. PCT/US2019/052137, dated Nov. 22, 2019, 2 pages.
Maassab et al., "Evaluation of a Cold-Recombinant Influenza Virus Vaccine in Ferrets," J. Infect. Dis., Dec. 1982, 146(6):780-790.
Sweet et al., "Pathogenicity of Influenza Virus," Microbiological Reviews, Jun. 1980, 44(2):303-330.
Weaver et al., "Protection against Divergent Influenza H1N1 Virus by a Centralized Influenza Hemagglutinin," PLoS One, Mar. 28, 2011, 6(3):e18314, 12 pages.
Partial Supplementary European Search Report in European Appln. No. 19861574.2, dated Jun. 3, 2022, 11 pages.
Office Action in Chinese Appln. No. 201980074988.7, dated Sep. 28, 2023, 16 pages (with English translation).
GenBank Accession No. AID70330.1, "hemagglutinin [Influenza A virus (A/swine/USA/2013028053/2013(H3N1))]," dated Sep. 5, 2014, 2 pages.
Office Action in Chinese Appln. No. 201980074988.7, dated Apr. 29, 2024, 13 pages (with English translation).

* cited by examiner

*Primary Examiner* — Rachel B Gill
(74) *Attorney, Agent, or Firm* — Fish & Richardson P.C.

(57) ABSTRACT

This document describes a number of different polypeptide sequences, and the nucleic acid sequences encoding such polypeptide sequences, that can be used alone or in combination as universal vaccines against viruses including influenza A or influenza B in humans or influenza in swine.

14 Claims, 49 Drawing Sheets

Specification includes a Sequence Listing.

~ 0.001 changes

38A Manitoba/2005
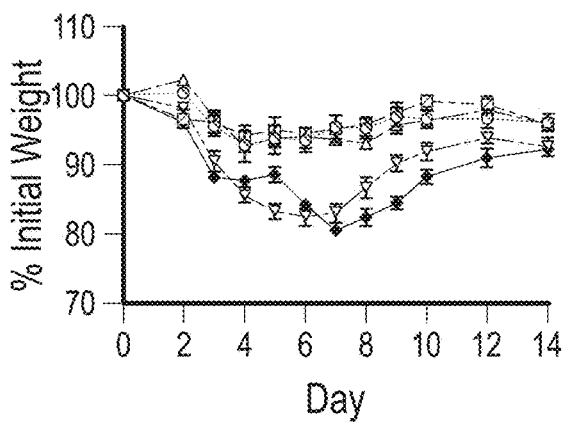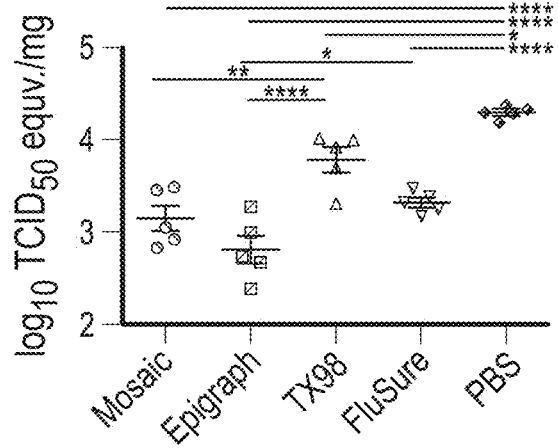
Colorado/1977
38B
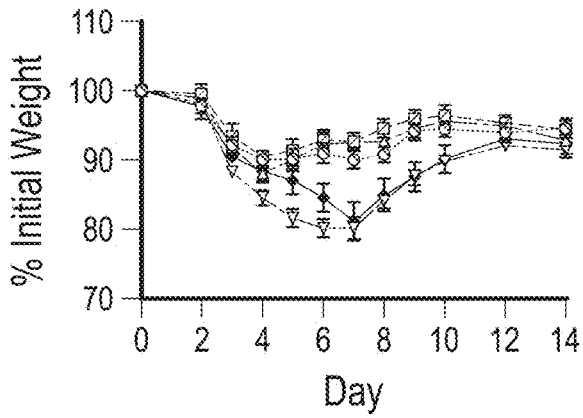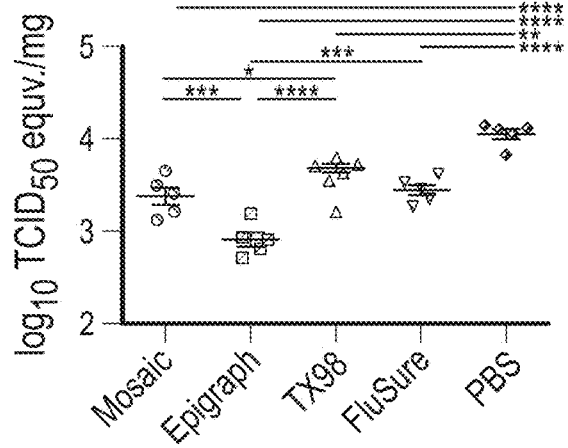
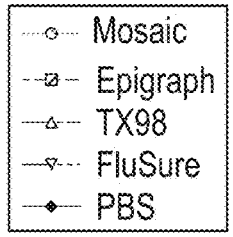
FIG. 38A-38B

SEQUENCE LISTING

```
<160> NUMBER OF SEQ ID NOS: 122

<210> SEQ ID NO 1
<211> LENGTH: 572
<212> TYPE: PRT
<213> ORGANISM: Artificial
<220> FEATURE:
<223> OTHER INFORMATION: synthetically-generated protein

<400> SEQUENCE: 1
```

-continued

```
Met Lys Ala Ile Leu Val Val Leu Leu Tyr Thr Phe Ala Thr Ala Asn
1               5                   10                  15

Ala Asp Thr Leu Cys Ile Gly Tyr His Ala Asn Asn Ser Thr Asp Thr
                20                  25                  30

Val Asp Thr Val Leu Glu Lys Asn Val Thr Val Thr His Ser Val Asn
                35                  40                  45

Leu Leu Glu Asp Lys His Asn Gly Lys Leu Cys Lys Leu Arg Gly Val
50                  55                  60

Ala Pro Leu His Leu Gly Lys Cys Asn Ile Ala Gly Trp Ile Leu Gly
65                  70                  75                  80

Asn Pro Glu Cys Glu Ser Leu Ser Thr Ala Ser Ser Trp Ser Tyr Ile
                85                  90                  95

Val Glu Thr Ser Ser Ser Asp Asn Gly Thr Cys Tyr Pro Gly Asp Phe
                100                 105                 110

Ile Asp Tyr Glu Glu Leu Arg Glu Gln Leu Ser Ser Val Ser Ser Phe
                115                 120                 125

Glu Arg Phe Glu Ile Phe Pro Lys Thr Ser Ser Trp Pro Asn His Asp
                130                 135                 140

Ser Asn Lys Gly Val Thr Ala Ala Cys Pro His Ala Gly Ala Lys Ser
145                 150                 155                 160

Phe Tyr Lys Asn Leu Ile Trp Leu Val Lys Lys Gly Asn Ser Tyr Pro
                165                 170                 175

Lys Leu Ser Lys Ser Tyr Ile Asn Asp Lys Gly Lys Glu Val Leu Val
                180                 185                 190

Leu Trp Gly Ile His His Pro Ser Thr Ala Asp Gln Gln Ser Leu Tyr
                195                 200                 205

Gln Asn Ala Asp Ala Tyr Val Phe Val Gly Thr Ser Arg Tyr Ser Lys
                210                 215                 220

Lys Phe Lys Pro Glu Ile Ala Ile Arg Pro Lys Val Arg Asp Gln Glu
225                 230                 235                 240

Gly Arg Met Asn Tyr Tyr Trp Thr Leu Val Glu Pro Gly Asp Lys Ile
                245                 250                 255

Thr Phe Glu Ala Thr Gly Asn Leu Val Val Pro Arg Tyr Ala Phe Ala
                260                 265                 270

Met Glu Arg Asn Ala Gly Ser Gly Ile Ile Ile Ser Asp Thr Pro Val
                275                 280                 285

His Asp Cys Asn Thr Thr Cys Gln Thr Pro Lys Gly Ala Ile Asn Thr
                290                 295                 300

Ser Leu Thr Ser Leu Pro Phe Gln Asn Ile His Pro Ile Thr Ile Gly
305                 310                 315                 320

Lys Cys Pro Lys Tyr Val Lys Ser Thr Lys Leu Arg Leu Ala Thr Gly
                325                 330                 335

Leu Arg Asn Val Pro Ser Ile Gln Ser Arg Gly Leu Phe Gly Ala Ile
                340                 345                 350

Ala Gly Phe Ile Glu Gly Gly Trp Thr Gly Met Val Asp Gly Trp Tyr
                355                 360                 365

Gly Tyr His His Gln Asn Glu Gln Gly Ser Gly Tyr Ala Ala Asp Leu
                370                 375                 380

Lys Ser Thr Gln Asn Ala Ile Asp Ile Thr Asn Lys Val Asn Ser Val
385                 390                 395                 400

Ile Glu Lys Met Asn Thr Gln Phe Thr Ala Val Gly Lys Glu Phe Asn
                405                 410                 415

His Leu Glu Lys Arg Ile Glu Asn Leu Asn Lys Lys Val Asp Asp Gly
```

```
                    420             425             430
Phe Leu Asp Ile Trp Thr Tyr Asn Ala Glu Leu Leu Val Leu Leu Glu
            435                 440             445

Asn Glu Arg Thr Leu Asp Tyr His Asp Ser Asn Val Lys Asn Leu Tyr
            450                 455             460

Glu Lys Val Arg Ser Gln Leu Lys Asn Asn Ala Lys Glu Ile Gly Asn
465                 470             475                 480

Gly Cys Phe Glu Phe Tyr His Lys Cys Asp Asn Thr Cys Met Glu Ser
            485                 490             495

Val Lys Asn Gly Thr Tyr Asp Tyr Pro Lys Tyr Ser Glu Glu Ala Lys
            500             505             510

Leu Asn Arg Glu Glu Ile Asp Gly Val Lys Leu Glu Ser Thr Arg Ile
            515             520             525

Tyr Gln Ile Leu Ala Ile Tyr Ser Thr Val Ala Ser Ser Leu Val Leu
            530             535             540

Val Val Ser Leu Gly Ala Ile Ser Phe Trp Met Cys Ser Asn Gly Ser
545             550             555                 560

Ser Val Glu Tyr Ser Leu Gln Cys Arg Ile Cys Ile
                565             570

<210> SEQ ID NO 2
<211> LENGTH: 560
<212> TYPE: PRT
<213> ORGANISM: Artificial
<220> FEATURE:
<223> OTHER INFORMATION: synthetically-generated protein

<400> SEQUENCE: 2

Met Lys Val Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
                20                  25                  30

Val Asp Thr Val Leu Glu Lys Asn Val Thr Val Thr His Ser Val Asn
            35                  40                  45

Leu Leu Glu Asp Ser His Asn Gly Lys Leu Cys Leu Leu Lys Gly Ile
50                  55                  60

Ala Pro Leu Gln Leu Gly Asn Cys Ser Val Ala Gly Trp Ile Leu Gly
65                  70                  75                  80

Asn Pro Glu Cys Glu Leu Leu Ile Ser Lys Glu Ser Trp Ser Tyr Ile
                85                  90                  95

Val Glu Thr Pro Asn Pro Glu Asn Gly Thr Cys Tyr Pro Gly Phe Ala
            100                 105                 110

Asp Tyr Glu Glu Leu Arg Glu Gln Leu Ser Ser Val Ser Ser Phe Glu
            115                 120                 125

Arg Phe Glu Ile Phe Pro Lys Glu Ser Ser Trp Pro Asn His Thr Val
            130                 135                 140

Thr Lys Gly Val Ser Ala Ser Cys Ser His Asn Gly Ser Ser Phe Tyr
145                 150                 155                 160

Arg Asn Leu Leu Trp Leu Thr Gly Lys Asn Gly Leu Tyr Pro Asn Leu
                165                 170                 175

Ser Lys Ser Tyr Ala Asn Asn Lys Glu Lys Glu Val Leu Val Leu Trp
            180                 185                 190

Gly Val His His Pro Pro Asn Ile Gly Asp Gln Leu Tyr His Thr Glu
            195                 200                 205

Asn Ala Tyr Val Ser Val Val Ser Ser His Tyr Ser Arg Phe Thr Pro
```

```
                210                 215                 220
Glu Ile Ala Lys Arg Pro Lys Val Arg Asp Gln Glu Gly Arg Ile Asn
225                 230                 235                 240

Tyr Tyr Trp Thr Leu Leu Glu Pro Gly Asp Thr Ile Ile Phe Glu Ala
                245                 250                 255

Asn Gly Asn Leu Ile Ala Pro Arg Tyr Ala Phe Ala Leu Ser Arg Gly
                260                 265                 270

Phe Gly Ser Gly Ile Ile Ser Asn Ala Pro Met Asp Glu Cys Asp Ala
            275                 280                 285

Lys Cys Gln Thr Pro Gln Gly Ala Ile Asn Ser Ser Leu Pro Phe Gln
            290                 295                 300

Asn Val His Pro Val Thr Ile Gly Glu Cys Pro Lys Tyr Val Arg Ser
305                 310                 315                 320

Ala Lys Leu Arg Met Val Thr Gly Leu Arg Asn Ile Pro Ser Ile Gln
                325                 330                 335

Ser Arg Gly Leu Phe Gly Ala Ile Ala Gly Phe Ile Glu Gly Gly Trp
                340                 345                 350

Thr Gly Met Val Asp Gly Trp Tyr Gly Tyr His His Gln Asn Glu Gln
            355                 360                 365

Gly Ser Gly Tyr Ala Ala Asp Gln Lys Ser Thr Gln Asn Ala Ile Asn
            370                 375                 380

Gly Ile Thr Asn Lys Val Asn Ser Val Ile Glu Lys Met Asn Thr Gln
385                 390                 395                 400

Phe Thr Ala Val Gly Lys Glu Phe Asn Lys Leu Glu Arg Arg Met Glu
                405                 410                 415

Asn Leu Asn Lys Lys Val Asp Asp Gly Phe Leu Asp Ile Trp Thr Tyr
                420                 425                 430

Asn Ala Glu Leu Leu Val Leu Leu Glu Asn Glu Arg Thr Leu Asp Phe
            435                 440                 445

His Asp Ser Asn Val Lys Asn Leu Tyr Glu Lys Val Lys Ser Gln Leu
            450                 455                 460

Lys Asn Asn Ala Lys Glu Ile Gly Asn Gly Cys Phe Glu Phe Tyr His
465                 470                 475                 480

Lys Cys Asn Asp Glu Cys Met Glu Ser Val Lys Asn Gly Thr Tyr Asp
                485                 490                 495

Tyr Pro Lys Tyr Ser Glu Glu Ser Lys Leu Asn Arg Glu Lys Ile Asp
            500                 505                 510

Gly Val Lys Leu Glu Ser Met Gly Val Tyr Gln Ile Leu Ala Ile Tyr
            515                 520                 525

Ser Thr Val Ala Ser Ser Leu Val Leu Val Ser Leu Gly Ala Ile
530                 535                 540

Ser Phe Trp Met Cys Ser Asn Gly Ser Leu Gln Cys Arg Ile Cys Ile
545                 550                 555                 560

<210> SEQ ID NO 3
<211> LENGTH: 565
<212> TYPE: PRT
<213> ORGANISM: Artificial
<220> FEATURE:
<223> OTHER INFORMATION: synthetically-generated protein

<400> SEQUENCE: 3

Met Lys Val Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
```

-continued

```
                20                  25                  30
Val Asp Thr Val Leu Glu Lys Asn Val Thr Val Thr His Ser Val Asn
                35                  40                  45
Leu Leu Glu Asn Ser His Asn Gly Lys Leu Cys Leu Leu Lys Gly Ile
                50                  55                  60
Ala Pro Leu Gln Leu Gly Asn Cys Ser Val Ala Gly Trp Ile Leu Gly
65                  70                  75                  80
Asn Pro Glu Cys Glu Leu Leu Ile Ser Lys Glu Ser Trp Ser Tyr Ile
                85                  90                  95
Val Glu Lys Pro Asn Pro Glu Asn Gly Thr Cys Tyr Pro Gly His Phe
                100                 105                 110
Ala Asp Tyr Glu Glu Leu Arg Glu Gln Leu Ser Ser Val Ser Ser Leu
                115                 120                 125
Glu Arg Phe Glu Ile Phe Pro Lys Glu Ser Ser Trp Pro Asn His Thr
                130                 135                 140
Val Thr Gly Val Ser Ala Ser Cys Ser His Asn Gly Glu Ser Ser Phe
145                 150                 155                 160
Tyr Arg Asn Leu Leu Trp Leu Thr Gly Lys Asn Gly Leu Tyr Pro Asn
                165                 170                 175
Leu Ser Lys Ser Tyr Ala Asn Asn Lys Glu Lys Glu Val Leu Val Leu
                180                 185                 190
Trp Gly Val His His Pro Pro Asn Ile Gly Asp Gln Arg Ala Leu Tyr
                195                 200                 205
His Thr Glu Asn Ala Tyr Val Ser Val Ser Ser His Tyr Ser Arg
                210                 215                 220
Lys Phe Thr Pro Glu Ile Ala Lys Arg Pro Lys Val Arg Asp Gln Glu
225                 230                 235                 240
Gly Arg Ile Asn Tyr Tyr Trp Thr Leu Leu Glu Pro Gly Asp Thr Ile
                245                 250                 255
Ile Phe Glu Ala Asn Gly Asn Leu Ile Ala Pro Arg Tyr Ala Phe Ala
                260                 265                 270
Leu Ser Arg Gly Phe Gly Ser Gly Ile Ile Asn Ser Asn Ala Pro Met
                275                 280                 285
Asp Lys Cys Asp Ala Lys Cys Gln Thr Pro Gln Gly Ala Ile Asn Ser
                290                 295                 300
Ser Leu Pro Phe Gln Asn Val His Pro Val Thr Ile Gly Glu Cys Pro
305                 310                 315                 320
Lys Tyr Val Arg Ser Ala Lys Leu Arg Met Val Thr Gly Leu Arg Asn
                325                 330                 335
Ile Pro Ser Val Gln Ser Arg Gly Leu Phe Gly Ala Ile Ala Gly Phe
                340                 345                 350
Ile Glu Gly Gly Trp Thr Gly Met Ile Asp Gly Trp Tyr Gly Tyr His
                355                 360                 365
His Gln Asn Glu Gln Gly Ser Gly Tyr Ala Ala Asp Gln Lys Ser Thr
                370                 375                 380
Gln Asn Ala Ile Asn Gly Ile Thr Asn Lys Val Asn Ser Val Ile Glu
385                 390                 395                 400
Lys Met Asn Ile Gln Phe Thr Ala Val Gly Lys Glu Phe Asn Lys Leu
                405                 410                 415
Glu Arg Arg Met Glu Asn Leu Asn Lys Lys Val Asp Asp Gly Phe Ile
                420                 425                 430
Asp Ile Trp Thr Tyr Asn Ala Glu Leu Leu Val Leu Leu Glu Asn Glu
                435                 440                 445
```

```
Arg Thr Leu Asp Phe His Asp Ser Asn Val Lys Asn Leu Tyr Glu Lys
            450                 455                 460

Val Lys Ser Gln Leu Lys Asn Asn Ala Lys Glu Val Gly Asn Gly Cys
465                 470                 475                 480

Phe Glu Phe Tyr His Lys Cys Asn Asp Glu Cys Met Glu Ser Val Lys
                    485                 490                 495

Asn Glu Thr Tyr Asp Tyr Pro Lys Tyr Ser Glu Glu Ser Lys Leu Asn
            500                 505                 510

Arg Glu Lys Ile Asp Gly Val Lys Leu Asp Ser Met Gly Val Tyr Gln
            515                 520                 525

Ile Leu Thr Ile Tyr Ser Thr Val Ala Ser Ser Leu Val Leu Leu Val
            530                 535                 540

Ser Leu Gly Ala Ile Ser Phe Trp Met Cys Ser Asn Gly Ser Leu Gln
545                 550                 555                 560

Cys Lys Ile Cys Ile
                565

<210> SEQ ID NO 4
<211> LENGTH: 566
<212> TYPE: PRT
<213> ORGANISM: Artificial
<220> FEATURE:
<223> OTHER INFORMATION: synthetically-generated protein

<400> SEQUENCE: 4

Met Lys Ala Ile Leu Val Val Leu Leu Tyr Thr Phe Thr Thr Ala Asn
1               5                   10                  15

Ala Asp Thr Leu Cys Ile Gly Tyr His Ala Asn Asn Ser Thr Asp Thr
            20                  25                  30

Val Asp Thr Ile Leu Glu Lys Asn Val Thr Val Thr His Ser Val Asn
        35                  40                  45

Leu Leu Glu Asp Lys His Asn Gly Lys Leu Cys Lys Leu Arg Gly Val
    50                  55                  60

Ala Pro Leu His Leu Gly Lys Cys Asn Ile Ala Gly Trp Ile Leu Gly
65                  70                  75                  80

Asn Pro Glu Cys Glu Ser Leu Ser Thr Ala Ser Ser Trp Ser Tyr Ile
                85                  90                  95

Val Glu Thr Ser Asn Ser Asp Asn Gly Thr Cys Tyr Pro Gly Asp Phe
            100                 105                 110

Ile Asn Tyr Glu Glu Leu Arg Glu Gln Leu Ser Ser Val Ser Ser Phe
        115                 120                 125

Glu Arg Phe Glu Ile Phe Pro Lys Thr Ser Ser Trp Pro Asn His Asp
    130                 135                 140

Pro Asn Lys Gly Val Thr Thr Ala Cys Pro His Ala Gly Ala Lys Ser
145                 150                 155                 160

Phe Tyr Lys Asn Leu Ile Trp Leu Val Glu Lys Gly Asn Ser Tyr Pro
                165                 170                 175

Lys Leu Ser Lys Ser Tyr Ile Asn Asp Lys Gly Lys Glu Ile Leu Val
            180                 185                 190

Leu Trp Gly Ile His His Pro Ser Thr Ser Ala Asp Gln Gln Ser Leu
        195                 200                 205

Tyr Gln Asn Ala Asp Thr Tyr Val Phe Val Gly Thr Ser Lys Tyr Ser
    210                 215                 220

Lys Lys Phe Lys Pro Glu Ile Ala Ile Arg Pro Lys Val Arg Asp Gln
225                 230                 235                 240
```

Glu Gly Arg Met Asn Tyr Tyr Trp Thr Leu Ile Pro Gly Asp Lys
            245                 250                 255

Ile Thr Phe Glu Thr Thr Gly Asn Leu Val Val Pro Arg Tyr Ala Phe
            260                 265                 270

Ala Met Glu Arg Asn Ala Gly Ser Gly Ile Ile Ile Ser Asp Thr Ser
            275                 280                 285

Val His Asp Cys Asn Thr Thr Cys Gln Thr Pro Lys Gly Ala Ile Asn
            290                 295                 300

Thr Ser Leu Pro Phe His Asn Ile His Pro Ile Thr Ile Gly Glu Cys
305                 310                 315                 320

Pro Lys Tyr Val Arg Ser Thr Lys Leu Arg Met Val Thr Gly Leu Arg
            325                 330                 335

Asn Ile Pro Ser Ile Gln Ser Arg Gly Leu Phe Gly Ala Ile Ala Gly
            340                 345                 350

Phe Ile Glu Gly Gly Trp Thr Gly Met Val Asp Gly Trp Tyr Gly Tyr
            355                 360                 365

His His Gln Asn Ala Gln Gly Ser Gly Tyr Ala Ala Asp Gln Lys Ser
            370                 375                 380

Thr Gln Asn Ala Ile Asp Glu Ile Thr Asn Lys Val Asn Ser Val Ile
385                 390                 395                 400

Glu Lys Met Asn Thr Gln Phe Thr Ala Val Gly Lys Glu Phe Asn Lys
            405                 410                 415

Leu Glu Lys Arg Met Glu Asn Leu Asn Lys Lys Val Asp Asp Gly Phe
            420                 425                 430

Leu Asp Ile Trp Thr Tyr Asn Ala Glu Leu Leu Ile Leu Leu Glu Asn
            435                 440                 445

Glu Arg Thr Leu Asp Tyr His Asp Ser Asn Val Lys Asn Leu Tyr Glu
            450                 455                 460

Lys Val Arg Ser Gln Leu Lys Asn Asn Ala Lys Glu Thr Gly Asn Gly
465                 470                 475                 480

Cys Phe Glu Phe Tyr His Lys Cys Asp Asn Thr Cys Met Glu Ser Val
            485                 490                 495

Lys Asn Gly Thr Tyr Asn Tyr Pro Lys Tyr Ser Glu Glu Ala Lys Leu
            500                 505                 510

Asn Arg Glu Lys Ile Asp Gly Val Lys Leu Glu Ser Met Gly Val Tyr
            515                 520                 525

Gln Ile Leu Ala Ile Tyr Ser Thr Val Ala Ser Ser Leu Val Leu Val
            530                 535                 540

Val Ser Leu Gly Ala Val Ser Phe Trp Met Cys Ser Asn Gly Ser Leu
545                 550                 555                 560

Arg Cys Arg Ile Cys Ile
            565

<210> SEQ ID NO 5
<211> LENGTH: 566
<212> TYPE: PRT
<213> ORGANISM: Artificial
<220> FEATURE:
<223> OTHER INFORMATION: synthetically-generated protein

<400> SEQUENCE: 5

Met Glu Ala Ile Leu Val Val Leu Leu Tyr Thr Phe Ala Thr Ala Asn
1               5                   10                  15

Ala Asp Thr Leu Cys Val Gly Tyr His Ala Asn Asn Ser Thr Asp Thr
            20                  25                  30

```
Val Asp Thr Leu Leu Glu Lys Asn Val Thr Val Thr His Ser Val Asn
        35                  40                  45

Leu Leu Glu Asp Ser His Asn Gly Lys Leu Cys Arg Leu Lys Gly Ile
50                  55                  60

Ala Pro Leu Gln Leu Gly Lys Cys Ser Ile Ala Gly Trp Ile Leu Gly
65                  70                  75                  80

Asn Pro Glu Cys Glu Thr Leu Ser Thr Ala Ser Ser Trp Ser Tyr Ile
                85                  90                  95

Val Glu Thr Ser Ser Ser Asp Asn Gly Thr Cys Tyr Pro Gly Asp Phe
                100                 105                 110

Ile Asp Tyr Glu Glu Leu Arg Glu Gln Leu Ser Ser Val Ser Ser Phe
            115                 120                 125

Glu Arg Phe Glu Met Phe Pro Lys Thr Ser Ser Trp Pro Asn His Asp
        130                 135                 140

Ser Asn Lys Gly Val Thr Ala Ala Cys Pro His Ala Gly Ala Lys Gly
145                 150                 155                 160

Phe Tyr Lys Asn Leu Ile Trp Leu Val Lys Lys Gly Asn Ser Tyr Pro
                165                 170                 175

Lys Leu Ser Gln Ser Tyr Ile Asn Asp Lys Gly Lys Glu Val Leu Val
                180                 185                 190

Leu Trp Gly Ile His His Pro Ser Thr Thr Ala Asp Gln Gln Ser Leu
            195                 200                 205

Tyr Gln Asn Ala Asp Ala Tyr Val Phe Val Gly Thr Ser Arg Tyr Ser
        210                 215                 220

Lys Lys Phe Lys Pro Glu Ile Ala Thr Arg Pro Lys Val Arg Asp Gln
225                 230                 235                 240

Glu Arg Arg Met Asn Tyr Tyr Trp Thr Leu Val Glu Pro Gly Asp Lys
                245                 250                 255

Ile Thr Phe Glu Ala Thr Gly Asn Leu Val Val Pro Arg Tyr Ala Phe
                260                 265                 270

Thr Met Glu Arg Asn Ala Gly Ser Gly Ile Ile Ile Ser Asp Thr Pro
            275                 280                 285

Val His Asp Cys Asn Thr Thr Cys Gln Thr Pro Glu Gly Ala Ile Asn
        290                 295                 300

Thr Ser Leu Pro Phe Gln Asn Ile His Pro Ile Thr Ile Gly Lys Cys
305                 310                 315                 320

Pro Lys Tyr Val Lys Ser Thr Lys Leu Arg Leu Ala Thr Gly Leu Arg
                325                 330                 335

Asn Val Pro Ser Ile Gln Ser Arg Gly Leu Leu Gly Ala Ile Ala Gly
                340                 345                 350

Phe Ile Glu Gly Gly Trp Thr Gly Met Met Asp Gly Trp Tyr Gly Tyr
            355                 360                 365

His His Gln Asn Gly Gln Gly Ser Gly Tyr Ala Ala Asp Leu Lys Ser
        370                 375                 380

Thr Gln Asn Ala Ile Asp Lys Ile Thr Asn Lys Val Asn Ser Val Ile
385                 390                 395                 400

Asp Lys Met Asn Thr Gln Phe Thr Ala Val Gly Lys Glu Phe Asn His
                405                 410                 415

Leu Glu Lys Arg Ile Glu Asn Leu Asn Lys Lys Val Asp Asp Gly Phe
                420                 425                 430

Ile Asp Val Trp Thr Tyr Asn Ala Glu Leu Leu Val Val Leu Glu Asn
            435                 440                 445
```

```
Glu Arg Thr Leu Glu Tyr His Asp Ser Asn Val Lys Asn Leu Tyr Glu
    450                 455                 460

Lys Val Arg Asn Gln Leu Lys Asn Asn Ala Lys Glu Ile Gly Asn Gly
465                 470                 475                 480

Cys Phe Glu Phe Tyr His Lys Cys Asn Asn Glu Cys Met Glu Ser Val
                485                 490                 495

Lys Asn Gly Thr Tyr Asp Tyr Pro Lys Tyr Ser Glu Ala Lys Leu
                500                 505                 510

Asn Arg Glu Glu Ile Asp Gly Val Lys Leu Glu Ser Thr Arg Ile Tyr
                515                 520                 525

Gln Ile Leu Ala Ile Tyr Ser Thr Ala Ala Ser Ser Leu Val Leu Val
            530                 535                 540

Val Ser Leu Gly Ala Ile Ser Phe Trp Met Cys Ser Asn Gly Ser Leu
545                 550                 555                 560

Gln Cys Arg Ile Cys Ile
                565
```

```
<210> SEQ ID NO 6
<211> LENGTH: 566
<212> TYPE: PRT
<213> ORGANISM: Artificial
<220> FEATURE:
<223> OTHER INFORMATION: synthetically-generated protein

<400> SEQUENCE: 6

Met Lys Ala Ile Leu Val Val Leu Leu Tyr Thr Phe Ala Thr Ala Asn
1               5                   10                  15

Ala Asp Thr Leu Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Lys His Asn Gly Lys Leu Cys Lys Leu Arg Gly Val
50                  55                  60

Ala Pro Leu His Leu Gly Lys Cys Asn Ile Ala Gly Trp Ile Leu Gly
65              70                  75                  80

Asn Pro Glu Cys Glu Ser Leu Ser Thr Ala Ser Ser Trp Ser Tyr Ile
                85                  90                  95

Val Glu Thr Ser Ser Ser Asp Asn Gly Thr Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Arg Phe Glu Ile Phe Pro Lys Thr Ser Ser Trp Pro Asn His Asp
130                 135                 140

Ser Asn Lys Gly Val Thr Ala Ala Cys Pro His Ala Gly Ala Lys Ser
145                 150                 155                 160

Phe Tyr Lys Asn Leu Ile Trp Leu Val Lys Lys Gly Asn Ser Tyr Pro
                165                 170                 175

Lys Leu Ser Lys Ser Tyr Ile Asn Asp Lys Gly Lys Glu Val Leu Val
            180                 185                 190

Leu Trp Gly Ile His His Pro Ser Thr Ser Ala Asp Gln Gln Ser Leu
        195                 200                 205

Tyr Gln Asn Ala Asp Ala Tyr Val Phe Val Gly Thr Ser Arg Tyr Ser
    210                 215                 220

Lys Lys Phe Lys Pro Glu Ile Ala Ile Arg Pro Lys Val Arg Asp Gln
225                 230                 235                 240
```

```
Glu Gly Arg Met Asn Tyr Tyr Trp Thr Leu Val Pro Gly Asp Lys
                245                 250                 255

Ile Thr Phe Glu Ala Thr Gly Asn Leu Val Val Pro Arg Tyr Ala Phe
        260                 265                 270

Ala Met Glu Arg Asn Ala Gly Ser Gly Ile Ile Ile Ser Asp Thr Pro
    275                 280                 285

Val His Asp Cys Asn Thr Thr Cys Gln Thr Pro Lys Gly Ala Ile Asn
290                 295                 300

Thr Ser Leu Pro Phe Gln Asn Ile His Pro Ile Thr Ile Gly Lys Cys
305                 310                 315                 320

Pro Lys Tyr Val Lys Ser Thr Lys Leu Arg Leu Ala Thr Gly Leu Arg
                325                 330                 335

Asn Val Pro Ser Ile Gln Ser Arg Gly Leu Phe Gly Ala Ile Ala Gly
            340                 345                 350

Phe Ile Glu Gly Gly Trp Thr Gly Met Val Asp Gly Trp Tyr Gly Tyr
        355                 360                 365

His His Gln Asn Glu Gln Gly Ser Gly Tyr Ala Ala Asp Leu Lys Ser
    370                 375                 380

Thr Gln Asn Ala Ile Asp Lys Ile Thr Asn Lys Val Asn Ser Val Ile
385                 390                 395                 400

Glu Lys Met Asn Thr Gln Phe Thr Ala Val Gly Lys Glu Phe Asn His
                405                 410                 415

Leu Glu Lys Arg Ile Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
        435                 440                 445

Glu Arg Thr Leu Asp Tyr His Asp Ser Asn Val Lys Asn Leu Tyr Glu
    450                 455                 460

Lys Val Arg Ser Gln Leu Lys Asn Asn Ala Lys Glu Ile Gly Asn Gly
465                 470                 475                 480

Cys Phe Glu Phe Tyr His Lys Cys Asp Asn Thr Cys Met Glu Ser Val
                485                 490                 495

Lys Asn Gly Thr Tyr Asp Tyr Pro Lys Tyr Ser Glu Glu Ala Lys Leu
            500                 505                 510

Asn Arg Glu Glu Ile Asp Gly Val Lys Leu Glu Ser Thr Arg Ile Tyr
        515                 520                 525

Gln Ile Leu Ala Ile Tyr Ser Thr Val Ala Ser Ser Leu Val Leu Val
    530                 535                 540

Val Ser Leu Gly Ala Ile Ser Phe Trp Met Cys Ser Asn Gly Ser Leu
545                 550                 555                 560

Gln Cys Arg Ile Cys Ile
                565

<210> SEQ ID NO 7
<211> LENGTH: 563
<212> TYPE: PRT
<213> ORGANISM: Artificial
<220> FEATURE:
<223> OTHER INFORMATION: synthetically-generated protein

<400> SEQUENCE: 7

Met Lys Val Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30
```

```
Val Asp Thr Ile Leu Glu Lys Asn Val Thr Val Thr His Ser Val Asn
    35                  40                  45

Leu Leu Glu Asn Ser His Asn Gly Lys Leu Cys Leu Leu Lys Gly Ile
 50                  55                  60

Ala Pro Leu Gln Leu Gly Asn Cys Ser Val Ala Gly Trp Ile Leu Gly
 65                  70                  75                  80

Asn Pro Glu Cys Glu Leu Leu Ile Ser Lys Glu Ser Trp Ser Tyr Ile
                 85                  90                  95

Val Glu Lys Pro Asn Pro Glu Asn Gly Thr Cys Tyr Pro Gly Asp Phe
            100                 105                 110

Ile Asn Tyr Glu Glu Leu Arg Glu Gln Leu Ser Ser Val Ser Ser Leu
        115                 120                 125

Glu Arg Phe Glu Ile Phe Pro Lys Glu Ser Ser Trp Pro Asn His Thr
    130                 135                 140

Val Thr Gly Val Ser Ala Ser Cys Ser His Asn Gly Glu Ser Ser Phe
145                 150                 155                 160

Tyr Arg Asn Leu Leu Trp Leu Thr Gly Lys Asn Gly Leu Tyr Pro Asn
                165                 170                 175

Leu Ser Lys Ser Tyr Ala Asn Asn Lys Glu Lys Glu Val Leu Val Leu
            180                 185                 190

Trp Gly Val His His Pro Pro Asn Ile Gly Asp Gln Arg Ala Leu Tyr
        195                 200                 205

His Thr Glu Asn Ala Tyr Val Ser Val Val Ser Ser His Tyr Ser Arg
    210                 215                 220

Lys Phe Thr Pro Glu Ile Ala Lys Arg Pro Lys Val Arg Asp Gln Glu
225                 230                 235                 240

Gly Arg Ile Asn Tyr Tyr Trp Thr Leu Leu Glu Pro Gly Asp Thr Ile
                245                 250                 255

Ile Phe Glu Ala Asn Gly Asn Leu Ile Ala Pro Arg Tyr Ala Phe Ala
            260                 265                 270

Leu Ser Arg Gly Phe Gly Ser Gly Ile Ile Asn Ser Asn Ala Pro Met
        275                 280                 285

Asp Lys Cys Asp Ala Lys Cys Gln Thr Pro Gln Gly Ala Ile Asn Ser
    290                 295                 300

Ser Leu Pro Phe Gln Asn Val His Pro Val Thr Ile Gly Glu Cys Pro
305                 310                 315                 320

Lys Tyr Val Arg Ser Ala Lys Leu Arg Met Val Thr Gly Leu Arg Asn
                325                 330                 335

Ile Pro Ser Ile Gln Ser Arg Gly Leu Leu Gly Ala Ile Ala Gly Phe
            340                 345                 350

Ile Glu Gly Gly Trp Thr Gly Met Ile Asp Gly Trp Tyr Gly Tyr His
        355                 360                 365

His Gln Asn Ala Gln Gly Ser Gly Tyr Ala Ala Asp Gln Lys Ser Thr
    370                 375                 380

Gln Asn Ala Ile Asp Glu Ile Thr Asn Lys Val Asn Ser Val Ile Glu
385                 390                 395                 400

Lys Met Asn Ile Gln Phe Thr Ala Val Gly Lys Glu Phe Asn Lys Leu
                405                 410                 415

Glu Arg Arg Met Glu Asn Leu Asn Lys Lys Val Asp Asp Gly Phe Ile
            420                 425                 430

Asp Ile Trp Thr Tyr Asn Ala Glu Leu Leu Ile Leu Leu Glu Asn Glu
        435                 440                 445

Arg Thr Leu Asp Phe His Asp Ser Asn Val Lys Asn Leu Tyr Glu Lys
```

```
            450                 455                 460
Val Arg Asn Gln Leu Lys Asn Asn Ala Lys Glu Val Gly Asn Gly Cys
465                 470                 475                 480

Phe Glu Phe Tyr His Lys Cys Asn Asp Glu Cys Met Glu Ser Val Lys
                    485                 490                 495

Asn Gly Ile Tyr Asp Tyr Pro Lys Tyr Ser Glu Ser Lys Leu Asn
                500                 505                 510

Arg Glu Lys Ile Asp Gly Val Lys Leu Glu Ser Met Gly Val Tyr Gln
                515                 520                 525

Ile Leu Ala Ile Tyr Ser Thr Val Ala Ser Ser Leu Val Leu Leu Val
                530                 535                 540

Ser Leu Gly Ala Ile Ser Phe Trp Met Cys Ser Gly His Ser Cys Arg
545                 550                 555                 560

Ile Cys Ile

<210> SEQ ID NO 8
<211> LENGTH: 566
<212> TYPE: PRT
<213> ORGANISM: Artificial
<220> FEATURE:
<223> OTHER INFORMATION: synthetically-generated protein

<400> SEQUENCE: 8

Met Glu Ala Ile Leu Val Val Leu Leu Tyr Thr Phe Thr Thr Ala Asn
1               5                   10                  15

Ala Asp Thr Leu Cys Val Gly Tyr His Ala Asn Asn Ser Thr Asp Thr
                20                  25                  30

Val Asp Thr Val Leu Glu Arg Asn Val Thr Val Thr His Ser Val Asn
                35                  40                  45

Leu Leu Glu Asp Ser His Asn Gly Lys Leu Cys Arg Leu Lys Gly Ile
            50                  55                  60

Ala Pro Leu Gln Leu Gly Lys Cys Asn Ile Ala Gly Trp Leu Leu Gly
65                  70                  75                  80

Asn Pro Glu Cys Glu Ser Leu Phe Ser Lys Glu Ser Trp Ser Tyr Ile
                85                  90                  95

Val Glu Thr Pro Asn Pro Glu Asn Gly Thr Cys Tyr Pro Gly His Phe
                100                 105                 110

Ala Asp Tyr Glu Glu Leu Arg Glu Gln Leu Asn Ser Val Ser Ser Phe
                115                 120                 125

Glu Arg Phe Glu Met Phe Pro Lys Thr Ser Ser Trp Pro Asp His Asp
130                 135                 140

Ser Asn Lys Gly Val Thr Thr Ala Cys Pro His Ala Gly Ala Lys Gly
145                 150                 155                 160

Phe Tyr Lys Asn Leu Ile Trp Leu Thr Lys Lys Gly Asn Ser Tyr Pro
                165                 170                 175

Lys Leu Ser Gln Ser Tyr Ile Asn Asp Lys Gly Lys Glu Ile Leu Val
                180                 185                 190

Leu Trp Gly Ile His His Pro Ser Thr Thr Ala Asp Gln Gln Ser Leu
                195                 200                 205

Tyr Gln Asn Ala Asp Thr Tyr Val Phe Val Gly Thr Ser Lys Tyr Ser
210                 215                 220

Lys Lys Phe Lys Pro Glu Ile Ala Thr Arg Pro Lys Val Arg Asp Gln
225                 230                 235                 240

Glu Arg Arg Met Asn Tyr Tyr Trp Thr Leu Ile Glu Pro Gly Asp Lys
                245                 250                 255
```

```
Ile Thr Phe Glu Ala Asn Gly Asn Leu Val Val Pro Arg Tyr Ala Phe
            260                 265                 270

Thr Met Glu Arg Asn Ala Gly Ser Gly Ile Ile Ile Ser Asp Thr Ser
            275                 280                 285

Val His Asp Cys Asn Thr Thr Cys Gln Thr Pro Glu Gly Ala Ile Asn
        290                 295                 300

Thr Ser Leu Pro Phe His Asn Ile His Pro Ile Thr Ile Gly Glu Cys
305                 310                 315                 320

Pro Lys Tyr Val Arg Ser Thr Lys Leu Arg Met Val Thr Gly Leu Arg
                325                 330                 335

Asn Val Pro Ser Val Gln Ser Arg Gly Leu Phe Gly Ala Ile Ala Gly
            340                 345                 350

Phe Ile Glu Gly Gly Trp Thr Gly Met Met Asp Gly Trp Tyr Gly Tyr
            355                 360                 365

His His Gln Asn Gly Gln Gly Ser Gly Tyr Ala Ala Asp Gln Lys Ser
        370                 375                 380

Thr Gln Asn Ala Ile Asn Gly Ile Thr Asn Lys Val Asn Ser Val Ile
385                 390                 395                 400

Asp Lys Met Asn Thr Gln Phe Thr Ala Val Gly Lys Glu Phe Asn Lys
                405                 410                 415

Leu Glu Lys Arg Met Glu Asn Leu Asn Lys Lys Val Asp Asp Gly Phe
            420                 425                 430

Ile Asp Val Trp Thr Tyr Asn Ala Glu Leu Leu Ile Leu Leu Glu Asn
            435                 440                 445

Glu Arg Thr Leu Asp Tyr His Asp Ser Lys Val Lys Asn Leu Tyr Glu
        450                 455                 460

Lys Val Lys Ser Gln Leu Lys Asn Asn Ala Lys Glu Thr Gly Asn Gly
465                 470                 475                 480

Cys Phe Glu Phe Tyr His Lys Cys Asn Asn Glu Cys Met Glu Ser Val
                485                 490                 495

Lys Asn Gly Thr Tyr Asp Tyr Pro Arg Tyr Ser Glu Glu Ala Lys Leu
            500                 505                 510

Asn Arg Glu Lys Ile Asp Gly Val Lys Leu Glu Ser Thr Arg Val Tyr
            515                 520                 525

Gln Ile Leu Ala Ile Tyr Ser Thr Ala Ala Ser Ser Leu Val Leu Val
        530                 535                 540

Val Ser Leu Gly Glu Ile Ser Phe Trp Met Cys Ser Asn Gly Ser Leu
545                 550                 555                 560

Arg Cys Arg Ile Cys Ile
                565

<210> SEQ ID NO 9
<211> LENGTH: 558
<212> TYPE: PRT
<213> ORGANISM: Artificial
<220> FEATURE:
<223> OTHER INFORMATION: synthetically-generated protein

<400> SEQUENCE: 9

Met Ala Ile Ile Tyr Leu Ile Leu Leu Phe Thr Ala Val Arg Gly Asp
1               5                   10                  15

Gln Ile Cys Ile Gly Tyr His Ala Asn Asn Ser Thr Glu Lys Val Asp
            20                  25                  30

Thr Ile Leu Glu Arg Asn Val Thr Val Thr His Ala Lys Asp Ile Leu
        35                  40                  45
```

```
Glu Lys Thr His Asn Gly Lys Leu Cys Lys Leu Asn Gly Ile Pro Pro
     50                  55                  60
Leu Glu Leu Gly Asp Cys Ser Ile Ala Gly Trp Leu Leu Gly Asn Pro
 65                  70                  75                  80
Glu Cys Asp Arg Leu Leu Val Pro Glu Trp Ser Tyr Ile Met Glu Lys
                 85                  90                  95
Glu Asn Pro Arg Gly Leu Cys Tyr Pro Gly Ser Phe Asn Asp Tyr Glu
             100                 105                 110
Glu Leu Lys His Leu Leu Ser Ser Val Lys His Phe Glu Lys Val Lys
             115                 120                 125
Ile Leu Pro Lys Asp Arg Trp Thr Gln His Thr Thr Thr Gly Gly Ser
130                 135                 140
Arg Ala Cys Ala Val Ser Gly Asn Pro Ser Phe Phe Arg Asn Met Val
145                 150                 155                 160
Trp Leu Thr Lys Lys Gly Ser Asn Tyr Pro Val Ala Lys Gly Ser Tyr
                 165                 170                 175
Asn Asn Thr Ser Gly Glu Gln Met Leu Ile Ile Trp Gly Val His His
             180                 185                 190
Pro Asn Asp Glu Thr Glu Gln Arg Thr Leu Tyr Gln Asn Val Gly Thr
             195                 200                 205
Tyr Val Ser Val Thr Ser Thr Leu Asn Lys Arg Ser Thr Pro Glu Ile
210                 215                 220
Ala Arg Pro Lys Val Asn Gly Leu Gly Ser Arg Met Glu Phe Ser Trp
225                 230                 235                 240
Thr Leu Leu Asp Met Trp Asp Thr Ile Asn Phe Glu Ser Thr Gly Asn
                 245                 250                 255
Leu Ile Ala Pro Glu Tyr Gly Phe Lys Ile Ser Lys Arg Gly Ser Ser
             260                 265                 270
Gly Ile Met Lys Thr Glu Gly Thr Leu Glu Asn Cys Glu Thr Lys Cys
             275                 280                 285
Gln Thr Pro Leu Gly Ala Ile Asn Thr Thr Leu Pro Phe His Asn Val
290                 295                 300
His Pro Leu Thr Ile Gly Glu Cys Pro Lys Tyr Val Lys Ser Glu Lys
305                 310                 315                 320
Leu Val Leu Ala Thr Gly Leu Arg Asn Val Pro Gln Ile Glu Ser Arg
                 325                 330                 335
Gly Leu Phe Gly Ala Ile Ala Gly Phe Ile Glu Gly Gly Trp Gln Gly
             340                 345                 350
Met Val Asp Gly Trp Tyr Gly Tyr His His Ser Asn Asp Gln Gly Ser
             355                 360                 365
Gly Tyr Ala Ala Asp Lys Glu Ser Thr Gln Lys Ala Phe Asp Gly Ile
370                 375                 380
Thr Asn Lys Val Asn Ser Val Ile Glu Lys Met Asn Thr Gln Phe Glu
385                 390                 395                 400
Ala Val Gly Lys Glu Phe Ser Asn Leu Glu Arg Arg Leu Glu Asn Leu
                 405                 410                 415
Asn Lys Lys Met Glu Asp Gly Phe Leu Asp Val Trp Thr Tyr Asn Ala
             420                 425                 430
Glu Leu Leu Val Leu Met Glu Asn Glu Arg Thr Leu Asp Phe His Asp
             435                 440                 445
Ser Asn Val Lys Asn Leu Tyr Asp Lys Val Arg Met Gln Leu Arg Asp
450                 455                 460
```

Asn Val Lys Glu Leu Gly Asn Gly Cys Phe Glu Phe Tyr His Lys Cys
465                 470                 475                 480

Asp Asp Glu Cys Met Asn Ser Val Lys Asn Gly Thr Tyr Asp Tyr Pro
            485                 490                 495

Lys Tyr Glu Glu Glu Ser Lys Leu Asn Arg Asn Glu Ile Lys Gly Val
        500                 505                 510

Lys Leu Ser Ser Met Gly Val Tyr Gln Ile Leu Ala Ile Tyr Ala Thr
    515                 520                 525

Val Ala Gly Ser Leu Ser Leu Ala Ile Met Met Ala Gly Ile Ser Phe
530                 535                 540

Trp Met Cys Ser Asn Gly Ser Leu Gln Cys Arg Ile Cys Ile
545                 550                 555

<210> SEQ ID NO 10
<211> LENGTH: 562
<212> TYPE: PRT
<213> ORGANISM: Artificial
<220> FEATURE:
<223> OTHER INFORMATION: synthetically-generated protein

<400> SEQUENCE: 10

Met Val Ile Ile Tyr Leu Ile Leu Leu Phe Thr Ala Val Arg Gly Asp
1               5                   10                  15

Lys Ile Cys Ile Gly Tyr His Ala Asn Asn Ser Thr Glu Met Val Asp
            20                  25                  30

Thr Ile Leu Glu Arg Asn Val Thr Val Thr His Ala Lys Asp Ile Leu
        35                  40                  45

Glu Lys Thr His Asn Gly Lys Leu Cys Lys Leu Asn Gly Ile Pro Pro
    50                  55                  60

Leu Glu Leu Gly Asn Cys Ser Ile Ala Gly Trp Leu Leu Gly Asn Pro
65                  70                  75                  80

Glu Cys Asp Arg Leu Leu Arg Val Pro Glu Trp Ser Tyr Ile Met Glu
                85                  90                  95

Lys Glu Asn Pro Arg Asp Gly Leu Cys Tyr Pro Gly Ser Phe Asn Asp
            100                 105                 110

Tyr Glu Glu Leu Lys His Phe Leu Ser Ser Val Lys His Phe Glu Lys
        115                 120                 125

Val Lys Ile Leu Pro Lys Asp Arg Trp Thr Gln His Thr Thr Thr Gly
    130                 135                 140

Gly Ser Arg Ala Cys Ala Val Ser Gly Asn Pro Ser Phe Phe Arg Asn
145                 150                 155                 160

Met Val Trp Leu Thr Lys Lys Gly Ser Asn Tyr Pro Val Ala Gln Gly
                165                 170                 175

Ser Tyr Asn Asn Thr Ser Gly Glu Lys Met Leu Ile Ile Trp Gly Val
            180                 185                 190

His His Pro Asn Asp Glu Thr Glu Gln Arg Thr Leu Tyr Gln Asn Val
        195                 200                 205

Gly Thr Tyr Val Ser Val Gly Thr Ser Thr Leu Asn Lys Arg Ser Thr
    210                 215                 220

Pro Asp Ile Ala Thr Arg Pro Lys Val Asn Gly Leu Gly Gly Arg Met
225                 230                 235                 240

Glu Phe Ser Trp Thr Leu Leu Asp Met Trp Asp Thr Ile Asn Phe Glu
                245                 250                 255

Ser Thr Gly Asn Leu Ile Ala Pro Glu Tyr Gly Phe Lys Ile Ser Lys
            260                 265                 270

```
Arg Gly Arg Ser Gly Ile Met Lys Thr Glu Gly Thr Leu Glu Asn Cys
            275                 280                 285

Glu Thr Lys Cys Gln Thr Pro Leu Gly Ala Ile Asn Thr Thr Leu Pro
        290                 295                 300

Phe His Asn Val His Pro Leu Ala Ile Gly Glu Cys Pro Lys Tyr Val
305                 310                 315                 320

Arg Ser Glu Lys Leu Val Leu Ala Thr Gly Leu Arg Asn Val Pro Gln
                325                 330                 335

Ile Glu Ser Arg Gly Leu Phe Gly Ala Ile Ala Gly Phe Ile Glu Gly
                340                 345                 350

Gly Trp Gln Gly Met Ile Asp Gly Trp Tyr Gly Tyr His His Ser Asn
        355                 360                 365

Asp Gln Gly Ser Gly Tyr Ala Ala Asp Lys Glu Ser Thr Gln Arg Ala
    370                 375                 380

Phe Asp Gly Ile Thr Asn Lys Val Asn Ser Val Ile Glu Lys Met Asn
385                 390                 395                 400

Thr Gln Phe Glu Ser Val Gly Lys Glu Phe Ser Asn Leu Glu Arg Arg
                405                 410                 415

Leu Glu Asn Leu Asn Lys Lys Met Glu Asp Gly Phe Leu Asp Val Trp
                420                 425                 430

Thr Tyr Asn Ala Glu Leu Leu Val Leu Met Glu Asn Glu Arg Thr Leu
        435                 440                 445

Gly Phe His Asp Ser Asn Val Lys Asn Leu Tyr Asn Lys Val Arg Met
    450                 455                 460

Gln Leu Arg Asp Asn Val Lys Glu Leu Gly Asp Gly Cys Phe Glu Phe
465                 470                 475                 480

Tyr His Lys Cys Asn Asp Glu Cys Met Asn Ser Val Lys Asn Gly Thr
                485                 490                 495

Tyr Tyr Tyr Pro Lys Tyr Glu Glu Ser Lys Leu Asn Arg Asn Glu
                500                 505                 510

Ile Lys Gly Val Lys Leu Ser Ser Met Gly Ile Tyr Gln Ile Leu Ala
        515                 520                 525

Ile Tyr Ala Thr Val Ala Gly Ser Leu Ser Leu Ala Ile Met Met Ala
    530                 535                 540

Gly Ile Ser Phe Trp Met Cys Ser Asn Gly Ser Leu Gln Phe Arg Ile
545                 550                 555                 560

Cys Ile

<210> SEQ ID NO 11
<211> LENGTH: 562
<212> TYPE: PRT
<213> ORGANISM: Artificial
<220> FEATURE:
<223> OTHER INFORMATION: synthetically-generated protein

<400> SEQUENCE: 11

Met Ala Ile Ile Tyr Leu Ile Leu Leu Phe Ala Thr Val Arg Gly Asp
1               5                   10                  15

Gln Ile Cys Ile Gly Tyr His Ala Asn Asn Ser Thr Glu Thr Val Asp
                20                  25                  30

Thr Ile Leu Glu Arg Asn Val Thr Val Thr His Ala Lys Asp Ile Leu
            35                  40                  45

Glu Lys Ala His Asn Gly Lys Leu Cys Lys Leu Asn Gly Ile Pro Pro
        50                  55                  60

Leu Glu Leu Gly Asp Cys Ser Ile Ala Gly Trp Leu Leu Gly Asn Pro
```

```
                65                  70                  75                  80
Lys Cys Asp Arg Leu Leu Ser Val Pro Glu Trp Ser Tyr Ile Met Glu
                    85                  90                  95
Lys Glu Asn Pro Lys Tyr Ser Leu Cys Tyr Pro Gly Ser Leu Asn Asp
                    100                 105                 110
Tyr Glu Glu Leu Lys His Leu Leu Ser Ser Val Lys His Phe Glu Lys
                    115                 120                 125
Val Arg Ile Leu Pro Lys Asp Gly Trp Thr Gln His Thr Thr Thr Gly
            130                 135                 140
Gly Ser Lys Ala Cys Ala Val Ser Gly Lys Pro Ser Phe Phe Arg Asn
145                 150                 155                 160
Met Val Trp Leu Thr Glu Lys Gly Ser Asn Tyr Pro Val Ala Lys Gly
                    165                 170                 175
Ser Tyr Asn Asn Thr Ser Gly Glu Gln Met Leu Ile Ile Trp Gly Val
                180                 185                 190
His His Pro Ile Asp Glu Ala Glu Gln Arg Ala Leu Tyr Gln Glu Val
            195                 200                 205
Gly Thr Tyr Val Ser Ala Ser Thr Ser Thr Leu Asn Lys Arg Ser Ile
        210                 215                 220
Pro Glu Ile Ala Ala Arg Pro Lys Val Asn Gly Leu Gly Ser Arg Met
225                 230                 235                 240
Glu Phe Phe Trp Thr Leu Leu Asp Val Trp Asp Thr Ile Asn Phe Glu
                    245                 250                 255
Ser Thr Gly Asn Leu Val Val Pro Glu Tyr Gly Phe Lys Ile Ser Lys
                260                 265                 270
Arg Gly Ser Ser Gly Ile Met Lys Thr Glu Gly Thr Leu Gly Asn Cys
            275                 280                 285
Glu Thr Lys Cys Gln Thr Pro Leu Gly Ala Ile Asn Thr Thr Leu Pro
        290                 295                 300
Phe His Asn Val His Pro Leu Thr Ile Gly Glu Cys Pro Arg Tyr Val
305                 310                 315                 320
Lys Ser Glu Lys Leu Val Leu Ala Thr Gly Leu Arg Asn Ile Pro Gln
                    325                 330                 335
Ile Glu Ser Arg Gly Leu Phe Gly Ala Ile Ala Gly Phe Ile Glu Gly
                340                 345                 350
Gly Trp Gln Gly Met Val Asp Gly Trp Tyr Gly Tyr His His Ser Asn
            355                 360                 365
Glu Gln Gly Ser Gly Tyr Ala Ala Asp Lys Glu Ser Thr Gln Lys Ala
        370                 375                 380
Phe Asp Gly Ile Thr Asn Lys Glu Asn Ser Val Ile Glu Lys Met Asn
385                 390                 395                 400
Thr Gln Phe Glu Ala Val Gly Lys Glu Phe Asn Asn Leu Glu Lys Arg
                    405                 410                 415
Leu Glu Asn Leu Asn Lys Arg Met Glu Asp Gly Phe Leu Asp Val Trp
                420                 425                 430
Thr Tyr Asn Ala Glu Leu Leu Val Leu Met Glu Asn Glu Arg Thr Leu
            435                 440                 445
Asp Phe His Asp Ser Asn Val Lys Asn Leu Tyr Glu Lys Val Arg Met
        450                 455                 460
Gln Leu Arg Asp Asn Val Lys Glu Leu Gly Asn Gly Cys Phe Glu Phe
465                 470                 475                 480
Tyr His Lys Cys Asp Asn Glu Cys Met Asp Ser Val Lys Asn Gly Thr
                    485                 490                 495
```

Tyr Asp Tyr Pro Lys Tyr Glu Glu Ser Lys Ala Lys Arg Asn Glu
            500                 505                 510

Ile Lys Gly Val Lys Leu Ser Ser Met Gly Val Tyr Gln Ile Leu Ala
            515                 520                 525

Ile Tyr Ala Thr Val Ala Gly Ser Leu Ser Leu Ala Ile Met Val Ala
            530                 535                 540

Gly Ile Ser Phe Trp Met Cys Ser Asn Gly Ser Leu Gln Cys Arg Ile
545                 550                 555                 560

Cys Ile

<210> SEQ ID NO 12
<211> LENGTH: 562
<212> TYPE: PRT
<213> ORGANISM: Artificial
<220> FEATURE:
<223> OTHER INFORMATION: synthetically-generated protein

<400> SEQUENCE: 12

Met Ala Ile Ile Tyr Phe Ile Leu Leu Phe Thr Ala Val Arg Gly Asp
1               5                   10                  15

Gln Ile Cys Ile Gly Tyr His Ala Asn Asn Ser Thr Glu Lys Val Asp
            20                  25                  30

Thr Ile Leu Glu Arg Asn Val Thr Val Thr His Ala Lys Asn Ile Leu
        35                  40                  45

Glu Lys Thr His Asn Gly Arg Leu Cys Lys Leu Asn Gly Ile Pro Pro
    50                  55                  60

Leu Glu Leu Gly Asp Cys Ser Ile Thr Gly Trp Leu Leu Gly Asn Pro
65                  70                  75                  80

Glu Cys Asp Arg Leu Leu Ser Val Pro Glu Trp Ser Tyr Ile Met Glu
                85                  90                  95

Lys Glu Asn Pro Arg Tyr Ser Leu Cys Tyr Pro Gly Ser Phe Asn Asp
            100                 105                 110

Tyr Glu Glu Leu Lys His Leu Leu Ser Ser Val Lys His Leu Glu Lys
        115                 120                 125

Val Lys Ile Leu Pro Lys Asp Gly Trp Thr Gln His Glu Thr Asp Gly
    130                 135                 140

Gly Ser Lys Ala Cys Ala Val Ser Gly Glu Pro Ser Phe Phe Arg Asn
145                 150                 155                 160

Met Val Trp Leu Thr Lys Lys Gly Pro Asn Tyr Pro Val Ala Lys Arg
                165                 170                 175

Ser Tyr Asn Asn Thr Ser Gly Glu Gln Met Leu Ile Ile Trp Gly Val
            180                 185                 190

His His Pro Asn Asp Glu Ala Glu Gln Arg Ala Leu Tyr Gln Lys Val
        195                 200                 205

Gly Thr Tyr Val Ser Ala Ser Thr Ser Thr Leu Asn Lys Arg Ser Thr
    210                 215                 220

Pro Glu Ile Ala Ala Arg Pro Glu Val Asn Gly Leu Gly Ser Arg Met
225                 230                 235                 240

Glu Phe Ser Trp Thr Leu Leu Asp Val Trp Asp Thr Ile Ser Phe Glu
                245                 250                 255

Ser Thr Gly Asn Leu Val Ala Pro Glu Tyr Gly Phe Lys Ile Ser Lys
            260                 265                 270

Arg Gly Ser Ser Gly Ile Ile Lys Thr Glu Gly Thr Leu Gly Asn Cys
        275                 280                 285

```
Glu Thr Lys Cys Gln Thr Pro Leu Gly Ala Ile Asn Thr Thr Leu Pro
        290                 295                 300

Phe His Asn Val His Pro Leu Thr Ile Gly Glu Cys Pro Lys Tyr Val
305                 310                 315                 320

Lys Ser Glu Lys Leu Val Leu Ala Thr Gly Pro Arg Asn Val Pro Gln
                325                 330                 335

Ile Glu Ser Arg Gly Leu Phe Gly Ala Ile Ala Gly Phe Ile Glu Gly
                340                 345                 350

Gly Trp Gln Gly Met Val Asp Gly Trp Tyr Gly Tyr His His Ser Lys
        355                 360                 365

Glu Gln Gly Ser Gly Tyr Ala Ala Asp Lys Glu Ser Thr Gln Lys Ala
    370                 375                 380

Phe Asp Arg Ile Thr Asn Lys Val Asn Ser Val Ile Glu Lys Ile Asn
385                 390                 395                 400

Thr Gln Phe Glu Ala Val Gly Lys Glu Phe Ser Asn Leu Glu Lys Arg
                405                 410                 415

Leu Glu Asn Leu Asn Lys Lys Met Glu Asp Gly Phe Ile Asp Val Trp
                420                 425                 430

Thr Tyr Asn Ala Glu Leu Leu Val Leu Met Glu Asn Glu Arg Ile Leu
        435                 440                 445

Asp Phe His Asp Ser Asn Val Lys Asn Leu Tyr Asp Lys Val Arg Met
    450                 455                 460

Gln Leu Arg Asp Asn Ala Lys Glu Leu Gly Asn Gly Cys Phe Glu Phe
465                 470                 475                 480

Tyr His Lys Cys Asp Asp Glu Cys Met Asn Ser Val Lys Asn Gly Thr
                485                 490                 495

Tyr Asp Tyr Pro Lys Tyr Glu Glu Ser Lys Leu Lys Arg Asn Glu
                500                 505                 510

Ile Lys Gly Val Glu Leu Ser Ser Met Gly Val Tyr Gln Ile Leu Val
        515                 520                 525

Ile Tyr Ala Thr Val Ala Gly Ser Leu Ser Leu Ala Ile Met Ile Ala
    530                 535                 540

Gly Ile Ser Phe Trp Met Cys Ser Asn Gly Ser Leu Gln Cys Arg Val
545                 550                 555                 560

Cys Ile
```

<210> SEQ ID NO 13
<211> LENGTH: 562
<212> TYPE: PRT
<213> ORGANISM: Artificial
<220> FEATURE:
<223> OTHER INFORMATION: synthetically-generated protein

<400> SEQUENCE: 13

```
Met Ala Ile Ile Tyr Leu Ile Leu Leu Phe Thr Ala Val Arg Gly Asp
1               5                   10                  15

Gln Ile Cys Ile Gly Tyr His Ala Asn Asn Ser Thr Glu Lys Val Asp
                20                  25                  30

Thr Ile Leu Glu Arg Asn Val Thr Val Thr His Ala Lys Asp Ile Leu
            35                  40                  45

Glu Lys Thr His Asn Gly Lys Leu Cys Lys Leu Asn Gly Ile Pro Pro
        50                  55                  60

Leu Glu Leu Gly Asp Cys Ser Ile Ala Gly Trp Leu Leu Gly Asn Pro
65                  70                  75                  80

Glu Cys Asp Arg Leu Leu Ser Val Pro Glu Trp Ser Tyr Ile Met Glu
```

```
            85                  90                  95
Lys Glu Asn Pro Arg Asp Gly Leu Cys Tyr Pro Gly Ser Phe Asn Asp
            100                 105                 110

Tyr Glu Glu Leu Lys His Leu Leu Ser Ser Val Lys His Phe Glu Lys
            115                 120                 125

Val Lys Ile Leu Pro Lys Asp Arg Trp Thr Gln His Thr Thr Thr Gly
            130                 135                 140

Gly Ser Arg Ala Cys Ala Val Ser Gly Asn Pro Ser Phe Phe Arg Asn
145                 150                 155                 160

Met Val Trp Leu Thr Lys Lys Gly Ser Asn Tyr Pro Val Ala Lys Gly
                165                 170                 175

Ser Tyr Asn Asn Thr Ser Gly Glu Gln Met Leu Ile Ile Trp Gly Val
                180                 185                 190

His His Pro Asn Asp Glu Thr Glu Gln Arg Thr Leu Tyr Gln Asn Val
                195                 200                 205

Gly Thr Tyr Val Ser Val Gly Thr Ser Thr Leu Asn Lys Arg Ser Thr
            210                 215                 220

Pro Glu Ile Ala Thr Arg Pro Lys Val Asn Gly Leu Gly Ser Arg Met
225                 230                 235                 240

Glu Phe Ser Trp Thr Leu Leu Asp Met Trp Asp Thr Ile Asn Phe Glu
                245                 250                 255

Ser Thr Gly Asn Leu Ile Ala Pro Glu Tyr Gly Phe Lys Ile Ser Lys
                260                 265                 270

Arg Gly Ser Ser Gly Ile Met Lys Thr Glu Gly Thr Leu Glu Asn Cys
                275                 280                 285

Glu Thr Lys Cys Gln Thr Pro Leu Gly Ala Ile Asn Thr Thr Leu Pro
            290                 295                 300

Phe His Asn Val His Pro Leu Thr Ile Gly Glu Cys Pro Lys Tyr Val
305                 310                 315                 320

Lys Ser Glu Lys Leu Val Leu Ala Thr Gly Leu Arg Asn Val Pro Gln
                325                 330                 335

Ile Glu Ser Arg Gly Leu Phe Gly Ala Ile Ala Gly Phe Ile Glu Gly
                340                 345                 350

Gly Trp Gln Gly Met Val Asp Gly Trp Tyr Gly Tyr His His Ser Asn
                355                 360                 365

Asp Gln Gly Ser Gly Tyr Ala Ala Asp Lys Glu Ser Thr Gln Lys Ala
            370                 375                 380

Phe Asp Gly Ile Thr Asn Lys Val Asn Ser Val Ile Glu Lys Met Asn
385                 390                 395                 400

Thr Gln Phe Glu Ala Val Gly Lys Glu Phe Ser Asn Leu Glu Arg Arg
                405                 410                 415

Leu Glu Asn Leu Asn Lys Lys Met Glu Asp Gly Phe Leu Asp Val Trp
                420                 425                 430

Thr Tyr Asn Ala Glu Leu Leu Val Leu Met Glu Asn Glu Arg Thr Leu
                435                 440                 445

Asp Phe His Asp Ser Asn Val Lys Asn Leu Tyr Asp Lys Val Arg Met
            450                 455                 460

Gln Leu Arg Asp Asn Val Lys Glu Leu Gly Asn Gly Cys Phe Glu Phe
465                 470                 475                 480

Tyr His Lys Cys Asp Asp Glu Cys Met Asn Ser Val Lys Asn Gly Thr
                485                 490                 495

Tyr Asp Tyr Pro Lys Tyr Glu Glu Glu Ser Lys Leu Asn Arg Asn Glu
                500                 505                 510
```

-continued

```
Ile Lys Gly Val Lys Leu Ser Ser Met Gly Val Tyr Gln Ile Leu Ala
        515                 520                 525
Ile Tyr Ala Thr Val Ala Gly Ser Leu Ser Leu Ala Ile Met Met Ala
        530                 535                 540
Gly Ile Ser Phe Trp Met Cys Ser Asn Gly Ser Leu Gln Cys Arg Ile
545                 550                 555                 560
Cys Ile

<210> SEQ ID NO 14
<211> LENGTH: 562
<212> TYPE: PRT
<213> ORGANISM: Artificial
<220> FEATURE:
<223> OTHER INFORMATION: synthetically-generated protein

<400> SEQUENCE: 14

Met Ala Ile Ile Tyr Leu Ile Leu Leu Phe Ala Thr Val Arg Gly Asp
1               5                   10                  15
Gln Ile Cys Ile Gly Tyr His Ala Asn Asn Ser Thr Glu Thr Val Asp
                20                  25                  30
Thr Ile Leu Glu Arg Asn Val Thr Val Thr His Ala Lys Asn Ile Leu
            35                  40                  45
Glu Lys Thr His Asn Gly Lys Leu Cys Lys Leu Asn Gly Ile Pro Pro
    50                  55                  60
Leu Glu Leu Gly Asp Cys Ser Ile Ala Gly Trp Leu Leu Gly Asn Pro
65                  70                  75                  80
Glu Cys Asp Arg Leu Leu Arg Val Pro Glu Trp Ser Tyr Ile Met Glu
                85                  90                  95
Lys Glu Asn Pro Arg Tyr Ser Leu Cys Tyr Pro Gly Ser Leu Asn Asp
                100                 105                 110
Tyr Glu Glu Leu Lys His Leu Leu Ser Ser Val Lys His Phe Glu Lys
            115                 120                 125
Val Arg Ile Leu Pro Lys Asp Gly Trp Thr Gln His Thr Thr Thr Gly
    130                 135                 140
Gly Ser Lys Ala Cys Ala Val Ser Gly Lys Pro Ser Phe Phe Arg Asn
145                 150                 155                 160
Met Val Trp Leu Thr Lys Lys Gly Pro Asn Tyr Pro Val Ala Lys Arg
                165                 170                 175
Ser Tyr Asn Asn Thr Ser Gly Glu Gln Met Leu Ile Ile Trp Gly Val
                180                 185                 190
His His Pro Asn Asp Glu Ala Glu Gln Arg Ala Leu Tyr Gln Lys Val
            195                 200                 205
Gly Thr Tyr Val Ser Ala Ser Thr Ser Thr Leu Asn Lys Arg Ser Thr
    210                 215                 220
Pro Asp Ile Ala Thr Arg Pro Lys Val Asn Gly Gln Gly Gly Arg Met
225                 230                 235                 240
Glu Phe Ser Trp Thr Leu Leu Asp Val Trp Asp Thr Ile Asn Phe Glu
                245                 250                 255
Ser Thr Gly Asn Leu Val Ala Pro Glu Tyr Gly Phe Lys Ile Ser Lys
                260                 265                 270
Arg Gly Ser Ser Gly Ile Met Lys Thr Glu Gly Thr Leu Gly Asn Cys
            275                 280                 285
Glu Thr Lys Cys Gln Thr Pro Leu Gly Ala Ile Asn Thr Thr Leu Pro
    290                 295                 300
```

```
Phe His Asn Val His Pro Leu Thr Ile Gly Glu Cys Pro Lys Tyr Val
305                 310                 315                 320

Lys Ser Glu Lys Leu Val Leu Ala Thr Gly Pro Arg Asn Val Pro Gln
            325                 330                 335

Ile Glu Ser Arg Gly Leu Phe Gly Ala Ile Ala Gly Phe Ile Glu Gly
            340                 345                 350

Gly Trp Gln Gly Met Val Asp Gly Trp Tyr Gly Tyr His His Ser Asn
            355                 360                 365

Asp Gln Gly Ser Gly Tyr Ala Ala Asp Lys Glu Ser Thr Gln Lys Ala
            370                 375                 380

Phe Asp Arg Ile Thr Asn Lys Val Asn Ser Val Ile Glu Lys Met Asn
385                 390                 395                 400

Thr Gln Phe Glu Ala Val Gly Lys Glu Phe Asn Asn Leu Glu Lys Arg
            405                 410                 415

Leu Glu Asn Leu Asn Lys Lys Met Glu Asp Gly Phe Leu Asp Val Trp
            420                 425                 430

Thr Tyr Asn Ala Glu Leu Leu Val Leu Met Glu Asn Glu Arg Thr Leu
            435                 440                 445

Asp Phe His Asp Ser Asn Val Lys Asn Leu Tyr Glu Lys Val Arg Met
450                 455                 460

Gln Leu Arg Asp Asn Val Lys Glu Leu Gly Asn Gly Cys Phe Glu Phe
465                 470                 475                 480

Tyr His Lys Cys Asp Asn Glu Cys Met Asp Ser Val Lys Asn Gly Thr
            485                 490                 495

Tyr Asp Tyr Pro Lys Tyr Glu Glu Ser Lys Leu Leu Arg Asn Glu
            500                 505                 510

Ile Lys Gly Val Lys Leu Ser Ser Met Gly Ile Tyr Gln Ile Leu Ala
            515                 520                 525

Ile Tyr Ala Thr Val Ala Gly Ser Leu Ser Leu Ala Ile Met Ile Ala
            530                 535                 540

Gly Ile Ser Phe Trp Met Cys Ser Asn Gly Ser Leu Gln Cys Arg Ile
545                 550                 555                 560

Cys Ile

<210> SEQ ID NO 15
<211> LENGTH: 562
<212> TYPE: PRT
<213> ORGANISM: Artificial
<220> FEATURE:
<223> OTHER INFORMATION: synthetically-generated protein

<400> SEQUENCE: 15

Met Ala Ile Ile Tyr Phe Ile Leu Leu Phe Thr Ala Val Arg Gly Asp
1               5                   10                  15

Gln Ile Cys Ile Gly Tyr His Ala Asn Asn Ser Thr Glu Lys Val Asp
            20                  25                  30

Thr Ile Leu Glu Arg Asn Val Thr Val Thr His Ala Lys Asn Ile Leu
            35                  40                  45

Glu Lys Thr His Asn Gly Lys Leu Cys Lys Leu Asn Gly Ile Pro Pro
        50                  55                  60

Leu Glu Leu Gly Asp Cys Ser Ile Ala Gly Trp Leu Leu Gly Asn Pro
65                  70                  75                  80

Glu Cys Asp Arg Leu Leu Ser Val Pro Glu Trp Ser Tyr Ile Met Glu
                85                  90                  95

Lys Glu Asn Pro Lys Tyr Ser Leu Cys Tyr Pro Gly Ser Phe Asn Asp
```

```
                100                 105                 110
Tyr Glu Glu Leu Lys His Leu Leu Ser Ser Val Lys His Phe Glu Lys
            115                 120                 125
Val Lys Ile Leu Pro Lys Asp Gly Trp Thr Gln His Glu Thr Asp Gly
            130                 135                 140
Gly Ser Lys Ala Cys Ala Val Ser Gly Glu Pro Ser Phe Phe Arg Asn
145                 150                 155                 160
Met Val Trp Leu Thr Glu Lys Gly Ser Asn Tyr Pro Val Ala Lys Gly
                165                 170                 175
Ser Tyr Asn Asn Thr Ser Gly Glu Gln Met Leu Ile Ile Trp Gly Val
            180                 185                 190
His His Pro Ile Asp Glu Ala Glu Gln Arg Ala Leu Tyr Gln Glu Val
        195                 200                 205
Gly Thr Tyr Val Ser Ala Ser Thr Ser Thr Leu Asn Lys Arg Ser Ile
    210                 215                 220
Pro Glu Ile Ala Ala Arg Pro Lys Val Asn Gly Leu Gly Gly Arg Met
225                 230                 235                 240
Glu Phe Ser Trp Thr Leu Leu Asp Val Trp Asp Thr Ile Ser Phe Glu
                245                 250                 255
Ser Thr Gly Asn Leu Val Ala Pro Glu Tyr Gly Phe Lys Ile Ser Lys
            260                 265                 270
Arg Gly Ser Ser Gly Ile Met Lys Thr Glu Gly Thr Leu Glu Asn Cys
        275                 280                 285
Glu Thr Lys Cys Gln Thr Pro Leu Gly Ala Ile Asn Thr Thr Leu Pro
    290                 295                 300
Phe His Asn Val His Pro Leu Thr Ile Gly Glu Cys Pro Lys Tyr Val
305                 310                 315                 320
Lys Ser Glu Lys Leu Val Leu Ala Thr Gly Pro Arg Asn Val Pro Gln
                325                 330                 335
Ile Glu Ser Arg Gly Leu Phe Gly Ala Ile Ala Gly Phe Ile Glu Gly
            340                 345                 350
Gly Trp Gln Gly Met Val Asp Gly Trp Tyr Gly Tyr His His Ser Asn
        355                 360                 365
Asp Gln Gly Ser Gly Tyr Ala Ala Asp Lys Glu Ser Thr Gln Arg Ala
    370                 375                 380
Phe Asp Gly Ile Thr Asn Lys Val Asn Ser Val Ile Glu Lys Met Asn
385                 390                 395                 400
Thr Gln Phe Glu Ala Val Gly Lys Glu Phe Ser Asn Leu Glu Lys Arg
                405                 410                 415
Leu Glu Asn Leu Asn Lys Lys Met Glu Asp Gly Phe Leu Asp Val Trp
            420                 425                 430
Thr Tyr Asn Ala Glu Leu Leu Val Leu Met Glu Asn Glu Arg Thr Leu
        435                 440                 445
Asp Phe His Asp Ser Asn Val Lys Asn Leu Tyr Asn Lys Val Arg Met
    450                 455                 460
Gln Leu Arg Asp Asn Val Lys Glu Leu Gly Asn Gly Cys Phe Glu Phe
465                 470                 475                 480
Tyr His Lys Cys Asp Asp Glu Cys Met Ser Ser Val Lys Asn Gly Thr
                485                 490                 495
Tyr Asp Tyr Pro Lys Tyr Glu Glu Ser Lys Leu Lys Arg Asn Glu
            500                 505                 510
Ile Lys Gly Val Lys Leu Ser Ser Met Gly Val Tyr Gln Ile Leu Ala
        515                 520                 525
```

```
Ile Tyr Ala Thr Val Ala Gly Ser Leu Ser Leu Ala Ile Met Val Ala
            530                 535                 540

Gly Ile Ser Phe Trp Met Cys Ser Asn Gly Ser Leu Gln Cys Arg Ile
545                 550                 555                 560

Cys Ile

<210> SEQ ID NO 16
<211> LENGTH: 564
<212> TYPE: PRT
<213> ORGANISM: Artificial
<220> FEATURE:
<223> OTHER INFORMATION: synthetically-generated protein

<400> SEQUENCE: 16

Met Lys Thr Ile Ile Ala Leu Ser Tyr Ile Cys Leu Val Phe Ala
1               5                   10                  15

Gln Lys Leu Pro Gly Asn Asp Asn Ser Thr Ala Thr Leu Cys Leu
                20                  25                  30

Gly His Ala Val Pro Asn Gly Thr Ile Val Lys Thr Ile Thr Asn
            35                  40                  45

Asp Gln Ile Glu Val Thr Asn Ala Thr Glu Leu Val Gln Ser Ser Thr
50                  55                  60

Gly Glu Ile Cys Asp Ser Pro His Gln Ile Leu Asp Gly Glu Asn Cys
65                  70                  75                  80

Thr Leu Ile Asp Ala Leu Leu Gly Asp Pro Gln Cys Asp Gly Phe Gln
                85                  90                  95

Asn Lys Lys Trp Asp Leu Phe Val Glu Arg Ser Lys Ala Tyr Ser Asn
                100                 105                 110

Cys Tyr Pro Tyr Asp Val Pro Asp Tyr Ala Ser Leu Arg Ser Leu Val
                115                 120                 125

Ala Ser Ser Gly Thr Leu Glu Phe Asn Asn Glu Ser Phe Asn Trp Thr
130                 135                 140

Gly Val Thr Gln Asn Gly Thr Ser Ser Ala Cys Ile Arg Arg Ser Asn
145                 150                 155                 160

Ser Phe Phe Ser Arg Leu Asn Trp Leu Thr His Leu Asn Phe Lys Tyr
                165                 170                 175

Pro Ala Leu Asn Val Thr Met Pro Asn Asn Glu Gln Phe Asp Lys Leu
                180                 185                 190

Tyr Ile Trp Gly Val His His Pro Gly Thr Asp Lys Asp Gln Ile Phe
                195                 200                 205

Leu Tyr Ala Gln Ser Gly Arg Ile Thr Val Ser Thr Lys Arg Ser Gln
210                 215                 220

Gln Ala Val Ile Pro Asn Ile Gly Ser Arg Pro Arg Ile Pro Ser
225                 230                 235                 240

Arg Ile Ser Ile Tyr Trp Thr Ile Val Lys Pro Gly Asp Ile Leu Leu
                245                 250                 255

Ile Asn Ser Thr Gly Asn Leu Ile Ala Pro Arg Gly Tyr Phe Lys Ile
                260                 265                 270

Arg Ser Gly Lys Ser Ser Ile Met Arg Ser Asp Ala Pro Ile Gly Lys
                275                 280                 285

Cys Ser Glu Cys Ile Thr Pro Asn Gly Ser Ile Pro Asn Asp Lys Pro
                290                 295                 300

Phe Gln Asn Val Asn Arg Ile Thr Tyr Gly Ala Cys Pro Arg Tyr Val
305                 310                 315                 320
```

Lys Gln Thr Leu Lys Leu Ala Thr Gly Met Arg Asn Val Pro Glu Lys
            325                 330                 335

Gln Thr Arg Gly Ile Phe Gly Ala Ile Ala Gly Phe Ile Glu Asn Gly
            340                 345                 350

Trp Glu Gly Met Val Asp Gly Trp Tyr Gly Phe Arg His Gln Asn Ser
            355                 360                 365

Glu Gly Arg Gly Gln Ala Ala Asp Leu Lys Ser Thr Gln Ala Ala Ile
            370                 375                 380

Asp Gln Ile Asn Gly Lys Leu Asn Arg Leu Ile Gly Lys Thr Asn Glu
385                 390                 395                 400

Lys Phe His Gln Ile Glu Lys Glu Phe Ser Glu Val Glu Gly Arg Ile
                405                 410                 415

Gln Asp Leu Glu Lys Tyr Val Glu Asp Thr Lys Ile Asp Leu Trp Ser
            420                 425                 430

Tyr Asn Ala Glu Leu Leu Val Ala Leu Glu Asn Gln His Thr Ile Asp
            435                 440                 445

Leu Thr Asp Ser Glu Met Asn Lys Leu Phe Glu Lys Thr Lys Lys Gln
            450                 455                 460

Leu Arg Glu Asn Ala Glu Asp Met Gly Asn Gly Cys Phe Lys Ile Tyr
465                 470                 475                 480

His Lys Cys Asp Asn Ala Cys Ile Gly Ser Ile Arg Asn Gly Thr Tyr
                485                 490                 495

Asp His Asp Val Tyr Arg Asp Glu Ala Leu Asn Asn Arg Phe Gln Ile
            500                 505                 510

Lys Gly Val Glu Leu Lys Ser Gly Tyr Lys Asp Trp Ile Leu Trp Ile
            515                 520                 525

Ser Phe Ala Ile Ser Cys Phe Leu Leu Cys Val Ala Leu Leu Gly Phe
            530                 535                 540

Ile Met Trp Ala Cys Gln Lys Gly Asn Ile Arg Cys Asn Ile Arg Cys
545                 550                 555                 560

Asn Ile Cys Ile

<210> SEQ ID NO 17
<211> LENGTH: 566
<212> TYPE: PRT
<213> ORGANISM: Artificial
<220> FEATURE:
<223> OTHER INFORMATION: synthetically-generated protein

<400> SEQUENCE: 17

Met Lys Thr Ile Ile Ala Leu Ser His Ile Leu Cys Leu Val Phe Ala
1               5                   10                  15

Gln Lys Ile Pro Gly Asn Asp Asn Ser Thr Ala Thr Leu Cys Ile Gly
            20                  25                  30

His His Ala Val Pro Asn Gly Met Ile Val Lys Thr Ile Thr Asn Asp
            35                  40                  45

Arg Ile Glu Val Thr Asn Ala Thr Glu Leu Val Gln Asn Ser Ser Ile
        50                  55                  60

Gly Glu Ile Cys Asp Ser Pro His Gln Ile Leu Asp Gly Glu Asn Cys
65                  70                  75                  80

Thr Leu Ile Asp Ala Leu Leu Gly Asp Pro His Cys Asp Gly Phe Gln
                85                  90                  95

Asn Glu Lys Trp Asp Leu Phe Val Glu Arg Ser Lys Ala Phe Ser Asn
            100                 105                 110

Cys Tyr Pro Tyr Asp Val Pro Asp Tyr Ala Ser Leu Arg Ser Leu Val

```
            115                 120                 125
Ala Ser Ser Gly Thr Leu Glu Phe Lys Asn Glu Ser Phe Asn Trp Thr
130                 135                 140

Gly Val Ala Gln Asn Gly Thr Ser Ser Ala Cys Ile Arg Arg Ser Ser
145                 150                 155                 160

Ser Ser Phe Phe Ser Arg Leu Asn Trp Leu Thr His Leu Asn Tyr Thr
                165                 170                 175

Tyr Pro Ala Leu Asn Val Thr Met Pro Asn Lys Glu Gln Phe Asp Lys
            180                 185                 190

Leu Tyr Ile Trp Gly Val His His Pro Gly Thr Asp Lys Asp Gln Ile
        195                 200                 205

Phe Leu Tyr Ala Gln Ser Ser Gly Arg Ile Thr Val Ser Thr Lys Arg
210                 215                 220

Ser Gln Gln Thr Ala Ile Pro Asn Ile Gly Ser Arg Pro Arg Ile Arg
225                 230                 235                 240

Asp Ile Pro Ser Arg Ile Ser Ile Tyr Trp Thr Ile Val Lys Pro Gly
                245                 250                 255

Asp Val Leu Val Ile Asn Ser Asn Gly Asn Leu Ile Ala Pro Arg Gly
            260                 265                 270

Tyr Phe Lys Ile Gln Ser Gly Lys Ser Ser Ile Met Arg Ser Asp Ala
        275                 280                 285

Pro Ile Gly Lys Cys Lys Ser Glu Cys Ile Thr Pro Asn Gly Ser Ile
290                 295                 300

Ser Asn Asp Lys Pro Phe Gln Asn Val Asn Lys Ile Thr Tyr Gly Ala
305                 310                 315                 320

Cys Pro Arg Tyr Val Lys His Ser Thr Leu Lys Leu Ala Thr Gly Met
                325                 330                 335

Arg Asn Val Pro Glu Lys Gln Thr Arg Gly Leu Phe Gly Ala Ile Ala
            340                 345                 350

Gly Phe Ile Glu Asn Gly Trp Glu Gly Met Lys Asp Gly Trp Tyr Gly
        355                 360                 365

Phe Arg His Gln Asn Ser Glu Gly Arg Gly Gln Ala Ala Asp Leu Lys
370                 375                 380

Ser Thr Gln Ala Ala Ile Asn Gln Ile Asn Gly Lys Leu Asn Arg Leu
385                 390                 395                 400

Ile Gly Lys Thr Asn Glu Lys Phe His Gln Ile Glu Lys Glu Phe Ser
                405                 410                 415

Glu Val Glu Gly Arg Val Gln Asp Leu Glu Lys Tyr Val Glu Asp Ser
            420                 425                 430

Lys Ile Asp Leu Trp Ser Tyr Asn Ala Gly Leu Leu Val Ala Leu Glu
        435                 440                 445

Asn Gln His Thr Ile Asp Leu Thr Asp Ser Glu Met Asn Lys Leu Phe
450                 455                 460

Glu Arg Thr Arg Lys Gln Leu Arg Glu Asn Ala Glu Asp Met Gly Asn
465                 470                 475                 480

Gly Cys Phe Thr Ile Tyr His Lys Cys Asp Asn Ala Cys Ile Gly Ser
                485                 490                 495

Ile Arg Asn Gly Thr Tyr Asp His Asn Val Tyr Arg Asp Glu Ala Leu
            500                 505                 510

Asn Lys Arg Phe Gln Ile Lys Gly Ile Glu Leu Lys Ser Gly Tyr Lys
        515                 520                 525

Asp Trp Ile Leu Trp Ile Ser Phe Ala Ile Ser Cys Phe Leu Leu Cys
530                 535                 540
```

```
Val Ala Leu Leu Gly Phe Ile Met Trp Ala Cys Gln Lys Gly Asn Ile
545                 550                 555                 560

Arg Cys Asn Ile Cys Ile
                565
```

<210> SEQ ID NO 18
<211> LENGTH: 566
<212> TYPE: PRT
<213> ORGANISM: Artificial
<220> FEATURE:
<223> OTHER INFORMATION: synthetically-generated protein

<400> SEQUENCE: 18

```
Met Lys Thr Ile Ile Ala Leu Ser Tyr Ile Phe Cys Leu Val Phe Ala
1               5                   10                  15

Gln Lys Leu Pro Gly Asn Asp Asn Ser Thr Ala Met Leu Cys Leu Gly
                20                  25                  30

His His Ala Val Pro Asn Gly Thr Leu Val Lys Thr Ile Thr Asn Asp
            35                  40                  45

Gln Ile Glu Val Thr Asn Ala Thr Glu Leu Val Gln Ser Ser Ser Thr
50                  55                  60

Gly Arg Ile Cys Asp Ser Pro His Arg Ile Leu Asp Gly Lys Asn Cys
65                  70                  75                  80

Thr Leu Met Asp Ala Leu Leu Gly Asp Pro His Cys Asp Gly Phe Gln
                85                  90                  95

Asn Lys Glu Trp Asp Leu Phe Val Glu Arg Ser Lys Ala Tyr Ser Asn
            100                 105                 110

Cys Tyr Pro Tyr Asp Val Pro Asp Tyr Val Ser Leu Arg Ser Leu Val
            115                 120                 125

Ala Ser Ser Gly Thr Leu Glu Phe Asn Asn Glu Ser Phe Asn Trp Ala
130                 135                 140

Gly Val Thr Gln Asn Gly Thr Ser Ser Ala Cys Lys Arg Arg Ser Asn
145                 150                 155                 160

Ser Ser Phe Phe Ser Arg Leu Asn Trp Leu Thr His Leu Asn Phe Lys
                165                 170                 175

Tyr Pro Ala Leu Asn Val Thr Met Pro Asn Asn Glu Gln Phe Asp Lys
            180                 185                 190

Leu Tyr Ile Trp Gly Val His His Pro Ser Thr Asp Ser Asp Gln Ile
            195                 200                 205

Ser Leu Tyr Ala Gln Ala Ser Gly Arg Val Thr Val Ser Thr Lys Arg
210                 215                 220

Ser Gln Gln Ala Val Ile Pro Asn Ile Gly Ser Arg Pro Arg Ile Arg
225                 230                 235                 240

Asn Ile Pro Ser Arg Ile Ser Ile Tyr Trp Thr Ile Val Lys Pro Gly
                245                 250                 255

Asp Ile Leu Val Ile Asn Ser Asn Gly Asn Leu Ile Ala Pro Arg Gly
            260                 265                 270

Tyr Phe Lys Ile Arg Asn Gly Lys Ser Ser Ile Met Arg Ser Asn Ala
            275                 280                 285

Pro Ile Gly Lys Cys Asn Ser Glu Cys Ile Thr Pro Asn Gly Ser Ile
290                 295                 300

Pro Asn Asp Lys Pro Phe Gln Asn Val Asn Arg Val Thr Tyr Gly Ala
305                 310                 315                 320

Cys Pro Arg Tyr Val Lys Gln Ser Thr Leu Lys Leu Ala Thr Gly Met
                325                 330                 335
```

```
Arg Asn Val Pro Glu Lys Gln Thr Arg Gly Ile Phe Gly Ala Ile Ala
            340                 345                 350

Val Phe Ile Glu Asn Gly Trp Glu Gly Met Val Asp Gly Trp Tyr Gly
        355                 360                 365

Phe Arg His Gln Asn Ser Glu Gly Thr Gly Gln Ala Ala Asp Leu Lys
    370                 375                 380

Ser Thr Gln Ala Ala Val Asp Gln Ile Asn Gly Lys Leu Asn Arg Leu
385                 390                 395                 400

Ile Glu Lys Thr Asn Glu Lys Phe His Gln Ile Glu Lys Glu Phe Thr
            405                 410                 415

Glu Val Glu Gly Arg Ile Gln Asp Leu Glu Lys Tyr Val Glu Asp Thr
        420                 425                 430

Lys Val Asp Leu Trp Ser Tyr Asn Ala Glu Leu Leu Val Ala Leu Glu
    435                 440                 445

Asn Gln His Thr Ile Asp Leu Thr Asp Ala Glu Met Asn Lys Leu Phe
450                 455                 460

Glu Arg Thr Lys Lys Gln Leu Arg Glu Asn Ala Glu Asp Ile Gly Asn
465                 470                 475                 480

Gly Cys Phe Lys Ile Tyr His Lys Cys Asp Asn Ala Cys Ile Glu Ser
            485                 490                 495

Ile Arg Asn Gly Thr Tyr Asp His Asp Val Tyr Arg Asp Glu Ala Leu
        500                 505                 510

Asn Asn Arg Phe His Ile Lys Gly Val Glu Leu Lys Ser Gly Tyr Lys
    515                 520                 525

Asn Trp Ile Leu Trp Ile Ser Phe Ala Ile Ser Cys Phe Leu Leu Cys
530                 535                 540

Val Val Leu Leu Gly Phe Ile Met Trp Ala Cys Gln Lys Gly Asn Ile
545                 550                 555                 560

Arg Cys Ser Ile Cys Ile
            565

<210> SEQ ID NO 19
<211> LENGTH: 566
<212> TYPE: PRT
<213> ORGANISM: Artificial
<220> FEATURE:
<223> OTHER INFORMATION: synthetically-generated protein

<400> SEQUENCE: 19

Met Lys Thr Ile Ile Ala Leu Ser Tyr Ile Leu Cys Leu Val Phe Ala
1               5                   10                  15

Gln Lys Leu Pro Glu Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Gln Thr Glu Val Thr Asn Ala Thr Glu Leu Val Gln Ser Ser Ser Thr
    50                  55                  60

Gly Glu Ile Cys Asn Ser Pro His Gln Ile Leu Asp Gly Lys Asn Cys
65                  70                  75                  80

Thr Leu Ile Asp Ala Leu Leu Gly Asp Pro Gln Cys Asp Gly Phe Gln
            85                  90                  95

Asn Lys Lys Trp Asp Leu Phe Val Glu Arg Ser Lys Ala His Ser Asn
        100                 105                 110

Cys Tyr Pro Tyr Asp Val Pro Asp Tyr Ala Ser Leu Arg Ser Leu Ile
    115                 120                 125
```

```
Ala Ser Ser Gly Thr Leu Glu Phe Asn Asn Glu Ser Phe Asn Trp Thr
    130                 135                 140

Gly Val Thr Gln Asn Gly Thr Ser Ser Ala Cys Ile Arg Arg Ser Asn
145                 150                 155                 160

Asn Ser Phe Phe Ser Arg Leu Asn Trp Leu Thr His Leu Lys Phe Lys
                165                 170                 175

Tyr Pro Ala Leu Asn Val Thr Met Pro Asn Asn Glu Lys Phe Asp Lys
            180                 185                 190

Leu Tyr Ile Trp Gly Val His His Pro Gly Thr Asp Asn Asp Gln Ile
        195                 200                 205

Phe Leu Tyr Ala Gln Ala Ser Gly Arg Ile Thr Val Ser Thr Lys Arg
    210                 215                 220

Ser Gln Gln Thr Val Ile Pro Asn Ile Gly Ser Arg Pro Arg Val Arg
225                 230                 235                 240

Asn Ile Pro Ser Arg Val Ser Ile Tyr Trp Thr Ile Val Lys Pro Gly
                245                 250                 255

Asp Ile Leu Leu Ile Asn Ser Thr Gly Asn Leu Ile Ala Pro Arg Gly
            260                 265                 270

Tyr Phe Lys Ile Arg Ser Gly Lys Ser Ser Ile Met Arg Ser Asp Ala
        275                 280                 285

Pro Ile Gly Lys Cys Asn Ser Ala Cys Ile Thr Pro Asn Gly Ser Ile
    290                 295                 300

Pro Asn Gly Lys Pro Phe Gln Asn Val Asn Arg Ile Thr Tyr Gly Ala
305                 310                 315                 320

Cys Pro Arg Tyr Val Lys Gln Asn Thr Leu Lys Leu Ala Thr Gly Met
                325                 330                 335

Arg Asn Val Pro Glu Arg Gln Thr Arg Gly Ile Phe Gly Ala Ile Ala
            340                 345                 350

Gly Phe Ile Glu Asn Gly Trp Glu Gly Met Met Asp Gly Trp Tyr Gly
        355                 360                 365

Phe Arg His Gln Asn Ser Glu Gly Ile Gly Gln Ala Ala Asp Leu Lys
    370                 375                 380

Ser Thr Gln Ala Ala Ile Asp Gln Ile Asn Gly Lys Leu Asn Arg Val
385                 390                 395                 400

Ile Glu Lys Thr Asn Glu Lys Phe His Gln Ile Glu Lys Glu Phe Ser
                405                 410                 415

Glu Val Glu Gly Arg Ile Gln Asp Ile Glu Lys Tyr Val Glu Asp Thr
            420                 425                 430

Lys Ile Asp Leu Trp Ser Tyr Asn Ala Glu Phe Leu Val Ala Leu Glu
        435                 440                 445

Asn Gln His Thr Ile His Leu Thr Asp Ser Glu Met Asn Lys Leu Phe
    450                 455                 460

Glu Lys Thr Lys Lys Gln Leu Arg Glu Asn Ala Glu Asp Met Gly Asn
465                 470                 475                 480

Gly Cys Phe Lys Ile Tyr His Lys Cys Asn Asn Ala Cys Ile Gly Ser
                485                 490                 495

Ile Arg Asn Glu Thr Tyr Asp His Asn Val Tyr Arg Asp Glu Ala Leu
            500                 505                 510

Asn Asn Arg Phe Gln Ile Lys Gly Val Glu Leu Lys Ser Gly Tyr Lys
        515                 520                 525

Asp Trp Val Leu Trp Ile Ser Phe Ala Ile Ser Cys Phe Leu Leu Cys
    530                 535                 540
```

Ile Val Leu Leu Gly Phe Ile Met Trp Ala Cys Gln Arg Gly Asn Ile
545                 550                 555                 560

Arg Cys Asn Ile Cys Ile
            565

<210> SEQ ID NO 20
<211> LENGTH: 566
<212> TYPE: PRT
<213> ORGANISM: Artificial
<220> FEATURE:
<223> OTHER INFORMATION: synthetically-generated protein

<400> SEQUENCE: 20

Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Gln Ile Glu Val Thr Asn Ala Thr Glu Leu Val Gln Asn Ser Ser Ile
    50                  55                  60

Gly Glu Ile Cys Asp Ser Pro His Gln Ile Leu Asp Gly Glu Asn Cys
65                  70                  75                  80

Thr Leu Ile Asp Ala Leu Leu Gly Asp Pro Gln Cys Asp Gly Phe Gln
                85                  90                  95

Asn Lys Lys Trp Asp Leu Phe Val Glu Arg Ser Lys Ala Tyr Ser Asn
            100                 105                 110

Cys Tyr Pro Tyr Asp Val Pro Asp Tyr Ala Ser Leu Arg Ser Leu Val
        115                 120                 125

Ala Ser Ser Gly Thr Leu Glu Phe Asn Asn Glu Ser Phe Asn Trp Thr
    130                 135                 140

Gly Val Thr Gln Asn Gly Thr Ser Ser Ala Cys Ile Arg Arg Ser Asn
145                 150                 155                 160

Asn Ser Phe Phe Ser Arg Leu Asn Trp Leu Thr His Leu Asn Phe Lys
                165                 170                 175

Tyr Pro Ala Leu Asn Val Thr Met Pro Asn Asn Glu Gln Phe Asp Lys
            180                 185                 190

Leu Tyr Ile Trp Gly Val His His Pro Gly Thr Asp Lys Asp Gln Ile
        195                 200                 205

Phe Leu Tyr Ala Gln Ser Ser Gly Arg Ile Thr Val Ser Thr Lys Arg
    210                 215                 220

Ser Gln Gln Ala Val Ile Pro Asn Ile Gly Ser Arg Pro Arg Ile Arg
225                 230                 235                 240

Asp Ile Pro Ser Arg Ile Ser Ile Tyr Trp Thr Ile Val Lys Pro Gly
                245                 250                 255

Asp Ile Leu Leu Ile Asn Ser Thr Gly Asn Leu Ile Ala Pro Arg Gly
            260                 265                 270

Tyr Phe Lys Ile Arg Ser Gly Lys Ser Ser Ile Met Arg Ser Asp Ala
        275                 280                 285

Pro Ile Gly Lys Cys Lys Ser Glu Cys Ile Thr Pro Asn Gly Ser Ile
    290                 295                 300

Pro Asn Asp Lys Pro Phe Gln Asn Val Asn Arg Ile Thr Tyr Gly Ala
305                 310                 315                 320

Cys Pro Arg Tyr Val Lys Gln Asn Thr Leu Lys Leu Ala Thr Gly Met
                325                 330                 335

```
Arg Asn Val Pro Glu Lys Gln Thr Arg Gly Ile Phe Gly Ala Ile Ala
            340                 345                 350

Gly Phe Ile Glu Asn Gly Trp Glu Gly Met Val Asp Gly Trp Tyr Gly
        355                 360                 365

Phe Arg His Gln Asn Ser Glu Gly Arg Gly Gln Ala Ala Asp Leu Lys
        370                 375                 380

Ser Thr Gln Ala Ala Ile Asp Gln Ile Asn Gly Lys Leu Asn Arg Leu
385                 390                 395                 400

Ile Gly Lys Thr Asn Glu Lys Phe His Gln Ile Glu Lys Glu Phe Ser
                405                 410                 415

Glu Val Glu Gly Arg Ile Gln Asp Leu Glu Lys Tyr Val Glu Asp Thr
            420                 425                 430

Lys Ile Asp Leu Trp Ser Tyr Asn Ala Glu Leu Leu Val Ala Leu Glu
        435                 440                 445

Asn Gln His Thr Ile Asp Leu Thr Asp Ser Glu Met Asn Lys Leu Phe
        450                 455                 460

Glu Lys Thr Lys Lys Gln Leu Arg Glu Asn Ala Glu Asp Met Gly Asn
465                 470                 475                 480

Gly Cys Phe Lys Ile Tyr His Lys Cys Asp Asn Ala Cys Ile Gly Ser
                485                 490                 495

Ile Arg Asn Gly Thr Tyr Asp His Asp Val Tyr Arg Asp Glu Ala Leu
            500                 505                 510

Asn Asn Arg Phe Gln Ile Lys Gly Val Glu Leu Lys Ser Gly Tyr Lys
        515                 520                 525

Asp Trp Ile Leu Trp Ile Ser Phe Ala Ile Ser Cys Phe Leu Leu Cys
        530                 535                 540

Val Ala Leu Leu Gly Phe Ile Met Trp Ala Cys Gln Lys Gly Asn Ile
545                 550                 555                 560

Arg Cys Asn Ile Cys Ile
                565

<210> SEQ ID NO 21
<211> LENGTH: 566
<212> TYPE: PRT
<213> ORGANISM: Artificial
<220> FEATURE:
<223> OTHER INFORMATION: synthetically-generated protein

<400> SEQUENCE: 21

Met Lys Thr Ile Ile Ala Leu Ser His Ile Leu Cys Leu Val Phe Ala
1               5                   10                  15

Gln Lys Ile Pro Gly Asn Asp Asn Ser Thr Ala Met Leu Cys Leu Gly
            20                  25                  30

His His Ala Val Ser Asn Gly Thr Ile Val Lys Thr Ile Thr Asn Asp
        35                  40                  45

Arg Ile Glu Val Thr Asn Ala Thr Glu Leu Val Gln Ser Ser Ser Thr
50                  55                  60

Gly Glu Ile Cys Asp Ser Pro His Arg Ile Leu Asp Gly Lys Asn Cys
65                  70                  75                  80

Thr Leu Ile Asp Ala Leu Leu Gly Asp Pro His Cys Asp Gly Phe Gln
                85                  90                  95

Asn Lys Glu Trp Asp Leu Phe Val Glu Arg Ser Lys Ala His Ser Asn
            100                 105                 110

Cys Tyr Pro Tyr Asp Val Pro Asp Tyr Val Ser Leu Arg Ser Leu Val
        115                 120                 125
```

```
Ala Ser Ser Gly Thr Leu Glu Phe Lys Asn Glu Ser Phe Asn Trp Thr
130                 135                 140

Gly Val Ala Gln Asn Gly Thr Ser Ser Ala Cys Ile Arg Arg Ser Ser
145                 150                 155                 160

Ser Ser Phe Phe Ser Arg Leu Asn Trp Leu Thr His Leu Asn Tyr Thr
                165                 170                 175

Tyr Pro Ala Leu Asn Val Thr Met Pro Asn Asn Glu Lys Phe Asp Lys
            180                 185                 190

Leu Tyr Ile Trp Gly Val His His Pro Gly Thr Asp Asn Asp Gln Ile
        195                 200                 205

Phe Leu Tyr Ala Gln Ala Ser Gly Arg Ile Thr Val Ser Thr Lys Arg
210                 215                 220

Ser Gln Gln Thr Val Ile Pro Asn Ile Gly Ser Arg Pro Arg Val Arg
225                 230                 235                 240

Asn Ile Pro Ser Arg Ile Ser Ile Tyr Trp Thr Ile Val Lys Pro Gly
                245                 250                 255

Asp Val Leu Val Ile Asn Ser Asn Gly Asn Leu Ile Ala Pro Arg Gly
            260                 265                 270

Tyr Phe Lys Ile Gln Ser Gly Lys Ser Ser Ile Met Arg Ser Asp Ala
        275                 280                 285

Pro Ile Gly Lys Cys Asn Ser Glu Cys Ile Thr Pro Asn Gly Ser Ile
290                 295                 300

Ser Asn Asp Lys Pro Phe Gln Asn Val Asn Lys Ile Thr Tyr Gly Ala
305                 310                 315                 320

Cys Pro Arg Tyr Val Lys His Ser Thr Leu Lys Leu Ala Thr Gly Met
                325                 330                 335

Arg Asn Val Pro Glu Arg Gln Thr Arg Gly Ile Phe Gly Ala Ile Ala
            340                 345                 350

Val Phe Ile Glu Asn Gly Trp Glu Gly Met Met Asp Gly Trp Tyr Gly
        355                 360                 365

Phe Arg His Gln Asn Ser Glu Gly Thr Gly Gln Ala Ala Asp Leu Lys
370                 375                 380

Ser Thr Gln Ala Ala Ile Asn Gln Ile Asn Gly Lys Leu Asn Arg Leu
385                 390                 395                 400

Ile Glu Lys Thr Asn Glu Lys Phe His Gln Ile Glu Lys Glu Phe Ser
                405                 410                 415

Glu Val Glu Gly Arg Val Gln Asp Leu Glu Lys Tyr Val Glu Asp Ser
            420                 425                 430

Lys Ile Asp Leu Trp Ser Tyr Asn Ala Gly Leu Leu Val Ala Leu Glu
        435                 440                 445

Asn Gln His Thr Ile His Leu Thr Asp Ser Glu Met Asn Lys Leu Phe
450                 455                 460

Glu Arg Thr Lys Lys Gln Leu Arg Glu Asn Ala Glu Asp Met Gly Asn
465                 470                 475                 480

Gly Cys Phe Thr Ile Tyr His Lys Cys Asp Asn Ala Cys Ile Glu Ser
                485                 490                 495

Ile Arg Asn Gly Thr Tyr Asp His Asn Val Tyr Arg Asp Glu Ala Leu
            500                 505                 510

Asn Lys Arg Phe Gln Ile Lys Gly Ile Glu Leu Lys Ser Gly Tyr Lys
        515                 520                 525

Asp Trp Val Leu Trp Ile Ser Phe Ala Ile Ser Cys Phe Leu Leu Cys
530                 535                 540

Val Val Leu Leu Gly Phe Ile Met Trp Ala Cys Gln Arg Gly Asn Ile
```

```
                545                 550                 555                 560

Arg Cys Asn Ile Cys Ile
                565

<210> SEQ ID NO 22
<211> LENGTH: 566
<212> TYPE: PRT
<213> ORGANISM: Artificial
<220> FEATURE:
<223> OTHER INFORMATION: synthetically-generated protein

<400> SEQUENCE: 22

Met Arg Thr Ile Ile Ala Leu Ser Tyr Ile Phe Cys Leu Val Phe Ala
1               5                   10                  15

Gln Lys Leu Pro Glu Asn Asp Asn Ser Thr Ala Thr Leu Cys Ile Gly
            20                  25                  30

His His Ala Val Pro Asn Gly Thr Leu Val Lys Thr Ile Thr Asn Asp
        35                  40                  45

Gln Val Glu Val Thr Asn Ala Thr Glu Leu Val Gln Ser Ser Ser Thr
    50                  55                  60

Gly Gly Ile Cys Asp Ser Pro His Gln Ile Leu Asp Gly Lys Asn Cys
65                  70                  75                  80

Thr Leu Val Asp Ala Leu Leu Gly Asp Pro His Cys Asp Gly Phe Gln
                85                  90                  95

Asn Glu Lys Trp Asp Leu Phe Val Glu Arg Ser Lys Ala Phe Ser Asn
            100                 105                 110

Cys Tyr Pro Tyr Asp Val Gln Asp Tyr Ala Ser Leu Arg Ser Leu Ile
        115                 120                 125

Ala Ser Ser Gly Thr Leu Glu Phe Asn Asn Glu Ser Phe Asn Trp Ala
    130                 135                 140

Gly Val Thr Gln Asn Gly Thr Ser Ser Ala Cys Lys Arg Arg Ser Asn
145                 150                 155                 160

Ser Ser Phe Phe Ser Arg Leu Asn Trp Leu Thr His Leu Lys Phe Lys
                165                 170                 175

Tyr Pro Ala Leu Asn Val Thr Met Pro Asn Lys Glu Gln Phe Asp Lys
            180                 185                 190

Leu Tyr Ile Trp Gly Val His His Pro Ser Thr Asp Ser Asp Gln Ile
        195                 200                 205

Ser Leu Tyr Ala Gln Ala Ser Gly Arg Val Thr Val Ser Thr Lys Arg
    210                 215                 220

Ser Gln Gln Thr Ala Ile Pro Asn Ile Gly Ser Arg Pro Arg Ile Arg
225                 230                 235                 240

Asn Ile Pro Ser Arg Val Ser Ile Tyr Trp Thr Ile Val Lys Pro Gly
                245                 250                 255

Asp Ile Leu Leu Ile Asn Cys Thr Gly Asn Leu Ile Ala Pro Arg Gly
            260                 265                 270

Tyr Phe Lys Ile Arg Asn Gly Lys Ser Ser Ile Met Arg Ser Asn Ala
        275                 280                 285

Pro Ile Gly Lys Cys Asn Ser Ala Cys Ile Thr Pro Asn Gly Ser Ile
    290                 295                 300

Pro Asn Gly Lys Pro Phe Gln Asn Val Asn Arg Val Thr Tyr Gly Ala
305                 310                 315                 320

Cys Pro Arg Tyr Val Lys Gln Ser Thr Leu Lys Leu Ala Thr Gly Met
                325                 330                 335

Arg Asn Val Pro Glu Lys Gln Thr Arg Gly Leu Phe Gly Ala Ile Ala
```

```
                340                 345                 350
Gly Phe Ile Glu Asn Gly Trp Glu Gly Met Lys Asp Gly Trp Tyr Gly
            355                 360                 365

Phe Arg His Gln Asn Ser Glu Gly Ile Gly Gln Ala Ala Asp Leu Lys
        370                 375                 380

Ser Thr Gln Ala Ala Val Asp Gln Ile Asn Gly Lys Leu Asn Arg Val
385                 390                 395                 400

Ile Glu Lys Thr Asn Glu Lys Phe His Gln Ile Glu Lys Glu Phe Thr
                405                 410                 415

Glu Val Glu Gly Arg Ile Gln Asp Ile Glu Lys Tyr Val Glu Asp Thr
            420                 425                 430

Lys Val Asp Leu Trp Ser Tyr Asn Ala Glu Leu Leu Val Ser Leu Glu
        435                 440                 445

Asn Gln His Thr Ile Asp Met Thr Asp Ser Glu Met Asn Lys Leu Phe
    450                 455                 460

Glu Arg Thr Arg Lys Gln Leu Arg Glu Asn Ala Glu Asp Ile Gly Asn
465                 470                 475                 480

Gly Cys Phe Lys Ile Tyr His Lys Cys Asn Asn Ala Cys Ile Gly Ser
                485                 490                 495

Ile Arg Asn Glu Thr Tyr Asp His Asn Val Tyr Arg Asp Glu Ala Leu
            500                 505                 510

Asn Asn Arg Phe His Ile Lys Gly Val Glu Leu Lys Ser Gly Tyr Lys
        515                 520                 525

Asn Trp Ile Leu Trp Ile Ser Phe Ala Thr Ser Cys Phe Leu Leu Cys
    530                 535                 540

Ile Val Leu Leu Gly Phe Ile Met Trp Ala Cys Gln Lys Gly Asn Ile
545                 550                 555                 560

Lys Cys Asn Ile Cys Ile
                565

<210> SEQ ID NO 23
<211> LENGTH: 573
<212> TYPE: PRT
<213> ORGANISM: Artificial
<220> FEATURE:
<223> OTHER INFORMATION: synthetically-generated protein

<400> SEQUENCE: 23

Met Glu Lys Ile Val Leu Leu Leu Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asp Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

Glu Lys Ala Asn Pro Ala Asn Asp Leu Cys Tyr Pro Gly Asn Phe Asn
            100                 105                 110

Asp Tyr Glu Glu Leu Lys His Leu Leu Ser Arg Ile Asn His Phe Glu
        115                 120                 125

Lys Ile Gln Ile Ile Pro Lys Ser Ser Trp Ser Asp His Glu Ala Ser
```

```
                130               135               140
Ser Gly Val Ser Ser Ala Cys Pro Tyr Gln Gly Ser Ser Phe Phe Arg
145                 150               155                 160

Asn Val Val Trp Leu Ile Lys Lys Asn Asn Thr Tyr Pro Thr Ile Lys
                165               170                 175

Arg Ser Tyr Asn Asn Thr Asn Gln Glu Asp Leu Leu Val Leu Trp Gly
                180               185                 190

Ile His His Pro Asn Asp Ala Ala Glu Gln Thr Leu Tyr Gln Asn Pro
                195               200                 205

Thr Thr Tyr Ile Ser Val Gly Thr Ser Thr Leu Asn Gln Arg Leu Val
    210                215                220

Pro Lys Ile Ala Thr Arg Ser Lys Val Asn Gly Gln Ser Gly Arg Met
225                 230               235                 240

Glu Phe Phe Trp Thr Ile Leu Lys Pro Asn Asp Ala Ile Asn Phe Glu
                245               250                 255

Ser Asn Gly Asn Phe Ile Ala Pro Glu Tyr Ala Tyr Lys Ile Val Lys
                260               265                 270

Lys Gly Asp Ser Thr Ile Met Lys Ser Glu Leu Glu Tyr Gly Asn Cys
            275               280               285

Asn Thr Lys Cys Gln Thr Pro Ile Gly Ala Ile Asn Ser Ser Met Pro
    290                295                300

Phe His Asn Ile His Pro Leu Thr Ile Gly Glu Cys Pro Lys Tyr Val
305                 310               315                 320

Lys Ser Asn Arg Leu Val Leu Ala Thr Gly Leu Arg Asn Ser Pro Gln
                325               330                 335

Arg Glu Arg Arg Arg Lys Lys Arg Gly Leu Phe Gly Ala Ile Ala Gly
                340               345                 350

Phe Ile Glu Gly Gly Trp Gln Gly Met Val Asp Gly Trp Tyr Gly Tyr
            355               360               365

His His Ser Asn Glu Gln Gly Ser Gly Tyr Ala Ala Asp Lys Glu Ser
    370                375                380

Thr Gln Lys Ala Ile Asp Gly Val Thr Asn Lys Val Asn Ser Ile Ile
385                 390               395                 400

Asp Lys Met Asn Thr Gln Phe Glu Ala Val Gly Arg Glu Phe Asn Asn
                405               410                 415

Leu Glu Arg Arg Ile Glu Asn Leu Asn Lys Lys Met Glu Asp Gly Phe
                420               425                 430

Leu Asp Val Trp Thr Tyr Asn Ala Glu Leu Leu Val Leu Met Glu Asn
            435               440               445

Glu Arg Thr Leu Asp Phe His Asp Ser Asn Val Lys Asn Leu Tyr Asp
    450                455                460

Lys Val Arg Leu Gln Leu Arg Asp Asn Ala Lys Glu Leu Gly Asn Gly
465                 470               475                 480

Cys Phe Glu Phe Tyr His Lys Cys Asp Asn Glu Cys Met Glu Ser Val
                485               490                 495

Arg Asn Gly Thr Tyr Asp Tyr Pro Gln Tyr Ser Glu Glu Ala Arg Leu
                500               505                 510

Lys Arg Glu Glu Ile Ser Gly Val Lys Leu Glu Ser Ile Gly Thr Tyr
            515               520               525

Gln Ile Leu Ser Ile Tyr Ser Thr Val Ala Ser Ser Leu Ala Leu Ala
    530                535                540

Ile Met Val Ala Gly Leu Ser Leu Trp Met Cys Ser Asn Gly Ser Leu
545                 550               555                 560
```

```
                Gln Cys Arg Ile Cys Ile Lys Phe Cys Glu Phe Arg Leu
                                565                 570

<210> SEQ ID NO 24
<211> LENGTH: 566
<212> TYPE: PRT
<213> ORGANISM: Artificial
<220> FEATURE:
<223> OTHER INFORMATION: synthetically-generated protein

<400> SEQUENCE: 24

Met Glu Lys Ile Val Leu Leu Ala Ile Val Ser Ile Val Lys Ser
1               5                   10                  15

Asp Gln Ile Cys Ile Gly Tyr His Ala Asn Asn Ser Ser Glu Gln Val
                20                  25                  30

Asp Thr Ile Met Glu Arg Asn Val Thr Val Thr His Ala Gln Asp Ile
                35                  40                  45

Leu Glu Lys Thr His Asn Gly Lys Leu Cys Asn Leu Asp Gly Val Lys
        50                  55                  60

Pro Leu Ile Leu Arg Asp Cys Ser Val Ala Gly Trp Leu Leu Gly Asn
65                  70                  75                  80

Pro Met Cys Asp Glu Phe Leu Asn Val Pro Glu Trp Ser Tyr Ile Val
                85                  90                  95

Glu Lys Ile Asn Pro Ala Asn Asp Leu Cys Tyr Pro Gly Asn Phe Asn
                100                 105                 110

Asp Tyr Glu Glu Leu Lys His Leu Leu Ser Arg Ile Thr His Phe Glu
                115                 120                 125

Lys Ile Gln Ile Ile Pro Lys Asn Ser Trp Ser Asp His Glu Ala Ser
            130                 135                 140

Gly Val Ser Ser Ala Cys Pro Tyr Gln Gly Arg Ser Ser Phe Phe Arg
145                 150                 155                 160

Asn Val Val Trp Leu Thr Lys Lys Asp Asn Ala Tyr Pro Thr Ile Lys
                165                 170                 175

Arg Ser Tyr Asn Asn Thr Asn Gln Glu Asp Leu Leu Val Leu Trp Gly
                180                 185                 190

Ile His His Pro Asn Asp Ala Ala Glu Gln Thr Arg Leu Tyr Gln Asn
            195                 200                 205

Pro Thr Thr Tyr Ile Ser Val Gly Thr Ser Thr Leu Asn Gln Arg Leu
        210                 215                 220

Val Pro Arg Ile Ala Thr Arg Ser Lys Ile Asn Gly Gln Ser Gly Arg
225                 230                 235                 240

Ile Glu Phe Phe Trp Thr Ile Leu Lys Ser Asn Asp Ala Ile Asn Phe
                245                 250                 255

Glu Ser Asn Gly Asn Phe Ile Ala Pro Glu Asn Ala Tyr Lys Ile Val
                260                 265                 270

Lys Lys Gly Asp Ser Thr Ile Met Lys Ser Glu Leu Glu Tyr Gly Asn
            275                 280                 285

Cys Asn Thr Lys Cys Gln Thr Pro Ile Gly Ala Ile Asn Ser Ser Met
        290                 295                 300

Pro Leu His Asn Ile His Pro Leu Thr Ile Gly Glu Cys Pro Lys Tyr
305                 310                 315                 320

Val Lys Ser Asn Arg Leu Val Leu Ala Thr Gly Leu Arg Asn Ser Pro
                325                 330                 335

Gln Gly Glu Arg Arg Arg Lys Lys Arg Gly Leu Phe Gly Ala Ile Ala
                340                 345                 350
```

```
Cys Phe Ile Glu Gly Gly Trp Gln Gly Met Val Asp Gly Trp Tyr Gly
        355                 360                 365

Ser His His Ser Asn Asp Gln Gly Ser Gly Tyr Ala Ala Asp Lys Glu
    370                 375                 380

Ser Thr Gln Arg Ala Ile Asp Gly Val Thr Asn Lys Val Asn Ser Ile
385                 390                 395                 400

Ile Asn Lys Met Asn Thr Gln Phe Glu Ala Val Gly Arg Glu Phe Asn
                405                 410                 415

Asn Leu Glu Arg Arg Ile Gly Asn Leu Asn Lys Lys Met Glu Asp Gly
                420                 425                 430

Phe Leu Asp Val Trp Thr Tyr Asn Ala Glu Leu Leu Val Leu Met Gly
            435                 440                 445

Asn Glu Arg Thr Leu Asp Phe His Asp Ser Asn Val Lys Asn Leu Tyr
    450                 455                 460

Asp Lys Val Arg Leu Gln Leu Lys Asp Asn Ala Lys Glu Leu Gly Asn
465                 470                 475                 480

Gly Cys Phe Glu Phe Tyr His Arg Cys Asp Asn Glu Cys Met Glu Ser
                485                 490                 495

Val Arg Asn Gly Thr Tyr Asp Tyr Pro Gln Tyr Ser Glu Glu Ala Arg
            500                 505                 510

Leu Arg Arg Glu Glu Ile Ser Gly Val Lys Leu Glu Ser Ile Gly Val
            515                 520                 525

Tyr Gln Ile Leu Ser Ile Tyr Ser Thr Ala Ala Ser Ser Leu Ala Leu
    530                 535                 540

Ala Ile Met Val Ala Gly Leu Phe Leu Trp Met Cys Ser Asn Gly Ser
545                 550                 555                 560

Leu His Ala Asp Cys Ile
                565

<210> SEQ ID NO 25
<211> LENGTH: 568
<212> TYPE: PRT
<213> ORGANISM: Artificial
<220> FEATURE:
<223> OTHER INFORMATION: synthetically-generated protein

<400> SEQUENCE: 25

Met Glu Lys Ile Val Leu Leu Phe Ala Ile Val Ser Leu Val Lys Ser
1               5                   10                  15

Asp Gln Ile Cys Ile Gly Tyr His Ala Asn Asn Ser Thr Lys Gln Val
            20                  25                  30

Asp Thr Ile Met Glu Lys Asn Val Thr Val Thr His Ala Gln Asp Ile
        35                  40                  45

Leu Glu Lys Lys His Asn Gly Lys Leu Cys Asp Leu Asp Gly Val Arg
    50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

Glu Lys Ala Asn Pro Val Asn Asp Leu Cys Tyr Pro Gly Asp Phe Asn
            100                 105                 110

Asp Tyr Glu Glu Leu Lys His Leu Leu Ser Arg Ile Asn His Phe Glu
        115                 120                 125

Lys Ile Gln Ile Ile Pro Lys Ser Ser Trp Ser Ser His Glu Ala Ser
    130                 135                 140
```

```
Leu Gly Val Ser Ser Ala Cys Pro Tyr Gln Gly Lys Ser Phe Phe
145                 150                 155                 160

Arg Asn Val Val Trp Leu Ile Lys Lys Asn Asn Thr Tyr Pro Thr Ile
                165                 170                 175

Lys Arg Ser Tyr Asn Asn Thr Asn Gln Glu Asp Leu Leu Val Met Trp
            180                 185                 190

Gly Ile His His Pro Asn Asp Glu Ala Glu Gln Ile Lys Leu Tyr Gln
        195                 200                 205

Asn Pro Thr Thr Tyr Val Ser Val Gly Thr Ser Thr Leu Asn Gln Arg
    210                 215                 220

Leu Thr Pro Arg Ile Ala Thr Arg Ser Lys Val Asn Gly Gln Ser Gly
225                 230                 235                 240

Arg Met Glu Phe Phe Trp Thr Ile Leu Lys Pro Asn Asp Ala Ile Asn
                245                 250                 255

Phe Glu Ser Asn Gly Asn Phe Val Ala Pro Glu Tyr Ala Tyr Lys Ile
            260                 265                 270

Val Lys Lys Gly Asp Ser Ala Ile Met Lys Ser Glu Leu Glu Tyr Ser
        275                 280                 285

Asn Cys Asn Thr Lys Cys Gln Thr Pro Met Gly Ala Ile Asn Ser Ser
    290                 295                 300

Met Pro Phe His His Ile His Pro Leu Thr Ile Gly Glu Cys Pro Lys
305                 310                 315                 320

Tyr Val Lys Ser Thr Arg Leu Val Leu Ala Thr Gly Leu Arg Asn Ser
                325                 330                 335

Pro Gln Arg Glu Ser Arg Arg Lys Lys Arg Gly Leu Phe Gly Ala Ile
            340                 345                 350

Ala Gly Phe Ile Glu Ala Gly Trp Gln Gly Met Val Asp Gly Trp Tyr
        355                 360                 365

Gly Tyr His His Ser Asn Glu Gln Gly Ser Gly Tyr Ala Ala Asp Lys
    370                 375                 380

Glu Ser Thr Gln Lys Ala Ile Asp Gly Val Thr Asn Lys Val Asn Ser
385                 390                 395                 400

Ile Ile Asp Lys Met Asn Thr Gln Phe Glu Ala Ile Gly Arg Glu Phe
                405                 410                 415

Asn Asn Leu Glu Arg Arg Ile Glu Asn Leu Asn Lys Lys Met Glu Asp
            420                 425                 430

Gly Phe Leu Asp Val Trp Thr Tyr Lys Ala Glu Leu Leu Val Leu Met
        435                 440                 445

Glu Asn Glu Arg Thr Leu Asp Tyr His Asp Ser Asn Val Arg Asn Leu
    450                 455                 460

Tyr Asp Lys Val Arg Leu Gln Leu Arg Asp Asn Thr Lys Glu Leu Gly
465                 470                 475                 480

Asn Gly Cys Phe Glu Phe Tyr His Lys Cys Asp Asp Glu Cys Met Glu
                485                 490                 495

Ser Val Lys Asn Gly Thr Tyr Asp Tyr Pro Gln Tyr Ser Glu Glu Ala
            500                 505                 510

Arg Leu Asn Arg Glu Glu Ile Ser Gly Val Lys Leu Glu Ser Ile Gly
        515                 520                 525

Ile Tyr Gln Ile Leu Ser Ile Tyr Ser Thr Val Ala Ser Ser Leu Val
    530                 535                 540

Leu Ala Ile Met Val Ala Gly Leu Ser Leu Trp Met Cys Ser Asn Gly
545                 550                 555                 560
```

Ser Leu Gln Cys Arg Val Cys Ile
            565

<210> SEQ ID NO 26
<211> LENGTH: 574
<212> TYPE: PRT
<213> ORGANISM: Artificial
<220> FEATURE:
<223> OTHER INFORMATION: synthetically-generated protein

<400> SEQUENCE: 26

Met Glu Gln Ile Val Leu Leu Ala Ile Val Ser Leu Val Lys Ser
1               5                   10                  15

Asp His Ile Cys Ile Gly Tyr His Ala Asn Asn Ser Thr Glu Gln Val
            20                  25                  30

Asp Thr Ile Met Glu Lys Asn Val Thr Val Thr His Ala Gln Asn Ile
        35                  40                  45

Leu Glu Lys Thr His Asn Gly Lys Leu Cys Asp Leu Asp Gly Val Lys
    50                  55                  60

Pro Leu Ile Leu Lys Asp Cys Ser Val Ala Gly Trp Leu Leu Gly Asn
65                  70                  75                  80

Pro Met Cys Asp Glu Phe Ile Arg Val Pro Glu Trp Ser Tyr Ile Val
                85                  90                  95

Glu Lys Ala Asn Pro Ala Asn Asp Leu Cys Tyr Pro Gly Ser Phe Asn
            100                 105                 110

Asp Tyr Glu Glu Leu Lys His Leu Leu Ser Arg Ile Asn His Phe Glu
        115                 120                 125

Lys Leu Gln Ile Ile Pro Lys Ser Ser Trp Ser Asp His Glu Ala Ser
    130                 135                 140

Ser Gly Val Ser Ser Ala Cys Pro Tyr Gln Gly Thr Pro Ser Phe Phe
145                 150                 155                 160

Arg Asn Val Val Trp Leu Ile Lys Lys Asn Ser Thr Tyr Pro Thr Ile
                165                 170                 175

Lys Lys Ser Tyr Asn Asn Thr Asn Gln Glu Asp Leu Leu Ile Leu Trp
            180                 185                 190

Gly Ile His His Ser Asn Asp Ala Ala Glu Gln Thr Lys Leu Tyr Gln
        195                 200                 205

Asn Pro Thr Thr Tyr Ile Ser Ile Gly Thr Ser Thr Leu Asn Gln Arg
    210                 215                 220

Leu Val Pro Lys Ile Ala Thr Arg Ser Lys Val Asn Gly Gln Ser Gly
225                 230                 235                 240

Arg Met Asp Phe Phe Trp Thr Ile Leu Lys Pro Asn Asp Ala Ile His
                245                 250                 255

Phe Glu Ser Asn Gly Asn Phe Ile Ala Pro Glu Tyr Ala Tyr Lys Ile
            260                 265                 270

Val Lys Glu Gly Asp Ser Ala Ile Met Lys Ser Glu Val Glu Tyr Gly
        275                 280                 285

Asn Cys Asn Thr Lys Cys Gln Thr Pro Val Gly Ala Ile Asn Ser Ser
    290                 295                 300

Met Pro Phe His Asn Ile His Pro Leu Thr Ile Gly Glu Cys Pro Lys
305                 310                 315                 320

Tyr Val Lys Ser Asn Lys Leu Val Leu Ala Thr Gly Leu Arg Asn Ser
                325                 330                 335

Pro Leu Arg Glu Arg Arg Arg Lys Arg Gly Leu Phe Gly Ala Ile Ala
            340                 345                 350

```
Gly Phe Ile Glu Gly Gly Trp Gln Gly Met Val Asp Gly Trp Tyr Gly
            355                 360                 365

Phe His His Ser Asn Glu Gln Gly Ser Gly Tyr Ala Ala Asp Arg Glu
            370                 375                 380

Ser Thr Gln Lys Ala Ile Asp Gly Val Thr Asn Lys Val Asn Ser Ile
385                 390                 395                 400

Ile Asp Lys Met Asn Thr Gln Phe Glu Val Val Gly Arg Glu Phe Asn
            405                 410                 415

Asn Leu Glu Ser Arg Ile Glu Asn Leu Asn Lys Lys Met Glu Asp Gly
            420                 425                 430

Phe Leu Asp Val Trp Thr Tyr Asn Ala Glu Leu Leu Val Leu Met Glu
            435                 440                 445

Asn Glu Arg Thr Leu Asp Phe His Asp Ser Asn Val Lys Asn Leu Tyr
            450                 455                 460

Asp Arg Val Arg Leu Gln Leu Arg Asp Asn Ala Lys Glu Leu Gly Asn
465                 470                 475                 480

Gly Cys Phe Glu Phe Tyr His Lys Cys Asp Asn Glu Cys Met Glu Ser
            485                 490                 495

Ile Arg Asn Gly Thr Tyr Asn Tyr Pro Gln Tyr Ser Glu Glu Ala Arg
            500                 505                 510

Leu Lys Arg Glu Glu Ile Ser Gly Val Lys Leu Glu Ser Ile Gly Thr
            515                 520                 525

Tyr Gln Ile Leu Ser Ile Tyr Ser Thr Val Ala Ser Ser Leu Ala Leu
            530                 535                 540

Ala Ile Met Ile Ala Gly Leu Ser Leu Trp Met Cys Ser Asn Gly Ser
545                 550                 555                 560

Leu Gln Cys Arg Ile Cys Ile Tyr Phe Cys Glu Phe Arg Leu
            565                 570

<210> SEQ ID NO 27
<211> LENGTH: 569
<212> TYPE: PRT
<213> ORGANISM: Artificial
<220> FEATURE:
<223> OTHER INFORMATION: synthetically-generated protein

<400> SEQUENCE: 27

Met Glu Lys Ile Val Leu Leu Leu Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
            35                  40                  45

Leu Glu Lys Thr His Asn Gly Lys Leu Cys Asp Leu Asp Gly Val Lys
50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
            85                  90                  95

Glu Lys Ala Asn Pro Ala Asn Asp Leu Cys Tyr Pro Gly Asn Phe Asn
            100                 105                 110

Asp Tyr Glu Glu Leu Lys His Leu Leu Ser Arg Ile Asn His Phe Glu
            115                 120                 125

Lys Ile Gln Ile Ile Pro Lys Ser Ser Trp Ser Asp His Glu Ala Ser
            130                 135                 140
```

```
Ser Gly Val Ser Ser Ala Cys Pro Tyr Gln Gly Arg Ser Ser Phe Phe
145                 150                 155                 160

Arg Asn Val Val Trp Leu Ile Lys Lys Asn Asn Thr Tyr Pro Thr Ile
                165                 170                 175

Lys Arg Ser Tyr Asn Asn Thr Asn Gln Glu Asp Leu Leu Val Leu Trp
            180                 185                 190

Gly Ile His His Pro Asn Asp Ala Ala Glu Gln Thr Arg Leu Tyr Gln
        195                 200                 205

Asn Pro Thr Thr Tyr Ile Ser Val Gly Thr Ser Thr Leu Asn Gln Arg
    210                 215                 220

Leu Val Pro Lys Ile Ala Thr Arg Ser Lys Val Asn Gly Gln Ser Gly
225                 230                 235                 240

Arg Met Glu Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
            260                 265                 270

Val Lys Lys Gly Asp Ser Thr Ile Met Lys Ser Glu Leu Glu Tyr Gly
        275                 280                 285

Asn Cys Asn Thr Lys Cys Gln Thr Pro Ile Gly Ala Ile Asn Ser Ser
    290                 295                 300

Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Ser
                325                 330                 335

Pro Gln Gly Glu Arg Arg Arg Lys Lys Arg Gly Leu Phe Gly Ala Ile
            340                 345                 350

Ala Gly Phe Ile Glu Gly Gly Trp Gln Gly Met Val Asp Gly Trp Tyr
        355                 360                 365

Gly Tyr His His Ser Asn Glu Gln Gly Ser Gly Tyr Ala Ala Asp Lys
    370                 375                 380

Glu Ser Thr Gln Lys Ala Ile Asp Gly Val Thr Asn Lys Val Asn Ser
385                 390                 395                 400

Ile Ile Asp Lys Met Asn Thr Gln Phe Glu Ala Val Gly Arg Glu Phe
                405                 410                 415

Asn Asn Leu Glu Arg Arg Ile Glu Asn Leu Asn Lys Lys Met Glu Asp
            420                 425                 430

Gly Phe Leu Asp Val Trp Thr Tyr Asn Ala Glu Leu Leu Val Leu Met
        435                 440                 445

Glu Asn Glu Arg Thr Leu Asp Phe His Asp Ser Asn Val Lys Asn Leu
    450                 455                 460

Tyr Asp Lys Val Arg Leu Gln Leu Arg Asp Asn Ala Lys Glu Leu Gly
465                 470                 475                 480

Asn Gly Cys Phe Glu Phe Tyr His Lys Cys Asp Asn Glu Cys Met Glu
                485                 490                 495

Ser Val Arg Asn Gly Thr Tyr Asp Tyr Pro Gln Tyr Ser Glu Glu Ala
            500                 505                 510

Arg Leu Lys Arg Glu Glu Ile Ser Gly Val Lys Leu Glu Ser Ile Gly
        515                 520                 525

Thr Tyr Gln Ile Leu Ser Ile Tyr Ser Thr Val Ala Ser Ser Leu Ala
    530                 535                 540

Leu Ala Ile Met Val Ala Gly Leu Ser Leu Trp Met Cys Ser Asn Gly
545                 550                 555                 560

Ser Leu Gln Cys Arg Ile Cys Ile Lys
```

-continued

```
<210> SEQ ID NO 28
<211> LENGTH: 566
<212> TYPE: PRT
<213> ORGANISM: Artificial
<220> FEATURE:
<223> OTHER INFORMATION: synthetically-generated protein

<400> SEQUENCE: 28
```

Met Glu Lys Ile Val Leu Leu Phe Ala Ile Val Ser Leu Val Lys Ser
1               5                   10                  15

Asp Gln Ile Cys Ile Gly Tyr His Ala Asn Asn Ser Thr Lys Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asn Leu Asp Gly Val Lys
    50                  55                  60

Pro Leu Ile Leu Lys Asp Cys Ser Val Ala Gly Trp Leu Leu Gly Asn
65                  70                  75                  80

Pro Met Cys Asp Glu Phe Leu Asn Val Pro Glu Trp Ser Tyr Ile Val
                85                  90                  95

Glu Lys Ile Asn Pro Ala Asn Asp Leu Cys Tyr Pro Gly Asp Phe Asn
            100                 105                 110

Asp Tyr Glu Glu Leu Lys His Leu Leu Ser Arg Ile Asn His Phe Glu
        115                 120                 125

Lys Ile Gln Ile Ile Pro Lys Asn Ser Trp Ser Asp His Glu Ala Ser
    130                 135                 140

Gly Val Ser Ser Ala Cys Pro Tyr Gln Gly Thr Pro Ser Phe Phe Arg
145                 150                 155                 160

Asn Val Val Trp Leu Ile Lys Lys Asn Ser Thr Tyr Pro Thr Ile Lys
                165                 170                 175

Lys Ser Tyr Asn Asn Thr Asn Gln Glu Asp Leu Leu Ile Leu Trp Gly
            180                 185                 190

Ile His His Ser Asn Asp Ala Ala Glu Gln Thr Lys Leu Tyr Gln Asn
        195                 200                 205

Pro Thr Thr Tyr Ile Ser Ile Gly Thr Ser Thr Leu Asn Gln Arg Leu
    210                 215                 220

Thr Pro Arg Ile Ala Thr Arg Ser Lys Val Asn Gly Gln Ser Gly Arg
225                 230                 235                 240

Met Asp Phe Phe Trp Thr Ile Leu Lys Ser Asn Asp Ala Ile Asn Phe
                245                 250                 255

Glu Ser Asn Gly Asn Phe Ile Ala Pro Glu Asn Ala Tyr Lys Ile Val
            260                 265                 270

Lys Lys Gly Asp Ser Ala Ile Met Lys Ser Glu Val Glu Tyr Gly Asn
        275                 280                 285

Cys Asn Thr Lys Cys Gln Thr Pro Met Gly Ala Ile Asn Ser Ser Met
    290                 295                 300

Pro Phe His Asn Ile His Pro Leu Thr Ile Gly Glu Cys Pro Lys Tyr
305                 310                 315                 320

Val Lys Ser Asn Lys Leu Val Leu Ala Thr Gly Leu Arg Asn Ser Pro
                325                 330                 335

Leu Arg Glu Arg Arg Arg Lys Arg Gly Leu Phe Gly Ala Ile Ala Gly
            340                 345                 350

Phe Ile Glu Gly Gly Trp Gln Gly Met Val Asp Gly Trp Tyr Gly Phe

```
                    355                 360                 365
His His Ser Asn Glu Gln Gly Ser Gly Tyr Ala Ala Asp Lys Glu Ser
    370                 375                 380

Thr Gln Arg Ala Ile Asp Gly Val Thr Asn Lys Val Asn Ser Ile Ile
385                 390                 395                 400

Asn Lys Met Asn Thr Gln Phe Glu Ala Val Gly Arg Glu Phe Asn Asn
                405                 410                 415

Leu Glu Arg Arg Ile Glu Asn Leu Asn Lys Lys Met Glu Asp Gly Phe
            420                 425                 430

Leu Asp Val Trp Thr Tyr Asn Ala Glu Leu Leu Val Leu Met Glu Asn
        435                 440                 445

Glu Arg Thr Leu Asp Phe His Asp Ser Asn Val Lys Asn Leu Tyr Asp
    450                 455                 460

Lys Val Arg Leu Gln Leu Lys Asp Asn Ala Lys Glu Leu Gly Asn Gly
465                 470                 475                 480

Cys Phe Glu Phe Tyr His Arg Cys Asp Asn Glu Cys Met Glu Ser Ile
                485                 490                 495

Arg Asn Gly Thr Tyr Asn Tyr Pro Gln Tyr Ser Glu Glu Ala Arg Leu
            500                 505                 510

Asn Arg Glu Glu Ile Ser Gly Val Lys Leu Glu Ser Ile Gly Ile Tyr
        515                 520                 525

Gln Ile Leu Ser Ile Tyr Ser Thr Ala Ala Ser Ser Leu Ala Leu Ala
    530                 535                 540

Ile Met Val Ala Gly Leu Phe Leu Trp Met Cys Ser Asn Gly Ser Leu
545                 550                 555                 560

Gln Cys Arg Val Cys Ile
                565

<210> SEQ ID NO 29
<211> LENGTH: 568
<212> TYPE: PRT
<213> ORGANISM: Artificial
<220> FEATURE:
<223> OTHER INFORMATION: synthetically-generated protein

<400> SEQUENCE: 29

Met Glu Lys Ile Val Leu Leu Leu Ala Ile Val Ser Ile Val Lys Ser
1               5                   10                  15

Asp Gln Ile Cys Ile Gly Tyr His Ala Asn Asn Ser Thr Lys Gln Val
                20                  25                  30

Asp Thr Ile Met Glu Lys Asn Val Thr Val Thr His Ala Gln Asp Ile
            35                  40                  45

Leu Glu Lys Lys His Asn Gly Lys Leu Cys Asp Leu Asp Gly Val Arg
        50                  55                  60

Pro Leu Ile Leu Arg Asp Cys Ser Val Ala Gly Trp Leu Leu Gly Asn
65                  70                  75                  80

Pro Met Cys Asp Glu Phe Ile Arg Val Pro Trp Ser Tyr Ile Val
                85                  90                  95

Glu Lys Ala Asn Pro Val Asn Asp Leu Cys Tyr Pro Gly Val Phe Asn
            100                 105                 110

Asp Tyr Glu Glu Leu Lys His Leu Leu Ser Arg Ile Asn His Phe Glu
        115                 120                 125

Lys Leu Gln Ile Ile Pro Lys Ser Ser Trp Ser Ser His Glu Ala Ser
    130                 135                 140

Leu Gly Val Ser Ser Ala Cys Pro Tyr Gln Gly Lys Ser Ser Phe Phe
```

```
            145                 150                 155                 160
        Arg Asn Val Val Trp Leu Thr Lys Lys Asp Asn Ala Tyr Pro Thr Ile
                        165                 170                 175
        Lys Arg Ser Tyr Asn Asn Thr Asn Gln Glu Asp Leu Leu Val Met Trp
                        180                 185                 190
        Gly Ile His His Pro Asn Asp Ala Ala Glu Gln Thr Lys Leu Tyr Gln
                        195                 200                 205
        Asn Pro Thr Thr Tyr Val Ser Val Gly Thr Ser Thr Leu Asn Gln Arg
                        210                 215                 220
        Leu Val Pro Arg Ile Ala Thr Arg Ser Lys Val Asn Gly Gln Asn Gly
        225                 230                 235                 240
        Arg Met Glu Phe Phe Trp Thr Ile Leu Lys Ser Asn Asp Val Ile Asn
                        245                 250                 255
        Phe Glu Ser Asn Gly Asn Phe Ile Ala Pro Glu Tyr Ala Tyr Lys Ile
                        260                 265                 270
        Val Lys Glu Gly Asp Ser Ala Ile Met Lys Ser Glu Leu Glu Tyr Ser
                        275                 280                 285
        Asn Cys Asn Thr Lys Cys Gln Thr Pro Met Gly Ala Ile Asn Ser Ser
                        290                 295                 300
        Met Pro Phe His Asn Ile His Pro Leu Thr Ile Gly Glu Cys Pro Lys
        305                 310                 315                 320
        Tyr Val Lys Ser Thr Arg Leu Val Leu Ala Thr Gly Leu Arg Asn Ser
                        325                 330                 335
        Pro Gln Arg Glu Ser Arg Arg Lys Lys Arg Gly Leu Phe Gly Ala Ile
                        340                 345                 350
        Ala Gly Phe Ile Glu Gly Gly Trp Gln Gly Met Val Asp Gly Trp Tyr
                        355                 360                 365
        Gly Phe His His Ser Asn Glu Gln Gly Ser Gly Tyr Ala Ala Asp Arg
                        370                 375                 380
        Glu Ser Thr Gln Lys Ala Ile Asp Gly Val Thr Asn Lys Val Asn Ser
        385                 390                 395                 400
        Ile Ile Asn Lys Met Asn Thr Gln Phe Glu Ala Val Gly Arg Glu Phe
                        405                 410                 415
        Asn Asn Leu Glu Arg Arg Ile Glu Asn Leu Asn Lys Lys Met Glu Asp
                        420                 425                 430
        Gly Phe Leu Asp Val Trp Thr Tyr Asn Ala Glu Leu Leu Val Leu Met
                        435                 440                 445
        Glu Asn Glu Arg Thr Leu Asp Phe His Asp Ser Asn Val Lys Asn Leu
        450                 455                 460
        Tyr Asp Lys Val Arg Leu Gln Leu Arg Asp Asn Ala Lys Glu Leu Gly
        465                 470                 475                 480
        Asn Gly Cys Phe Glu Phe Tyr His Lys Cys Asp Asn Glu Cys Met Glu
                        485                 490                 495
        Ser Val Lys Asn Gly Thr Tyr Asp Tyr Pro Gln Tyr Ser Glu Glu Ala
                        500                 505                 510
        Arg Leu Asn Arg Glu Glu Ile Ser Gly Val Lys Leu Glu Ser Ile Gly
                        515                 520                 525
        Val Tyr Gln Ile Leu Ser Ile Tyr Ser Thr Val Ala Ser Ser Leu Ala
                        530                 535                 540
        Leu Ala Ile Met Ile Ala Gly Leu Ser Leu Trp Met Cys Ser Asn Gly
        545                 550                 555                 560
        Ser Leu Gln Cys Arg Ile Cys Ile
                        565
```

<210> SEQ ID NO 30
<211> LENGTH: 472
<212> TYPE: PRT
<213> ORGANISM: Artificial
<220> FEATURE:
<223> OTHER INFORMATION: synthetically-generated protein

<400> SEQUENCE: 30

| | | | | | | | | | | | | | | | |
|---|---|---|---|---|---|---|---|---|---|---|---|---|---|---|---|
| Met | Asn | Pro | Asn | Gln | Lys | Ile | Ile | Thr | Ile | Gly | Ser | Val | Cys | Met | Thr |
| 1 | | | | 5 | | | | | 10 | | | | | 15 | |
| Ile | Gly | Met | Ala | Asn | Leu | Ile | Leu | Gln | Ile | Gly | Asn | Ile | Ile | Ser | Ile |
| | | | 20 | | | | | 25 | | | | | 30 | | |
| Trp | Ser | His | Ser | Ile | Gln | Leu | Gly | Asn | Gln | Asn | Gln | Ile | Glu | Thr | Cys |
| | | | 35 | | | | | 40 | | | | | 45 | | |
| Thr | Ile | Cys | Asn | Gln | Ser | Val | Ile | Thr | Tyr | Glu | Asn | Asn | Thr | Trp | Val |
| | 50 | | | | | 55 | | | | | 60 | | | | |
| Asn | Gln | Thr | Tyr | Val | Asn | Ile | Ser | Asn | Thr | Asn | Phe | Ala | Ala | Gly | Gln |
| 65 | | | | | 70 | | | | | 75 | | | | | 80 |
| Ser | Val | Val | Ser | Val | Lys | Leu | Ala | Gly | Asn | Ser | Ser | Leu | Cys | Pro | Val |
| | | | | 85 | | | | | 90 | | | | | 95 | |
| Ser | Gly | Trp | Ala | Ile | Tyr | Ser | Lys | Asp | Asn | Ser | Ile | Arg | Ile | Gly | Ser |
| | | | 100 | | | | | 105 | | | | | 110 | | |
| Lys | Gly | Asp | Val | Phe | Val | Ile | Arg | Glu | Pro | Phe | Ile | Ser | Cys | Ser | Pro |
| | | 115 | | | | | 120 | | | | | 125 | | | |
| Leu | Glu | Cys | Arg | Thr | Phe | Phe | Leu | Thr | Gln | Gly | Ala | Leu | Leu | Asn | Asp |
| 130 | | | | | 135 | | | | | 140 | | | | | |
| Lys | His | Ser | Asn | Gly | Thr | Ile | Lys | Asp | Arg | Ser | Pro | Tyr | Arg | Thr | Leu |
| 145 | | | | | 150 | | | | | 155 | | | | | 160 |
| Met | Ser | Cys | Pro | Ile | Gly | Glu | Val | Pro | Ser | Pro | Tyr | Asn | Ser | Arg | Phe |
| | | | | 165 | | | | | 170 | | | | | 175 | |
| Glu | Ser | Val | Ala | Trp | Ser | Ala | Ser | Ala | Cys | His | Asp | Gly | Ile | Asn | Trp |
| | | | 180 | | | | | 185 | | | | | 190 | | |
| Leu | Thr | Ile | Gly | Ile | Ser | Gly | Pro | Asp | Asn | Gly | Ala | Val | Ala | Val | Leu |
| | | | | 195 | | | | | 200 | | | | | 205 | |
| Lys | Tyr | Asn | Gly | Ile | Ile | Thr | Asp | Thr | Ile | Lys | Ser | Trp | Arg | Asn | Asn |
| | 210 | | | | | 215 | | | | | 220 | | | | |
| Ile | Leu | Arg | Thr | Gln | Glu | Ser | Glu | Cys | Ala | Cys | Val | Asn | Gly | Ser | Cys |
| 225 | | | | | 230 | | | | | 235 | | | | | 240 |
| Phe | Thr | Ile | Met | Thr | Asp | Gly | Pro | Ser | Asp | Gly | Gln | Ala | Ser | Tyr | Lys |
| | | | | 245 | | | | | 250 | | | | | 255 | |
| Ile | Phe | Arg | Ile | Glu | Lys | Gly | Lys | Ile | Val | Lys | Ser | Val | Glu | Met | Asn |
| | | | 260 | | | | | 265 | | | | | 270 | | |
| Ala | Pro | Asn | Tyr | His | Tyr | Glu | Glu | Cys | Ser | Cys | Tyr | Pro | Asp | Ser | Ser |
| | | | | 275 | | | | | 280 | | | | | 285 | |
| Glu | Ile | Thr | Cys | Val | Cys | Arg | Asp | Asn | Trp | His | Gly | Ser | Asn | Arg | Pro |
| | | 290 | | | | | 295 | | | | | 300 | | | |
| Trp | Val | Ser | Phe | Asn | Gln | Asn | Leu | Glu | Tyr | Gln | Ile | Gly | Tyr | Ile | Cys |
| 305 | | | | | 310 | | | | | 315 | | | | | 320 |
| Ser | Gly | Val | Phe | Gly | Asp | Asn | Pro | Arg | Pro | Asn | Asp | Lys | Thr | Gly | Ser |
| | | | | 325 | | | | | 330 | | | | | 335 | |
| Cys | Gly | Pro | Val | Ser | Ser | Asn | Gly | Ala | Asn | Gly | Val | Lys | Gly | Phe | Ser |
| | | | 340 | | | | | 345 | | | | | 350 | | |
| Phe | Lys | Tyr | Gly | Asn | Gly | Val | Trp | Ile | Gly | Arg | Thr | Lys | Ser | Ile | Ser |
| | | 355 | | | | | 360 | | | | | 365 | | | |

```
Ser Arg Lys Gly Phe Glu Met Ile Trp Asp Pro Asn Gly Trp Thr Gly
    370                 375                 380

Thr Asp Asn Phe Ser Ile Lys Gln Asp Ile Val Gly Ile Asn Glu Trp
385                 390                 395                 400

Ser Gly Tyr Ser Gly Ser Phe Val Gln His Pro Glu Leu Thr Gly Leu
                405                 410                 415

Asp Cys Ile Arg Pro Cys Phe Trp Val Glu Leu Ile Arg Gly Arg Pro
                420                 425                 430

Lys Glu Asn Thr Thr Ile Trp Thr Ser Gly Ser Ser Ile Ser Phe Cys
                435                 440                 445

Gly Val Asn Ser Asp Thr Val Gly Trp Ser Trp Pro Asp Gly Ala Glu
    450                 455                 460

Leu Pro Phe Thr Ile Asp Lys Tyr
465                 470

<210> SEQ ID NO 31
<211> LENGTH: 470
<212> TYPE: PRT
<213> ORGANISM: Artificial
<220> FEATURE:
<223> OTHER INFORMATION: synthetically-generated protein

<400> SEQUENCE: 31

Met Asn Pro Asn Gln Lys Ile Ile Thr Ile Gly Ser Ile Ser Ile Ala
1               5                   10                  15

Ile Gly Ile Ile Ser Leu Met Leu Gln Ile Gly Asn Ile Ile Ser Ile
                20                  25                  30

Trp Ala Ser His Ser Ile Gln Thr Gly Ser Gln Asn His Thr Gly Ile
                35                  40                  45

Cys Asn Gln Arg Ile Ile Thr Tyr Glu Asn Ser Thr Trp Val Asn His
50                  55                  60

Thr Tyr Val Ser Ile Asn Asn Thr Asn Val Val Ala Gly Lys Asp Lys
65                  70                  75                  80

Thr Ser Val Thr Leu Ala Gly Asn Ser Ser Leu Cys Ser Ile Ser Gly
                85                  90                  95

Trp Ala Ile Tyr Thr Lys Asp Asn Ser Ile Arg Ile Gly Ser Lys Gly
                100                 105                 110

Asp Val Phe Val Ile Arg Glu Pro Phe Ile Ser Cys Ser His Leu Glu
                115                 120                 125

Cys Lys Thr Phe Phe Leu Thr Gln Gly Ala Leu Leu Asn Asp Lys His
                130                 135                 140

Ser Asn Gly Thr Val Lys Asp Arg Ser Pro Tyr Arg Ala Leu Met Ser
145                 150                 155                 160

Cys Pro Leu Gly Glu Ala Pro Ser Pro Tyr Asn Ser Arg Phe Glu Ser
                165                 170                 175

Ile Ala Trp Ser Ala Ser Ala Cys His Asp Gly Ile Asn Trp Leu Thr
                180                 185                 190

Ile Gly Ile Ser Gly Pro Asp Asp Gly Ala Val Ala Val Leu Lys Tyr
                195                 200                 205

Asn Gly Ile Ile Thr Gly Thr Ile Lys Ser Trp Lys Lys Gln Ile Leu
                210                 215                 220

Arg Thr Gln Glu Ser Glu Cys Val Cys Val Asn Gly Ser Cys Phe Thr
225                 230                 235                 240

Val Met Thr Asp Gly Pro Ser Asn Gly Gln Ala Ser Tyr Lys Ile Phe
                245                 250                 255
```

```
Arg Ile Glu Lys Gly Lys Ile Val Lys Ser Val Met Asn Ala Pro
            260                 265                 270

Asn Tyr His Tyr Glu Glu Cys Ser Cys Tyr Pro Asp Ser Glu Ile
            275                 280                 285

Thr Cys Val Cys Arg Asp Asn Trp His Ala Ser Asn Arg Pro Trp Val
290                 295                 300

Ser Phe Asn Gln Asn Leu Asp Tyr Gln Ile Gly Tyr Ile Cys Ser Gly
305                 310                 315                 320

Val Phe Gly Asp Asn Pro Arg Pro Glu Asp Gly Gly Ser Cys Asn
            325                 330                 335

Pro Val Thr Val Asp Gly Ala Asn Gly Val Lys Gly Phe Ser Tyr Lys
            340                 345                 350

Tyr Asp Asn Gly Val Trp Ile Gly Arg Thr Lys Ser Asn Arg Leu Arg
            355                 360                 365

Lys Gly Phe Glu Met Ile Trp Asp Pro Asn Gly Trp Thr Asn Thr Asp
    370                 375                 380

Ser Asp Phe Ser Val Lys Gln Asp Val Val Ala Ile Thr Asp Trp Ser
385                 390                 395                 400

Gly Tyr Ser Gly Ser Phe Val Gln Tyr Pro Glu Leu Thr Gly Leu Asp
            405                 410                 415

Cys Met Arg Pro Cys Phe Trp Val Glu Leu Val Arg Gly Leu Pro Arg
            420                 425                 430

Glu Asn Thr Thr Ile Trp Thr Ser Gly Ser Ser Ile Ser Phe Cys Gly
            435                 440                 445

Val Asn Ser Asp Thr Ala Asn Trp Ser Trp Pro Asp Gly Ala Glu Leu
    450                 455                 460

Pro Phe Thr Ile Asp Lys
465                 470

<210> SEQ ID NO 32
<211> LENGTH: 469
<212> TYPE: PRT
<213> ORGANISM: Artificial
<220> FEATURE:
<223> OTHER INFORMATION: synthetically-generated protein

<400> SEQUENCE: 32

Met Asn Pro Thr Gln Lys Ile Ile Thr Ile Gly Ser Val Cys Met Thr
1               5                   10                  15

Ile Gly Met Ala Asn Leu Ile Leu Gln Ile Gly Asn Ile Ile Ser Ile
            20                  25                  30

Trp Ile Ser His Ser Ile Gln Leu Gly Asn Gln Asn Gln Ile Glu Thr
        35                  40                  45

Cys Asn Gln Ser Ile Ile Thr Tyr Glu Asn Asn Thr Trp Val Asn Gln
    50                  55                  60

Thr Tyr Val Asn Ile Ser Asn Thr Asn Phe Ala Ala Gly Gln Ser Val
65                  70                  75                  80

Val Ser Val Lys Leu Ala Gly Asn Ser Ser Leu Cys Pro Val Ser Gly
                85                  90                  95

Trp Ala Ile Tyr Ser Lys Asp Asn Ser Ile Arg Ile Gly Ser Arg Gly
            100                 105                 110

Asp Val Phe Val Ile Arg Glu Ser Phe Ile Ser Cys Ser His Leu Glu
        115                 120                 125

Cys Arg Thr Phe Phe Leu Thr Gln Gly Ala Leu Leu Asn Asp Arg His
    130                 135                 140
```

Ser Asn Gly Thr Val Lys Asp Arg Ser Pro His Arg Thr Leu Met Ser
145                 150                 155                 160

Cys Pro Val Gly Glu Ala Pro Ser Pro Tyr Asn Ser Lys Phe Glu Ser
                165                 170                 175

Val Ala Trp Ser Ala Ser Ala Cys His Asp Gly Met Gly Trp Leu Thr
            180                 185                 190

Ile Gly Ile Ser Gly Pro Asp Asn Gly Ala Val Ala Val Leu Lys Tyr
        195                 200                 205

Asn Gly Ile Ile Thr Glu Thr Ile Lys Ser Trp Lys Lys Arg Ile Leu
210                 215                 220

Arg Thr Gln Glu Ser Glu Cys Val Cys Met Asn Gly Ser Cys Phe Thr
225                 230                 235                 240

Ile Met Thr Asp Gly Pro Ser Asn Gly Ala Ala Ser Tyr Lys Ile Phe
                245                 250                 255

Lys Ile Glu Lys Gly Lys Val Thr Lys Ser Ile Glu Leu Asn Ala Pro
                260                 265                 270

Asn Phe His Tyr Glu Glu Cys Ser Cys Tyr Pro Asp Thr Gly Thr Val
            275                 280                 285

Met Cys Val Cys Arg Asp Asn Trp His Gly Ala Asn Arg Pro Trp Val
        290                 295                 300

Ser Phe Asn Gln Asn Leu Glu Tyr Gln Ile Gly Tyr Ile Cys Ser Gly
305                 310                 315                 320

Ile Phe Gly Asp Asn Pro Arg Pro Asn Asp Lys Thr Gly Ser Cys Gly
                325                 330                 335

Pro Val Ser Ser Asn Gly Ala Asn Gly Val Lys Gly Phe Ser Phe Lys
                340                 345                 350

Tyr Gly Asn Gly Val Trp Ile Gly Arg Thr Lys Ser Ile Ser Ser Arg
            355                 360                 365

Asn Gly Phe Glu Met Ile Trp Asp Pro Asn Gly Trp Thr Gly Thr Asp
370                 375                 380

Asn Asn Phe Ser Ile Lys Gln Asp Ile Val Gly Ile Lys Glu Trp Ser
385                 390                 395                 400

Gly Tyr Ser Gly Ser Phe Ile Gln His Pro Glu Leu Thr Gly Leu Asn
                405                 410                 415

Cys Ile Arg Pro Cys Phe Trp Val Glu Leu Ile Arg Gly Arg Pro Lys
                420                 425                 430

Glu Asn Thr Ile Trp Thr Ser Gly Ser Ser Ile Ser Phe Cys Gly Val
            435                 440                 445

Asp Ser Asp Thr Ala Asn Trp Ser Trp Pro Asp Gly Ala Glu Leu Pro
        450                 455                 460

Phe Ile Ile Asp Lys
465

<210> SEQ ID NO 33
<211> LENGTH: 469
<212> TYPE: PRT
<213> ORGANISM: Artificial
<220> FEATURE:
<223> OTHER INFORMATION: synthetically-generated protein

<400> SEQUENCE: 33

Met Asn Pro Asn Lys Lys Ile Ile Thr Ile Gly Ser Ile Cys Met Thr
1               5                   10                  15

Ile Gly Met Ala Asn Leu Met Leu Gln Ile Gly Asn Ile Ile Ser Ile
            20                  25                  30

```
Trp Val Ser His Ser Ile Gln Ile Gly Asn Gln Ser Gln Ile Glu Thr
        35                  40                  45

Cys Asn Gln Ser Val Ile Thr Tyr Glu Asn Asn Thr Trp Val Asn His
    50                  55                  60

Thr Tyr Val Asn Ile Asn Asn Thr Asn Val Val Ala Gly Glu Asp Lys
65              70                  75                      80

Thr Ser Val Thr Leu Ala Gly Asn Ser Ser Leu Cys Pro Ile Arg Gly
                85                  90                  95

Trp Ala Ile Tyr Ser Lys Asp Asn Ser Val Arg Ile Gly Ser Lys Gly
            100                 105                 110

Asp Val Phe Val Met Arg Glu Pro Phe Ile Ser Cys Ser Pro Leu Glu
        115                 120                 125

Cys Arg Thr Phe Phe Leu Thr Gln Gly Thr Leu Leu Asn Asp Lys His
    130                 135                 140

Ser Asn Gly Thr Ile Lys Asp Arg Ser Pro Tyr Arg Thr Leu Met Ser
145             150                 155                     160

Cys Pro Ile Gly Glu Val Pro Ser Pro Tyr Asn Ser Arg Phe Glu Ser
                165                 170                 175

Val Ala Trp Ser Ala Ser Ala Cys His Asp Gly Thr Ser Trp Leu Thr
            180                 185                 190

Ile Gly Ile Ser Gly Pro Asp Ser Gly Ala Val Ala Val Leu Lys Tyr
        195                 200                 205

Asn Gly Ile Ile Thr Asp Thr Ile Lys Ser Trp Arg Asn Asn Ile Leu
    210                 215                 220

Arg Thr Gln Glu Ser Glu Cys Ala Cys Val Asn Gly Ser Cys Phe Thr
225             230                 235                     240

Ile Met Thr Asp Gly Pro Ser Asp Gly Gln Ala Ser Tyr Lys Ile Phe
                245                 250                 255

Arg Ile Glu Lys Gly Lys Ile Ile Lys Ser Val Glu Met Lys Ala Pro
            260                 265                 270

Asn Tyr His Tyr Glu Glu Cys Ser Cys Tyr Pro Asp Thr Gly Ile Val
        275                 280                 285

Met Cys Val Cys Arg Asp Asn Trp His Gly Ser Asn Arg Pro Trp Val
    290                 295                 300

Ser Phe Asn Gln Asn Leu Glu Tyr Gln Met Gly Tyr Ile Cys Ser Gly
305             310                 315                     320

Val Phe Gly Asp Asn Pro Arg Pro Lys Asp Gly Lys Gly Ser Cys Asn
                325                 330                 335

Pro Val Thr Val Asp Gly Ala Asp Gly Val Lys Gly Phe Ser Tyr Lys
            340                 345                 350

Tyr Gly Asn Gly Val Trp Ile Gly Arg Thr Lys Ser Ile Ser Ser Arg
        355                 360                 365

Lys Gly Phe Glu Met Ile Trp Asp Thr Asn Gly Trp Thr Gly Thr Asp
    370                 375                 380

Asn Lys Phe Ser Ile Lys Gln Asp Ile Val Gly Ile Asn Glu Trp Ser
385             390                 395                     400

Gly Tyr Ser Gly Ser Phe Val Gln His Pro Glu Leu Thr Gly Leu Asp
                405                 410                 415

Cys Ile Arg Pro Cys Phe Trp Val Glu Leu Ile Arg Gly Arg Pro Glu
            420                 425                 430

Glu Asn Thr Ile Trp Thr Ser Gly Ser Ile Ile Ser Phe Cys Gly Val
    435                 440                 445
```

Asn Ser Asp Thr Val Gly Trp Ser Trp Pro Asp Gly Ala Glu Leu Pro
    450                 455                 460

Phe Thr Val Asp Lys
465

<210> SEQ ID NO 34
<211> LENGTH: 469
<212> TYPE: PRT
<213> ORGANISM: Artificial
<220> FEATURE:
<223> OTHER INFORMATION: synthetically-generated protein

<400> SEQUENCE: 34

Met Asn Pro Asn Gln Lys Ile Ile Thr Ile Gly Ser Val Cys Met Thr
1               5                   10                  15

Ile Gly Met Ala Asn Leu Ile Leu Gln Ile Gly Asn Ile Ile Ser Ile
            20                  25                  30

Trp Ile Ser His Ser Ile Gln Leu Gly Asn Gln Asn Gln Ile Glu Thr
        35                  40                  45

Cys Asn Gln Ser Val Ile Thr Tyr Glu Asn Asn Thr Trp Val Asn Gln
    50                  55                  60

Thr Tyr Val Asn Ile Ser Asn Thr Asn Phe Ala Ala Gly Gln Ser Val
65                  70                  75                  80

Val Ser Val Lys Leu Ala Gly Asn Ser Ser Leu Cys Pro Val Ser Gly
                85                  90                  95

Trp Ala Ile Tyr Ser Lys Asp Asn Ser Ile Arg Ile Gly Ser Lys Gly
            100                 105                 110

Asp Val Phe Val Ile Arg Glu Pro Phe Ile Ser Cys Ser Pro Leu Glu
        115                 120                 125

Cys Arg Thr Phe Phe Leu Thr Gln Gly Ala Leu Leu Asn Asp Lys His
    130                 135                 140

Ser Asn Gly Thr Ile Lys Asp Arg Ser Pro Tyr Arg Thr Leu Met Ser
145                 150                 155                 160

Cys Pro Ile Gly Glu Val Pro Ser Pro Tyr Asn Ser Arg Phe Glu Ser
                165                 170                 175

Val Ala Trp Ser Ala Ser Ala Cys His Asp Gly Ile Asn Trp Leu Thr
            180                 185                 190

Ile Gly Ile Ser Gly Pro Asp Asn Gly Ala Val Ala Val Leu Lys Tyr
        195                 200                 205

Asn Gly Ile Ile Thr Asp Thr Ile Lys Ser Trp Arg Asn Asn Ile Leu
    210                 215                 220

Arg Thr Gln Glu Ser Glu Cys Ala Cys Val Asn Gly Ser Cys Phe Thr
225                 230                 235                 240

Ile Met Thr Asp Gly Pro Ser Asp Gly Gln Ala Ser Tyr Lys Ile Phe
                245                 250                 255

Arg Ile Glu Lys Gly Lys Ile Val Lys Ser Val Glu Met Asn Ala Pro
            260                 265                 270

Asn Tyr His Tyr Glu Glu Cys Ser Cys Tyr Pro Asp Ser Ser Glu Ile
        275                 280                 285

Thr Cys Val Cys Arg Asp Asn Trp His Gly Ser Asn Arg Pro Trp Val
    290                 295                 300

Ser Phe Asn Gln Asn Leu Glu Tyr Gln Ile Gly Tyr Ile Cys Ser Gly
305                 310                 315                 320

Ile Phe Gly Asp Asn Pro Arg Pro Asn Asp Lys Thr Gly Ser Cys Gly
                325                 330                 335

-continued

```
Pro Val Ser Ser Asn Gly Ala Asn Gly Val Lys Gly Phe Ser Phe Lys
            340                 345                 350

Tyr Gly Asn Gly Val Trp Ile Gly Arg Thr Lys Ser Ile Ser Ser Arg
            355                 360                 365

Lys Gly Phe Glu Met Ile Trp Asp Pro Asn Gly Trp Thr Gly Thr Asp
    370                 375                 380

Asn Asn Phe Ser Ile Lys Gln Asp Ile Val Gly Ile Asn Glu Trp Ser
385                 390                 395                 400

Gly Tyr Ser Gly Ser Phe Val Gln His Pro Glu Leu Thr Gly Leu Asp
                405                 410                 415

Cys Ile Arg Pro Cys Phe Trp Val Glu Leu Ile Arg Gly Arg Pro Lys
            420                 425                 430

Glu Asn Thr Ile Trp Thr Ser Gly Ser Ser Ile Ser Phe Cys Gly Val
            435                 440                 445

Asn Ser Asp Thr Val Gly Trp Ser Trp Pro Asp Gly Ala Glu Leu Pro
    450                 455                 460

Phe Thr Ile Asp Lys
465

<210> SEQ ID NO 35
<211> LENGTH: 470
<212> TYPE: PRT
<213> ORGANISM: Artificial
<220> FEATURE:
<223> OTHER INFORMATION: synthetically-generated protein

<400> SEQUENCE: 35

Met Asn Pro Thr Gln Lys Ile Ile Thr Ile Gly Ser Ile Ser Ile Ala
1               5                   10                  15

Ile Gly Ile Ile Ser Leu Met Leu Gln Ile Gly Asn Ile Ser Ile
            20                  25                  30

Trp Ala Ser His Ser Ile Gln Thr Gly Ser Gln Asn His Thr Gly Ile
            35                  40                  45

Cys Asn Gln Arg Ile Ile Thr Tyr Glu Asn Ser Thr Trp Val Asn His
    50                  55                  60

Thr Tyr Val Asn Ile Asn Asn Thr Asn Val Val Ala Gly Lys Asp Lys
65                  70                  75                  80

Thr Ser Val Thr Leu Ala Gly Asn Ser Ser Leu Cys Pro Ile Arg Gly
            85                  90                  95

Trp Ala Ile Tyr Ser Lys Asp Asn Ser Val Arg Ile Gly Ser Lys Gly
            100                 105                 110

Asp Val Phe Val Met Arg Glu Pro Phe Ile Ser Cys Ser His Leu Glu
            115                 120                 125

Cys Arg Thr Phe Phe Leu Thr Gln Gly Thr Leu Leu Asn Asp Lys His
    130                 135                 140

Ser Asn Gly Thr Val Lys Asp Arg Ser Pro Tyr Arg Ala Leu Met Ser
145                 150                 155                 160

Cys Pro Leu Gly Glu Ala Pro Ser Pro Tyr Asn Ser Lys Phe Glu Ser
            165                 170                 175

Val Ala Trp Ser Ala Ser Ala Cys His Asp Gly Met Gly Trp Leu Thr
            180                 185                 190

Ile Gly Ile Ser Gly Pro Asp Ser Gly Ala Val Ala Val Leu Lys Tyr
            195                 200                 205

Asn Gly Ile Ile Thr Gly Thr Ile Lys Ser Trp Lys Lys Gln Ile Leu
    210                 215                 220
```

```
Arg Thr Gln Glu Ser Glu Cys Val Cys Val Asn Gly Ser Cys Phe Thr
225                 230                 235                 240

Val Met Thr Asp Gly Pro Ser Asn Gly Ala Ala Ser Tyr Lys Ile Phe
            245                 250                 255

Lys Ile Glu Lys Gly Lys Val Thr Lys Ser Ile Glu Leu Asn Ala Pro
        260                 265                 270

Asn Phe His Tyr Glu Glu Cys Ser Cys Tyr Pro Asp Thr Gly Thr Val
    275                 280                 285

Met Cys Val Cys Arg Asp Asn Trp His Gly Ala Asn Arg Pro Trp Val
290                 295                 300

Ser Phe Asn Gln Asn Leu Asp Tyr Gln Ile Gly Tyr Ile Cys Ser Gly
305                 310                 315                 320

Val Phe Gly Asp Asn Pro Arg Pro Glu Asp Gly Glu Gly Ser Cys Asn
                325                 330                 335

Pro Val Thr Val Asp Gly Ala Asn Gly Val Lys Gly Phe Ser Tyr Lys
            340                 345                 350

Tyr Gly Asn Gly Val Trp Ile Gly Arg Thr Lys Ser Ile Ser Ser Arg
        355                 360                 365

Asn Gly Phe Glu Met Ile Trp Asp Pro Asn Gly Trp Thr Asn Thr Asp
    370                 375                 380

Ser Asp Phe Ser Val Lys Gln Asp Val Val Ala Ile Thr Asp Trp Ser
385                 390                 395                 400

Gly Tyr Ser Gly Ser Phe Ile Gln His Pro Glu Leu Thr Gly Leu Asp
                405                 410                 415

Cys Met Arg Pro Cys Phe Trp Val Glu Leu Val Arg Gly Leu Pro Arg
            420                 425                 430

Glu Asn Thr Thr Ile Trp Thr Ser Gly Ser Ser Met Ser Phe Cys Gly
        435                 440                 445

Val Asn Ser Asp Thr Ala Asn Trp Ser Trp Pro Asp Gly Ala Glu Leu
    450                 455                 460

Pro Phe Ile Ile Asp Lys
465             470

<210> SEQ ID NO 36
<211> LENGTH: 469
<212> TYPE: PRT
<213> ORGANISM: Artificial
<220> FEATURE:
<223> OTHER INFORMATION: synthetically-generated protein

<400> SEQUENCE: 36

Met Asn Pro Asn Lys Lys Ile Ile Thr Ile Gly Ser Ile Cys Met Thr
1               5                   10                  15

Ile Gly Met Ala Asn Leu Met Leu Gln Ile Gly Asn Ile Ile Ser Ile
            20                  25                  30

Trp Val Ser His Ser Ile Gln Ile Gly Asn Gln Ser Gln Ile Glu Thr
        35                  40                  45

Cys Asn Gln Ser Ile Ile Thr Tyr Glu Asn Asn Thr Trp Val Asn His
    50                  55                  60

Thr Tyr Val Ser Ile Asn Asn Thr Asn Val Val Ala Gly Glu Asp Lys
65                  70                  75                  80

Thr Ser Val Thr Leu Ala Gly Asn Ser Ser Leu Cys Ser Ile Ser Gly
            85                  90                  95

Trp Ala Ile Tyr Thr Lys Asp Asn Ser Ile Arg Ile Gly Ser Arg Gly
            100                 105                 110
```

Asp Val Phe Val Ile Arg Glu Pro Phe Ile Ser Cys Ser His Leu Glu
            115                 120                 125

Cys Lys Thr Phe Phe Leu Thr Gln Gly Ala Leu Leu Asn Asp Arg His
    130                 135                 140

Ser Asn Gly Thr Val Lys Asp Arg Ser Pro His Arg Thr Leu Met Ser
145                 150                 155                 160

Cys Pro Val Gly Glu Ala Pro Ser Pro Tyr Asn Ser Arg Phe Glu Ser
                165                 170                 175

Val Ala Trp Ser Ala Ser Ala Cys His Asp Gly Thr Ser Trp Leu Thr
            180                 185                 190

Ile Gly Ile Ser Gly Pro Asp Asp Gly Ala Val Ala Val Leu Lys Tyr
        195                 200                 205

Asn Gly Ile Ile Thr Glu Thr Ile Lys Ser Trp Lys Lys Arg Ile Leu
    210                 215                 220

Arg Thr Gln Glu Ser Glu Cys Val Cys Met Asn Gly Ser Cys Phe Thr
225                 230                 235                 240

Ile Met Thr Asp Gly Pro Ser Asn Gly Gln Ala Ser Tyr Lys Ile Phe
                245                 250                 255

Arg Ile Glu Lys Gly Lys Ile Ile Lys Ser Val Glu Met Lys Ala Pro
            260                 265                 270

Asn Tyr His Tyr Glu Glu Cys Ser Cys Tyr Pro Asp Thr Gly Ile Val
        275                 280                 285

Met Cys Val Cys Arg Asp Asn Trp His Gly Ser Asn Arg Pro Trp Ile
    290                 295                 300

Ser Phe Asn Gln Asn Leu Glu Tyr Gln Met Gly Tyr Ile Cys Ser Gly
305                 310                 315                 320

Val Phe Gly Asp Asn Pro Arg Pro Lys Asp Gly Lys Gly Ser Cys Asn
                325                 330                 335

Pro Val Thr Val Asp Gly Ala Asp Gly Val Lys Gly Phe Ser Tyr Lys
            340                 345                 350

Tyr Asp Asn Gly Val Trp Ile Gly Arg Thr Lys Ser Asn Arg Leu Arg
        355                 360                 365

Lys Gly Phe Glu Met Ile Trp Asp Ser Asn Gly Trp Thr Gly Thr Asp
    370                 375                 380

Asn Lys Phe Ser Ile Lys Gln Asp Ile Val Gly Ile Lys Glu Trp Ser
385                 390                 395                 400

Gly Tyr Ser Gly Ser Phe Ile Gln His Pro Glu Leu Thr Gly Leu Asn
                405                 410                 415

Cys Ile Arg Pro Cys Phe Trp Val Glu Leu Ile Arg Gly Arg Pro Glu
            420                 425                 430

Glu Asn Thr Ile Trp Thr Ser Gly Ser Ser Ile Ser Phe Cys Gly Val
        435                 440                 445

Asp Ser Asp Thr Ala Asn Trp Ser Trp Pro Asp Gly Ala Glu Leu Pro
    450                 455                 460

Phe Thr Val Asp Lys
465

<210> SEQ ID NO 37
<211> LENGTH: 469
<212> TYPE: PRT
<213> ORGANISM: Artificial
<220> FEATURE:
<223> OTHER INFORMATION: synthetically-generated protein

<400> SEQUENCE: 37

```
Met Asn Pro Asn Gln Lys Ile Ile Thr Ile Gly Ser Val Ser Leu Thr
1               5                   10                  15

Ile Ser Thr Ile Cys Phe Phe Met Gln Ile Ala Ile Leu Ile Thr Thr
            20                  25                  30

Val Thr Leu His Phe Lys Gln Tyr Glu Phe Asn Ser Pro Pro Asn Asn
        35                  40                  45

Gln Val Met Leu Cys Glu Pro Thr Thr Ile Ile Glu Arg Asn Ile Thr
    50                  55                  60

Glu Ile Val Tyr Leu Thr Asn Thr Thr Ile Glu Lys Glu Ile Cys Pro
65                  70                  75                  80

Lys Pro Ala Glu Tyr Arg Asn Trp Ser Lys Pro Gln Cys Ile Thr Gly
                85                  90                  95

Phe Ala Pro Phe Ser Lys Asp Asn Ser Ile Arg Leu Ser Ala Gly Gly
            100                 105                 110

Asp Ile Trp Val Thr Arg Glu Pro Tyr Val Ser Cys Asp Pro Asp Lys
        115                 120                 125

Cys Tyr Gln Phe Ala Leu Gly Gln Gly Thr Thr Leu Asn Asn Val His
130                 135                 140

Ser Asn Asn Thr Val Arg Asp Arg Thr Pro Tyr Arg Thr Leu Leu Met
145                 150                 155                 160

Asn Glu Leu Gly Val Pro Phe His Leu Gly Thr Lys Gln Val Cys Ile
                165                 170                 175

Ala Trp Ser Ser Ser Ser Cys His Asp Gly Lys Ala Trp Leu His Val
            180                 185                 190

Cys Ile Thr Gly Asp Asp Lys Asn Ala Thr Ala Ser Phe Ile Tyr Asn
        195                 200                 205

Gly Arg Leu Val Asp Ser Val Val Ser Trp Ser Lys Tyr Ile Leu Arg
210                 215                 220

Thr Gln Glu Ser Glu Cys Val Cys Ile Asn Gly Thr Cys Thr Val Val
225                 230                 235                 240

Met Thr Asp Gly Ser Ala Ser Gly Lys Ala Asp Thr Lys Ile Leu Phe
                245                 250                 255

Ile Glu Glu Gly Lys Ile Val His Thr Ser Thr Leu Ser Gly Ser Ala
            260                 265                 270

Gln His Val Glu Glu Cys Ser Cys Tyr Pro Arg Tyr Pro Gly Val Arg
        275                 280                 285

Cys Val Cys Arg Asp Asn Trp Lys Gly Ser Asn Arg Pro Ile Val Asp
    290                 295                 300

Ile Asn Ile Lys Asp His Ser Ile Val Ser Ser Tyr Val Cys Ser Gly
305                 310                 315                 320

Leu Val Gly Asp Thr Pro Arg Lys Asn Asp Ser Ser Ser Ser His
                325                 330                 335

Cys Leu Asp Pro Asn Asn Glu Glu Gly Gly His Gly Val Lys Gly Trp
            340                 345                 350

Ala Phe Asp Asp Gly Asn Asp Val Trp Met Gly Arg Thr Ile Asn Glu
        355                 360                 365

Thr Ser Arg Leu Gly Tyr Glu Thr Phe Lys Val Ile Glu Gly Trp Ser
    370                 375                 380

Asn Pro Lys Ser Lys Leu Gln Ile Asn Arg Gln Val Ile Val Asp Arg
385                 390                 395                 400

Gly Asp Arg Ser Gly Tyr Ser Gly Ile Phe Ser Val Glu Gly Lys Ser
                405                 410                 415

Cys Ile Asn Arg Cys Phe Tyr Val Glu Leu Ile Arg Gly Arg Lys Glu
```

```
                420             425             430
Glu Thr Glu Val Leu Trp Thr Ser Asn Ser Ile Val Phe Cys Gly
            435             440             445
Thr Ser Gly Thr Tyr Gly Thr Gly Ser Trp Pro Asp Gly Ala Asp Leu
        450             455             460
Asn Leu Met Pro Ile
465

<210> SEQ ID NO 38
<211> LENGTH: 469
<212> TYPE: PRT
<213> ORGANISM: Artificial
<220> FEATURE:
<223> OTHER INFORMATION: synthetically-generated protein

<400> SEQUENCE: 38

Met Asn Pro Asn Gln Lys Ile Ile Ala Ile Gly Ser Val Ser Leu Thr
1               5                   10                  15
Ile Ala Thr Ile Cys Phe Leu Met Gln Ile Ala Ile Leu Val Thr Thr
            20                  25                  30
Val Thr Leu His Phe Lys Gln Tyr Glu Cys Asn Ser Pro Pro Asn Asn
        35                  40                  45
Gln Val Met Pro Cys Glu Pro Ile Ile Ile Glu Arg Asn Ile Thr Glu
    50                  55                  60
Ile Val Tyr Leu Asn Asn Thr Thr Ile Glu Lys Glu Ile Cys Pro Lys
65                  70                  75                  80
Leu Ala Glu Tyr Arg Asn Trp Ser Lys Pro Gln Cys Asn Ile Thr Gly
                85                  90                  95
Phe Ala Pro Phe Ser Lys Asp Asn Ser Ile Arg Leu Ser Ala Ser Gly
            100                 105                 110
Asp Ile Trp Val Thr Arg Glu Pro Tyr Val Ser Cys Asp Pro Asp Lys
        115                 120                 125
Cys Tyr Gln Phe Ala Leu Gly Gln Gly Thr Thr Leu Asn Asn Gly His
    130                 135                 140
Ser Asn Asp Thr Val His Asp Arg Ile Pro His Arg Thr Leu Leu Met
145                 150                 155                 160
Asn Glu Leu Gly Val Pro Phe His Leu Gly Thr Arg Gln Val Cys Ile
                165                 170                 175
Ala Trp Ser Ser Ser Ser Cys His Asp Gly Lys Ala Trp Leu His Val
            180                 185                 190
Cys Val Thr Gly His Asp Glu Asn Ala Thr Ala Ser Phe Ile Tyr Asp
        195                 200                 205
Gly Arg Leu Val Asp Ser Ile Gly Ser Trp Ser Lys Lys Ile Leu Arg
    210                 215                 220
Thr Gln Glu Ser Glu Cys Val Cys Ile Asn Gly Thr Cys Thr Val Val
225                 230                 235                 240
Met Thr Asp Gly Ser Ala Ser Gly Arg Ala Asp Thr Lys Ile Leu Phe
                245                 250                 255
Ile Glu Glu Gly Lys Ile Val His Ile Ser Pro Leu Ser Gly Ser Ala
            260                 265                 270
Gln His Val Glu Glu Cys Ser Cys Tyr Pro Arg Tyr Ser Gly Val Arg
        275                 280                 285
Cys Val Cys Arg Asp Asn Trp Lys Gly Ser Asn Arg Pro Ile Val Asp
    290                 295                 300
Ile Asn Val Lys Asp Tyr Ser Ile Val Ser Ser Tyr Val Cys Ser Gly
```

```
305                 310                 315                 320
Leu Val Gly Asp Thr Pro Arg Lys Asn Asp Arg Ser Ser Ser Tyr
                325                 330                 335

Cys Arg Asn Pro Asn Glu Lys Gly Ser His Gly Val Lys Gly Trp
                340                 345                 350

Ala Phe Asp Asn Gly Asp Val Trp Met Gly Arg Thr Ile Ser Glu
                355                 360                 365

Lys Leu Arg Ser Gly Tyr Glu Thr Phe Lys Val Ile Glu Gly Trp Ser
    370                 375                 380

Lys Pro Asn Ser Lys Leu Gln Ile Asn Arg Gln Val Ile Val Glu Arg
385                 390                 395                 400

Gly Asn Arg Ser Gly Tyr Ser Gly Ile Phe Ser Val Glu Gly Lys Asn
                405                 410                 415

Cys Ile Asn Arg Cys Phe Tyr Val Glu Leu Ile Arg Gly Arg Glu Gln
                420                 425                 430

Glu Thr Arg Val Trp Trp Thr Ser Asn Ser Ile Val Phe Cys Gly
                435                 440                 445

Thr Ser Gly Thr Tyr Gly Thr Gly Ser Trp Pro Asp Gly Ala Asp Ile
    450                 455                 460

Asn Leu Met Pro Ile
465

<210> SEQ ID NO 39
<211> LENGTH: 469
<212> TYPE: PRT
<213> ORGANISM: Artificial
<220> FEATURE:
<223> OTHER INFORMATION: synthetically-generated protein

<400> SEQUENCE: 39

Met Asn Pro Asn Lys Lys Ile Ile Thr Ile Gly Ser Val Ser Leu Thr
1               5                   10                  15

Ile Ser Thr Ile Cys Phe Phe Met Gln Ile Ala Ile Leu Ile Thr Thr
                20                  25                  30

Val Thr Leu His Phe Lys Gln His Glu Cys Asn Ser Pro Pro Asn Asn
                35                  40                  45

Gln Val Met Leu Cys Glu Pro Thr Ile Ile Glu Arg Asn Met Thr Glu
    50                  55                  60

Ile Val Tyr Leu Thr Asn Ile Thr Ile Glu Lys Glu Ile Cys Pro Lys
65                  70                  75                  80

Pro Ala Glu Tyr Arg Asn Trp Ser Lys Pro Gln Cys Gly Ile Thr Gly
                85                  90                  95

Phe Ala Pro Phe Ser Arg Asp Asn Ser Ile Arg Leu Ser Ala Gly Gly
                100                 105                 110

Asn Ile Trp Val Thr Arg Glu Pro Tyr Val Ser Cys Asp Pro Asn Lys
                115                 120                 125

Cys Tyr Gln Phe Ala Leu Gly Gln Gly Thr Thr Leu Asn Asn Val His
                130                 135                 140

Ser Asn Asn Thr Val Arg Asp Arg Thr Pro Tyr Arg Thr Leu Leu Met
145                 150                 155                 160

Ser Glu Leu Gly Val Pro Phe His Leu Gly Thr Lys Gln Val Cys Met
                165                 170                 175

Ala Trp Ser Ser Ser Ser Cys His Asp Gly Lys Ala Trp Leu His Val
                180                 185                 190

Cys Ile Thr Gly Asp Asp Lys Asn Ala Thr Ala Ser Ile Ile Tyr Asn
```

```
                195                 200                 205
Gly Arg Leu Val Asp Ser Val Ser Trp Ser Lys Asp Ile Leu Arg
    210                 215                 220

Thr Gln Glu Ser Glu Cys Val Cys Ile Asp Gly Thr Cys Thr Val Val
225                 230                 235                 240

Met Thr Asp Gly Asn Ala Thr Gly Lys Ala Asp Thr Lys Ile Leu Phe
                245                 250                 255

Ile Lys Glu Gly Lys Ile Val His Thr Ser Lys Leu Ser Gly Ser Ala
                260                 265                 270

Gln His Val Glu Glu Cys Ser Cys Tyr Pro Arg Tyr Pro Asp Val Arg
                275                 280                 285

Cys Ile Cys Arg Asp Asn Trp Lys Gly Ser Asn Arg Pro Ile Val Asp
                290                 295                 300

Ile Asn Ile Lys Asp His Ser Ile Val Ser Ser Tyr Val Cys Ser Gly
305                 310                 315                 320

Leu Val Gly Asp Thr Pro Arg Lys Ser Asp Ser Ser Ser Ser His
                325                 330                 335

Cys Leu Asn Pro Asn Asn Glu Glu Gly Gly His Arg Val Lys Gly Trp
                340                 345                 350

Ala Phe Asp Asp Gly Asp Val Trp Met Gly Arg Thr Ile Asn Glu
                355                 360                 365

Thr Ser Arg Leu Gly Tyr Glu Thr Phe Lys Val Val Glu Gly Trp Ser
370                 375                 380

Asn Pro Lys Ser Lys Leu Gln Ile Asn Arg Gln Val Ile Val Asp Arg
385                 390                 395                 400

Gly Asp Arg Ser Gly Tyr Ser Gly Ile Phe Ser Val Glu Ser Lys Ser
                405                 410                 415

Cys Ile Asn Arg Cys Phe Tyr Val Glu Leu Ile Arg Gly Arg Lys Gln
                420                 425                 430

Glu Thr Glu Val Trp Trp Thr Ser Asn Ser Ile Val Val Phe Cys Gly
                435                 440                 445

Thr Ser Gly Thr Tyr Gly Thr Gly Ser Trp Pro Asp Gly Ala Asp Leu
    450                 455                 460

Asn Leu Met His Ile
465

<210> SEQ ID NO 40
<211> LENGTH: 469
<212> TYPE: PRT
<213> ORGANISM: Artificial
<220> FEATURE:
<223> OTHER INFORMATION: synthetically-generated protein

<400> SEQUENCE: 40

Met Asn Pro Asn Gln Lys Ile Ile Thr Ile Gly Ser Val Ser Leu Thr
1               5                   10                  15

Ile Ala Thr Val Cys Phe Leu Met Gln Ile Ala Ile Leu Ala Thr Thr
                20                  25                  30

Val Thr Leu His Phe Lys Gln Tyr Glu Phe Asn Ser Pro Pro Asn Asn
            35                  40                  45

Gln Val Val Leu Cys Glu Pro Thr Ile Ile Glu Arg Asn Ile Thr Glu
        50                  55                  60

Ile Val Tyr Leu Thr Asn Thr Thr Ile Glu Lys Glu Ile Cys Pro Lys
65                  70                  75                  80

Leu Val Glu Tyr Arg Asn Trp Ser Lys Pro Gln Cys Asp Ile Thr Gly
```

```
                    85                  90                  95
Phe Ala Pro Phe Ser Lys Asp Asn Ser Ile Arg Leu Ser Ala Gly Gly
                100                 105                 110

Asp Ile Trp Val Thr Arg Glu Pro Tyr Val Ser Cys Asp Pro Gly Lys
            115                 120                 125

Cys Tyr Gln Phe Ala Leu Gly Gln Gly Thr Thr Leu Asn Asn Arg His
        130                 135                 140

Ser Asn Asp Thr Val His Asp Arg Thr Pro Tyr Arg Thr Leu Leu Met
145                 150                 155                 160

Asn Glu Leu Gly Ile Pro Phe His Leu Gly Thr Lys Gln Val Cys Ile
                165                 170                 175

Ala Trp Ser Ser Ser Cys Tyr Asp Gly Lys Ala Trp Leu His Val
                180                 185                 190

Cys Val Thr Gly Asp Asp Lys Asn Ala Thr Ala Ser Phe Ile Tyr Asn
            195                 200                 205

Gly Arg Leu Val Asp Ser Ile Val Ser Trp Ser Lys Glu Ile Leu Arg
        210                 215                 220

Thr Gln Glu Ser Glu Cys Val Cys Ile Asn Gly Thr Cys Ala Val Val
225                 230                 235                 240

Met Thr Asp Gly Ser Ala Ser Gly Lys Ala Asp Thr Lys Ile Leu Phe
                245                 250                 255

Ile Glu Glu Gly Lys Ile Val His Thr Ser Thr Leu Ser Gly Ser Ala
            260                 265                 270

Gln His Val Glu Glu Cys Ser Cys Tyr Pro Arg Tyr Pro Gly Val Arg
        275                 280                 285

Cys Val Cys Arg Asp Asn Trp Arg Gly Ser Asn Arg Pro Ile Val Asp
    290                 295                 300

Ile Asn Ile Lys Asp Tyr Ser Ile Val Ser Arg Tyr Val Cys Ser Gly
305                 310                 315                 320

Leu Val Gly Asp Thr Pro Arg Lys Asn Asp Ser Ser Ser Ser His
                325                 330                 335

Cys Leu Asp Pro Asn Asn Glu Glu Gly Gly His Gly Val Lys Gly Trp
            340                 345                 350

Ala Phe Asp Asp Gly Asn Asp Val Trp Met Gly Arg Thr Ile Ser Glu
        355                 360                 365

Lys Ser Arg Leu Gly Tyr Glu Thr Phe Lys Val Ile Glu Gly Trp Ser
    370                 375                 380

Asn Pro Lys Ser Lys Leu Gln Thr Asn Arg Gln Val Ile Val Asp Arg
385                 390                 395                 400

Gly Asn Arg Ser Gly Tyr Ser Gly Ile Phe Ser Val Glu Gly Lys Ser
                405                 410                 415

Cys Ile Asn Arg Cys Phe Phe Val Glu Leu Ile Arg Gly Arg Lys Glu
            420                 425                 430

Glu Thr Glu Val Leu Trp Thr Ser Asn Ser Ile Val Val Leu Cys Gly
        435                 440                 445

Thr Ser Gly Thr Tyr Gly Ala Gly Ser Trp Pro Asp Gly Ala Asp Leu
    450                 455                 460

Asn Leu Met Pro Ile
465

<210> SEQ ID NO 41
<211> LENGTH: 469
<212> TYPE: PRT
<213> ORGANISM: Artificial
```

```
<220> FEATURE:
<223> OTHER INFORMATION: synthetically-generated protein

<400> SEQUENCE: 41

Met Asn Pro Asn Gln Lys Ile Ile Thr Ile Gly Ser Val Ser Leu Thr
1               5                   10                  15

Ile Ser Thr Ile Cys Phe Phe Met Gln Ile Ala Ile Leu Ile Thr Thr
            20                  25                  30

Val Thr Leu His Phe Lys Gln Tyr Glu Phe Asn Ser Pro Pro Asn Asn
        35                  40                  45

Gln Val Met Leu Cys Glu Pro Thr Ile Ile Glu Arg Asn Ile Thr Glu
    50                  55                  60

Ile Val Tyr Leu Thr Asn Thr Thr Ile Glu Lys Glu Ile Cys Pro Lys
65              70                  75                  80

Pro Ala Glu Tyr Arg Asn Trp Ser Lys Pro Gln Cys Gly Ile Thr Gly
                85                  90                  95

Phe Ala Pro Phe Ser Lys Asp Asn Ser Ile Arg Leu Ser Ala Gly Gly
            100                 105                 110

Asp Ile Trp Val Thr Arg Glu Pro Tyr Val Ser Cys Asp Pro Asp Lys
        115                 120                 125

Cys Tyr Gln Phe Ala Leu Gly Gln Gly Thr Thr Leu Asn Asn Val His
    130                 135                 140

Ser Asn Asn Thr Val Arg Asp Arg Thr Pro Tyr Arg Thr Leu Leu Met
145                 150                 155                 160

Asn Glu Leu Gly Val Pro Phe His Leu Gly Thr Lys Gln Val Cys Ile
                165                 170                 175

Ala Trp Ser Ser Ser Ser Cys His Asp Gly Lys Ala Trp Leu His Val
            180                 185                 190

Cys Ile Thr Gly Asp Asp Lys Asn Ala Thr Ala Ser Phe Ile Tyr Asn
        195                 200                 205

Gly Arg Leu Val Asp Ser Val Val Ser Trp Ser Lys Glu Ile Leu Arg
    210                 215                 220

Thr Gln Glu Ser Glu Cys Val Cys Ile Asn Gly Thr Cys Thr Val Val
225                 230                 235                 240

Met Thr Asp Gly Ser Ala Ser Gly Lys Ala Asp Thr Lys Ile Leu Phe
                245                 250                 255

Ile Glu Glu Gly Lys Ile Val His Thr Ser Thr Leu Ser Gly Ser Ala
            260                 265                 270

Gln His Val Glu Glu Cys Ser Cys Tyr Pro Arg Tyr Pro Gly Val Arg
        275                 280                 285

Cys Val Cys Arg Asp Asn Trp Lys Gly Ser Asn Arg Pro Ile Val Asp
    290                 295                 300

Ile Asn Ile Lys Asp His Ser Ile Val Ser Ser Tyr Val Cys Ser Gly
305                 310                 315                 320

Leu Val Gly Asp Thr Pro Arg Lys Asn Asp Ser Ser Ser Ser His
                325                 330                 335

Cys Leu Asp Pro Asn Asn Glu Glu Gly Gly His Gly Val Lys Gly Trp
            340                 345                 350

Ala Phe Asp Asp Gly Asn Asp Val Trp Met Gly Arg Thr Ile Asn Glu
        355                 360                 365

Thr Ser Arg Leu Gly Tyr Glu Thr Phe Lys Val Ile Glu Gly Trp Ser
    370                 375                 380

Asn Pro Lys Ser Lys Leu Gln Ile Asn Arg Gln Val Ile Val Asp Arg
385                 390                 395                 400
```

-continued

```
Gly Asp Arg Ser Gly Tyr Ser Gly Ile Phe Ser Val Glu Gly Lys Ser
            405                 410                 415

Cys Ile Asn Arg Cys Phe Tyr Val Glu Leu Ile Arg Gly Arg Lys Glu
            420                 425                 430

Glu Thr Glu Val Leu Trp Thr Ser Asn Ser Ile Val Val Phe Cys Gly
            435                 440                 445

Thr Ser Gly Thr Tyr Gly Thr Gly Ser Trp Pro Asp Gly Ala Asp Leu
            450                 455                 460

Asn Leu Met Pro Ile
465

<210> SEQ ID NO 42
<211> LENGTH: 469
<212> TYPE: PRT
<213> ORGANISM: Artificial
<220> FEATURE:
<223> OTHER INFORMATION: synthetically-generated protein

<400> SEQUENCE: 42

Met Asn Pro Asn Gln Lys Ile Ile Ser Ile Gly Ser Val Ser Leu Thr
1               5                   10                  15

Ile Ala Thr Ile Cys Phe Leu Met Gln Ile Ala Ile Leu Val Thr Thr
            20                  25                  30

Val Thr Leu His Phe Lys Gln Tyr Glu Cys Asn Ser Pro Pro Asn Asn
            35                  40                  45

Gln Val Met Pro Cys Glu Pro Ile Ile Ile Glu Arg Asn Ile Thr Glu
        50                  55                  60

Ile Val Tyr Leu Asn Asn Thr Thr Ile Glu Lys Glu Ile Cys Pro Lys
65              70                  75                  80

Leu Ala Glu Tyr Arg Asn Trp Ser Lys Pro Gln Cys Asp Ile Thr Gly
                85                  90                  95

Phe Ala Pro Phe Ser Arg Asp Asn Ser Ile Arg Leu Ser Ala Gly Gly
            100                 105                 110

Asn Ile Trp Val Thr Arg Glu Pro Tyr Val Ser Cys Asp Pro Gly Lys
        115                 120                 125

Cys Tyr Gln Phe Ala Leu Gly Gln Gly Thr Thr Leu Asn Asn Gly His
    130                 135                 140

Ser Asn Asp Thr Val His Asp Arg Thr Pro Tyr Arg Thr Leu Leu Met
145                 150                 155                 160

Ser Glu Leu Gly Val Pro Phe His Leu Gly Thr Arg Gln Val Cys Ile
                165                 170                 175

Ala Trp Ser Ser Ser Ser Cys Tyr Asp Gly Lys Ala Trp Leu His Val
            180                 185                 190

Cys Val Thr Gly Asp Asp Glu Asn Ala Thr Ala Ser Phe Ile Tyr Asp
        195                 200                 205

Gly Arg Leu Val Asp Ser Val Val Ser Trp Ser Lys Asp Ile Leu Arg
    210                 215                 220

Thr Gln Glu Ser Glu Cys Val Cys Ile Asp Gly Thr Cys Thr Val Val
225                 230                 235                 240

Met Thr Asp Gly Asn Ala Thr Gly Lys Ala Asp Thr Lys Ile Leu Phe
                245                 250                 255

Ile Lys Glu Gly Lys Ile Val His Thr Ser Lys Leu Ser Gly Ser Ala
            260                 265                 270

Gln His Val Glu Glu Cys Ser Cys Tyr Pro Arg Tyr Pro Asp Val Arg
        275                 280                 285
```

```
Cys Ile Cys Arg Asp Asn Trp Lys Gly Ser Asn Arg Pro Ile Val Asp
            290                 295                 300

Ile Asn Val Lys Asp Tyr Ser Ile Val Ser Ser Tyr Val Cys Ser Gly
305                 310                 315                 320

Leu Val Gly Asp Thr Pro Arg Lys Ser Asp Ser Ser Ser Ser His
                325                 330                 335

Cys Leu Asn Pro Asn Asn Glu Glu Gly His Gly Val Lys Gly Trp
                340                 345                 350

Ala Phe Asp Asn Gly Asp Val Trp Met Gly Arg Thr Ile Ser Glu
                355                 360                 365

Lys Ser Arg Leu Gly Tyr Glu Thr Phe Lys Val Val Glu Gly Trp Ser
370                 375                 380

Asn Pro Lys Ser Lys Leu Gln Thr Asn Arg Gln Val Ile Val Asp Arg
385                 390                 395                 400

Gly Asn Arg Ser Gly Tyr Ser Gly Ile Phe Ser Val Glu Ser Lys Ser
                405                 410                 415

Cys Ile Asn Arg Cys Phe Phe Val Glu Leu Ile Arg Gly Arg Lys Gln
                420                 425                 430

Glu Thr Glu Val Trp Trp Thr Ser Asn Ser Ile Val Leu Cys Gly
                435                 440                 445

Thr Ser Gly Thr Tyr Gly Ala Gly Ser Trp Pro Asp Gly Ala Asp Ile
450                 455                 460

Asn Leu Met Pro Ile
465

<210> SEQ ID NO 43
<211> LENGTH: 469
<212> TYPE: PRT
<213> ORGANISM: Artificial
<220> FEATURE:
<223> OTHER INFORMATION: synthetically-generated protein

<400> SEQUENCE: 43

Met Asn Pro Asn Lys Lys Ile Ile Thr Ile Gly Ser Val Ser Leu Thr
1               5                   10                  15

Ile Ala Thr Val Cys Phe Leu Met Gln Ile Ala Ile Leu Ala Thr Thr
                20                  25                  30

Val Thr Leu His Phe Lys Gln His Glu Cys Asn Ser Pro Pro Asn Asn
            35                  40                  45

Gln Val Val Leu Cys Glu Pro Thr Ile Ile Glu Arg Asn Met Thr Glu
50                  55                  60

Ile Val Tyr Leu Thr Asn Ile Thr Ile Glu Lys Glu Ile Cys Pro Lys
65                  70                  75                  80

Leu Val Glu Tyr Arg Asn Trp Ser Lys Pro Gln Cys Asn Ile Thr Gly
                85                  90                  95

Phe Ala Pro Phe Ser Lys Asp Asn Ser Val Arg Leu Ser Ala Gly Gly
                100                 105                 110

Asp Ile Trp Val Ala Arg Glu Pro Tyr Val Ser Cys Asp Pro Asn Lys
            115                 120                 125

Cys Tyr Gln Phe Ala Leu Gly Gln Gly Thr Thr Leu Asn Asn Arg His
            130                 135                 140

Ser Asn Asp Thr Val His Asp Arg Ile Pro His Arg Thr Leu Leu Met
145                 150                 155                 160

Asn Glu Leu Gly Ile Pro Phe His Leu Gly Thr Lys Gln Val Cys Met
                165                 170                 175
```

Ala Trp Ser Ser Ser Cys His Asp Gly Lys Ala Trp Leu His Val
                180                 185                 190

Cys Val Thr Gly Asp Asp Lys Asn Ala Thr Ala Ser Ile Ile Tyr Asn
            195                 200                 205

Gly Arg Leu Val Asp Ser Ile Gly Ser Trp Ser Lys Lys Ile Leu Arg
    210                 215                 220

Thr Gln Glu Ser Glu Cys Val Cys Ile Asn Gly Thr Cys Ala Val Val
225                 230                 235                 240

Met Thr Asp Gly Ser Ala Ser Gly Arg Ala Asp Thr Lys Ile Leu Phe
                245                 250                 255

Ile Glu Glu Gly Lys Ile Val His Ile Ser Pro Leu Ser Gly Ser Ala
            260                 265                 270

Gln His Val Glu Glu Cys Ser Cys Tyr Pro Arg Tyr Pro Gly Val Arg
        275                 280                 285

Cys Ile Cys Arg Asp Asn Trp Lys Gly Ser Asn Arg Pro Ile Val Asp
    290                 295                 300

Ile Asn Ile Lys Asp Tyr Ser Ile Val Ser Arg Tyr Val Cys Ser Gly
305                 310                 315                 320

Leu Val Gly Asp Thr Pro Arg Lys Asn Asp Arg Ser Ser Ser Ser Tyr
                325                 330                 335

Cys Arg Asn Pro Asn Asn Glu Lys Gly Ser His Gly Val Lys Gly Trp
            340                 345                 350

Ala Phe Asp Asp Gly Asp Asp Val Trp Met Gly Arg Thr Ile Ser Glu
        355                 360                 365

Lys Leu Arg Ser Gly Tyr Glu Thr Phe Lys Val Ile Glu Gly Trp Ser
    370                 375                 380

Lys Pro Asn Ser Lys Leu Gln Ile Asn Arg Gln Val Ile Val Glu Arg
385                 390                 395                 400

Gly Asn Arg Ser Gly Tyr Ser Gly Ile Phe Ser Val Glu Gly Lys Asn
                405                 410                 415

Cys Ile Asn Arg Cys Phe Tyr Val Glu Leu Ile Arg Gly Arg Glu Gln
            420                 425                 430

Glu Thr Arg Val Trp Trp Thr Ser Asn Ser Ile Ile Val Phe Cys Gly
        435                 440                 445

Thr Ser Gly Thr Tyr Gly Thr Gly Pro Trp Pro Asp Gly Ala Asp Leu
    450                 455                 460

Asn Leu Met His Ile
465

<210> SEQ ID NO 44
<211> LENGTH: 584
<212> TYPE: PRT
<213> ORGANISM: Artificial
<220> FEATURE:
<223> OTHER INFORMATION: synthetically-generated protein

<400> SEQUENCE: 44

Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
            20                  25                  30

Thr Ala Thr Gln Gly Glu Val Asn Val Thr Gly Val Ile Pro Leu Thr
        35                  40                  45

Thr Thr Pro Thr Lys Ser His Phe Ala Asn Leu Lys Gly Thr Glu Thr
    50                  55                  60

```
Arg Gly Lys Leu Cys Pro Lys Cys Leu Asn Cys Thr Asp Leu Asp Val
 65                  70                  75                  80

Ala Leu Gly Arg Pro Lys Cys Thr Gly Lys Ile Pro Ser Ala Arg Val
                 85                  90                  95

Ser Ile Leu His Glu Val Arg Pro Val Thr Ser Gly Cys Phe Pro Ile
            100                 105                 110

Met His Asp Arg Thr Lys Ile Arg Gln Leu Pro Asn Leu Leu Arg Gly
            115                 120                 125

Tyr Glu His Val Arg Leu Ser Thr His Asn Val Ile Asn Ala Glu Ala
            130                 135                 140

Pro Gly Gly Pro Tyr Lys Ile Gly Thr Ser Ser Cys Pro Asn Ile
145                 150                 155                 160

Thr Asn Gly Asn Gly Phe Phe Ala Thr Met Ala Trp Ala Val Pro Lys
                165                 170                 175

Asn Asp Lys Asn Lys Thr Ala Thr Asn Pro Leu Thr Ile Glu Val Pro
            180                 185                 190

Tyr Ile Cys Thr Glu Gly Glu Asp Gln Ile Thr Val Trp Gly Phe His
            195                 200                 205

Ser Asp Asn Glu Thr Gln Met Ala Lys Leu Tyr Gly Asp Ser Lys Pro
210                 215                 220

Gln Lys Phe Thr Ser Ser Ala Asn Gly Val Thr Thr His Tyr Val Ser
225                 230                 235                 240

Gln Ile Gly Gly Phe Pro Asn Gln Thr Glu Asp Gly Gly Leu Pro Gln
                245                 250                 255

Ser Gly Arg Ile Val Val Asp Tyr Met Val Gln Lys Ser Gly Lys Thr
            260                 265                 270

Gly Thr Ile Thr Tyr Gln Arg Gly Ile Leu Leu Pro Gln Lys Val Trp
            275                 280                 285

Cys Ala Ser Gly Arg Ser Lys Val Ile Lys Gly Ser Leu Pro Leu Ile
290                 295                 300

Gly Glu Ala Asp Cys Leu His Glu Lys Tyr Gly Gly Leu Asn Lys Ser
305                 310                 315                 320

Lys Pro Tyr Tyr Thr Gly Glu His Ala Lys Ala Ile Gly Asn Cys Pro
                325                 330                 335

Ile Trp Val Lys Thr Pro Leu Lys Leu Ala Asn Gly Thr Lys Tyr Arg
            340                 345                 350

Pro Pro Ala Lys Leu Leu Lys Glu Arg Gly Phe Phe Gly Ala Ile Ala
            355                 360                 365

Gly Phe Leu Glu Gly Gly Trp Glu Gly Met Ile Ala Gly Trp His Gly
            370                 375                 380

Tyr Thr Ser His Gly Ala His Gly Val Ala Val Ala Ala Asp Leu Lys
385                 390                 395                 400

Ser Thr Gln Glu Ala Ile Asn Lys Ile Thr Lys Asn Leu Asn Ser Leu
                405                 410                 415

Ser Glu Leu Glu Val Lys Asn Leu Gln Arg Leu Ser Gly Ala Met Asp
            420                 425                 430

Glu Leu His Asn Glu Ile Leu Glu Leu Asp Glu Lys Val Asp Asp Leu
            435                 440                 445

Arg Ala Asp Thr Ile Ser Ser Gln Ile Glu Leu Ala Val Leu Leu Ser
            450                 455                 460

Asn Glu Gly Ile Ile Asn Ser Glu Asp Glu His Leu Leu Ala Leu Glu
465                 470                 475                 480
```

```
Arg Lys Leu Lys Lys Met Leu Gly Pro Ser Ala Val Glu Ile Gly Asn
                485                 490                 495
Gly Cys Phe Glu Thr Lys His Lys Cys Asn Gln Thr Cys Leu Asp Arg
            500                 505                 510
Ile Ala Ala Gly Thr Phe Asp Ala Gly Glu Phe Ser Leu Pro Thr Phe
            515                 520                 525
Asp Ser Leu Asn Ile Thr Ala Ala Ser Leu Asn Asp Asp Gly Leu Asp
            530                 535                 540
Asn His Thr Ile Leu Leu Tyr Tyr Ser Thr Ala Ala Ser Ser Leu Ala
545                 550                 555                 560
Val Thr Leu Met Ile Ala Ile Phe Val Val Tyr Met Val Ser Arg Asp
                565                 570                 575
Asn Val Ser Cys Ser Ile Cys Leu
            580

<210> SEQ ID NO 45
<211> LENGTH: 584
<212> TYPE: PRT
<213> ORGANISM: Artificial
<220> FEATURE:
<223> OTHER INFORMATION: synthetically-generated protein

<400> SEQUENCE: 45

Met Lys Ala Ile Ile Val Leu Leu Met Val Val Thr Ser Asn Ala Asp
1               5                   10                  15
Arg Ile Cys Thr Gly Ile Thr Ser Ser Asn Ser Pro His Val Val Lys
                20                  25                  30
Thr Ala Thr Gln Gly Glu Val Asn Val Thr Gly Val Ile Pro Leu Thr
            35                  40                  45
Thr Thr Pro Thr Lys Ser His Phe Ala Asn Leu Lys Gly Thr Glu Thr
        50                  55                  60
Arg Gly Lys Leu Cys Pro Lys Cys Leu Asn Cys Thr Asp Leu Asp Val
65                  70                  75                  80
Ala Leu Gly Arg Pro Lys Cys Thr Gly Lys Ile Pro Ser Ala Arg Val
                85                  90                  95
Ser Ile Leu His Glu Val Arg Pro Val Thr Ser Gly Cys Phe Pro Ile
            100                 105                 110
Met His Asp Arg Thr Lys Ile Arg Gln Leu Pro Asn Leu Leu Arg Gly
        115                 120                 125
Tyr Glu His Ile Arg Leu Ser Thr His Asn Val Ile Asn Ala Glu Ala
130                 135                 140
Pro Gly Gly Pro Tyr Lys Ile Gly Thr Ser Gly Ser Cys Pro Asn Ile
145                 150                 155                 160
Thr Asn Gly Asn Gly Phe Phe Ala Thr Met Ala Trp Ala Val Pro Lys
                165                 170                 175
Asn Asp Lys Asn Lys Thr Ala Thr Asn Pro Leu Thr Ile Glu Val Pro
            180                 185                 190
Tyr Ile Cys Thr Glu Gly Glu Asp Gln Ile Thr Val Trp Gly Phe His
        195                 200                 205
Ser Asp Asn Glu Thr Gln Met Ala Lys Leu Tyr Gly Asp Ser Lys Pro
    210                 215                 220
Gln Lys Phe Thr Ser Ser Ala Asn Gly Val Thr Thr His Tyr Val Ser
225                 230                 235                 240
Gln Ile Gly Gly Phe Pro Asn Gln Thr Glu Asp Gly Gly Leu Pro Gln
                245                 250                 255
```

```
Ser Gly Arg Ile Val Val Asp Tyr Met Val Gln Lys Ser Gly Lys Thr
            260                 265                 270

Gly Thr Ile Thr Tyr Gln Arg Gly Ile Leu Leu Pro Gln Lys Val Trp
        275                 280                 285

Cys Ala Ser Gly Arg Ser Lys Val Ile Lys Gly Ser Leu Pro Leu Ile
    290                 295                 300

Gly Glu Ala Asp Cys Leu His Glu Lys Tyr Gly Gly Leu Asn Lys Ser
305                 310                 315                 320

Lys Pro Tyr Tyr Thr Gly Glu His Ala Lys Ala Ile Gly Asn Cys Pro
                325                 330                 335

Ile Trp Val Lys Thr Pro Leu Lys Leu Ala Asn Gly Thr Lys Tyr Arg
            340                 345                 350

Pro Pro Ala Lys Leu Leu Lys Glu Arg Gly Phe Phe Gly Ala Ile Ala
        355                 360                 365

Gly Phe Leu Glu Gly Gly Trp Glu Gly Met Ile Ala Gly Trp His Gly
    370                 375                 380

Tyr Thr Ser His Gly Ala His Gly Val Ala Val Ala Ala Asp Leu Lys
385                 390                 395                 400

Ser Thr Gln Glu Ala Ile Asn Lys Ile Thr Lys Asn Leu Asn Ser Leu
                405                 410                 415

Ser Glu Leu Glu Val Lys Asn Leu Gln Arg Leu Ser Gly Ala Met Asp
            420                 425                 430

Glu Leu His Asn Glu Ile Leu Glu Leu Asp Glu Lys Val Asp Asp Leu
        435                 440                 445

Arg Ala Asp Thr Ile Ser Ser Gln Ile Glu Leu Ala Val Leu Leu Ser
450                 455                 460

Asn Glu Gly Ile Ile Asn Ser Glu Asp Glu His Leu Leu Ala Leu Glu
465                 470                 475                 480

Arg Lys Leu Lys Lys Met Leu Gly Pro Ser Ala Val Glu Ile Gly Asn
                485                 490                 495

Gly Cys Phe Glu Thr Lys His Lys Cys Asn Gln Thr Cys Leu Asp Arg
            500                 505                 510

Ile Ala Ala Gly Thr Phe Asp Ala Gly Glu Phe Ser Leu Pro Thr Phe
        515                 520                 525

Asp Ser Leu Asn Ile Thr Ala Ala Ser Leu Asn Asp Asp Gly Leu Asp
    530                 535                 540

Asn His Thr Ile Leu Leu Tyr Tyr Ser Thr Ala Ala Ser Ser Leu Ala
545                 550                 555                 560

Val Thr Leu Met Ile Ala Ile Phe Val Val Tyr Met Val Ser Arg Asp
                565                 570                 575

Asn Val Ser Cys Ser Ile Cys Leu
            580

<210> SEQ ID NO 46
<211> LENGTH: 585
<212> TYPE: PRT
<213> ORGANISM: Artificial
<220> FEATURE:
<223> OTHER INFORMATION: synthetically-generated protein

<400> SEQUENCE: 46

Met Lys Ala Ile Ile Val Leu Leu Met Val Val Thr Ser Ser Ala Asp
1               5                   10                  15

Arg Ile Cys Thr Gly Ile Thr Ser Ser Ser Pro His Val Val Lys
            20                  25                  30
```

-continued

Thr Ala Thr Gln Gly Glu Ile Asn Val Thr Gly Val Ile Pro Leu Thr
         35                  40                  45
Thr Thr Pro Ile Lys Ser His Phe Ala Asn Leu Lys Gly Thr Glu Thr
 50                  55                  60
Arg Gly Lys Leu Cys Pro Lys Cys Pro Asn Cys Thr Asp Leu Asp Val
 65                  70                  75                  80
Ala Leu Gly Arg Pro Lys Cys Thr Gly Lys Ile Pro Ser Ala Arg Val
                 85                  90                  95
Ser Ile Leu His Glu Ala Arg Pro Val Thr Ser Gly Cys Phe Pro Ile
             100                 105                 110
Met His Asp Arg Thr Lys Ile Arg Gln Leu Pro Asn Leu Leu Arg Gly
         115                 120                 125
Tyr Glu His Val Arg Leu Ser Thr His Asn Val Ile Asn Ala Glu Asp
 130                 135                 140
Ala Pro Gly Gly Pro Tyr Lys Ile Gly Thr Ser Gly Ser Cys Pro Asn
 145                 150                 155                 160
Ile Thr Asn Gly Asn Gly Phe Phe Ala Thr Met Ala Trp Ala Val Pro
                 165                 170                 175
Lys Asn Asp Lys Asn Lys Thr Ala Thr Asn Pro Leu Thr Ile Glu Val
             180                 185                 190
Pro Tyr Val Cys Thr Glu Gly Glu Asp Gln Ile Thr Val Trp Gly Phe
         195                 200                 205
His Ser Asp Asn Glu Ala Gln Met Ala Lys Leu Tyr Gly Asp Ser Lys
 210                 215                 220
Pro Gln Lys Phe Thr Ser Ser Ala Asn Gly Val Ala Thr His Tyr Val
225                 230                 235                 240
Ser Gln Ile Gly Gly Phe Pro Asn Gln Thr Glu Asp Gly Gly Leu Pro
                 245                 250                 255
Gln Ser Gly Arg Ile Ile Val Asp Tyr Met Val Gln Lys Pro Gly Lys
             260                 265                 270
Thr Gly Thr Ile Val Tyr Gln Arg Gly Ile Leu Leu Pro Gln Lys Val
         275                 280                 285
Trp Cys Thr Ser Gly Arg Ser Lys Val Ile Lys Gly Phe Leu Pro Leu
 290                 295                 300
Ile Gly Glu Ala Asp Cys Leu His Glu Lys Tyr Gly Gly Leu Asn Lys
305                 310                 315                 320
Ser Arg Pro Tyr Tyr Thr Gly Glu His Ala Lys Ala Val Gly Asn Cys
                 325                 330                 335
Pro Ile Trp Val Lys Thr Pro Leu Lys Leu Ala Asn Gly Thr Lys Tyr
             340                 345                 350
Arg Pro Pro Ala Lys Leu Leu Lys Glu Lys Gly Phe Phe Gly Ala Ile
         355                 360                 365
Ala Gly Phe Leu Glu Gly Gly Trp Glu Gly Met Val Ala Gly Trp His
 370                 375                 380
Gly Tyr Thr Ser His Gly Ala His Gly Ile Ala Val Ala Ala Asp Leu
385                 390                 395                 400
Lys Ser Thr Gln Glu Ala Ile Asn Arg Ile Thr Lys Asn Leu Asn Ser
                 405                 410                 415
Leu Ser Glu Leu Glu Val Lys Asn Leu Gln Arg Leu Ser Ser Ala Met
             420                 425                 430
Asp Glu Leu His Asn Glu Ile Leu Glu Leu Asp Glu Lys Val Asp Asp
         435                 440                 445
Leu Arg Ala Asp Thr Ile Ser Ser Gln Ile Ala Glu Ala Val His Phe

```
                450             455             460
Ser Asn Glu Gly Ile Ile Asn Ser Glu Asp Glu His Leu Met Ala Leu
465                 470                 475                 480

Glu Arg Lys Leu Lys Lys Met Leu Gly Pro Ser Ala Val Glu Ile Gly
                485                 490                 495

Asn Gly Cys Phe Glu Thr Gln His Lys Cys Asn Gln Thr Cys Leu Asp
                500                 505                 510

Lys Ile Ala Ala Gly Thr Phe Asp Ala Glu Glu Phe Ser Leu Pro Thr
                515                 520                 525

Phe Asp Ser Leu Asn Ile Thr Ala Ala Ser Leu Asp Asp Asp Gly Leu
                530                 535                 540

Asp Asn His Thr Ile Leu Leu Tyr Tyr Ser Thr Ala Ala Ser Ser Leu
545                 550                 555                 560

Ala Val Thr Leu Met Ile Ala Ile Phe Ile Val Tyr Met Ile Ser Arg
                565                 570                 575

Asp Asn Val Ser Cys Ser Ile Cys Leu
                580                 585
```

<210> SEQ ID NO 47
<211> LENGTH: 583
<212> TYPE: PRT
<213> ORGANISM: Artificial
<220> FEATURE:
<223> OTHER INFORMATION: synthetically-generated protein

<400> SEQUENCE: 47

```
Met Lys Ala Met Ile Val Leu Leu Met Val Val Thr Ser Asn Ala Asp
1               5                   10                  15

Arg Ile Cys Thr Gly Ile Thr Ser Ser Asn Ser Pro His Ile Val Lys
                20                  25                  30

Thr Ala Thr Gln Gly Glu Val Asn Val Thr Gly Val Ile Pro Leu Thr
                35                  40                  45

Thr Thr Pro Thr Lys Ser His Phe Ala Asn Leu Lys Gly Thr Lys Thr
            50                  55                  60

Arg Gly Lys Leu Cys Pro Lys Cys Leu Asn Cys Thr Asp Leu Asp Val
65                  70                  75                  80

Ala Leu Gly Arg Pro Lys Cys Thr Gly Asn Ile Pro Ser Ala Arg Val
                85                  90                  95

Ser Ile Leu His Glu Val Arg Pro Val Thr Ser Gly Cys Phe Pro Ile
                100                 105                 110

Met His Asp Arg Thr Lys Ile Thr Gln Leu Pro Asn Leu Leu Arg Gly
                115                 120                 125

Tyr Glu His Ile Arg Leu Ser Thr His Asn Val Ile Asn Ala Glu Asn
130                 135                 140

Ala Pro Gly Gly Pro Tyr Lys Ile Gly Thr Ser Gly Ser Cys Pro Asn
145                 150                 155                 160

Val Thr Asn Gly Asn Gly Phe Phe Ala Thr Met Ala Trp Ala Val Pro
                165                 170                 175

Asp Lys Asn Lys Thr Ala Thr Asn Ser Leu Thr Ile Glu Val Pro Tyr
                180                 185                 190

Ile Cys Thr Glu Gly Glu Asp Gln Ile Thr Ile Trp Gly Phe His Ser
                195                 200                 205

Asp Asn Glu Thr Gln Met Ala Lys Leu Tyr Gly Asp Ser Asn Pro Gln
210                 215                 220

Lys Phe Thr Ser Ser Ala Asn Gly Ile Thr Thr His Tyr Val Ser Gln
```

```
            225                 230                 235                 240
    Ile Gly Gly Phe Pro Asp Gln Thr Glu Asp Gly Gly Leu Pro Gln Ser
                    245                 250                 255

Gly Arg Ile Val Val Asp Tyr Met Val Gln Lys Ser Gly Lys Thr Gly
                    260                 265                 270

Thr Ile Thr Tyr Gln Arg Gly Ile Leu Leu Pro Gln Lys Val Trp Cys
                    275                 280                 285

Val Ser Gly Arg Ser Lys Val Ile Lys Gly Ser Leu Pro Leu Ile Gly
            290                 295                 300

Glu Ala Asp Cys Leu His Glu Lys Tyr Gly Gly Leu Asn Lys Ser Lys
    305                 310                 315                 320

Pro Tyr Tyr Thr Gly Glu His Ala Lys Ala Ile Gly Asn Cys Pro Ile
                    325                 330                 335

Trp Val Lys Thr Pro Leu Thr Leu Ala Asn Gly Thr Lys Tyr Arg Pro
                    340                 345                 350

Pro Ala Lys Leu Leu Arg Glu Arg Gly Phe Phe Gly Ala Ile Ala Gly
                    355                 360                 365

Phe Leu Glu Gly Gly Trp Glu Gly Met Ile Ala Gly Trp His Gly Tyr
            370                 375                 380

Thr Ser His Gly Ala His Gly Val Ala Val Ala Ala Asp Leu Lys Ser
    385                 390                 395                 400

Thr Gln Glu Ala Ile Asn Lys Ile Thr Gln Asn Leu Asn Ser Leu Ser
                    405                 410                 415

Glu Leu Glu Ile Lys Asn Leu Gln Arg Leu Ser Gly Ala Met Asp Glu
                    420                 425                 430

Leu His Asn Glu Ile Ile Glu Leu Asp Glu Lys Val Asp Asp Leu Arg
            435                 440                 445

Ala Asp Thr Ile Ser Ser Gln Ile Glu Leu Thr Val Leu Leu Ser Asn
            450                 455                 460

Glu Gly Ile Ile Asn Asn Glu Asp Glu His Leu Leu Ala Leu Glu Arg
    465                 470                 475                 480

Lys Leu Lys Lys Met Leu Gly Pro Ser Ala Ile Glu Ile Gly Asn Gly
                    485                 490                 495

Cys Phe Glu Thr Lys His Lys Cys Asn Gln Thr Cys Ile Asp Arg Ile
                    500                 505                 510

Ala Ala Gly Thr Phe Asp Ala Gly Glu Phe Ser Leu Pro Thr Phe Asp
                    515                 520                 525

Ser Leu Asn Ile Thr Ala Ala Ser Leu Asn Asp Asp Gly Leu Asp Asn
            530                 535                 540

His Thr Ile Met Leu Tyr Tyr Ser Thr Ala Ala Ser Ser Leu Ala Val
    545                 550                 555                 560

Thr Leu Met Ile Ala Ile Phe Val Val Tyr Met Val Ser Arg Asp Asn
                    565                 570                 575

Phe Ser Cys Ser Ile Cys Leu
                    580

<210> SEQ ID NO 48
<211> LENGTH: 584
<212> TYPE: PRT
<213> ORGANISM: Artificial
<220> FEATURE:
<223> OTHER INFORMATION: synthetically-generated protein

<400> SEQUENCE: 48

Met Lys Thr Ile Ile Val Leu Leu Met Val Val Thr Ser Lys Ala Asp
```

-continued

```
1               5               10              15
Arg Ile Cys Thr Gly Ile Thr Ser Ser Asn Ser Pro His Val Val Lys
                20              25              30
Thr Ala Thr Gln Gly Glu Val Asn Val Thr Gly Ala Ile Pro Leu Thr
                35              40              45
Thr Thr Pro Thr Lys Ser Tyr Phe Ala Asn Leu Lys Gly Thr Arg Thr
 50              55                  60
Arg Gly Lys Leu Cys Pro Asp Cys Leu Asn Cys Thr Asp Leu Asp Val
 65              70              75              80
Ala Leu Gly Arg Pro Met Cys Val Gly Thr Thr Pro Ser Ala Lys Ala
                85              90              95
Ser Ile Leu His Glu Val Arg Pro Ala Thr Ser Gly Cys Phe Pro Ile
                100             105             110
Met His Asp Arg Thr Lys Ile Arg Gln Leu Ala Asn Leu Leu Arg Gly
                115             120             125
Tyr Glu Asn Ile Arg Leu Ser Thr Gln Asn Val Ile Asp Ala Glu Lys
 130             135             140
Ala Pro Gly Gly Pro Tyr Arg Leu Gly Thr Ser Gly Ser Cys Pro Asn
 145             150             155             160
Ala Thr Ser Lys Ser Gly Phe Phe Ala Thr Met Ala Trp Ala Val Pro
                165             170             175
Lys Asp Asn Asn Lys Asn Ala Thr Asn Pro Leu Thr Val Glu Val Pro
                180             185             190
Tyr Ile Cys Thr Glu Gly Glu Asp Gln Ile Thr Val Trp Gly Phe His
                195             200             205
Ser Asp Asn Lys Thr Gln Met Lys Asn Leu Tyr Gly Asp Ser Asn Pro
 210             215             220
Gln Arg Phe Thr Ser Ser Ala Asn Gly Val Thr Thr His Tyr Val Ser
 225             230             235             240
Gln Ile Gly Asp Phe Pro Asp Gln Thr Glu Asp Gly Gly Leu Pro Gln
                245             250             255
Ser Gly Arg Ile Val Val Asp Tyr Met Met Gln Lys Pro Gly Lys Thr
                260             265             270
Gly Thr Ile Val Tyr Gln Arg Gly Val Leu Leu Pro Gln Lys Val Trp
                275             280             285
Cys Ala Ser Gly Arg Ser Lys Val Ile Lys Gly Ser Leu Pro Leu Ile
                290             295             300
Gly Glu Ala Asp Cys Leu His Glu Glu Tyr Gly Gly Leu Asn Lys Ser
 305             310             315             320
Lys Pro Tyr Tyr Thr Gly Lys His Ala Lys Ala Ile Gly Asn Cys Pro
                325             330             335
Ile Trp Val Lys Ala Pro Leu Lys Leu Ala Asn Gly Thr Lys Tyr Arg
                340             345             350
Pro Pro Ala Lys Leu Leu Lys Glu Arg Gly Phe Phe Gly Ala Ile Ala
                355             360             365
Gly Phe Leu Glu Gly Gly Trp Glu Gly Met Ile Thr Gly Trp His Gly
 370             375             380
Tyr Thr Ser His Gly Ala His Gly Val Ala Ile Ala Ala Asp Leu Lys
 385             390             395             400
Ser Thr Gln Glu Ala Ile Asn Lys Ile Thr Lys Asn Leu Asn Ser Leu
                405             410             415
Ser Glu Leu Glu Val Lys Asn Leu Gln Arg Leu Ser Gly Ala Met Asn
                420             425             430
```

Glu Leu His Asn Glu Ile Leu Glu Leu Asp Glu Lys Val Asp Asp Leu
                435                 440                 445

Arg Ala Asp Thr Ile Ser Ser Gln Ile Glu Leu Ala Val Leu Leu Ser
            450                 455                 460

Asn Glu Gly Ile Ile Asn Ser Glu Asp Glu His Leu Leu Ala Leu Glu
465                 470                 475                 480

Arg Arg Leu Lys Lys Met Leu Gly Pro Ser Ala Val Asp Ile Gly Asn
                485                 490                 495

Gly Cys Phe Glu Thr Lys His Lys Cys Asn Gln Thr Cys Leu Asp Arg
            500                 505                 510

Ile Ala Ala Gly Thr Phe Asn Ala Gly Glu Phe Ser Leu Pro Thr Phe
                515                 520                 525

Asp Ser Leu Asn Ile Thr Ala Ala Ser Leu Asn Glu Asp Gly Leu Asp
            530                 535                 540

Asn His Thr Ile Leu Leu Tyr Tyr Ser Thr Val Ala Ser Ser Leu Ala
545                 550                 555                 560

Val Thr Leu Met Leu Ala Ile Phe Ile Val Tyr Met Val Ser Arg Asp
                565                 570                 575

Asn Val Ser Cys Ser Val Cys Leu
            580

<210> SEQ ID NO 49
<211> LENGTH: 585
<212> TYPE: PRT
<213> ORGANISM: Artificial
<220> FEATURE:
<223> OTHER INFORMATION: synthetically-generated protein

<400> SEQUENCE: 49

Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
                20                  25                  30

Thr Ala Thr Gln Gly Glu Val Asn Val Thr Gly Val Ile Pro Leu Thr
            35                  40                  45

Thr Thr Pro Thr Lys Ser His Phe Ala Asn Leu Lys Gly Thr Glu Thr
        50                  55                  60

Arg Gly Lys Leu Cys Pro Lys Cys Leu Asn Cys Thr Asp Leu Asp Val
65                  70                  75                  80

Ala Leu Gly Arg Pro Lys Cys Thr Gly Lys Ile Pro Ser Ala Arg Val
                85                  90                  95

Ser Ile Leu His Glu Val Arg Pro Val Thr Ser Gly Cys Phe Pro Ile
            100                 105                 110

Met His Asp Arg Thr Lys Ile Arg Gln Leu Pro Asn Leu Leu Arg Gly
        115                 120                 125

Tyr Glu His Val Arg Leu Ser Thr His Asn Val Ile Asn Ala Glu Asp
        130                 135                 140

Ala Pro Gly Gly Pro Tyr Lys Ile Gly Thr Ser Gly Ser Cys Pro Asn
145                 150                 155                 160

Ile Thr Asn Gly Asn Gly Phe Phe Ala Thr Met Ala Trp Ala Val Pro
                165                 170                 175

Lys Asn Asp Lys Asn Lys Thr Ala Thr Asn Pro Leu Thr Ile Glu Val
            180                 185                 190

Pro Tyr Ile Cys Thr Glu Gly Glu Asp Gln Ile Thr Val Trp Gly Phe
        195                 200                 205

His Ser Asp Asn Glu Thr Gln Met Ala Lys Leu Tyr Gly Asp Ser Lys
        210                 215                 220

Pro Gln Lys Phe Thr Ser Ser Ala Asn Gly Val Thr Thr His Tyr Val
225                 230                 235                 240

Ser Gln Ile Gly Gly Phe Pro Asn Gln Thr Glu Asp Gly Gly Leu Pro
                245                 250                 255

Gln Ser Gly Arg Ile Val Val Asp Tyr Met Val Gln Lys Ser Gly Lys
            260                 265                 270

Thr Gly Thr Ile Thr Tyr Gln Arg Gly Ile Leu Leu Pro Gln Lys Val
        275                 280                 285

Trp Cys Ala Ser Gly Arg Ser Lys Val Ile Lys Gly Ser Leu Pro Leu
    290                 295                 300

Ile Gly Glu Ala Asp Cys Leu His Glu Lys Tyr Gly Gly Leu Asn Lys
305                 310                 315                 320

Ser Lys Pro Tyr Tyr Thr Gly Glu His Ala Lys Ala Ile Gly Asn Cys
                325                 330                 335

Pro Ile Trp Val Lys Thr Pro Leu Lys Leu Ala Asn Gly Thr Lys Tyr
            340                 345                 350

Arg Pro Pro Ala Lys Leu Leu Lys Glu Arg Gly Phe Phe Gly Ala Ile
        355                 360                 365

Ala Gly Phe Leu Glu Gly Gly Trp Glu Gly Met Ile Ala Gly Trp His
    370                 375                 380

Gly Tyr Thr Ser His Gly Ala His Gly Val Ala Val Ala Ala Asp Leu
385                 390                 395                 400

Lys Ser Thr Gln Glu Ala Ile Asn Lys Ile Thr Lys Asn Leu Asn Ser
                405                 410                 415

Leu Ser Glu Leu Glu Val Lys Asn Leu Gln Arg Leu Ser Gly Ala Met
            420                 425                 430

Asp Glu Leu His Asn Glu Ile Leu Glu Leu Asp Glu Lys Val Asp Asp
        435                 440                 445

Leu Arg Ala Asp Thr Ile Ser Ser Gln Ile Glu Leu Ala Val Leu Leu
    450                 455                 460

Ser Asn Glu Gly Ile Ile Asn Ser Glu Asp Glu His Leu Leu Ala Leu
465                 470                 475                 480

Glu Arg Lys Leu Lys Lys Met Leu Gly Pro Ser Ala Val Glu Ile Gly
                485                 490                 495

Asn Gly Cys Phe Glu Thr Lys His Lys Cys Asn Gln Thr Cys Leu Asp
            500                 505                 510

Arg Ile Ala Ala Gly Thr Phe Asp Ala Gly Glu Phe Ser Leu Pro Thr
        515                 520                 525

Phe Asp Ser Leu Asn Ile Thr Ala Ala Ser Leu Asn Asp Asp Gly Leu
    530                 535                 540

Asp Asn His Thr Ile Leu Leu Tyr Tyr Ser Thr Ala Ala Ser Ser Leu
545                 550                 555                 560

Ala Val Thr Leu Met Ile Ala Ile Phe Val Val Tyr Met Val Ser Arg
                565                 570                 575

Asp Asn Val Ser Cys Ser Ile Cys Leu
            580                 585

<210> SEQ ID NO 50
<211> LENGTH: 584
<212> TYPE: PRT
<213> ORGANISM: Artificial
<220> FEATURE:

<223> OTHER INFORMATION: synthetically-generated protein

<400> SEQUENCE: 50

```
Met Lys Thr Ile Ile Val Leu Leu Met Val Val Thr Ser Ser Ala Asp
1               5                   10                  15

Arg Ile Cys Thr Gly Ile Thr Ser Ser Asn Ser Pro His Ile Val Lys
            20                  25                  30

Thr Ala Thr Gln Gly Glu Val Asn Val Thr Gly Ala Ile Pro Leu Thr
        35                  40                  45

Thr Thr Pro Thr Lys Ser Tyr Phe Ala Asn Leu Lys Gly Thr Arg Thr
    50                  55                  60

Arg Gly Lys Leu Cys Pro Asp Cys Leu Asn Cys Thr Asp Leu Asp Val
65                  70                  75                  80

Ala Leu Gly Arg Pro Met Cys Val Gly Thr Thr Pro Ser Ala Lys Ala
                85                  90                  95

Ser Ile Leu His Glu Val Arg Pro Val Thr Ser Gly Cys Phe Pro Ile
            100                 105                 110

Met His Asp Arg Thr Lys Ile Arg Gln Leu Ala Asn Leu Leu Arg Gly
        115                 120                 125

Tyr Glu Asn Ile Arg Leu Ser Thr Gln Asn Val Ile Asp Ala Glu Lys
    130                 135                 140

Ala Pro Gly Gly Pro Tyr Arg Leu Gly Thr Ser Gly Ser Cys Pro Asn
145                 150                 155                 160

Ala Thr Ser Lys Ser Gly Phe Phe Ala Thr Met Ala Trp Ala Val Pro
                165                 170                 175

Lys Asp Asn Asn Lys Asn Ala Thr Asn Pro Leu Thr Val Glu Val Pro
            180                 185                 190

Tyr Val Cys Thr Glu Gly Glu Asp Gln Ile Thr Val Trp Gly Phe His
        195                 200                 205

Ser Asp Asn Lys Thr Gln Met Lys Asn Leu Tyr Gly Asp Ser Asn Pro
210                 215                 220

Gln Lys Phe Thr Ser Ser Ala Asn Gly Ile Thr Thr His Tyr Val Ser
225                 230                 235                 240

Gln Ile Gly Gly Phe Pro Asp Gln Thr Glu Asp Gly Gly Leu Pro Gln
                245                 250                 255

Ser Gly Arg Ile Val Val Asp Tyr Met Met Gln Lys Pro Gly Lys Thr
            260                 265                 270

Gly Thr Ile Val Tyr Gln Arg Gly Val Leu Leu Pro Gln Lys Val Trp
        275                 280                 285

Cys Val Ser Gly Arg Ser Lys Val Ile Lys Gly Ser Leu Pro Leu Ile
    290                 295                 300

Gly Glu Ala Asp Cys Leu His Glu Glu Tyr Gly Gly Leu Asn Lys Ser
305                 310                 315                 320

Lys Pro Tyr Tyr Thr Gly Lys His Ala Lys Ala Ile Gly Asn Cys Pro
                325                 330                 335

Ile Trp Val Lys Thr Pro Leu Lys Leu Ala Asn Gly Thr Lys Tyr Arg
            340                 345                 350

Pro Pro Ala Lys Leu Leu Arg Glu Arg Gly Phe Phe Gly Ala Ile Ala
        355                 360                 365

Gly Phe Leu Glu Gly Gly Trp Glu Gly Met Ile Ala Gly Trp His Gly
    370                 375                 380

Tyr Thr Ser His Gly Ala His Gly Ile Ala Val Ala Ala Asp Leu Lys
385                 390                 395                 400
```

```
Ser Thr Gln Glu Ala Ile Asn Lys Ile Thr Gln Asn Leu Asn Ser Leu
                405                 410                 415

Ser Glu Leu Glu Ile Lys Asn Leu Gln Arg Leu Ser Gly Ala Met Asn
            420                 425                 430

Glu Leu His Asn Glu Ile Leu Glu Leu Asp Glu Lys Val Asp Asp Leu
        435                 440                 445

Arg Ala Asp Thr Ile Ser Ser Gln Ile Glu Leu Ala Val Leu Leu Ser
    450                 455                 460

Asn Glu Gly Ile Ile Asn Ser Glu Asp Glu His Leu Met Ala Leu Glu
465                 470                 475                 480

Arg Lys Leu Lys Lys Met Leu Gly Pro Ser Ala Val Asp Ile Gly Asn
                485                 490                 495

Gly Cys Phe Glu Thr Lys His Lys Cys Asn Gln Thr Cys Ile Asp Arg
            500                 505                 510

Ile Ala Ala Gly Thr Phe Asn Ala Gly Glu Phe Ser Leu Pro Thr Phe
        515                 520                 525

Asp Ser Leu Asn Ile Thr Ala Ala Ser Leu Asp Asp Gly Leu Asp
    530                 535                 540

Asn His Thr Ile Leu Leu Tyr Tyr Ser Thr Ala Ala Ser Ser Leu Ala
545                 550                 555                 560

Val Thr Leu Met Leu Ala Ile Phe Ile Val Tyr Met Val Ser Arg Asp
                565                 570                 575

Asn Val Ser Cys Ser Ile Cys Leu
            580

<210> SEQ ID NO 51
<211> LENGTH: 584
<212> TYPE: PRT
<213> ORGANISM: Artificial
<220> FEATURE:
<223> OTHER INFORMATION: synthetically-generated protein

<400> SEQUENCE: 51

Met Lys Thr Ala Ile Ile Val Leu Leu Met Val Val Thr Ser Lys Ala
1               5                   10                  15

Asp Arg Ile Cys Thr Gly Ile Thr Ser Ser Ser Pro His Val Val
            20                  25                  30

Lys Thr Ala Thr Gln Gly Glu Ile Asn Val Thr Gly Val Ile Pro Leu
        35                  40                  45

Thr Thr Thr Pro Ile Lys Ser His Phe Ala Asn Leu Lys Gly Thr Lys
    50                  55                  60

Thr Arg Gly Lys Leu Cys Pro Lys Cys Pro Asn Cys Thr Asp Leu Asp
65                  70                  75                  80

Val Ala Leu Gly Arg Pro Lys Cys Thr Gly Asn Ile Pro Ser Ala Arg
                85                  90                  95

Val Ser Ile Leu His Glu Ala Arg Pro Val Thr Ser Gly Cys Phe Pro
            100                 105                 110

Ile Met His Asp Arg Thr Lys Ile Arg Gln Leu Pro Asn Leu Leu Arg
        115                 120                 125

Gly Tyr Glu His Ile Arg Leu Ser Thr His Asn Val Ile Asn Ala Glu
130                 135                 140

Asn Ala Pro Gly Gly Pro Tyr Lys Ile Gly Thr Ser Gly Ser Cys Pro
145                 150                 155                 160

Asn Val Thr Asn Gly Asn Gly Phe Phe Ala Thr Met Ala Trp Ala Val
                165                 170                 175
```

```
Pro Asp Lys Asn Lys Thr Ala Thr Asn Ser Leu Thr Ile Glu Val Pro
            180                 185                 190

Tyr Ile Cys Thr Glu Gly Glu Asp Gln Ile Thr Ile Trp Gly Phe His
        195                 200                 205

Ser Asp Asn Glu Ala Gln Met Ala Lys Leu Tyr Gly Asp Ser Lys Pro
    210                 215                 220

Gln Lys Phe Thr Ser Ser Ala Asn Gly Val Ala Thr His Tyr Val Ser
225                 230                 235                 240

Gln Ile Gly Asp Phe Pro Asp Gln Thr Glu Asp Gly Gly Leu Pro Gln
                245                 250                 255

Ser Gly Arg Ile Val Val Asp Tyr Met Val Gln Lys Pro Gly Lys Thr
            260                 265                 270

Gly Thr Ile Val Tyr Gln Arg Gly Ile Leu Leu Pro Gln Lys Val Trp
        275                 280                 285

Cys Val Ser Gly Arg Ser Lys Val Ile Lys Gly Ser Leu Pro Leu Ile
    290                 295                 300

Gly Glu Ala Asp Cys Leu His Glu Lys Tyr Gly Gly Leu Asn Lys Ser
305                 310                 315                 320

Lys Pro Tyr Tyr Thr Gly Glu Tyr Ala Lys Ala Ile Gly Asn Cys Pro
                325                 330                 335

Ile Trp Val Lys Thr Pro Leu Lys Leu Ala Asn Gly Thr Lys Tyr Arg
            340                 345                 350

Pro Pro Ala Lys Leu Leu Lys Glu Lys Gly Phe Phe Gly Ala Ile Ala
        355                 360                 365

Gly Phe Leu Glu Gly Gly Trp Glu Gly Met Ile Ala Gly Trp His Gly
    370                 375                 380

Tyr Thr Ser His Gly Ala His Gly Val Ala Val Ala Ala Asp Leu Lys
385                 390                 395                 400

Ser Thr Gln Glu Ala Ile Asn Lys Ile Thr Lys Asn Leu Asn Ser Leu
                405                 410                 415

Ser Glu Leu Glu Val Lys Asn Leu Gln Arg Leu Ser Ser Ala Met Asp
            420                 425                 430

Glu Leu His Asn Glu Ile Ile Glu Leu Asp Glu Lys Val Asp Asp Leu
        435                 440                 445

Arg Ala Asp Thr Ile Ser Ser Gln Ile Glu Leu Ala Val Leu Leu Ser
    450                 455                 460

Asn Glu Gly Ile Ile Asn Ser Glu Asp Glu His Leu Met Ala Leu Glu
465                 470                 475                 480

Arg Lys Leu Lys Lys Met Leu Gly Pro Ser Ala Ile Glu Ile Gly Asn
                485                 490                 495

Gly Cys Phe Glu Thr Lys His Lys Cys Asn Gln Thr Cys Leu Asp Lys
            500                 505                 510

Ile Ala Ala Gly Thr Phe Asp Ala Gly Glu Phe Ser Leu Pro Thr Phe
        515                 520                 525

Asp Ser Leu Asn Ile Thr Ala Ala Ser Leu Asn Glu Asp Gly Leu Asp
    530                 535                 540

Asn His Thr Ile Leu Leu Tyr Tyr Ser Thr Ala Ala Ser Ser Leu Ala
545                 550                 555                 560

Val Thr Leu Met Ile Ala Ile Phe Ile Val Tyr Met Ile Ser Arg Asp
                565                 570                 575

Asn Val Ser Cys Ser Ile Cys Leu
            580
```

-continued

<210> SEQ ID NO 52
<211> LENGTH: 586
<212> TYPE: PRT
<213> ORGANISM: Artificial
<220> FEATURE:
<223> OTHER INFORMATION: synthetically-generated protein

<400> SEQUENCE: 52

```
Met Lys Thr Ala Ile Ile Val Leu Leu Met Val Val Thr Ser Asn Ala
1               5                   10                  15

Asp Arg Val Cys Thr Gly Ile Thr Ser Ser Asn Ser Pro His Val Val
            20                  25                  30

Lys Thr Ala Thr Gln Gly Glu Ile Asn Val Thr Gly Val Ile Pro Leu
        35                  40                  45

Thr Thr Thr Pro Thr Arg Ser His Phe Ala Asn Leu Lys Gly Thr Lys
    50                  55                  60

Thr Arg Gly Lys Leu Cys Pro Thr Cys Leu Asn Cys Thr Asp Leu Asp
65                  70                  75                  80

Val Ala Leu Gly Arg Pro Met Cys Val Gly Ile Thr Pro Ser Ala Lys
                85                  90                  95

Ala Ser Ile Leu His Glu Val Lys Pro Val Thr Ser Gly Cys Phe Pro
            100                 105                 110

Ile Met His Asp Arg Thr Lys Ile Arg Gln Leu Pro Asn Leu Leu Arg
        115                 120                 125

Gly Tyr Glu Asn Val Arg Leu Ser Thr His Asn Val Ile Asn Ala Glu
    130                 135                 140

Gly Ala Pro Gly Gly Pro Tyr Lys Ile Gly Thr Ser Gly Ser Cys Pro
145                 150                 155                 160

Asn Ala Thr Ser Lys Ile Gly Phe Phe Ala Thr Met Ala Trp Ala Val
                165                 170                 175

Pro Lys Asn Asp Asn Asn Lys Thr Ala Thr Asn Pro Leu Thr Val Glu
            180                 185                 190

Val Pro Tyr Ile Cys Thr Glu Gly Glu Asp Gln Ile Thr Val Trp Gly
        195                 200                 205

Phe His Ser Asp Asn Lys Thr Gln Met Lys Ser Leu Tyr Gly Asp Ser
    210                 215                 220

Asn Pro Gln Lys Phe Thr Ser Ser Ala Asn Gly Met Thr Thr His Tyr
225                 230                 235                 240

Val Ser Gln Ile Gly Ser Phe Pro Asp Gln Thr Glu Asp Gly Gly Leu
                245                 250                 255

Pro Gln Ser Gly Arg Ile Ile Val Asp Tyr Met Val Gln Lys Ser Arg
            260                 265                 270

Lys Thr Gly Thr Ile Thr Tyr Gln Arg Gly Ile Leu Leu Pro Gln Lys
        275                 280                 285

Val Trp Cys Val Ser Gly Arg Ser Lys Val Ile Lys Gly Ser Leu Pro
    290                 295                 300

Leu Ile Gly Glu Ala Asp Cys Leu His Glu Lys Tyr Gly Gly Leu Asn
305                 310                 315                 320

Lys Ser Lys Pro Tyr Tyr Thr Gly Glu His Ala Lys Ala Val Gly Asn
                325                 330                 335

Cys Pro Ile Trp Val Lys Thr Pro Leu Lys Leu Ala Asn Gly Thr Lys
            340                 345                 350

Tyr Arg Pro Pro Ala Lys Leu Leu Arg Glu Arg Gly Phe Phe Gly Ala
        355                 360                 365

Ile Ala Gly Phe Leu Glu Gly Gly Trp Glu Gly Met Ile Ala Gly Trp
```

```
                370                 375                 380
His Gly Tyr Thr Ser His Gly Ala His Gly Val Ala Val Ala Ala Asp
385                 390                 395                 400

Leu Lys Ser Thr Gln Glu Ala Ile Asn Lys Ile Thr Lys Asn Leu Asn
                405                 410                 415

Ser Leu Ser Glu Leu Glu Val Lys Asn Leu Gln Arg Ile Ser Gly Ala
                420                 425                 430

Met Asp Glu Leu His Asn Glu Ile Leu Glu Leu Asp Glu Lys Val Asp
                435                 440                 445

Asp Leu Arg Ala Asp Thr Ile Ser Ser Gln Ile Glu Leu Ala Val Leu
                450                 455                 460

Leu Ser Asn Glu Gly Ile Ile Asn Ser Glu Asp Glu His Leu Met Ala
465                 470                 475                 480

Leu Glu Arg Lys Leu Lys Lys Met Leu Gly Pro Ser Ala Ile Glu Ile
                485                 490                 495

Gly Asn Gly Cys Phe Glu Thr Lys His Lys Cys Asn Gln Thr Cys Ile
                500                 505                 510

Asp Arg Ile Ala Ala Gly Thr Phe Asn Ala Gly Glu Phe Ser Leu Pro
                515                 520                 525

Thr Phe Asp Ser Leu Asn Ile Thr Ala Ala Ser Leu Asn Asp Asp Gly
                530                 535                 540

Leu Asp Ser His Thr Ile Leu Leu Tyr Tyr Ser Thr Ala Ala Ser Ser
545                 550                 555                 560

Leu Ala Val Thr Leu Met Ile Ala Ile Phe Val Val Tyr Met Ile Ser
                565                 570                 575

Arg Asp Asn Val Ser Cys Ser Ile Cys Leu
                580                 585

<210> SEQ ID NO 53
<211> LENGTH: 585
<212> TYPE: PRT
<213> ORGANISM: Artificial
<220> FEATURE:
<223> OTHER INFORMATION: synthetically-generated protein

<400> SEQUENCE: 53

Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
                20                  25                  30

Thr Ala Thr Gln Gly Glu Val Asn Val Thr Gly Val Ile Pro Leu Thr
                35                  40                  45

Thr Thr Pro Thr Lys Ser Tyr Phe Ala Asn Leu Lys Gly Thr Arg Thr
                50                  55                  60

Arg Gly Lys Leu Cys Pro Asp Cys Leu Asn Cys Thr Asp Leu Asp Val
65                  70                  75                  80

Ala Leu Gly Arg Pro Met Cys Val Gly Thr Thr Pro Ser Ala Lys Ala
                85                  90                  95

Ser Ile Leu His Glu Val Arg Pro Val Thr Ser Gly Cys Phe Pro Ile
                100                 105                 110

Met His Asp Arg Thr Lys Ile Arg Gln Leu Pro Asn Leu Leu Arg Gly
                115                 120                 125

Tyr Glu Lys Ile Arg Leu Ser Thr Gln Asn Val Ile Asp Ala Glu Lys
                130                 135                 140

Ala Pro Gly Gly Pro Tyr Arg Leu Gly Thr Ser Gly Ser Cys Pro Asn
```

```
        145                 150                 155                 160
Ala Thr Ser Lys Ile Gly Phe Phe Ala Thr Met Ala Trp Ala Val Pro
                    165                 170                 175
Lys Lys Asp Asn Tyr Lys Asn Ala Thr Asn Pro Gln Thr Val Glu Val
                    180                 185                 190
Pro Tyr Ile Cys Thr Glu Gly Glu Asp Gln Ile Thr Val Trp Gly Phe
            195                 200                 205
His Ser Asp Asn Lys Thr Gln Met Lys Ser Leu Tyr Gly Asp Ser Asn
            210                 215                 220
Pro Gln Lys Phe Thr Ser Ser Ala Asn Gly Val Thr Thr His Tyr Val
225                 230                 235                 240
Ser Gln Ile Gly Asp Phe Pro Asp Gln Thr Glu Asp Gly Gly Leu Pro
                    245                 250                 255
Gln Ser Gly Arg Ile Val Val Asp Tyr Met Val Gln Lys Pro Gly Lys
                    260                 265                 270
Thr Gly Thr Ile Val Tyr Gln Arg Gly Val Leu Leu Pro Gln Lys Val
                    275                 280                 285
Trp Cys Ala Ser Gly Arg Ser Lys Val Ile Lys Gly Ser Leu Pro Leu
            290                 295                 300
Ile Gly Glu Ala Asp Cys Leu His Glu Glu Tyr Gly Gly Leu Asn Lys
305                 310                 315                 320
Ser Lys Pro Tyr Tyr Thr Gly Lys His Ala Lys Ala Ile Gly Asn Cys
                    325                 330                 335
Pro Ile Trp Val Lys Thr Pro Leu Lys Leu Ala Asn Gly Thr Lys Tyr
                    340                 345                 350
Arg Pro Pro Ala Lys Leu Leu Lys Glu Arg Gly Phe Phe Gly Ala Ile
                    355                 360                 365
Ala Gly Phe Leu Glu Gly Gly Trp Glu Gly Met Ile Ala Gly Trp His
            370                 375                 380
Gly Tyr Thr Ser His Gly Ala His Gly Val Ala Val Ala Ala Asp Leu
385                 390                 395                 400
Lys Ser Thr Gln Glu Ala Ile Asn Lys Ile Thr Lys Asn Leu Asn Ser
                    405                 410                 415
Leu Ser Glu Leu Glu Val Lys Asn Leu Gln Arg Leu Ser Gly Ala Met
                    420                 425                 430
Asp Glu Leu His Asn Glu Ile Leu Glu Leu Asp Glu Lys Val Asp Asp
                    435                 440                 445
Leu Arg Ala Asp Thr Ile Ser Ser Gln Ile Glu Leu Ala Val Leu Leu
            450                 455                 460
Ser Asn Glu Gly Ile Ile Asn Ser Glu Asp Glu His Leu Leu Ala Leu
465                 470                 475                 480
Glu Arg Lys Leu Lys Lys Met Leu Gly Pro Ser Ala Val Asp Ile Gly
                    485                 490                 495
Asn Gly Cys Phe Glu Thr Lys His Lys Cys Asn Gln Thr Cys Leu Asp
                    500                 505                 510
Arg Ile Ala Ala Gly Thr Phe Asn Ala Gly Glu Phe Ser Leu Pro Thr
            515                 520                 525
Phe Asp Ser Leu Asn Ile Thr Ala Ala Ser Leu Asn Asp Asp Gly Leu
            530                 535                 540
Asp Asn His Thr Ile Leu Leu Tyr Tyr Ser Thr Ala Ala Ser Ser Leu
545                 550                 555                 560
Ala Val Thr Leu Met Leu Ala Ile Phe Ile Val Tyr Met Val Ser Arg
                    565                 570                 575
```

Asp Asn Val Ser Cys Ser Ile Cys Leu
            580                 585

<210> SEQ ID NO 54
<211> LENGTH: 584
<212> TYPE: PRT
<213> ORGANISM: Artificial
<220> FEATURE:
<223> OTHER INFORMATION: synthetically-generated protein

<400> SEQUENCE: 54

Met Lys Ala Ile Leu Val Leu Leu Met Val Val Thr Ser Asn Ala Asp
1               5                   10                  15

Arg Ile Cys Thr Gly Ile Thr Ser Ser Asn Ser Pro Tyr Val Val Lys
            20                  25                  30

Thr Ala Thr Gln Gly Glu Val Asn Val Thr Gly Ala Ile Pro Leu Thr
            35                  40                  45

Thr Thr Pro Thr Lys Ser His Phe Ala Asn Leu Lys Gly Thr Lys Thr
        50                  55                  60

Arg Gly Lys Leu Cys Pro Lys Cys Leu Asn Cys Thr Asp Leu Asp Val
65                  70                  75                  80

Ala Leu Gly Arg Pro Lys Cys Thr Gly Asn Ile Pro Ser Ala Glu Val
                85                  90                  95

Ser Ile Leu His Glu Val Arg Pro Val Thr Ser Gly Cys Phe Pro Ile
            100                 105                 110

Met His Asp Arg Thr Lys Ile Arg Gln Leu Ala Asn Leu Leu Arg Gly
        115                 120                 125

Tyr Glu Asn Ile Arg Leu Ser Thr Gln Asn Val Ile Asp Ala Glu Lys
    130                 135                 140

Ala Pro Gly Gly Pro Tyr Lys Leu Gly Thr Ser Gly Ser Cys Pro Asn
145                 150                 155                 160

Ala Thr Ser Lys Ser Gly Phe Phe Ala Thr Met Ala Trp Ala Val Pro
                165                 170                 175

Lys Asp Asn Asn Lys Asn Ala Thr Asn Pro Leu Thr Val Glu Val Pro
            180                 185                 190

Tyr Ile Cys Ala Glu Gly Glu Asp Gln Ile Thr Val Trp Gly Phe His
        195                 200                 205

Ser Asp Asn Lys Thr Gln Met Lys Asn Leu Tyr Gly Asp Ser Asn Pro
    210                 215                 220

Gln Lys Phe Thr Ser Ser Ala Asn Gly Val Thr Thr His Tyr Val Ser
225                 230                 235                 240

Gln Ile Gly Gly Phe Pro Asp Gln Thr Glu Asp Gly Gly Leu Ser Gln
                245                 250                 255

Ser Gly Arg Ile Val Val Asp Tyr Met Met Gln Lys Pro Gly Lys Thr
            260                 265                 270

Gly Thr Ile Thr Tyr Gln Arg Gly Ile Leu Leu Pro Gln Lys Val Trp
        275                 280                 285

Cys Ala Ser Gly Arg Ser Lys Val Ile Lys Gly Ser Leu Pro Leu Ile
    290                 295                 300

Gly Glu Ala Asp Cys Leu His Glu Lys Tyr Gly Gly Leu Asn Lys Ser
305                 310                 315                 320

Lys Pro Tyr Tyr Thr Gly Glu His Ala Lys Ala Ile Gly Asn Cys Pro
                325                 330                 335

Ile Trp Val Lys Thr Pro Leu Lys Leu Ala Asn Gly Thr Lys Tyr Arg
            340                 345                 350

```
Pro Pro Ala Arg Leu Leu Lys Glu Arg Gly Phe Phe Gly Ala Ile Ala
        355                 360                 365

Gly Phe Leu Glu Gly Gly Trp Glu Gly Met Val Ala Gly Trp His Gly
    370                 375                 380

Tyr Thr Ser His Gly Ala His Gly Val Ala Val Ala Ala Asp Leu Lys
385                 390                 395                 400

Ser Thr Gln Glu Ala Val Asn Lys Ile Thr Lys Asn Leu Asn Ser Leu
            405                 410                 415

Ser Glu Leu Glu Val Lys Asn Leu Gln Arg Leu Ser Gly Ala Met Asp
            420                 425                 430

Glu Leu His Asp Glu Ile Leu Glu Leu Asp Lys Val Asp Asp Leu
            435                 440                 445

Arg Ala Asp Thr Ile Ser Ser Gln Ile Glu Leu Ala Val Val Leu Ser
450                 455                 460

Asn Glu Gly Ile Ile Asn Ser Glu Asp Glu His Leu Leu Ser Leu Glu
465                 470                 475                 480

Arg Lys Leu Lys Lys Met Leu Gly Pro Ser Ala Val Glu Ile Gly Asn
                485                 490                 495

Gly Cys Phe Glu Thr Lys His Lys Cys Asn Gln Thr Cys Leu Asp Arg
            500                 505                 510

Ile Ala Ala Gly Thr Phe Asp Ala Gly Glu Phe Ser Leu Pro Thr Phe
            515                 520                 525

Asp Ser Leu Asn Ile Thr Ala Ala Ser Leu Asn Asp Asp Gly Leu Asp
            530                 535                 540

Asn His Thr Ile Leu Leu Tyr Tyr Ser Thr Ala Ser Ser Leu Thr
545                 550                 555                 560

Val Thr Leu Met Leu Ala Ile Phe Ile Val Tyr Met Val Ser Arg Asp
                565                 570                 575

Asn Ile Ser Cys Ser Ile Cys Leu
            580

<210> SEQ ID NO 55
<211> LENGTH: 584
<212> TYPE: PRT
<213> ORGANISM: Artificial
<220> FEATURE:
<223> OTHER INFORMATION: synthetically-generated protein

<400> SEQUENCE: 55

Met Lys Ala Ile Ile Val Leu Leu Met Val Val Thr Ser Asp Ala Asp
1               5                   10                  15

Arg Ile Cys Thr Gly Ile Thr Ser Ser Asn Ser Pro His Val Val Lys
            20                  25                  30

Thr Ala Thr Gln Gly Glu Ile Asn Val Thr Gly Val Ile Pro Leu Thr
        35                  40                  45

Thr Thr Pro Thr Lys Ser Tyr Phe Ala Asn Leu Lys Gly Ile Arg Thr
    50                  55                  60

Arg Gly Lys Leu Cys Pro Asp Cys Ile Asn Cys Thr Asp Leu Asp Val
65                  70                  75                  80

Ala Leu Gly Arg Pro Met Cys Met Gly Thr Thr Pro Ser Ala Lys Ala
                85                  90                  95

Ser Ile Leu His Glu Val Arg Pro Ile Thr Ser Gly Cys Phe Pro Ile
            100                 105                 110

Met His Asp Arg Thr Lys Ile Arg Gln Leu Pro Asn Leu Leu Arg Gly
        115                 120                 125
```

```
Tyr Glu Lys Ile Arg Leu Ser Thr Gln Asn Val Ile Asp Ala Glu Lys
            130                 135                 140

Ala Pro Arg Gly Pro Tyr Arg Leu Gly Thr Ser Gly Ser Cys Pro Asn
145                 150                 155                 160

Ala Thr Ser Lys Ile Gly Phe Phe Ala Thr Met Ala Trp Ala Val Pro
                165                 170                 175

Lys Asp Asn Tyr Lys Asn Ala Thr Asn Pro Gln Thr Val Glu Ile Pro
                180                 185                 190

Tyr Ile Cys Thr Glu Gly Glu Asp Gln Ile Thr Val Trp Gly Phe His
            195                 200                 205

Ser Asp Asp Lys Thr Gln Met Lys Ser Leu Tyr Gly Asp Ser Asn Pro
210                 215                 220

Gln Lys Phe Thr Ser Ser Ala Asn Gly Met Thr Thr His Tyr Val Ser
225                 230                 235                 240

Gln Ile Gly Asp Phe Pro Asp Gln Thr Glu Asp Gly Arg Leu Pro Gln
                245                 250                 255

Ser Gly Arg Ile Val Val Asp Tyr Met Val Gln Lys Pro Glu Lys Thr
            260                 265                 270

Gly Thr Ile Val Tyr Gln Arg Gly Val Leu Leu Pro Gln Lys Val Trp
            275                 280                 285

Cys Val Ser Gly Arg Ser Lys Val Ile Lys Gly Ala Leu Pro Leu Ile
290                 295                 300

Gly Glu Ala Asp Cys Leu His Glu Glu Tyr Gly Gly Leu Asn Lys Ser
305                 310                 315                 320

Lys Pro Tyr Tyr Thr Gly Lys His Ala Lys Ala Ile Gly Asp Cys Pro
                325                 330                 335

Ile Trp Val Lys Thr Pro Leu Glu Leu Ala Asn Gly Thr Lys Tyr Arg
                340                 345                 350

Ala Pro Ala Lys Leu Leu Lys Glu Arg Gly Phe Phe Gly Ala Ile Ala
            355                 360                 365

Gly Phe Leu Glu Gly Gly Trp Lys Gly Met Ile Ala Gly Trp His Gly
            370                 375                 380

Tyr Ile Ser His Gly Ala His Gly Val Ala Val Ala Ala Asp Leu Lys
385                 390                 395                 400

Ser Thr Gln Glu Ala Ile Asn Lys Ile Thr Arg Asn Leu Asn Ser Leu
                405                 410                 415

Ser Glu Leu Glu Val Lys Asn Leu Gln Arg Leu Ser Gly Ala Met Asp
            420                 425                 430

Glu Leu His Ser Glu Ile Leu Glu Leu Asp Glu Lys Val Asp Asp Leu
            435                 440                 445

Arg Ala Asp Thr Val Ser Ser Gln Ile Glu Leu Ala Val Leu Leu Ser
450                 455                 460

Asn Glu Gly Ile Ile Lys Ser Glu Asp Glu His Leu Leu Ala Leu Glu
465                 470                 475                 480

Arg Lys Leu Lys Lys Met Leu Gly Pro Ser Ala Ile Asp Ile Gly Asn
                485                 490                 495

Gly Cys Phe Glu Thr Thr His Lys Cys Asn Gln Thr Cys Leu Asp Arg
            500                 505                 510

Ile Ala Ala Gly Thr Phe Asn Ala Arg Glu Phe Ser Leu Pro Thr Phe
            515                 520                 525

Asp Ser Leu Asn Ile Thr Ala Ala Tyr Leu Asn Asp Asp Gly Leu Asp
530                 535                 540
```

-continued

```
Asn His Ala Ile Leu Leu Tyr Tyr Ser Thr Ala Ser Ser Leu Ala
545                 550                 555                 560

Val Thr Leu Met Leu Ala Ile Phe Ile Val Tyr Val Val Ser Arg Asp
                565                 570                 575

Asn Val Ser Cys Ser Ile Cys Leu
            580

<210> SEQ ID NO 56
<211> LENGTH: 584
<212> TYPE: PRT
<213> ORGANISM: Artificial
<220> FEATURE:
<223> OTHER INFORMATION: synthetically-generated protein

<400> SEQUENCE: 56

Met Lys Val Ile Ile Val Leu Leu Met Val Met Ser Asn Ala Asp
1               5                   10                  15

Arg Ile Cys Thr Gly Ile Thr Ser Ser Ser Pro His Val Val Lys
                20                  25                  30

Thr Ala Thr Gln Gly Glu Val Asn Val Thr Gly Val Ile Pro Leu Thr
                35                  40                  45

Ile Thr Pro Thr Lys Ser Tyr Phe Ala Asn Leu Lys Gly Thr Arg Thr
50                  55                  60

Arg Gly Lys Leu Cys Pro Asp Cys Leu Asn Cys Thr Asp Leu Asp Val
65                  70                  75                  80

Ala Leu Gly Arg Pro Met Cys Val Gly Thr Thr Pro Ser Ala Lys Ala
                85                  90                  95

Ser Ile Leu His Glu Val Lys Pro Val Thr Ser Gly Cys Phe Pro Ile
                100                 105                 110

Met His Asp Arg Thr Lys Ile Arg Gln Leu Pro Asn Phe Leu Arg Gly
                115                 120                 125

Tyr Glu Lys Ile Arg Leu Ser Thr Lys Asn Val Ile Asp Ala Glu Lys
130                 135                 140

Ala Pro Gly Gly Pro Tyr Arg Leu Gly Thr Ser Arg Ser Cys Pro Asn
145                 150                 155                 160

Ala Thr Ser Lys Val Gly Phe Phe Ala Thr Met Ala Trp Ala Val Pro
                165                 170                 175

Lys Asn Asn Tyr Lys Asn Ala Thr Asn Pro Gln Thr Val Glu Val Pro
                180                 185                 190

Tyr Ile Cys Thr Glu Gly Glu Asp Gln Ile Thr Val Trp Gly Phe His
                195                 200                 205

Ser Asp Asn Lys Thr Gln Met Lys Ser Leu Tyr Gly Asp Ser Asn Pro
210                 215                 220

Gln Arg Phe Thr Ser Ser Ala Asn Gly Val Thr Thr His Tyr Val Ser
225                 230                 235                 240

Gln Ile Gly Ser Phe Pro Asp Gln Thr Glu Asp Gly Gly Leu Pro Gln
                245                 250                 255

Ser Gly Arg Ile Val Val Asp Tyr Met Val Gln Lys Pro Gly Lys Thr
                260                 265                 270

Gly Thr Ile Val Tyr Gln Arg Gly Val Leu Phe Pro Gln Lys Val Trp
                275                 280                 285

Cys Ala Ser Gly Lys Ser Lys Val Ile Lys Gly Ser Leu Pro Leu Ile
                290                 295                 300

Gly Glu Ala Asp Cys Leu His Glu Glu Tyr Gly Gly Leu Thr Lys Ser
305                 310                 315                 320
```

```
Lys Pro Tyr Tyr Thr Gly Lys His Ala Lys Ala Ile Gly Asn Cys Pro
                325                 330                 335

Ile Trp Val Lys Thr Ser Leu Lys Leu Ala Asn Gly Thr Lys Tyr Arg
            340                 345                 350

Pro Pro Ala Lys Leu Leu Lys Glu Arg Gly Leu Phe Gly Ala Ile Ala
        355                 360                 365

Gly Phe Leu Glu Gly Gly Trp Glu Gly Met Ile Ala Gly Trp His Gly
370                 375                 380

Tyr Thr Ser His Gly Ala His Gly Val Ala Val Ala Ala Asp Leu Lys
385                 390                 395                 400

Ser Thr Gln Glu Ala Ile Asn Lys Ile Thr Lys Asn Leu Asn Phe Leu
                405                 410                 415

Ser Glu Leu Glu Val Lys Asn Leu Gln Arg Leu Ser Gly Ala Met Asp
            420                 425                 430

Glu Leu His Asn Glu Ile Leu Glu Leu Asp Glu Lys Val Asp Asp Leu
        435                 440                 445

Arg Ala Asp Thr Met Ser Ser Gln Ile Glu Leu Ala Val Leu Leu Ser
450                 455                 460

Asn Glu Gly Ile Ile Asn Ser Glu Asp Glu His Leu Leu Ala Leu Glu
465                 470                 475                 480

Arg Gln Leu Lys Lys Met Leu Gly Pro Ser Ala Val Asp Ile Gly Asn
                485                 490                 495

Gly Cys Phe Glu Thr Lys His Lys Cys Asn Gln Thr Cys Leu Asp Lys
            500                 505                 510

Ile Ala Ala Gly Thr Phe Asn Ala Gly Glu Phe Ser Leu Pro Thr Phe
        515                 520                 525

Asp Ser Leu Asn Ile Thr Ala Ala Ser Leu Asn Asn Asp Gly Leu Asp
530                 535                 540

Asn His Thr Ile Leu Leu Tyr Tyr Ser Thr Val Ala Ser Ser Leu Ala
545                 550                 555                 560

Val Thr Leu Met Ile Ala Ile Phe Val Val Tyr Met Val Ser Arg Asp
                565                 570                 575

Asn Val Ser Cys Ser Ile Cys Leu
            580

<210> SEQ ID NO 57
<211> LENGTH: 584
<212> TYPE: PRT
<213> ORGANISM: Artificial
<220> FEATURE:
<223> OTHER INFORMATION: synthetically-generated protein

<400> SEQUENCE: 57

Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
                20                  25                  30

Thr Ala Thr Gln Gly Glu Val Asn Val Thr Gly Val Ile Pro Leu Thr
            35                  40                  45

Thr Thr Pro Thr Lys Ser Tyr Phe Ala Asn Leu Lys Gly Thr Arg Thr
        50                  55                  60

Arg Gly Lys Leu Cys Pro Asp Cys Leu Asn Cys Thr Asp Leu Asp Val
65                  70                  75                  80

Ala Leu Gly Arg Pro Met Cys Val Gly Thr Thr Pro Ser Ala Lys Ala
                85                  90                  95
```

```
Ser Ile Leu His Glu Val Arg Pro Val Thr Ser Gly Cys Phe Pro Ile
            100                 105                 110

Met His Asp Arg Thr Lys Ile Arg Gln Leu Pro Asn Leu Leu Arg Gly
            115                 120                 125

Tyr Glu Lys Ile Arg Leu Ser Thr Gln Asn Val Ile Asp Ala Glu Lys
            130                 135                 140

Ala Pro Gly Gly Pro Tyr Arg Leu Gly Thr Ser Gly Ser Cys Pro Asn
145                 150                 155                 160

Ala Thr Ser Lys Ile Gly Phe Phe Ala Thr Met Ala Trp Ala Val Pro
                165                 170                 175

Lys Asp Asn Tyr Lys Asn Ala Thr Asn Pro Gln Thr Val Glu Val Pro
                180                 185                 190

Tyr Ile Cys Thr Glu Gly Glu Asp Gln Ile Thr Val Trp Gly Phe His
                195                 200                 205

Ser Asp Asn Lys Thr Gln Met Lys Ser Leu Tyr Gly Asp Ser Asn Pro
                210                 215                 220

Gln Lys Phe Thr Ser Ser Ala Asn Gly Val Thr Thr His Tyr Val Ser
225                 230                 235                 240

Gln Ile Gly Asp Phe Pro Asp Gln Thr Glu Asp Gly Gly Leu Pro Gln
                245                 250                 255

Ser Gly Arg Ile Val Val Asp Tyr Met Val Gln Lys Pro Gly Lys Thr
                260                 265                 270

Gly Thr Ile Val Tyr Gln Arg Gly Val Leu Leu Pro Gln Lys Val Trp
                275                 280                 285

Cys Ala Ser Gly Arg Ser Lys Val Ile Lys Gly Ser Leu Pro Leu Ile
290                 295                 300

Gly Glu Ala Asp Cys Leu His Glu Glu Tyr Gly Gly Leu Asn Lys Ser
305                 310                 315                 320

Lys Pro Tyr Tyr Thr Gly Lys His Ala Lys Ala Ile Gly Asn Cys Pro
                325                 330                 335

Ile Trp Val Lys Thr Pro Leu Lys Leu Ala Asn Gly Thr Lys Tyr Arg
                340                 345                 350

Pro Pro Ala Lys Leu Leu Lys Glu Arg Gly Phe Phe Gly Ala Ile Ala
                355                 360                 365

Gly Phe Leu Glu Gly Gly Trp Glu Gly Met Ile Ala Gly Trp His Gly
370                 375                 380

Tyr Thr Ser His Gly Ala His Gly Val Ala Val Ala Ala Asp Leu Lys
385                 390                 395                 400

Ser Thr Gln Glu Ala Ile Asn Lys Ile Thr Lys Asn Leu Asn Ser Leu
                405                 410                 415

Ser Glu Leu Glu Val Lys Asn Leu Gln Arg Leu Ser Gly Ala Met Asp
                420                 425                 430

Glu Leu His Asn Glu Ile Leu Glu Leu Asp Glu Lys Val Asp Asp Leu
                435                 440                 445

Arg Ala Asp Thr Ile Ser Ser Gln Ile Glu Leu Ala Val Leu Leu Ser
                450                 455                 460

Asn Glu Gly Ile Ile Asn Ser Glu Asp Glu His Leu Leu Ala Leu Glu
465                 470                 475                 480

Arg Lys Leu Lys Lys Met Leu Gly Pro Ser Ala Val Asp Ile Gly Asn
                485                 490                 495

Gly Cys Phe Glu Thr Lys His Lys Cys Asn Gln Thr Cys Leu Asp Arg
                500                 505                 510

Ile Ala Ala Gly Thr Phe Asn Ala Gly Glu Phe Ser Leu Pro Thr Phe
```

-continued

```
               515                 520                 525

Asp Ser Leu Asn Ile Thr Ala Ala Ser Leu Asn Asp Asp Gly Leu Asp
        530                 535                 540

Asn His Thr Ile Leu Leu Tyr Tyr Ser Thr Ala Ala Ser Ser Leu Ala
545                 550                 555                 560

Val Thr Leu Met Leu Ala Ile Phe Ile Val Tyr Met Val Ser Arg Asp
                565                 570                 575

Asn Val Ser Cys Ser Ile Cys Leu
            580

<210> SEQ ID NO 58
<211> LENGTH: 583
<212> TYPE: PRT
<213> ORGANISM: Artificial
<220> FEATURE:
<223> OTHER INFORMATION: synthetically-generated protein

<400> SEQUENCE: 58

Met Lys Val Ile Ile Val Leu Leu Met Val Val Thr Ser Asp Ala Asp
1               5                   10                  15

Arg Ile Cys Thr Gly Ile Thr Ser Ser Asn Ser Pro His Val Val Lys
            20                  25                  30

Thr Ala Thr Gln Gly Glu Val Asn Val Thr Gly Val Ile Pro Leu Thr
        35                  40                  45

Ile Thr Pro Thr Lys Ser Tyr Phe Ala Asn Leu Lys Gly Thr Lys Thr
    50                  55                  60

Arg Gly Lys Leu Cys Pro Asp Cys Phe Asn Cys Thr Asp Leu Asp Val
65                  70                  75                  80

Ala Leu Gly Arg Pro Met Cys Met Gly Thr Thr Pro Ser Ala Lys Ala
                85                  90                  95

Ser Ile Leu His Glu Val Lys Pro Val Thr Ser Gly Cys Phe Pro Ile
            100                 105                 110

Met His Asp Arg Thr Lys Ile Arg Gln Leu Ala Asn Leu Leu Arg Gly
        115                 120                 125

Tyr Glu Asn Ile Arg Leu Ser Thr Gln Asn Val Ile Asp Ala Glu Lys
    130                 135                 140

Ala Pro Arg Gly Pro Tyr Arg Leu Gly Thr Ser Arg Ser Cys Pro Asn
145                 150                 155                 160

Ala Thr Ser Lys Ser Gly Phe Phe Ala Thr Met Ala Trp Ala Val Pro
                165                 170                 175

Lys Asp Asn Asn Lys Asn Ala Thr Asn Pro Leu Thr Val Glu Val Pro
            180                 185                 190

Tyr Ile Cys Ala Glu Gly Glu Asp Gln Ile Thr Val Trp Gly Phe His
        195                 200                 205

Ser Asp Asp Lys Thr Gln Met Lys Asn Leu Tyr Gly Asp Ser Asn Pro
    210                 215                 220

Gln Arg Phe Thr Ser Ser Ala Asn Gly Val Thr Thr His Tyr Val Ser
225                 230                 235                 240

Gln Ile Gly Gly Phe Pro Asp Gln Thr Glu Asp Gly Gly Leu Pro Gln
                245                 250                 255

Ser Gly Arg Ile Val Val Asp Tyr Met Met Gln Lys Pro Gly Lys Thr
            260                 265                 270

Gly Thr Ile Val Tyr Gln Arg Gly Val Leu Phe Pro Gln Lys Val Trp
        275                 280                 285

Cys Ala Ser Gly Lys Ser Lys Val Ile Lys Gly Ser Leu Pro Leu Ile
```

```
                290                 295                 300
Gly Glu Ala Asp Cys Leu His Glu Lys Tyr Gly Gly Leu Asn Lys Ser
305                 310                 315                 320

Lys Pro Tyr Tyr Thr Gly Glu His Ala Lys Ala Ile Gly Asn Cys Pro
                325                 330                 335

Ile Trp Val Lys Thr Pro Leu Lys Leu Ala Asn Gly Thr Lys Tyr Arg
                340                 345                 350

Pro Pro Ala Lys Leu Leu Lys Glu Arg Gly Phe Phe Gly Ala Ile Ala
                355                 360                 365

Gly Phe Leu Glu Gly Gly Trp Glu Gly Met Ile Ala Gly Trp His Gly
                370                 375                 380

Tyr Thr Ser His Gly Ala His Gly Val Ala Val Ala Ala Asp Leu Lys
385                 390                 395                 400

Ser Thr Gln Glu Ala Ile Asn Lys Ile Thr Lys Asn Leu Asn Ser Leu
                405                 410                 415

Ser Glu Leu Glu Val Lys Asn Leu Gln Arg Leu Ser Gly Ala Met Asp
                420                 425                 430

Glu Leu His Ser Glu Ile Leu Glu Leu Asp Glu Lys Val Asp Asp Leu
                435                 440                 445

Arg Ala Asp Thr Ile Ser Ser Gln Ile Glu Leu Ala Val Leu Leu Ser
                450                 455                 460

Asn Glu Gly Ile Ile Asn Ser Glu Asp Glu His Leu Leu Ala Leu Glu
465                 470                 475                 480

Arg Lys Leu Lys Lys Met Leu Gly Pro Ser Ala Val Glu Ile Gly Asn
                485                 490                 495

Gly Cys Phe Glu Thr Lys His Lys Cys Asn Gln Thr Cys Leu Asp Lys
                500                 505                 510

Ile Ala Ala Gly Thr Phe Asn Ala Gly Glu Phe Ser Leu Pro Thr Phe
                515                 520                 525

Asp Ser Leu Asn Ile Thr Ala Ala Ser Leu Asn Asn Asp Gly Leu Asp
                530                 535                 540

Asn His Thr Ile Leu Leu Tyr Tyr Ser Thr Ala Ala Ser Ser Leu Thr
545                 550                 555                 560

Val Thr Leu Met Leu Ala Ile Phe Ile Val Tyr Val Val Ser Arg Asp
                565                 570                 575

Asn Val Ser Cys Ser Ile Cys
                580

<210> SEQ ID NO 59
<211> LENGTH: 583
<212> TYPE: PRT
<213> ORGANISM: Artificial
<220> FEATURE:
<223> OTHER INFORMATION: synthetically-generated protein

<400> SEQUENCE: 59

Met Lys Ala Ile Ile Val Leu Leu Met Val Val Met Ser Asn Ala Asp
1               5                   10                  15

Arg Ile Cys Thr Gly Ile Thr Ser Ser Asn Ser Pro His Val Val Lys
                20                  25                  30

Thr Ala Thr Gln Gly Glu Val Asn Val Thr Gly Val Ile Pro Leu Thr
                35                  40                  45

Thr Thr Pro Thr Lys Ser His Phe Ala Asn Leu Lys Gly Thr Lys Thr
                50                  55                  60

Arg Gly Lys Leu Cys Pro Asp Cys Ile Asn Cys Thr Asp Leu Asp Val
```

```
             65                  70                  75                  80
Ala Leu Gly Arg Pro Met Cys Val Gly Thr Ile Pro Ser Ala Lys Ala
                     85                  90                  95

Ser Ile Leu His Glu Val Arg Pro Val Thr Ser Gly Cys Phe Pro Ile
                    100                 105                 110

Met His Asp Arg Thr Lys Ile Arg Gln Leu Pro Asn Leu Leu Arg Gly
                    115                 120                 125

Tyr Glu Lys Ile Arg Leu Ser Thr Lys Asn Val Ile Asp Ala Glu Lys
                130                 135                 140

Ala Pro Arg Gly Pro Tyr Arg Leu Gly Thr Ser Gly Ser Cys Pro Asn
145                 150                 155                 160

Ala Thr Ser Lys Val Gly Phe Phe Ala Thr Met Ala Trp Ala Val Pro
                165                 170                 175

Lys Asn Asn Tyr Lys Asn Ala Thr Asn Pro Gln Thr Val Glu Ile Pro
                180                 185                 190

Tyr Ile Cys Thr Glu Gly Glu Asp Gln Ile Thr Val Trp Gly Phe His
                195                 200                 205

Ser Asp Asn Lys Ile Gln Met Lys Asn Leu Tyr Gly Asp Ser Asn Pro
    210                 215                 220

Gln Lys Phe Thr Ser Ser Ala Asn Gly Val Thr Thr His Tyr Val Ser
225                 230                 235                 240

Gln Ile Gly Ser Phe Pro Asp Gln Thr Glu Asp Gly Gly Leu Pro Gln
                245                 250                 255

Ser Gly Arg Ile Val Val Asp Tyr Met Val Gln Lys Pro Glu Lys Thr
                260                 265                 270

Gly Thr Ile Val Tyr Gln Arg Gly Ile Leu Leu Pro Gln Lys Val Trp
                275                 280                 285

Cys Val Ser Gly Arg Ser Lys Val Ile Lys Gly Ala Leu Pro Leu Ile
                290                 295                 300

Gly Glu Ala Asp Cys Leu His Glu Lys Tyr Gly Gly Leu Asn Lys Ser
305                 310                 315                 320

Lys Pro Tyr Tyr Thr Gly Lys His Ala Lys Ala Ile Gly Asn Cys Pro
                325                 330                 335

Ile Trp Val Lys Thr Pro Leu Lys Leu Ala Asn Gly Thr Lys Tyr Arg
                340                 345                 350

Pro Pro Ala Lys Leu Leu Lys Glu Arg Gly Phe Phe Gly Ala Ile Ala
                355                 360                 365

Gly Phe Leu Glu Gly Gly Trp Glu Gly Met Ile Ala Gly Trp His Gly
                370                 375                 380

Tyr Thr Ser His Gly Ala His Gly Val Ala Val Ala Ala Asp Leu Lys
385                 390                 395                 400

Ser Thr Gln Glu Ala Ile Asn Lys Ile Thr Lys Asn Leu Asn Ser Leu
                405                 410                 415

Ser Glu Leu Glu Val Lys Asn Leu Gln Arg Leu Ser Gly Ala Met Asp
                420                 425                 430

Glu Leu His Asp Glu Ile Leu Glu Leu Asp Glu Lys Val Asp Asp Leu
                435                 440                 445

Arg Ala Asp Thr Ile Ser Ser Gln Ile Glu Leu Ala Val Leu Leu Ser
                450                 455                 460

Asn Glu Gly Ile Ile Asn Ser Glu Asp Glu His Leu Leu Ala Leu Glu
465                 470                 475                 480

Arg Lys Leu Lys Lys Met Leu Gly Pro Ser Ala Ile Asp Ile Gly Asn
                485                 490                 495
```

Gly Cys Phe Glu Thr Lys His Lys Cys Asn Gln Thr Cys Leu Asp Arg
            500                 505                 510

Ile Ala Ala Gly Thr Phe Asp Ala Gly Glu Phe Ser Leu Pro Thr Phe
            515                 520                 525

Asp Ser Leu Asn Ile Thr Ala Ala Ser Leu Asn Glu Asp Gly Leu Asp
            530                 535                 540

Asn His Thr Ile Leu Leu Tyr Tyr Ser Thr Val Ala Ser Ser Leu Ala
545                 550                 555                 560

Val Thr Leu Met Ile Ala Ile Phe Val Val Tyr Met Val Ser Arg Asp
                565                 570                 575

Asn Val Ser Cys Ser Ile Cys
            580

<210> SEQ ID NO 60
<211> LENGTH: 584
<212> TYPE: PRT
<213> ORGANISM: Artificial
<220> FEATURE:
<223> OTHER INFORMATION: synthetically-generated protein

<400> SEQUENCE: 60

Met Lys Ala Ile Ile Val Leu Leu Met Val Val Ala Ser Asp Ala Asp
1               5                   10                  15

Arg Ile Cys Thr Gly Ile Thr Ser Ser Asn Ser Pro His Val Val Lys
                20                  25                  30

Thr Ala Thr Gln Gly Glu Val Asn Val Thr Gly Val Ile Pro Leu Thr
            35                  40                  45

Ile Thr Pro Thr Lys Ser Tyr Phe Ala Asn Leu Lys Gly Ile Arg Thr
        50                  55                  60

Arg Gly Lys Leu Cys Pro Asp Cys Phe Asn Cys Thr Asp Leu Asp Val
65                  70                  75                  80

Ala Leu Gly Arg Pro Met Cys Val Gly Ala Thr Pro Ser Ala Lys Ala
                85                  90                  95

Ser Ile Leu His Glu Val Arg Pro Val Thr Ser Gly Cys Phe Pro Ile
                100                 105                 110

Met His Asp Arg Thr Lys Ile Arg Gln Leu Pro Asn Leu Leu Arg Gly
            115                 120                 125

Tyr Glu Asn Ile Arg Leu Ser Thr Gln Asn Val Ile Asp Ala Glu Lys
        130                 135                 140

Ala Pro Arg Gly Pro Tyr Arg Leu Gly Thr Ser Gly Ser Cys Pro Asn
145                 150                 155                 160

Thr Thr Ser Lys Ile Gly Phe Phe Ala Thr Met Ala Trp Ala Val Pro
                165                 170                 175

Lys Asp Lys Tyr Lys Asn Ala Thr Asn Pro Gln Thr Leu Glu Ile Pro
            180                 185                 190

Tyr Ile Cys Thr Glu Gly Glu Asp Gln Ile Thr Val Trp Gly Phe His
        195                 200                 205

Ser Asp Asn Lys Thr Gln Met Lys Asn Leu Tyr Gly Asp Ser Asn Pro
    210                 215                 220

Gln Lys Phe Thr Ser Ser Ala Asn Gly Val Thr Thr His Tyr Val Ser
225                 230                 235                 240

Gln Ile Gly Asp Phe Pro Asn Gln Thr Glu Asp Gly Gly Leu Pro Gln
                245                 250                 255

Ser Gly Arg Ile Val Val Asp Tyr Met Val Gln Lys Pro Gly Arg Thr
            260                 265                 270

```
Gly Thr Ile Val Tyr Gln Arg Gly Ile Leu Leu Pro Gln Lys Val Trp
            275                 280                 285

Cys Ala Asn Gly Arg Ser Lys Val Ile Lys Gly Ala Leu Pro Leu Ile
        290                 295                 300

Gly Glu Ala Asp Cys Leu His Glu Lys Tyr Gly Gly Leu Asn Lys Ser
305                 310                 315                 320

Lys Pro Tyr Tyr Thr Gly Lys His Ala Lys Ala Ile Gly Asn Cys Pro
                325                 330                 335

Ile Trp Val Lys Thr Pro Leu Lys Leu Ala Asn Gly Thr Lys Tyr Arg
            340                 345                 350

Pro Pro Ala Lys Leu Leu Lys Glu Arg Gly Phe Phe Gly Ala Ile Ala
        355                 360                 365

Gly Phe Leu Glu Gly Gly Trp Glu Gly Met Ile Ala Gly Trp His Gly
    370                 375                 380

Tyr Thr Ser His Gly Ala His Gly Val Ala Val Ala Ala Asp Leu Lys
385                 390                 395                 400

Ser Thr Gln Glu Ala Ile Asn Lys Ile Thr Lys Asn Leu Asn Ser Leu
                405                 410                 415

Ser Glu Leu Glu Val Lys Asn Leu Gln Arg Leu Ser Gly Ala Met Asp
            420                 425                 430

Glu Leu His Ser Glu Ile Leu Glu Leu Asp Glu Lys Val Asp Asp Leu
        435                 440                 445

Arg Ala Asp Thr Ile Ser Ser Gln Ile Glu Leu Ala Val Leu Leu Ser
    450                 455                 460

Asn Glu Gly Ile Ile Asn Ser Glu Asp Glu His Leu Leu Ala Leu Glu
465                 470                 475                 480

Arg Lys Leu Lys Lys Met Leu Gly Pro Ser Ala Ile Asp Ile Gly Asn
                485                 490                 495

Gly Cys Phe Glu Thr Lys His Lys Cys Asn Gln Thr Cys Leu Asp Arg
            500                 505                 510

Ile Ala Ala Gly Thr Phe Ser Ala Gly Glu Phe Ser Leu Pro Thr Phe
        515                 520                 525

Asp Ser Leu Asn Ile Thr Ala Ala Ser Leu Asn Asp Asp Gly Leu Asp
    530                 535                 540

Asn His Ala Ile Leu Leu Tyr Tyr Ser Thr Ala Ala Ser Ser Leu Thr
545                 550                 555                 560

Val Thr Leu Met Leu Ala Ile Phe Ile Val Tyr Met Val Ser Lys Asp
                565                 570                 575

Asn Val Ser Cys Ser Ile Cys Leu
            580

<210> SEQ ID NO 61
<211> LENGTH: 467
<212> TYPE: PRT
<213> ORGANISM: Artificial
<220> FEATURE:
<223> OTHER INFORMATION: synthetically-generated protein

<400> SEQUENCE: 61

Met Leu Pro Ser Thr Ile Gln Thr Leu Thr Leu Phe Leu Thr Ser Gly
1               5                   10                  15

Gly Val Leu Leu Ser Leu Tyr Val Ser Ala Ser Leu Ser Tyr Leu Leu
            20                  25                  30

Tyr Ser Asp Ile Leu Leu Lys Phe Ser Pro Thr Glu Ile Thr Ala Pro
        35                  40                  45
```

```
Thr Met Pro Leu Asp Cys Ala Asn Ala Ser Asn Val Gln Ala Val Asn
    50                  55                  60

Arg Ser Ala Thr Lys Gly Val Thr Leu Leu Leu Pro Glu Pro Glu
 65              70                  75                  80

Trp Thr Tyr Pro Arg Leu Ser Cys Pro Gly Ser Thr Phe Gln Lys Ala
                85                  90                  95

Leu Leu Ile Ser Pro His Arg Phe Gly Glu Thr Lys Gly Asn Ser Ala
                100                 105                 110

Pro Leu Ile Ile Arg Glu Pro Phe Val Ala Cys Gly Pro Asn Glu Cys
                115                 120                 125

Lys His Phe Ala Leu Thr His Tyr Ala Ala Gln Pro Gly Gly Tyr Tyr
                130                 135                 140

Asn Gly Thr Arg Gly Asp Arg Asn Lys Leu Arg His Leu Ile Ser Val
145                 150                 155                 160

Lys Leu Gly Lys Ile Pro Thr Val Glu Asn Ser Ile Phe His Met Ala
                165                 170                 175

Ala Trp Ser Gly Ser Ala Cys His Asp Gly Lys Glu Trp Thr Tyr Ile
                180                 185                 190

Gly Val Asp Gly Pro Asp Asn Asn Ala Leu Leu Lys Val Lys Tyr Gly
                195                 200                 205

Glu Ala Tyr Thr Asp Thr Tyr His Ser Tyr Ala Asn Asn Ile Leu Arg
210                 215                 220

Thr Gln Glu Ser Ala Cys Asn Cys Ile Gly Gly Asn Cys Tyr Leu Met
225                 230                 235                 240

Ile Thr Asp Gly Ser Ala Ser Gly Val Ser Glu Cys Arg Phe Leu Lys
                245                 250                 255

Ile Arg Glu Gly Arg Ile Ile Lys Glu Ile Phe Pro Thr Gly Arg Val
                260                 265                 270

Lys His Thr Glu Glu Cys Thr Cys Gly Phe Ala Ser Asn Lys Thr Ile
                275                 280                 285

Glu Cys Ala Cys Arg Asp Asn Arg Tyr Thr Ala Lys Arg Pro Phe Val
290                 295                 300

Lys Leu Asn Val Glu Thr Asp Thr Ala Glu Ile Arg Leu Met Cys Thr
305                 310                 315                 320

Asp Thr Tyr Leu Asp Thr Pro Arg Pro Asn Asp Gly Ser Ile Thr Gly
                325                 330                 335

Pro Cys Glu Ser Asp Gly Asp Lys Gly Ser Gly Gly Ile Lys Gly Gly
                340                 345                 350

Phe Val His Gln Arg Met Lys Ser Lys Ile Gly Arg Trp Tyr Ser Arg
                355                 360                 365

Thr Met Ser Lys Thr Glu Arg Met Gly Met Gly Leu Tyr Val Lys Tyr
                370                 375                 380

Gly Gly Asp Pro Trp Ala Asp Ser Asp Ala Leu Ala Phe Ser Gly Val
385                 390                 395                 400

Met Val Ser Met Lys Glu Pro Gly Trp Tyr Ser Phe Gly Phe Glu Ile
                405                 410                 415

Lys Asp Lys Lys Cys Asp Val Pro Cys Ile Gly Ile Glu Met Val His
                420                 425                 430

Asp Gly Gly Lys Glu Thr Trp His Ser Ala Ala Thr Ala Ile Tyr Cys
                435                 440                 445

Leu Met Gly Ser Gly Gln Leu Leu Trp Asp Thr Val Thr Gly Val Asp
    450                 455                 460
```

Met Ala Leu
465

<210> SEQ ID NO 62
<211> LENGTH: 466
<212> TYPE: PRT
<213> ORGANISM: Artificial
<220> FEATURE:
<223> OTHER INFORMATION: synthetically-generated protein

<400> SEQUENCE: 62

Met Leu Pro Ser Thr Ile Gln Thr Leu Thr Leu Val Leu Thr Ser Gly
1               5                   10                  15

Gly Val Leu Leu Ser Leu Tyr Val Ser Ala Leu Leu Ser Tyr Leu Leu
            20                  25                  30

Tyr Ser Asp Ile Leu Leu Lys Phe Ser Arg Thr Glu Ile Thr Ala Pro
        35                  40                  45

Ile Met Pro Leu Asp Cys Ala Asn Ala Ser Asn Val Gln Ala Val Asn
    50                  55                  60

Arg Ser Ala Thr Lys Gly Val Thr Leu Leu Pro Gly Pro Glu Trp
65                  70                  75                  80

Thr Tyr Pro Arg Leu Ser Cys Gln Gly Ser Thr Phe Gln Lys Ala Leu
                85                  90                  95

Leu Ile Ser Pro His Arg Phe Gly Glu Ala Lys Gly Asn Ser Ala Pro
            100                 105                 110

Leu Ile Ile Arg Glu Pro Phe Ile Ala Cys Gly Pro Lys Glu Cys Lys
        115                 120                 125

His Phe Ala Leu Thr His Tyr Ala Ala Gln Pro Gly Gly Tyr Tyr Asn
    130                 135                 140

Gly Thr Arg Glu Asp Arg Asn Lys Leu Arg His Leu Ile Ser Val Asn
145                 150                 155                 160

Leu Gly Lys Ile Pro Thr Val Glu Asn Ser Ile Phe His Met Ala Ala
                165                 170                 175

Trp Ser Gly Ser Ala Cys His Asp Gly Arg Glu Trp Thr Tyr Ile Gly
            180                 185                 190

Val Asp Gly Pro Asp Ser Asn Ala Leu Leu Lys Ile Lys Tyr Gly Glu
        195                 200                 205

Ala Tyr Thr Asp Thr Tyr His Ser Tyr Ala Lys Asn Ile Leu Arg Thr
    210                 215                 220

Gln Glu Ser Ala Cys Asn Cys Ile Gly Gly Asp Cys Tyr Leu Met Ile
225                 230                 235                 240

Thr Asp Gly Pro Ala Ser Gly Ile Ser Glu Cys Arg Phe Leu Lys Ile
                245                 250                 255

Arg Lys Gly Arg Ile Ile Lys Glu Ile Phe Pro Thr Gly Arg Val Glu
            260                 265                 270

His Thr Glu Glu Cys Thr Cys Gly Phe Ala Ser Asn Lys Thr Ile Glu
        275                 280                 285

Cys Ala Cys Arg Asp Asn Ser Tyr Thr Ala Lys Arg Pro Phe Val Lys
    290                 295                 300

Leu Asn Val Glu Ile Asp Thr Ala Glu Ile Arg Leu Met Cys Thr Glu
305                 310                 315                 320

Thr Tyr Leu Asp Thr Pro Arg Pro Asp Asp Gly Ser Ile Thr Gly Pro
                325                 330                 335

Cys Glu Ser Asn Gly Asp Lys Gly Ser Gly Ile Lys Gly Gly Phe
            340                 345                 350

```
Val His Gln Arg Met Glu Ser Lys Ile Gly Arg Trp Tyr Ser Arg Thr
        355                 360                 365

Met Ser Lys Thr Glu Arg Met Gly Met Gly Leu Tyr Val Lys Tyr Asp
        370                 375                 380

Gly Asp Pro Trp Ala Asp Ser Gly Ala Leu Ala Phe Ser Gly Val Met
385                 390                 395                 400

Val Ser Met Lys Glu Pro Gly Trp Tyr Ser Phe Gly Phe Glu Ile Arg
                405                 410                 415

Asp Lys Lys Cys Asp Val Pro Cys Ile Gly Ile Glu Met Val His Asp
                420                 425                 430

Gly Gly Arg Glu Thr Trp His Ser Ala Ala Thr Thr Ile Tyr Cys Leu
        435                 440                 445

Met Gly Ser Gly Gln Leu Leu Trp Asp Thr Val Thr Gly Val Asn Met
        450                 455                 460

Thr Leu
465

<210> SEQ ID NO 63
<211> LENGTH: 466
<212> TYPE: PRT
<213> ORGANISM: Artificial
<220> FEATURE:
<223> OTHER INFORMATION: synthetically-generated protein

<400> SEQUENCE: 63

Met Leu Ser Ser Thr Ile Gln Thr Leu Thr Leu Leu Thr Ser Gly
1               5                   10                  15

Gly Val Leu Leu Ser Leu Tyr Val Ser Ala Ser Leu Ser Tyr Leu Leu
            20                  25                  30

Tyr Ser Asp Ile Leu Leu Lys Phe Ser Gln Thr Glu Ile Thr Ala Pro
        35                  40                  45

Ile Met Ser Leu Asp Cys Ala Asn Ala Ser Asn Val Gln Ala Val Asn
    50                  55                  60

Arg Ser Ala Ala Lys Gly Val Thr Leu Leu Leu Pro Glu Pro Glu Trp
65                  70                  75                  80

Thr Tyr Pro Arg Leu Ser Cys Pro Gly Ser Ile Phe Gln Lys Ala Leu
                85                  90                  95

Leu Ile Ser Pro His Arg Phe Gly Glu Ile Lys Gly Asn Ser Ala Pro
            100                 105                 110

Leu Ile Ile Arg Glu Pro Phe Ile Ala Cys Gly Pro Thr Glu Cys Lys
        115                 120                 125

His Phe Ala Leu Thr His Tyr Ala Ala Gln Pro Gly Gly Tyr Tyr Ser
    130                 135                 140

Gly Thr Arg Gly Asp Arg Asn Lys Leu Arg His Leu Ile Ser Val Lys
145                 150                 155                 160

Leu Gly Lys Ile Pro Thr Val Glu Thr Ser Ile Phe His Met Ala Ala
                165                 170                 175

Trp Ser Gly Ser Ser Cys His Asp Gly Lys Glu Trp Thr Tyr Ile Gly
            180                 185                 190

Val Asp Gly Pro Asp Asn Asn Ala Leu Leu Lys Ile Lys Tyr Gly Glu
        195                 200                 205

Ala Tyr Thr Asp Thr Tyr His Ser Tyr Ala Asn Lys Ile Leu Arg Thr
    210                 215                 220

Gln Glu Ser Ala Cys Asn Cys Ile Gly Gly Asn Cys Tyr Leu Met Ile
225                 230                 235                 240
```

```
Thr Asp Gly Pro Ala Ser Gly Val Ser Glu Cys Arg Phe Lys Ile
                245                 250                 255

Arg Glu Gly Arg Ile Ile Lys Glu Ile Phe Pro Thr Gly Arg Ile Lys
            260                 265                 270

His Thr Glu Glu Cys Thr Cys Gly Phe Ala Ser Asn Glu Thr Ile Glu
            275                 280                 285

Cys Ala Cys Arg Asp Asn Asn Tyr Thr Ala Lys Arg Pro Phe Val Lys
            290                 295                 300

Leu Asn Val Glu Thr Asp Thr Ala Glu Ile Arg Leu Met Cys Thr Lys
305                 310                 315                 320

Thr Tyr Leu Asp Thr Pro Arg Pro Asn Asp Gly Ser Thr Thr Gly Pro
                325                 330                 335

Cys Glu Ser Asp Gly Asp Lys Gly Ser Gly Gly Ile Lys Gly Gly Phe
            340                 345                 350

Val His Gln Arg Met Ala Ser Lys Ile Gly Arg Trp Tyr Ser Arg Thr
            355                 360                 365

Met Ser Lys Thr Lys Arg Met Gly Met Gly Leu Tyr Val Lys Tyr Asp
            370                 375                 380

Gly Asp Pro Trp Thr Asp Ser Glu Ala Leu Ala Leu Ser Gly Val Met
385                 390                 395                 400

Val Ser Met Glu Glu Pro Gly Trp Tyr Ser Phe Gly Phe Glu Ile Lys
                405                 410                 415

Asp Lys Lys Cys Asp Val Pro Cys Ile Gly Ile Glu Met Val His Asp
            420                 425                 430

Gly Gly Lys Thr Thr Trp His Ser Ala Ala Thr Ala Val Tyr Cys Leu
            435                 440                 445

Met Gly Ser Gly Gln Leu Leu Trp Asp Thr Val Thr Gly Val Asp Met
            450                 455                 460

Ala Leu
465

<210> SEQ ID NO 64
<211> LENGTH: 466
<212> TYPE: PRT
<213> ORGANISM: Artificial
<220> FEATURE:
<223> OTHER INFORMATION: synthetically-generated protein

<400> SEQUENCE: 64

Met Leu Pro Ser Thr Ile Gln Thr Leu Thr Leu Phe Leu Thr Ser Gly
1               5                   10                  15

Gly Val Leu Leu Ser Ile Tyr Val Ser Ala Ser Leu Ser Tyr Leu Ile
                20                  25                  30

Tyr Ser Asp Ile Leu Leu Lys Phe Ser Pro Thr Glu Ile Thr Ala Pro
            35                  40                  45

Thr Met Pro Leu Asp Cys Ala Asn Ala Ser Asn Val His Ala Val Asn
50                  55                  60

Arg Ser Ala Thr Lys Gly Val Thr Phe Leu Leu Pro Glu Pro Glu Trp
65                  70                  75                  80

Thr Tyr Pro Arg Leu Ser Cys Pro Gly Ser Thr Phe Gln Lys Ala Leu
                85                  90                  95

Leu Ile Ser Pro His Arg Phe Gly Glu Thr Lys Gly Asn Ser Ala Pro
            100                 105                 110

Leu Ile Ile Arg Glu Pro Phe Val Ala Cys Gly Pro Asn Glu Cys Lys
            115                 120                 125
```

His Phe Ala Leu Thr His Tyr Ala Thr Gln Pro Gly Gly Tyr Tyr Asn
130                 135                 140

Gly Thr Arg Gly Asp Arg Asn Lys Leu Arg His Leu Ile Ser Val Glu
145                 150                 155                 160

Leu Gly Lys Ile Pro Thr Val Glu Asn Ser Ile Phe His Met Thr Ala
                165                 170                 175

Trp Ser Gly Ser Ala Cys His Asp Gly Lys Glu Trp Thr Tyr Val Gly
                180                 185                 190

Val Asp Gly Pro Asp Asn Asn Ala Leu Leu Lys Val Lys Tyr Gly Glu
                195                 200                 205

Ala Tyr Thr Asp Thr Tyr His Ser Tyr Ala Asn Asn Ile Leu Arg Thr
210                 215                 220

Gln Glu Ser Ala Cys Asn Cys Ile Arg Gly Asn Cys Tyr Leu Met Ile
225                 230                 235                 240

Thr Asp Gly Ser Ala Ser Gly Val Ser Glu Cys Arg Phe Leu Lys Ile
                245                 250                 255

Gln Glu Gly Arg Ile Ile Lys Glu Ile Phe Pro Thr Gly Arg Val Lys
                260                 265                 270

His Thr Glu Glu Cys Thr Cys Gly Phe Ala Asn Asn Lys Thr Ile Glu
                275                 280                 285

Cys Ala Cys Arg Asp Asn Arg Tyr Thr Ala Lys Arg Pro Phe Val Lys
290                 295                 300

Leu Ser Val Glu Thr Asp Thr Ala Glu Ile Arg Leu Met Cys Thr Asp
305                 310                 315                 320

Thr Tyr Leu Asp Thr Pro Arg Pro Asn Asp Gly Ser Ile Thr Gly Pro
                325                 330                 335

Cys Glu Ser Asp Gly Asn Glu Gly Ser Gly Gly Ile Lys Gly Gly Phe
                340                 345                 350

Val His Gln Arg Met Lys Ser Lys Ile Gly Arg Trp Tyr Ser Arg Thr
                355                 360                 365

Met Ser Gln Thr Glu Arg Met Gly Met Gly Leu Tyr Val Lys Tyr Gly
370                 375                 380

Gly Asp Pro Trp Ala Asp Ser Asp Ala Leu Ala Phe Ser Gly Val Met
385                 390                 395                 400

Ile Ser Met Lys Glu Pro Gly Trp Tyr Ser Phe Gly Phe Glu Met Lys
                405                 410                 415

Asp Lys Lys Cys Asp Val Pro Cys Ile Gly Val Glu Met Val His Asp
                420                 425                 430

Gly Gly Lys Glu Thr Trp His Ser Ala Ala Thr Ala Ile Tyr Cys Leu
                435                 440                 445

Met Gly Ser Gly Lys Leu Leu Trp Asp Thr Val Thr Gly Val Asn Met
450                 455                 460

Ala Leu
465

<210> SEQ ID NO 65
<211> LENGTH: 466
<212> TYPE: PRT
<213> ORGANISM: Artificial
<220> FEATURE:
<223> OTHER INFORMATION: synthetically-generated protein

<400> SEQUENCE: 65

Met Leu Pro Ser Thr Ile Gln Thr Leu Thr Leu Phe Leu Thr Ser Gly
1               5                   10                  15

-continued

```
Gly Val Leu Leu Ser Leu Tyr Val Ala Ser Leu Ser Tyr Leu Leu
             20                  25                  30

Tyr Ser Asp Ile Leu Leu Lys Phe Ser Pro Thr Glu Ile Thr Ala Pro
         35                  40                  45

Thr Met Pro Leu Asp Cys Ala Asn Ala Ser Asn Val Gln Ala Val Asn
 50                  55                  60

Arg Ser Ala Thr Lys Gly Val Thr Leu Leu Pro Glu Pro Glu Trp
 65                  70                  75                  80

Thr Tyr Pro Arg Leu Ser Cys Pro Gly Ser Thr Phe Gln Lys Ala Leu
             85                  90                  95

Leu Ile Ser Pro His Arg Phe Gly Glu Thr Lys Gly Asn Ser Ala Pro
            100                 105                 110

Leu Ile Ile Arg Glu Pro Phe Val Ala Cys Gly Pro Asn Glu Cys Lys
            115                 120                 125

His Phe Ala Leu Thr His Tyr Ala Ala Gln Pro Gly Gly Tyr Tyr Asn
            130                 135                 140

Gly Thr Arg Gly Asp Arg Asn Lys Leu Arg His Leu Ile Ser Val Lys
145                 150                 155                 160

Leu Gly Lys Ile Pro Thr Val Glu Asn Ser Ile Phe His Met Ala Ala
            165                 170                 175

Trp Ser Gly Ser Ala Cys His Asp Gly Lys Glu Trp Thr Tyr Ile Gly
            180                 185                 190

Val Asp Gly Pro Asp Asn Asn Ala Leu Leu Lys Val Lys Tyr Gly Glu
            195                 200                 205

Ala Tyr Thr Asp Thr Tyr His Ser Tyr Ala Asn Asn Ile Leu Arg Thr
210                 215                 220

Gln Glu Ser Ala Cys Asn Cys Ile Gly Gly Asn Cys Tyr Leu Met Ile
225                 230                 235                 240

Thr Asp Gly Ser Ala Ser Gly Val Ser Glu Cys Arg Phe Leu Lys Ile
            245                 250                 255

Arg Glu Gly Arg Ile Ile Lys Glu Ile Phe Pro Thr Gly Arg Val Lys
            260                 265                 270

His Thr Glu Glu Cys Thr Cys Gly Phe Ala Ser Asn Lys Thr Ile Glu
            275                 280                 285

Cys Ala Cys Arg Asp Asn Arg Tyr Thr Ala Lys Arg Pro Phe Val Lys
290                 295                 300

Leu Asn Val Glu Thr Asp Thr Ala Glu Ile Arg Leu Met Cys Thr Asp
305                 310                 315                 320

Thr Tyr Leu Asp Thr Pro Arg Pro Asn Asp Gly Ser Ile Thr Gly Pro
            325                 330                 335

Cys Glu Ser Asp Gly Asp Lys Gly Ser Gly Gly Ile Lys Gly Gly Phe
            340                 345                 350

Val His Gln Arg Met Lys Ser Lys Ile Gly Arg Trp Tyr Ser Arg Thr
            355                 360                 365

Met Ser Lys Thr Glu Arg Met Gly Met Gly Leu Tyr Val Lys Tyr Gly
            370                 375                 380

Gly Asp Pro Trp Ala Asp Ser Asp Ala Leu Ala Phe Ser Gly Val Met
385                 390                 395                 400

Val Ser Met Lys Glu Pro Gly Trp Tyr Ser Phe Gly Phe Glu Ile Lys
            405                 410                 415

Asp Lys Lys Cys Asp Val Pro Cys Ile Gly Ile Glu Met Val His Asp
            420                 425                 430

Gly Gly Lys Glu Thr Trp His Ser Ala Ala Thr Ala Ile Tyr Cys Leu
```

```
              435                 440                 445
Met Gly Ser Gly Gln Leu Leu Trp Asp Thr Val Thr Gly Val Asp Met
            450                 455                 460

Ala Leu
465

<210> SEQ ID NO 66
<211> LENGTH: 466
<212> TYPE: PRT
<213> ORGANISM: Artificial
<220> FEATURE:
<223> OTHER INFORMATION: synthetically-generated protein

<400> SEQUENCE: 66

Met Leu Ser Ser Thr Ile Gln Thr Leu Thr Leu Val Leu Thr Ser Gly
1               5                   10                  15

Gly Val Leu Leu Ser Leu Tyr Val Ser Ala Leu Leu Ser Tyr Leu Leu
                20                  25                  30

Tyr Ser Asp Ile Leu Leu Lys Phe Ser Gln Thr Glu Ile Thr Ala Pro
            35                  40                  45

Ile Met Pro Leu Asp Cys Ala Asn Ala Pro Asn Val Gln Ala Val Asn
        50                  55                  60

Arg Ser Ala Ala Lys Gly Val Thr Leu Leu Pro Gly Pro Glu Trp
65                  70                  75                  80

Thr Tyr Pro Arg Leu Ser Cys Gln Gly Ser Thr Phe Gln Lys Ala Leu
                85                  90                  95

Leu Ile Ser Pro His Arg Phe Gly Glu Ile Lys Gly Asn Ser Ala Pro
            100                 105                 110

Leu Ile Ile Arg Glu Pro Phe Ile Ala Cys Gly Pro Lys Glu Cys Lys
        115                 120                 125

His Phe Ala Leu Thr His Tyr Ala Thr Gln Pro Gly Gly Tyr Tyr Asn
130                 135                 140

Gly Thr Arg Glu Asp Arg Asn Lys Leu Arg His Leu Ile Ser Val Asn
145                 150                 155                 160

Leu Gly Lys Ile Pro Thr Val Glu Asn Ser Ile Phe His Met Thr Ala
                165                 170                 175

Trp Ser Gly Ser Ala Cys His Asp Gly Arg Glu Trp Thr Tyr Ile Gly
            180                 185                 190

Val Asp Gly Pro Asp Ser Asn Ala Leu Leu Lys Ile Lys Tyr Gly Glu
        195                 200                 205

Ala Tyr Thr Asp Thr Tyr His Ser Tyr Ala Lys Asn Ile Leu Arg Thr
    210                 215                 220

Gln Glu Ser Ala Cys Asn Cys Ile Gly Gly Asp Cys Tyr Leu Met Ile
225                 230                 235                 240

Thr Asp Gly Pro Ala Ser Gly Ile Ser Glu Cys Arg Phe Leu Lys Ile
                245                 250                 255

Gln Glu Gly Arg Ile Ile Lys Glu Ile Phe Pro Thr Gly Arg Ile Lys
            260                 265                 270

His Thr Glu Glu Cys Thr Cys Gly Leu Ala Ser Asn Glu Thr Ile Glu
        275                 280                 285

Cys Ala Cys Arg Asp Asn Ser Tyr Thr Ala Lys Arg Pro Phe Val Lys
    290                 295                 300

Leu Asn Val Glu Ile Asp Thr Ala Glu Ile Arg Leu Met Cys Thr Glu
305                 310                 315                 320

Thr Tyr Leu Asp Thr Pro Arg Pro Asp Asp Gly Ser Ile Thr Gly Pro
```

```
            325                 330                 335
Cys Glu Ser Asn Gly Asp Lys Gly Gly Ile Lys Gly Gly Phe
            340                 345                 350

Val His Gln Arg Met Ala Ser Lys Ile Gly Arg Trp Tyr Ser Arg Thr
            355                 360                 365

Met Ser Lys Thr Lys Arg Met Gly Met Gly Leu Tyr Val Lys Tyr Asp
            370                 375                 380

Gly Asp Pro Trp Thr Asp Ser Glu Ala Leu Ala Leu Ser Gly Val Met
385                 390                 395                 400

Val Ser Met Glu Glu Pro Gly Trp Tyr Ser Phe Gly Phe Glu Ile Arg
                405                 410                 415

Asp Lys Lys Cys Asp Val Pro Cys Ile Gly Val Glu Met Val His Asp
                420                 425                 430

Gly Gly Lys Thr Thr Trp His Ser Ala Ala Thr Ala Val Tyr Cys Leu
                435                 440                 445

Met Gly Ser Gly Gln Leu Leu Trp Asp Thr Val Thr Gly Val Asn Met
            450                 455                 460

Thr Leu
465

<210> SEQ ID NO 67
<211> LENGTH: 466
<212> TYPE: PRT
<213> ORGANISM: Artificial
<220> FEATURE:
<223> OTHER INFORMATION: synthetically-generated protein

<400> SEQUENCE: 67

Met Leu Pro Ser Thr Ile Gln Met Leu Thr Leu Phe Leu Thr Ser Gly
1               5                   10                  15

Gly Val Leu Leu Ser Ile Tyr Val Ser Ala Ser Leu Ser Tyr Leu Ile
            20                  25                  30

Tyr Ser Asp Ile Leu Leu Lys Phe Ser Arg Thr Glu Ile Thr Ala Pro
        35                  40                  45

Ile Met Ser Leu Asp Cys Ala Asn Ala Ser Asn Val His Ala Val Asn
    50                  55                  60

Arg Ser Ala Thr Lys Gly Val Thr Phe Leu Leu Pro Glu Pro Glu Trp
65                  70                  75                  80

Thr Tyr Pro Arg Leu Ser Cys Ser Gly Ser Thr Phe Gln Lys Ala Leu
                85                  90                  95

Leu Ile Ser Pro His Arg Phe Gly Glu Ala Lys Gly Asn Ser Ala Pro
            100                 105                 110

Leu Ile Val Arg Glu Pro Phe Ile Ala Cys Gly Pro Thr Glu Cys Lys
        115                 120                 125

His Phe Ala Leu Thr His Tyr Ala Ala Gln Pro Gly Gly Tyr Tyr Ser
    130                 135                 140

Gly Thr Arg Gly Asp Arg Asn Lys Leu Arg His Leu Ile Ser Val Glu
145                 150                 155                 160

Leu Gly Lys Ile Pro Thr Val Glu Thr Ser Ile Phe His Met Ala Ala
                165                 170                 175

Trp Ser Gly Ser Ser Cys His Asp Gly Lys Glu Trp Thr Tyr Val Gly
            180                 185                 190

Val Asp Gly Pro Asp Asn Asn Ala Leu Leu Lys Ile Lys Tyr Gly Glu
        195                 200                 205

Ala Tyr Thr Asp Thr Tyr His Ser Tyr Ala Asn Lys Ile Leu Arg Thr
```

```
            210                 215                 220
Gln Glu Ser Ala Cys Asn Cys Ile Arg Gly Asn Cys Tyr Leu Met Ile
225                 230                 235                 240

Thr Asp Gly Pro Ala Ser Gly Val Ser Glu Cys Arg Phe Leu Lys Ile
                245                 250                 255

Arg Glu Gly Leu Ile Ile Lys Glu Ile Phe Pro Thr Gly Arg Val Glu
                260                 265                 270

His Thr Glu Glu Cys Thr Cys Gly Phe Ala Asn Asn Lys Thr Ile Glu
                275                 280                 285

Cys Ala Cys Arg Asp Asn Asn Tyr Thr Ala Lys Arg Pro Phe Val Lys
                290                 295                 300

Leu Ser Val Glu Thr Asp Thr Ala Glu Ile Arg Leu Met Cys Thr Lys
305                 310                 315                 320

Thr Tyr Leu Asp Thr Pro Arg Pro Asn Asp Gly Ser Thr Thr Gly Pro
                325                 330                 335

Cys Glu Ser Asp Gly Glu Lys Gly Ser Gly Gly Ile Lys Gly Gly Phe
                340                 345                 350

Val His Gln Arg Met Glu Ser Lys Ile Gly Arg Trp Tyr Ser Arg Thr
                355                 360                 365

Met Ser Gln Thr Glu Arg Met Gly Met Gly Leu Tyr Val Lys Tyr Asp
370                 375                 380

Gly Asp Pro Trp Ala Asp Ser Gly Ala Leu Ala Phe Ser Gly Val Met
385                 390                 395                 400

Ile Ser Met Lys Glu Pro Gly Trp Tyr Thr Phe Gly Phe Glu Ile Lys
                405                 410                 415

Asp Lys Lys Cys Asp Val Pro Cys Ile Gly Ile Glu Met Val His Asp
                420                 425                 430

Gly Gly Arg Glu Thr Trp His Ser Ala Ala Thr Thr Ile Tyr Cys Leu
                435                 440                 445

Met Gly Ser Gly Lys Leu Leu Trp Asp Thr Val Thr Gly Val Asn Met
450                 455                 460

Ala Leu
465

<210> SEQ ID NO 68
<211> LENGTH: 466
<212> TYPE: PRT
<213> ORGANISM: Artificial
<220> FEATURE:
<223> OTHER INFORMATION: synthetically-generated protein

<400> SEQUENCE: 68

Met Leu Pro Ser Thr Ile Gln Thr Leu Thr Leu Phe Leu Thr Ser Gly
1               5                   10                  15

Gly Val Leu Leu Ser Leu Tyr Val Ser Ala Ser Leu Ser Tyr Leu Leu
                20                  25                  30

Tyr Ser Asp Ile Leu Leu Lys Phe Ser Arg Thr Glu Val Thr Ala Pro
                35                  40                  45

Ile Met Pro Leu Asp Cys Ala Asn Ala Ser Asn Val Gln Ala Val Asn
                50                  55                  60

Arg Ser Ala Thr Lys Gly Val Thr Pro Leu Pro Glu Pro Glu Trp
65                  70                  75                  80

Thr Tyr Pro Arg Leu Ser Cys Pro Gly Ser Thr Phe Gln Lys Ala Leu
                85                  90                  95

Leu Ile Ser Pro His Arg Phe Gly Glu Thr Lys Gly Asn Ser Ala Pro
```

```
                    100                 105                 110
Leu Ile Ile Arg Glu Pro Phe Ile Ala Cys Gly Pro Lys Glu Cys Lys
            115                 120                 125
His Phe Ala Leu Thr His Tyr Ala Ala Gln Pro Gly Gly Tyr Tyr Asn
            130                 135                 140
Gly Thr Arg Glu Asp Arg Asn Lys Leu Arg His Leu Ile Ser Val Lys
145                 150                 155                 160
Leu Gly Lys Ile Pro Thr Val Glu Asn Ser Ile Phe His Met Ala Ala
                165                 170                 175
Trp Ser Gly Ser Ala Cys His Asp Gly Arg Glu Trp Thr Tyr Ile Gly
            180                 185                 190
Val Asp Gly Pro Asp Ser Asn Ala Leu Leu Lys Ile Lys Tyr Gly Glu
            195                 200                 205
Ala Tyr Thr Asp Thr Tyr His Ser Tyr Ala Lys Asn Ile Leu Arg Thr
            210                 215                 220
Gln Glu Ser Ala Cys Asn Cys Ile Gly Gly Asp Cys Tyr Leu Met Ile
225                 230                 235                 240
Thr Asp Gly Pro Ala Ser Gly Ile Ser Glu Cys Arg Phe Leu Lys Ile
                245                 250                 255
Arg Glu Gly Arg Ile Ile Lys Glu Ile Phe Pro Thr Gly Arg Val Lys
                260                 265                 270
His Thr Glu Glu Cys Thr Cys Gly Phe Ala Ser Asn Lys Thr Ile Glu
            275                 280                 285
Cys Ala Cys Arg Asp Asn Ser Tyr Thr Ala Lys Arg Pro Phe Val Lys
            290                 295                 300
Leu Asn Val Glu Thr Asp Thr Ala Glu Ile Arg Leu Met Cys Thr Lys
305                 310                 315                 320
Thr Tyr Leu Asp Thr Pro Arg Pro Asn Asp Gly Ser Ile Thr Gly Pro
                325                 330                 335
Cys Glu Ser Asp Gly Asn Glu Gly Ser Gly Ile Lys Gly Gly Phe
            340                 345                 350
Val His Gln Arg Met Ala Ser Lys Ile Gly Arg Trp Tyr Ser Arg Thr
            355                 360                 365
Met Ser Lys Thr Gln Arg Met Gly Met Gly Leu Tyr Val Lys Tyr Asp
            370                 375                 380
Gly Asp Pro Trp Thr Asp Ser Glu Ala Leu Ala Leu Ser Gly Val Met
385                 390                 395                 400
Val Ser Met Glu Glu Pro Gly Trp Tyr Ser Phe Gly Phe Glu Ile Lys
                405                 410                 415
Asp Lys Lys Cys Asp Val Pro Cys Ile Gly Ile Glu Met Val His Asp
                420                 425                 430
Gly Gly Lys Thr Thr Trp His Ser Ala Ala Thr Ala Ile Tyr Cys Leu
            435                 440                 445
Met Gly Ser Gly Gln Leu Leu Trp Asp Thr Val Thr Gly Val Asn Met
            450                 455                 460
Thr Leu
465

<210> SEQ ID NO 69
<211> LENGTH: 466
<212> TYPE: PRT
<213> ORGANISM: Artificial
<220> FEATURE:
<223> OTHER INFORMATION: synthetically-generated protein
```

<400> SEQUENCE: 69

```
Met Pro Pro Ser Thr Ile Gln Thr Leu Thr Leu Phe Leu Thr Ser Gly
1               5                   10                  15

Gly Val Leu Leu Ser Ile Tyr Val Ser Ala Ser Leu Ser Tyr Leu Leu
                20                  25                  30

Tyr Leu Asp Ile Leu Leu Lys Phe Pro Ser Thr Glu Ile Thr Ala Pro
            35                  40                  45

Thr Met Pro Leu Asp Cys Ala Asn Ala Ser Asn Val Gln Ala Val Asn
        50                  55                  60

His Ser Ala Thr Lys Gly Val Thr Leu Leu Pro Glu Pro Glu Trp
65                  70                  75                  80

Thr Tyr Pro Arg Leu Ser Cys Pro Gly Ser Thr Phe Gln Arg Ala Leu
                85                  90                  95

Leu Ile Ser Pro His Arg Phe Gly Glu Thr Lys Gly Asn Ser Ala Pro
            100                 105                 110

Leu Ile Met Arg Glu Pro Phe Ile Ala Cys Gly Pro Asn Glu Cys Lys
        115                 120                 125

His Phe Ala Leu Thr His Tyr Thr Ala Gln Pro Gly Gly Tyr Tyr Asn
    130                 135                 140

Gly Thr Arg Glu Asp Arg Asn Asn Leu Arg His Leu Ile Ser Val Lys
145                 150                 155                 160

Leu Gly Lys Ile Pro Thr Val Glu Asn Ser Ile Phe His Met Ala Ala
                165                 170                 175

Trp Ser Gly Ser Ala Cys His Asp Gly Lys Glu Trp Thr Tyr Ile Gly
            180                 185                 190

Val Asp Gly Pro Asp Asn Asn Ala Leu Leu Lys Val Lys Tyr Gly Glu
        195                 200                 205

Ala Tyr Thr Asp Thr Tyr His Ser Tyr Ala Asn Lys Ile Leu Arg Thr
    210                 215                 220

Gln Glu Ser Ala Cys Asn Cys Ile Gly Gly Asn Cys Tyr Leu Met Ile
225                 230                 235                 240

Thr Asp Gly Ser Ala Ser Gly Val Ser Glu Cys Arg Phe Leu Lys Ile
                245                 250                 255

Arg Glu Gly Arg Ile Met Lys Glu Ile Phe Pro Thr Gly Arg Thr Gln
            260                 265                 270

His Thr Glu Glu Cys Thr Cys Gly Phe Ala Ser Asn Lys Thr Ile Glu
        275                 280                 285

Cys Ala Cys Arg Asp Asn Ser Tyr Thr Ala Lys Arg Pro Phe Val Lys
    290                 295                 300

Leu Asn Val Glu Thr Asp Thr Ala Glu Ile Arg Leu Met Cys Thr Glu
305                 310                 315                 320

Thr Tyr Leu Asp Thr Pro Arg Pro Asp Asp Gly Ser Ile Thr Gly Pro
                325                 330                 335

Cys Glu Ser Asp Gly Asp Glu Gly Ser Gly Gly Ile Lys Gly Gly Phe
            340                 345                 350

Val His Gln Arg Met Glu Ser Lys Ile Gly Arg Trp Tyr Ser Arg Thr
        355                 360                 365

Met Ser Lys Thr Glu Arg Lys Gly Met Gly Leu Tyr Val Lys Tyr Asn
    370                 375                 380

Gly Asp Pro Trp Ala Asp Ser Asp Ala Leu Ala Phe Ser Gly Val Met
385                 390                 395                 400

Val Ser Met Lys Glu Pro Gly Trp Tyr Ser Phe Gly Phe Glu Ile Lys
                405                 410                 415
```

```
Asp Lys Lys Cys Asp Val Pro Cys Ile Gly Ile Glu Met Val His Asp
            420                 425                 430

Gly Gly Lys Glu Thr Trp His Ser Ala Ala Thr Ala Ile Tyr Cys Leu
            435                 440                 445

Met Gly Ser Gly Gln Leu Leu Trp Asp Thr Val Thr Gly Val Asp Met
            450                 455                 460

Ala Leu
465

<210> SEQ ID NO 70
<211> LENGTH: 466
<212> TYPE: PRT
<213> ORGANISM: Artificial
<220> FEATURE:
<223> OTHER INFORMATION: synthetically-generated protein

<400> SEQUENCE: 70

Met Leu Pro Ser Thr Ile Gln Thr Leu Thr Leu Leu Thr Ser Gly
1               5                   10                  15

Gly Val Leu Leu Ser Leu Tyr Val Ser Ala Ser Leu Ser Tyr Leu Leu
            20                  25                  30

Tyr Ser Asp Ile Leu Leu Lys Phe Ser Arg Thr Glu Val Thr Ala Pro
            35                  40                  45

Ile Met Pro Leu Asp Cys Ala Asn Ala Ser Asn Val Gln Ala Val Asn
50                  55                  60

Arg Ser Val Thr Lys Gly Val Thr Pro Leu Leu Pro Glu Pro Glu Trp
65                  70                  75                  80

Met Tyr Pro Arg Leu Ser Cys Pro Gly Ser Thr Phe Gln Lys Ala Leu
                85                  90                  95

Leu Ile Ser Pro His Arg Phe Gly Glu Ile Lys Gly Asn Ser Ala Pro
            100                 105                 110

Leu Ile Ile Arg Glu Pro Phe Ile Ala Cys Gly Pro Lys Glu Cys Lys
            115                 120                 125

His Phe Ala Leu Thr His Tyr Ala Thr Gln Pro Gly Gly Tyr Tyr Asn
130                 135                 140

Gly Thr Arg Glu Asp Arg Asn Lys Leu Arg His Leu Val Ser Val Lys
145                 150                 155                 160

Leu Gly Lys Ile Pro Thr Val Glu Asn Ser Met Phe His Met Ala Ala
                165                 170                 175

Trp Ser Gly Ser Ala Cys His Asp Gly Arg Glu Trp Thr Tyr Ile Gly
            180                 185                 190

Val Asp Gly Pro Asp Asn Asn Ala Leu Leu Lys Ile Lys Tyr Gly Glu
            195                 200                 205

Thr Tyr Thr Asp Thr Tyr His Ser Tyr Ala Lys Asn Ile Leu Arg Thr
210                 215                 220

Gln Glu Ser Ala Cys Asn Cys Ile Gly Gly Asp Cys Tyr Leu Met Ile
225                 230                 235                 240

Thr Asp Gly Pro Ala Ser Gly Val Ser Glu Cys Arg Phe Leu Lys Ile
                245                 250                 255

Arg Glu Gly Arg Ile Val Lys Glu Ile Phe Pro Thr Gly Arg Val Lys
            260                 265                 270

His Thr Glu Glu Cys Thr Cys Gly Phe Ala Asn Asn Lys Thr Ile Glu
            275                 280                 285

Cys Ala Cys Arg Asp Asn Arg Tyr Thr Ala Lys Arg Pro Phe Val Lys
290                 295                 300
```

```
Leu Asn Met Glu Thr Asp Thr Ala Glu Ile Arg Leu Met Cys Thr Lys
305                 310                 315                 320

Thr Tyr Leu Asp Asn Pro Arg Pro Asn Asp Gly Ser Ile Thr Gly Pro
                325                 330                 335

Cys Glu Ser Asp Gly Asn Glu Gly Ser Gly Gly Ile Lys Gly Gly Phe
            340                 345                 350

Val His Gln Arg Met Ala Ser Lys Ile Ala Arg Trp Tyr Ser Arg Thr
        355                 360                 365

Met Ser Lys Thr Lys Arg Met Gly Met Gly Leu Tyr Val Lys Tyr Asp
    370                 375                 380

Gly Asp Pro Trp Thr Asp Ser Glu Ala Leu Ala Leu Ser Gly Val Met
385                 390                 395                 400

Ile Ser Met Glu Glu Pro Gly Trp Tyr Ser Phe Gly Phe Glu Ile Arg
                405                 410                 415

Asp Lys Lys Cys Asp Val Pro Cys Ile Gly Val Glu Met Val His Asp
                420                 425                 430

Gly Gly Lys Lys Thr Trp His Ser Ala Ala Thr Ala Ile Tyr Cys Leu
            435                 440                 445

Met Gly Ser Gly Gln Pro Leu Trp Asp Thr Val Thr Gly Val Asn Ile
        450                 455                 460

Thr Leu
465

<210> SEQ ID NO 71
<211> LENGTH: 466
<212> TYPE: PRT
<213> ORGANISM: Artificial
<220> FEATURE:
<223> OTHER INFORMATION: synthetically-generated protein

<400> SEQUENCE: 71

Met Leu Pro Thr Thr Ile Gln Thr Leu Thr Leu Phe Leu Thr Ser Gly
1               5                   10                  15

Gly Val Leu Leu Ser Leu Tyr Met Ser Ala Ser Leu Ser Tyr Leu Leu
                20                  25                  30

Tyr Ser Asp Met Leu Leu Lys Phe Ser Arg Thr Glu Val Thr Ala Pro
            35                  40                  45

Met Met Pro Leu Asp Cys Ala Asn Ala Ser Asn Val Gln Ala Val Asn
        50                  55                  60

Arg Ser Ala Thr Lys Gly Val Thr Pro Leu Leu Pro Glu Pro Glu Trp
65                  70                  75                  80

Thr Tyr Pro Arg Leu Ser Cys Gln Gly Ser Thr Phe Gln Lys Ala Leu
                85                  90                  95

Leu Ile Ser Pro His Arg Phe Gly Glu Thr Arg Gly Asn Ser Ala Pro
            100                 105                 110

Leu Ile Ile Arg Glu Pro Phe Val Ala Cys Gly Pro Lys Glu Cys Lys
        115                 120                 125

His Phe Ala Leu Thr His Tyr Ala Ala Gln Pro Gly Gly Tyr Tyr Asn
    130                 135                 140

Gly Thr Arg Gly Asp Arg Asn Lys Leu Arg His Leu Ile Ser Val Lys
145                 150                 155                 160

Leu Gly Lys Val Pro Thr Val Glu Asn Ser Met Phe His Met Thr Ala
                165                 170                 175

Trp Ser Gly Ser Ala Cys His Asp Gly Arg Glu Trp Ile Tyr Ile Gly
            180                 185                 190
```

```
Val Asp Gly Pro Asp Ser Asn Ala Leu Leu Lys Ile Lys Tyr Gly Glu
        195                 200                 205

Ala Tyr Thr Asp Thr Tyr His Ser Tyr Ala Asn Asn Ile Leu Arg Thr
        210                 215                 220

Gln Glu Ser Ala Cys Asn Cys Ile Arg Gly Asp Cys Tyr Leu Met Ile
225                 230                 235                 240

Thr Asp Gly Pro Ala Ser Gly Ile Ser Glu Cys Arg Phe Leu Lys Ile
            245                 250                 255

Arg Glu Gly Arg Ile Ile Lys Glu Ile Phe Pro Thr Gly Arg Val Glu
            260                 265                 270

His Thr Glu Glu Cys Thr Cys Gly Phe Ala Ser Asn Lys Thr Ile Glu
        275                 280                 285

Cys Ala Cys Arg Asp Asn Asn Tyr Thr Ala Lys Arg Pro Phe Val Lys
        290                 295                 300

Leu Asn Val Glu Thr Asp Thr Ala Glu Ile Lys Leu Met Cys Thr Lys
305                 310                 315                 320

Thr Tyr Leu Asp Thr Pro Arg Pro Asn Asp Gly Ser Ile Thr Gly Pro
            325                 330                 335

Cys Glu Ser Asp Gly Lys Glu Gly Ser Gly Ile Lys Gly Gly Phe
            340                 345                 350

Val His Gln Arg Met Ala Ser Lys Ile Gly Arg Trp Tyr Ser Arg Thr
        355                 360                 365

Met Ser Lys Thr Gln Arg Met Gly Met Gly Leu Tyr Val Lys Tyr Asp
        370                 375                 380

Gly Asp Pro Trp Thr Asp Ser Asp Ala Leu Ala Leu Ser Gly Val Met
385                 390                 395                 400

Val Ser Met Glu Glu Pro Gly Trp Tyr Ser Phe Gly Phe Glu Val Lys
                405                 410                 415

Asp Lys Lys Cys Asp Val Pro Cys Ile Gly Met Glu Met Val His Asp
            420                 425                 430

Gly Gly Lys Thr Thr Trp His Ser Ala Ala Thr Ala Val Tyr Cys Leu
        435                 440                 445

Met Gly Ser Gly Gln Leu Leu Trp Asp Thr Val Thr Gly Val Asn Met
    450                 455                 460

Thr Leu
465

<210> SEQ ID NO 72
<211> LENGTH: 466
<212> TYPE: PRT
<213> ORGANISM: Artificial
<220> FEATURE:
<223> OTHER INFORMATION: synthetically-generated protein

<400> SEQUENCE: 72

Met Leu Pro Ser Thr Ile Gln Thr Leu Thr Leu Phe Leu Thr Ser Gly
1               5                   10                  15

Gly Val Leu Leu Ser Leu Tyr Val Ser Ala Ser Leu Ser Tyr Leu Leu
            20                  25                  30

Tyr Ser Asp Ile Leu Leu Lys Phe Ser Arg Thr Glu Val Thr Ala Pro
        35                  40                  45

Ile Met Pro Leu Asp Cys Ala Asn Ala Ser Asn Val Gln Ala Val Asn
    50                  55                  60

Arg Ser Ala Thr Lys Gly Val Pro Leu Leu Pro Glu Pro Glu Trp
65                  70                  75                  80
```

```
Thr Tyr Pro Arg Leu Ser Cys Pro Gly Ser Thr Phe Gln Lys Ala Leu
                85                  90                  95

Leu Ile Ser Pro His Arg Phe Gly Glu Thr Lys Gly Asn Ser Ala Pro
                100                 105                 110

Leu Ile Ile Arg Glu Pro Phe Ile Ala Cys Gly Pro Lys Glu Cys Lys
                115                 120                 125

His Phe Ala Leu Thr His Tyr Ala Ala Gln Pro Gly Tyr Tyr Asn
130                 135                 140

Gly Thr Arg Glu Asp Arg Asn Lys Leu Arg His Leu Ile Ser Val Lys
145                 150                 155                 160

Leu Gly Lys Ile Pro Thr Val Glu Asn Ser Ile Phe His Met Ala Ala
                165                 170                 175

Trp Ser Gly Ser Ala Cys His Asp Gly Arg Glu Trp Thr Tyr Ile Gly
                180                 185                 190

Val Asp Gly Pro Asp Ser Asn Ala Leu Leu Lys Ile Lys Tyr Gly Glu
                195                 200                 205

Ala Tyr Thr Asp Thr Tyr His Ser Tyr Ala Lys Asn Ile Leu Arg Thr
                210                 215                 220

Gln Glu Ser Ala Cys Asn Cys Ile Gly Gly Asp Cys Tyr Leu Met Ile
225                 230                 235                 240

Thr Asp Gly Pro Ala Ser Gly Ile Ser Glu Cys Arg Phe Leu Lys Ile
                245                 250                 255

Arg Glu Gly Arg Ile Ile Lys Glu Ile Phe Pro Thr Gly Arg Val Lys
                260                 265                 270

His Thr Glu Glu Cys Thr Cys Gly Phe Ala Ser Asn Lys Thr Ile Glu
                275                 280                 285

Cys Ala Cys Arg Asp Asn Ser Tyr Thr Ala Lys Arg Pro Phe Val Lys
290                 295                 300

Leu Asn Val Glu Thr Asp Thr Ala Glu Ile Arg Leu Met Cys Thr Lys
305                 310                 315                 320

Thr Tyr Leu Asp Thr Pro Arg Pro Asn Asp Gly Ser Ile Thr Gly Pro
                325                 330                 335

Cys Glu Ser Asp Gly Asn Glu Gly Ser Gly Ile Lys Gly Gly Phe
                340                 345                 350

Val His Gln Arg Met Ala Ser Lys Ile Gly Arg Trp Tyr Ser Arg Thr
                355                 360                 365

Met Ser Lys Thr Gln Arg Met Gly Met Gly Leu Tyr Val Lys Tyr Asp
                370                 375                 380

Gly Asp Pro Trp Thr Asp Ser Glu Ala Leu Ala Leu Ser Gly Val Met
385                 390                 395                 400

Val Ser Met Glu Glu Pro Gly Trp Tyr Ser Phe Gly Phe Glu Ile Lys
                405                 410                 415

Asp Lys Lys Cys Asp Val Pro Cys Ile Gly Ile Glu Met Val His Asp
                420                 425                 430

Gly Gly Lys Thr Thr Trp His Ser Ala Ala Thr Ala Ile Tyr Cys Leu
                435                 440                 445

Met Gly Ser Gly Gln Leu Leu Trp Asp Thr Val Thr Gly Val Asn Met
450                 455                 460

Thr Leu
465

<210> SEQ ID NO 73
<211> LENGTH: 466
```

```
<212> TYPE: PRT
<213> ORGANISM: Artificial
<220> FEATURE:
<223> OTHER INFORMATION: synthetically-generated protein

<400> SEQUENCE: 73

Met Leu Ser Ser Thr Ile Gln Thr Leu Thr Leu Leu Thr Ser Gly
1               5                   10                  15

Gly Val Leu Leu Ser Leu Tyr Val Ser Ala Leu Leu Ser Tyr Leu Leu
            20                  25                  30

Tyr Ser Asp Met Leu Leu Lys Phe Ser Arg Thr Glu Val Thr Ala Pro
                35                  40                  45

Met Met Pro Leu Asp Cys Ala Asn Ala Ser Asn Val Gln Ala Val Asn
    50                  55                  60

Arg Ser Val Thr Lys Gly Val Thr Pro Leu Leu Pro Glu Pro Glu Trp
65                  70                  75                  80

Met Tyr Pro Arg Leu Ser Cys Pro Gly Ser Thr Phe Gln Arg Ala Leu
                85                  90                  95

Leu Ile Ser Pro His Arg Phe Gly Glu Ile Lys Gly Asn Ser Ala Pro
                100                 105                 110

Leu Ile Ile Arg Glu Pro Phe Val Ala Cys Gly Pro Lys Glu Cys Lys
                115                 120                 125

His Phe Ala Leu Thr His Tyr Thr Ala Gln Pro Gly Gly Tyr Tyr Asn
130                 135                 140

Gly Thr Arg Gly Asp Arg Asn Lys Leu Arg His Leu Val Ser Val Lys
145                 150                 155                 160

Leu Gly Lys Ile Pro Thr Val Glu Asn Ser Met Phe His Met Ala Ala
                165                 170                 175

Trp Ser Gly Ser Ala Cys His Asp Gly Lys Glu Trp Thr Tyr Ile Gly
                180                 185                 190

Val Asp Gly Pro Asp Asn Asn Ala Leu Leu Lys Ile Lys Tyr Gly Glu
            195                 200                 205

Thr Tyr Thr Asp Thr Tyr His Ser Tyr Ala Asn Asn Ile Leu Arg Thr
        210                 215                 220

Gln Glu Ser Ala Cys Asn Cys Ile Gly Gly Asn Cys Tyr Leu Met Ile
225                 230                 235                 240

Thr Asp Gly Ser Ala Ser Gly Val Ser Glu Cys Arg Phe Leu Lys Ile
                245                 250                 255

Arg Glu Gly Arg Ile Val Lys Glu Ile Phe Pro Thr Gly Arg Thr Gln
                260                 265                 270

His Thr Glu Glu Cys Thr Cys Gly Phe Ala Asn Asn Lys Thr Ile Glu
                275                 280                 285

Cys Ala Cys Arg Asp Asn Arg Tyr Thr Ala Lys Arg Pro Phe Val Lys
                290                 295                 300

Leu Asn Val Glu Ile Asp Thr Ala Glu Ile Arg Leu Met Cys Thr Glu
305                 310                 315                 320

Thr Tyr Leu Asp Thr Pro Arg Pro Asp Asp Gly Ser Ile Thr Gly Pro
                325                 330                 335

Cys Glu Ser Asp Gly Lys Glu Gly Ser Gly Ile Lys Gly Gly Phe
                340                 345                 350

Val His Gln Arg Met Glu Ser Lys Ile Gly Arg Trp Tyr Ser Arg Thr
            355                 360                 365

Met Ser Lys Thr Lys Arg Met Gly Met Gly Leu Tyr Val Lys Tyr Asn
    370                 375                 380
```

```
Gly Asp Pro Trp Ala Asp Ser Asp Ala Leu Ala Leu Ser Gly Val Met
385                 390                 395                 400

Ile Ser Met Glu Glu Pro Gly Trp Tyr Ser Phe Gly Phe Glu Ile Arg
                405                 410                 415

Asp Lys Lys Cys Asp Val Pro Cys Ile Gly Val Glu Met Val His Asp
            420                 425                 430

Gly Gly Lys Glu Thr Trp His Ser Ala Ala Thr Ala Val Tyr Cys Leu
        435                 440                 445

Met Gly Ser Gly Gln Pro Leu Trp Asp Thr Val Thr Gly Val Asp Met
450                 455                 460

Ala Leu
465

<210> SEQ ID NO 74
<211> LENGTH: 466
<212> TYPE: PRT
<213> ORGANISM: Artificial
<220> FEATURE:
<223> OTHER INFORMATION: synthetically-generated protein

<400> SEQUENCE: 74

Met Leu Pro Thr Thr Ile Gln Thr Leu Thr Leu Phe Leu Thr Thr Gly
1               5                   10                  15

Gly Val Leu Leu Ser Leu Tyr Met Ser Ala Ser Leu Ser Tyr Leu Leu
            20                  25                  30

Tyr Leu Asp Ile Leu Leu Lys Phe Pro Ser Thr Glu Ile Thr Ala Pro
        35                  40                  45

Thr Met Pro Leu Asp Cys Ala Asn Ala Ser Asn Ala Gln Ala Val Asn
50                  55                  60

Arg Ser Ala Thr Lys Gly Val Thr Leu Leu Pro Glu Pro Glu Trp
65                  70                  75                  80

Thr Tyr Pro Arg Leu Ser Cys Gln Gly Ser Thr Phe Gln Lys Ala Leu
                85                  90                  95

Leu Ile Ser Ser His Arg Phe Gly Glu Thr Lys Gly Asn Ser Ala Pro
            100                 105                 110

Leu Ile Met Arg Glu Pro Phe Ile Ala Cys Gly Pro Asn Glu Cys Lys
        115                 120                 125

His Phe Ala Leu Thr His Tyr Ala Thr Gln Pro Gly Gly Tyr Tyr Asn
130                 135                 140

Gly Thr Arg Glu Asp Arg Asn Asn Leu Arg His Leu Ile Ser Val Lys
145                 150                 155                 160

Leu Gly Lys Val Pro Thr Val Glu Asn Ser Met Phe His Met Thr Ala
                165                 170                 175

Trp Ser Gly Ser Ala Cys His Asp Gly Arg Glu Trp Ile Tyr Ile Gly
            180                 185                 190

Val Asp Gly Pro Asp Asn Asn Ala Leu Leu Lys Val Lys Tyr Gly Glu
        195                 200                 205

Ala Tyr Thr Asp Thr Tyr His Ser Tyr Ala Asn Lys Ile Leu Arg Thr
210                 215                 220

Gln Glu Ser Ala Cys Asn Cys Ile Arg Gly Asp Cys Tyr Leu Met Ile
225                 230                 235                 240

Thr Asp Gly Pro Ala Ser Gly Val Ser Glu Cys Arg Phe Leu Lys Ile
                245                 250                 255

Arg Glu Gly Arg Ile Met Lys Glu Ile Phe Pro Thr Gly Arg Val Glu
            260                 265                 270
```

```
His Thr Glu Glu Cys Thr Cys Gly Phe Ala Ser Asn Lys Thr Ile Glu
            275                 280                 285

Cys Ala Cys Arg Asp Ile Pro Tyr Thr Ala Lys Arg Pro Phe Val Lys
        290                 295                 300

Leu Asn Val Glu Thr Asp Thr Ala Glu Ile Lys Leu Met Cys Thr Lys
305                 310                 315                 320

Thr Tyr Leu Asp Asn Pro Arg Pro Asn Asp Gly Ser Ile Thr Gly Pro
                325                 330                 335

Cys Glu Ser Asp Gly Asp Glu Gly Ser Gly Gly Ile Lys Gly Gly Leu
            340                 345                 350

Val His Gln Arg Met Ala Ser Lys Ile Ala Arg Trp Tyr Ser Arg Thr
            355                 360                 365

Met Ser Lys Thr Glu Arg Lys Gly Met Gly Leu Tyr Val Lys Tyr Asp
        370                 375                 380

Gly Asp Pro Trp Thr Asp Ser Asp Ala Leu Ala Leu Ser Gly Val Met
385                 390                 395                 400

Val Pro Met Glu Glu Pro Gly Trp Tyr Ser Phe Gly Phe Glu Ile Lys
                405                 410                 415

Asp Arg Lys Cys Asp Val Pro Cys Ile Gly Leu Glu Met Val His Asp
            420                 425                 430

Gly Gly Lys Lys Thr Trp His Ser Ala Ala Thr Ala Ile Tyr Cys Leu
        435                 440                 445

Met Gly Ser Gly Arg Leu Leu Trp Asp Thr Val Thr Gly Val Asn Ile
450                 455                 460

Thr Leu
465

<210> SEQ ID NO 75
<211> LENGTH: 548
<212> TYPE: PRT
<213> ORGANISM: Artificial
<220> FEATURE:
<223> OTHER INFORMATION: synthetically-generated protein
<220> FEATURE:
<221> NAME/KEY: misc_feature
<222> LOCATION: (180)..(181)
<223> OTHER INFORMATION: Xaa can be any naturally occurring amino acid

<400> SEQUENCE: 75

Met Met Lys Ala Ile Leu Val Leu Leu Thr Phe Thr Ala Ala Tyr Ala
1               5                   10                  15

Asp Thr Cys Ile Gly Tyr His Ala Asn Asn Ser Thr Asp Thr Val Asp
            20                  25                  30

Thr Val Leu Glu Lys Asn Val Thr Val Thr His Ser Val Asn Leu Leu
        35                  40                  45

Glu Asp His Asn Gly Lys Leu Cys Lys Leu Gly Ala Pro Leu Leu Gly
    50                  55                  60

Lys Cys Asn Ile Ala Gly Trp Ile Leu Gly Asn Pro Glu Cys Glu Ser
65                  70                  75                  80

Leu Thr Ala Ser Trp Ser Tyr Ile Val Glu Thr Ser Asn Ser Asp Asn
                85                  90                  95

Gly Thr Cys Tyr Pro Gly Asp Phe Asp Tyr Glu Glu Leu Arg Glu Gln
            100                 105                 110

Leu Ser Ser Val Ser Ser Phe Glu Arg Phe Glu Ile Phe Pro Lys Ser
        115                 120                 125

Ser Trp Pro Asn His Thr Gly Val Thr Ala Ala Cys His Asn Gly Ser
    130                 135                 140
```

```
Phe Tyr Arg Asn Leu Ile Trp Leu Val Lys Lys Gly Lys Glu Asn Ser
145                 150                 155                 160

Tyr Pro Lys Leu Ser Lys Ser Tyr Asn Asn Lys Lys Glu Val Leu Val
            165                 170                 175

Leu Trp Gly Xaa Xaa Ile His His Pro Ser Thr Asp Gln Gln Leu Tyr
        180                 185                 190

Gln Asn Ala Ala Tyr Val Phe Val Gly Ser Ser Tyr Ser Arg Lys Phe
    195                 200                 205

Pro Glu Ile Ala Arg Pro Lys Val Arg Asp Gln Gly Arg Met Asn Tyr
210                 215                 220

Tyr Trp Thr Leu Glu Pro Gly Asp Thr Ile Thr Phe Glu Ala Thr Gly
225                 230                 235                 240

Asn Leu Val Ala Pro Arg Tyr Ala Phe Ala Leu Arg Gly Gly Ser Gly
                245                 250                 255

Ile Ile Ser Asp Ala Pro Val His Asp Cys Asp Thr Cys Gln Thr Pro
            260                 265                 270

Gly Ala Ile Asn Thr Ser Leu Thr Ser Leu Pro Phe Gln Asn Val His
        275                 280                 285

Pro Val Thr Ile Gly Glu Cys Pro Lys Tyr Val Lys Ser Thr Lys Leu
    290                 295                 300

Arg Met Ala Thr Gly Leu Arg Asn Ile Pro Ser Ile Gln Ser Arg Gly
305                 310                 315                 320

Leu Phe Gly Ala Ile Ala Gly Phe Ile Glu Gly Gly Trp Thr Gly Met
                325                 330                 335

Ile Asp Gly Trp Tyr Gly Tyr His His Gln Asn Glu Gln Gly Ser Gly
            340                 345                 350

Tyr Ala Ala Asp Gln Lys Ser Thr Gln Asn Ala Ile Asp Gly Ile Thr
        355                 360                 365

Asn Lys Val Asn Ser Val Ile Glu Lys Met Asn Thr Gln Phe Thr Ala
    370                 375                 380

Val Gly Lys Glu Phe Asn Leu Glu Arg Arg Ile Glu Asn Leu Asn Lys
385                 390                 395                 400

Lys Val Asp Asp Gly Phe Leu Asp Ile Trp Thr Tyr Asn Ala Glu Leu
                405                 410                 415

Leu Val Leu Leu Glu Asn Glu Arg Thr Leu Asp Phe His Asp Ser Asn
            420                 425                 430

Val Lys Asn Leu Tyr Glu Lys Val Arg Ser Gln Leu Lys Asn Asn Ala
        435                 440                 445

Lys Glu Ile Gly Asn Gly Cys Phe Glu Phe Tyr His Lys Cys Asp Asn
450                 455                 460

Cys Met Glu Ser Val Lys Asn Gly Thr Tyr Asp Tyr Pro Lys Tyr Ser
465                 470                 475                 480

Glu Glu Ser Lys Leu Asn Arg Glu Glu Ile Asp Gly Val Lys Leu Glu
                485                 490                 495

Ser Arg Ile Tyr Gln Ile Leu Ala Ile Tyr Ser Thr Val Ala Ser Ser
            500                 505                 510

Leu Val Leu Leu Val Ser Leu Gly Ala Ile Ser Phe Trp Met Cys Ser
        515                 520                 525

Asn Gly Ser Leu Gln Cys Arg Ile Cys Ile Lys Asn Arg Asp Met Arg
    530                 535                 540

Lys Asn Thr Leu
545
```

<210> SEQ ID NO 76
<211> LENGTH: 566
<212> TYPE: PRT
<213> ORGANISM: Artificial
<220> FEATURE:
<223> OTHER INFORMATION: synthetically-generated protein

<400> SEQUENCE: 76

```
Met Lys Ala Ile Leu Val Val Leu Leu Tyr Thr Phe Thr Thr Ala Asn
1               5                   10                  15

Ala Asp Thr Leu Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asn Arg His Asn Gly Lys Leu Cys Lys Leu Arg Gly Val
    50                  55                  60

Ala Pro Leu His Leu Gly Lys Cys Asn Ile Ala Gly Trp Leu Leu Gly
65                  70                  75                  80

Asn Pro Glu Cys Glu Ser Leu Ser Thr Ala Ser Ser Trp Ser Tyr Ile
                85                  90                  95

Val Glu Thr Ser Asn Ser Asp Asn Gly Thr Cys Tyr Pro Gly Asp Phe
            100                 105                 110

Ile Asn Tyr Glu Glu Leu Arg Glu Gln Leu Ser Ser Val Ser Ser Phe
        115                 120                 125

Glu Arg Phe Glu Ile Phe Pro Lys Thr Ser Ser Trp Pro Asn His Asp
    130                 135                 140

Thr Asn Arg Gly Val Thr Ala Ala Cys Pro His Ala Gly Thr Asn Ser
145                 150                 155                 160

Phe Tyr Arg Asn Leu Ile Trp Leu Val Lys Lys Glu Asn Ser Tyr Pro
                165                 170                 175

Lys Ile Asn Lys Ser Tyr Ile Asn Asn Lys Glu Lys Glu Val Leu Val
            180                 185                 190

Leu Trp Ala Ile His His Pro Ser Thr Ser Ala Asp Gln Gln Ser Leu
        195                 200                 205

Tyr Lys Asn Ala Asp Ala Tyr Val Phe Val Gly Ser Ser Arg Tyr Ser
    210                 215                 220

Arg Lys Phe Glu Pro Glu Ile Ala Thr Arg Pro Lys Val Arg Asp Gln
225                 230                 235                 240

Ala Gly Arg Met Asn Tyr Tyr Trp Thr Leu Leu Asp Gln Gly Asp Thr
                245                 250                 255

Ile Thr Phe Glu Ala Thr Gly Asn Leu Val Ala Pro Arg Tyr Ala Phe
            260                 265                 270

Ala Leu Lys Arg Asn Ser Gly Ser Gly Ile Ile Ile Ser Asp Thr Ser
        275                 280                 285

Val His Asp Cys Asp Thr Thr Cys Gln Thr Pro Asn Gly Ala Ile Asn
    290                 295                 300

Thr Ser Leu Pro Phe Gln Asn Ile His Pro Val Thr Ile Gly Glu Cys
305                 310                 315                 320

Pro Lys Tyr Val Lys Ser Thr Lys Leu Arg Met Ala Thr Gly Leu Arg
                325                 330                 335

Asn Ile Pro Ser Val Gln Ser Arg Gly Leu Phe Gly Ala Ile Ala Gly
            340                 345                 350

Phe Ile Glu Gly Gly Trp Thr Gly Met Ile Asp Gly Trp Tyr Gly Tyr
        355                 360                 365
```

His His Arg Asn Glu Gln Gly Ser Gly Tyr Ala Ala Asp Leu Lys Ser
370                 375                 380

Thr Gln Asn Ala Ile Asp Gly Ile Thr Asn Lys Val Asn Ser Val Ile
385                 390                 395                 400

Glu Lys Met Asn Thr Gln Phe Thr Ala Val Gly Lys Glu Phe Ser His
                405                 410                 415

Leu Glu Arg Arg Ile Glu Asn Leu Asn Lys Lys Val Asp Asp Gly Phe
                420                 425                 430

Leu Asp Ile Trp Thr Tyr Asn Ala Glu Leu Leu Val Leu Leu Glu Asn
                435                 440                 445

Glu Arg Thr Leu Asp Tyr His Asp Ser Asn Val Lys Asn Leu Tyr Glu
450                 455                 460

Lys Val Arg Ser Gln Leu Lys Asn Asn Ala Lys Glu Val Gly Asn Gly
465                 470                 475                 480

Cys Phe Glu Phe Tyr His Lys Cys Asp Asp Thr Cys Met Glu Ser Val
                485                 490                 495

Lys Asn Gly Thr Tyr Asp Tyr Pro Lys Tyr Ser Glu Glu Ala Lys Leu
                500                 505                 510

Asn Arg Glu Glu Ile Asp Gly Val Lys Leu Glu Ser Thr Arg Ile Tyr
                515                 520                 525

Gln Ile Leu Ala Ile Tyr Ser Thr Val Ala Ser Ser Leu Val Leu Val
530                 535                 540

Val Ser Leu Gly Ala Ile Ser Phe Trp Met Cys Ser Asn Gly Ser Leu
545                 550                 555                 560

Gln Cys Lys Ile Cys Ile
                565

<210> SEQ ID NO 77
<211> LENGTH: 565
<212> TYPE: PRT
<213> ORGANISM: Artificial
<220> FEATURE:
<223> OTHER INFORMATION: synthetically-generated protein

<400> SEQUENCE: 77

Met Lys Val Lys Leu Leu Ile Leu Leu Cys Thr Phe Thr Ala Thr Tyr
1               5                   10                  15

Ala Asp Thr Ile Cys Ile Gly Tyr His Ala Asn Asn Ser Thr Glu Thr
                20                  25                  30

Val Asp Thr Val Leu Glu Lys Asn Val Ala Val Thr His Ser Val Asn
                35                  40                  45

Leu Leu Glu Asp Ser His Asn Gly Lys Leu Cys Leu Leu Lys Gly Ile
50                  55                  60

Ala Pro Leu Gln Leu Gly Asn Cys Ser Val Ala Gly Trp Ile Leu Gly
65                  70                  75                  80

Asn Pro Glu Cys Glu Ser Leu Ile Ser Lys Lys Ser Trp Ser Tyr Ile
                85                  90                  95

Val Glu Thr Pro Asn Pro Glu Asn Gly Ala Cys Tyr Pro Gly Glu Phe
                100                 105                 110

Ala Asp Tyr Glu Glu Leu Arg Glu Gln Leu Ser Ser Val Ser Ser Phe
                115                 120                 125

Lys Arg Phe Glu Ile Phe Pro Lys Glu Ser Ser Trp Pro Asn His Thr
130                 135                 140

Val Thr Gly Val Ser Ala Ser Cys Ser His Asn Gly Glu Arg Ser Phe
145                 150                 155                 160

```
Tyr Arg Asn Leu Ile Trp Leu Thr Val Lys Asn Gly Leu Tyr Pro Asn
            165                 170                 175

Leu Ser Lys Ser Tyr Glu Asn Asp Lys Gly Lys Glu Val Leu Ile Leu
            180                 185                 190

Trp Gly Val His His Pro Ser Asn Ile Gly Asp Gln Arg Thr Leu Tyr
            195                 200                 205

His Thr Glu Asn Ala Tyr Val Ser Val Val Ser Ser His Tyr Ser Arg
        210                 215                 220

Arg Phe Thr Pro Glu Ile Thr Lys Arg Pro Lys Val Arg Asp Gln Glu
225                 230                 235                 240

Gly Arg Ile Asn Tyr Tyr Trp Thr Leu Leu Glu Pro Gly Asp Thr Ile
                245                 250                 255

Ile Phe Glu Ala Asn Gly Asn Leu Ile Ala Pro Trp Tyr Ala Phe Ala
            260                 265                 270

Leu Ser Arg Gly Leu Gly Ser Gly Ile Ile Thr Ser Asn Ala Pro Met
        275                 280                 285

Asp Glu Cys Asp Ala Lys Cys Gln Thr Pro Gln Gly Ala Ile Asn Ser
    290                 295                 300

Ser Leu Pro Phe Gln Asn Val His Pro Val Thr Ile Gly Glu Cys Pro
305                 310                 315                 320

Lys Tyr Val Arg Ser Ala Lys Leu Arg Met Val Thr Gly Leu Arg Asn
                325                 330                 335

Ile Pro Ser Ile Gln Ser Arg Gly Leu Phe Gly Ala Ile Val Gly Phe
            340                 345                 350

Ile Glu Gly Gly Trp Thr Gly Met Val Asp Gly Trp Tyr Gly Tyr His
        355                 360                 365

His Gln Asn Gly Gln Gly Ser Gly Tyr Ala Ala Asp Gln Glu Ser Thr
    370                 375                 380

Gln Asn Ala Ile Asn Gly Ile Thr Asn Lys Val Asn Ser Ile Ile Glu
385                 390                 395                 400

Lys Met Asn Thr Gln Phe Thr Ala Val Gly Lys Glu Phe Asn Lys Leu
                405                 410                 415

Glu Arg Arg Met Glu Asn Leu Asn Lys Lys Val Asp Asp Gly Leu Leu
            420                 425                 430

Asp Val Trp Thr Tyr Asn Ala Glu Met Leu Val Leu Leu Glu Asn Glu
        435                 440                 445

Arg Thr Leu Asp Phe His Asp Ser Asn Val Lys Ser Leu Tyr Glu Lys
    450                 455                 460

Val Lys Ser Gln Leu Lys Asn Asn Ala Lys Glu Ile Gly Asn Gly Cys
465                 470                 475                 480

Phe Glu Phe Tyr His Lys Cys Asn Asn Glu Cys Met Glu Ser Val Arg
                485                 490                 495

Asn Gly Thr Tyr Asp Tyr Pro Lys Tyr Tyr Glu Glu Ser Lys Leu Asn
            500                 505                 510

Arg Glu Lys Ile Asp Gly Val Lys Leu Asp Ser Met Gly Val Tyr Arg
        515                 520                 525

Ile Leu Ala Ile Tyr Ser Thr Ala Ala Ser Ser Leu Val Leu Leu Val
    530                 535                 540

Ser Leu Gly Ala Ile Ser Phe Trp Val Cys Ser Asn Gly Ser Leu Gln
545                 550                 555                 560

Cys Arg Ile Cys Ile
            565
```

```
<210> SEQ ID NO 78
<211> LENGTH: 566
<212> TYPE: PRT
<213> ORGANISM: Artificial
<220> FEATURE:
<223> OTHER INFORMATION: synthetically-generated protein

<400> SEQUENCE: 78

Met Glu Ala Lys Leu Phe Val Leu Phe Cys Ala Phe Thr Ala Leu Lys
1               5                   10                  15

Ala Asp Thr Ile Cys Val Gly Tyr His Ala Asn Asn Ser Thr Asp Thr
            20                  25                  30

Val Asp Thr Ile Leu Glu Lys Asn Val Thr Val Thr His Ser Val Asn
        35                  40                  45

Leu Leu Glu Asp Lys His Asn Gly Lys Leu Cys Lys Leu Gly Gly Ile
    50                  55                  60

Ala Pro Leu His Leu Gly Lys Cys Asn Ile Ala Gly Trp Ile Leu Gly
65                  70                  75                  80

Asn Pro Glu Cys Glu Leu Leu Ile Ser Lys Glu Ser Trp Ser Tyr Ile
                85                  90                  95

Val Glu Thr Ser Ser Ser Asp Asn Gly Thr Cys Tyr Pro Gly Asp Phe
            100                 105                 110

Ile Asp Tyr Glu Glu Leu Arg Glu Gln Leu Ser Thr Val Ser Ser Phe
        115                 120                 125

Glu Arg Phe Glu Ile Phe Pro Lys Ala Ser Ser Trp Pro Asn His Asp
    130                 135                 140

Ser Asn Lys Gly Val Thr Ala Ala Cys Pro His Ala Gly Ala Lys Ser
145                 150                 155                 160

Phe Tyr Lys Asn Leu Ile Trp Leu Val Lys Lys Gly Asn Ser Tyr Pro
                165                 170                 175

Lys Leu Ser Lys Ser Tyr Ile Asn Asp Lys Gly Lys Glu Val Leu Val
            180                 185                 190

Leu Trp Gly Ile His His Pro Ser Thr Ser Ala Asp Gln Gln Ser Leu
        195                 200                 205

Tyr Gln Asn Ala Asp Ala Tyr Val Phe Val Gly Thr Ser Arg Tyr Ser
    210                 215                 220

Lys Lys Phe Lys Pro Glu Ile Ala Ile Arg Pro Lys Val Arg Asp Gln
225                 230                 235                 240

Glu Gly Arg Met Asn Tyr Tyr Trp Thr Leu Val Glu Pro Gly Asp Lys
                245                 250                 255

Ile Thr Phe Glu Ala Thr Gly Asn Leu Val Val Pro Arg Tyr Ala Phe
            260                 265                 270

Ala Met Glu Arg Asn Ala Gly Ser Gly Ile Ile Ile Ser Asp Thr Pro
        275                 280                 285

Val His Asp Cys Asn Thr Thr Cys Gln Thr Pro Lys Gly Ala Ile Asn
    290                 295                 300

Thr Ser Leu Pro Phe Gln Asn Ile His Pro Ile Thr Ile Gly Lys Cys
305                 310                 315                 320

Pro Lys Tyr Val Lys Ser Thr Lys Leu Arg Leu Ala Thr Gly Leu Arg
                325                 330                 335

Asn Val Pro Ser Ile Gln Ser Arg Gly Leu Phe Gly Ala Ile Ala Gly
            340                 345                 350

Phe Leu Glu Gly Gly Trp Thr Gly Met Val Asn Gly Trp Tyr Gly Tyr
        355                 360                 365

His His Gln Asn Glu Gln Gly Ser Gly Tyr Ala Ala Asp Gln Lys Ser
```

|   |   |   | 370 |   |   |   | 375 |   |   |   | 380 |   |
|---|---|---|---|---|---|---|---|---|---|---|---|---|

Thr Gln Ile Ala Ile Asp Gly Ile Ser Asn Lys Val Asn Ser Val Ile
385 390 395 400

Glu Lys Met Asn Ile Gln Phe Thr Ser Val Gly Lys Glu Phe Asn His
405 410 415

Leu Glu Lys Arg Ile Glu Asn Leu Asn Lys Lys Val Asp Asp Gly Phe
420 425 430

Leu Asp Val Trp Thr Tyr Asn Ala Glu Leu Leu Ile Leu Leu Glu Asn
435 440 445

Glu Arg Thr Leu Asp Phe His Asp Phe Asn Val Lys Asn Leu Tyr Glu
450 455 460

Lys Val Lys Ser Gln Leu Arg Asn Asn Ala Lys Glu Ile Gly Asn Gly
465 470 475 480

Cys Phe Glu Phe Tyr His Lys Cys Asp Asn Glu Cys Met Glu Ser Val
485 490 495

Lys Asn Gly Thr Tyr Asn Tyr Pro Lys Tyr Ser Glu Glu Ser Lys Leu
500 505 510

Asn Arg Glu Glu Ile Asp Gly Val Lys Leu Glu Ser Met Gly Val Tyr
515 520 525

Arg Ile Leu Ser Ile Tyr Ser Thr Val Ala Ser Ser Leu Val Leu Leu
530 535 540

Val Ser Leu Gly Ala Val Ser Phe Trp Met Cys Ser Asn Gly Ser Leu
545 550 555 560

Gln Cys Arg Val Cys Ile
565

<210> SEQ ID NO 79
<211> LENGTH: 566
<212> TYPE: PRT
<213> ORGANISM: Artificial
<220> FEATURE:
<223> OTHER INFORMATION: synthetically-generated protein

<400> SEQUENCE: 79

Met Lys Ala Ile Leu Val Val Leu Leu Tyr Thr Phe Thr Thr Ala Asn
1   5   10   15

Ala Asp Thr Leu Cys Ile Gly Tyr His Ala Asn Asn Ser Thr Asp Thr
20   25   30

Val Asp Thr Val Leu Glu Lys Asn Val Thr Val Thr His Ser Val Asn
35   40   45

Leu Leu Glu Asp Ser His Asn Gly Lys Leu Cys Lys Leu Arg Gly Val
50   55   60

Ala Pro Leu His Leu Gly Lys Cys Asn Ile Ala Gly Trp Leu Leu Gly
65   70   75   80

Asn Pro Glu Cys Glu Ser Leu Ser Thr Ala Ser Ser Trp Ser Tyr Ile
85   90   95

Val Glu Thr Ser Asn Ser Asp Asn Gly Thr Cys Tyr Pro Gly Asp Phe
100   105   110

Ile Asn Tyr Glu Glu Leu Arg Glu Gln Leu Ser Ser Val Ser Ser Phe
115   120   125

Glu Arg Phe Glu Ile Phe Pro Lys Thr Ser Ser Trp Pro Asn His Asp
130   135   140

Thr Asn Arg Gly Val Thr Ala Ala Cys Pro His Ala Gly Thr Asn Ser
145   150   155   160

Phe Tyr Arg Asn Leu Ile Trp Leu Val Lys Lys Gly Asn Ser Tyr Pro

```
                    165                 170                 175
Lys Leu Ser Lys Ser Tyr Ile Asn Asn Lys Glu Lys Glu Val Leu Val
            180                 185                 190

Leu Trp Ala Ile His His Pro Ser Thr Ser Ala Asp Gln Gln Ser Leu
            195                 200                 205

Tyr Gln Asn Ala Asp Ala Tyr Val Phe Val Gly Ser Ser Arg Tyr Ser
    210                 215                 220

Arg Lys Phe Glu Pro Glu Ile Ala Thr Arg Pro Lys Val Arg Asp Gln
225                 230                 235                 240

Ala Gly Arg Met Asn Tyr Tyr Trp Thr Leu Val Glu Pro Gly Asp Lys
            245                 250                 255

Ile Thr Phe Glu Ala Thr Gly Asn Leu Val Val Pro Arg Tyr Ala Phe
            260                 265                 270

Ala Leu Lys Arg Asn Ser Gly Ser Gly Ile Ile Ile Ser Asp Thr Ser
            275                 280                 285

Val His Asp Cys Asp Thr Thr Cys Gln Thr Pro Asn Gly Ala Ile Asn
    290                 295                 300

Thr Ser Leu Pro Phe Gln Asn Ile His Pro Val Thr Ile Gly Glu Cys
305                 310                 315                 320

Pro Lys Tyr Val Lys Ser Thr Lys Leu Arg Met Ala Thr Gly Leu Arg
            325                 330                 335

Asn Ile Pro Ser Ile Gln Ser Arg Gly Leu Phe Gly Ala Ile Ala Gly
            340                 345                 350

Phe Ile Glu Gly Gly Trp Thr Gly Met Ile Asp Gly Trp Tyr Gly Tyr
            355                 360                 365

His His Gln Asn Glu Gln Gly Ser Gly Tyr Ala Ala Asp Leu Lys Ser
    370                 375                 380

Thr Gln Asn Ala Ile Asp Gly Ile Thr Asn Lys Val Asn Ser Val Ile
385                 390                 395                 400

Glu Lys Met Asn Thr Gln Phe Thr Ala Val Gly Lys Glu Phe Asn Lys
            405                 410                 415

Leu Glu Arg Arg Met Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
            435                 440                 445

Glu Arg Thr Leu Asp Tyr His Asp Ser Asn Val Lys Asn Leu Tyr Glu
    450                 455                 460

Lys Val Arg Ser Gln Leu Lys Asn Asn Ala Lys Glu Ile Gly Asn Gly
465                 470                 475                 480

Cys Phe Glu Phe Tyr His Lys Cys Asn Asn Glu Cys Met Glu Ser Val
            485                 490                 495

Lys Asn Gly Thr Tyr Asp Tyr Pro Lys Tyr Ser Glu Glu Ala Lys Leu
            500                 505                 510

Asn Arg Glu Glu Ile Asp Gly Val Lys Leu Glu Ser Thr Arg Ile Tyr
            515                 520                 525

Gln Ile Leu Ala Ile Tyr Ser Thr Val Ala Ser Ser Leu Val Leu Leu
    530                 535                 540

Val Ser Leu Gly Ala Ile Ser Phe Trp Met Cys Ser Asn Gly Ser Leu
545                 550                 555                 560

Gln Cys Arg Ile Cys Ile
            565

<210> SEQ ID NO 80
```

<211> LENGTH: 565
<212> TYPE: PRT
<213> ORGANISM: Artificial
<220> FEATURE:
<223> OTHER INFORMATION: synthetically-generated protein

<400> SEQUENCE: 80

```
Met Lys Val Lys Leu Ile Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Ile Leu Glu Lys Asn Val Thr Val Thr His Ser Val Asn
                35                  40                  45

Leu Leu Glu Asn Arg His Asn Gly Lys Leu Cys Leu Leu Lys Gly Ile
    50                  55                  60

Ala Pro Leu Gln Leu Gly Asn Cys Ser Val Ala Gly Trp Ile Leu Gly
65                  70                  75                  80

Asn Pro Glu Cys Glu Ser Leu Ile Ser Lys Lys Ser Trp Ser Tyr Ile
                85                  90                  95

Val Glu Thr Pro Asn Pro Glu Asn Gly Ala Cys Tyr Pro Gly Glu Phe
                100                 105                 110

Ala Asp Tyr Glu Glu Leu Arg Glu Gln Leu Ser Thr Val Ser Ser Phe
            115                 120                 125

Glu Arg Phe Glu Ile Phe Pro Lys Glu Ser Ser Trp Pro Asn His Thr
    130                 135                 140

Val Thr Gly Val Ser Ala Ser Cys Ser His Asn Gly Glu Arg Ser Phe
145                 150                 155                 160

Tyr Arg Asn Leu Ile Trp Leu Thr Val Lys Asn Gly Leu Tyr Pro Asn
                165                 170                 175

Leu Ser Lys Ser Tyr Glu Asn Asp Lys Gly Lys Glu Val Leu Ile Leu
            180                 185                 190

Trp Gly Val His His Pro Ser Asn Ile Gly Asp Gln Arg Thr Leu Tyr
        195                 200                 205

His Thr Glu Asn Ala Tyr Val Ser Val Val Ser Ser His Tyr Ser Arg
    210                 215                 220

Arg Phe Thr Pro Glu Ile Thr Lys Arg Pro Lys Val Arg Asp Gln Glu
225                 230                 235                 240

Gly Arg Ile Asn Tyr Tyr Trp Thr Leu Leu Glu Pro Gly Asp Thr Ile
                245                 250                 255

Ile Phe Glu Ala Asn Gly Asn Leu Ile Ala Pro Trp Tyr Ala Phe Ala
            260                 265                 270

Leu Ser Arg Gly Leu Gly Ser Gly Ile Ile Thr Ser Asn Ala Pro Met
        275                 280                 285

Asp Glu Cys Asp Ala Lys Cys Gln Thr Pro Gln Gly Ala Ile Asn Ser
    290                 295                 300

Ser Leu Pro Phe Gln Asn Val His Pro Val Thr Ile Gly Glu Cys Pro
305                 310                 315                 320

Lys Tyr Val Arg Ser Ala Lys Leu Arg Met Val Thr Gly Leu Arg Asn
                325                 330                 335

Val Pro Ser Ile Gln Ser Arg Gly Leu Leu Gly Ala Ile Ala Gly Phe
            340                 345                 350

Ile Glu Gly Gly Trp Thr Gly Met Val Asp Gly Trp Tyr Gly Tyr His
        355                 360                 365

His Gln Asn Gly Gln Gly Ser Gly Tyr Ala Ala Asp Gln Glu Ser Thr
    370                 375                 380
```

```
Gln Asn Ala Ile Asn Gly Ile Thr Asn Lys Val Asn Ser Ile Ile Glu
385                 390                 395                 400

Lys Met Asn Ile Gln Phe Thr Ser Val Gly Lys Glu Phe Asn His Leu
            405                 410                 415

Glu Lys Arg Ile Glu Asn Leu Asn Lys Lys Val Asp Asp Gly Phe Leu
        420                 425                 430

Asp Val Trp Thr Tyr Asn Ala Glu Leu Leu Ile Leu Leu Glu Asn Glu
            435                 440                 445

Arg Thr Leu Asp Phe His Asp Ser Asn Val Lys Ser Leu Tyr Glu Lys
    450                 455                 460

Val Lys Ser Gln Leu Lys Asn Asn Ala Lys Glu Val Gly Asn Gly Cys
465                 470                 475                 480

Phe Glu Phe Tyr His Lys Cys Asp Asp Thr Cys Met Glu Ser Val Lys
                485                 490                 495

Asn Gly Thr Tyr Asn Tyr Pro Lys Tyr Ser Glu Glu Ser Lys Leu Asn
            500                 505                 510

Arg Glu Lys Ile Asp Gly Val Lys Leu Asp Ser Met Gly Val Tyr Arg
        515                 520                 525

Ile Leu Ala Ile Tyr Ser Thr Val Ala Ser Ser Leu Val Leu Val Val
            530                 535                 540

Ser Leu Gly Ala Ile Ser Phe Trp Met Cys Ser Asn Gly Ser Leu Gln
545                 550                 555                 560

Cys Arg Val Cys Ile
                565

<210> SEQ ID NO 81
<211> LENGTH: 566
<212> TYPE: PRT
<213> ORGANISM: Artificial
<220> FEATURE:
<223> OTHER INFORMATION: synthetically-generated protein

<400> SEQUENCE: 81

Met Glu Ala Lys Leu Phe Val Leu Phe Cys Ala Phe Thr Ala Leu Lys
1               5                   10                  15

Ala Asp Thr Ile Cys Val Gly Tyr His Ala Asn Asn Ser Thr Glu Thr
            20                  25                  30

Val Asp Thr Val Leu Glu Lys Asn Val Ala Val Thr His Ser Val Asn
        35                  40                  45

Leu Leu Glu Asp Lys His Asn Gly Lys Leu Cys Lys Leu Gly Gly Ile
    50                  55                  60

Ala Pro Leu His Leu Gly Lys Cys Asn Ile Ala Gly Trp Ile Leu Gly
65                  70                  75                  80

Asn Pro Glu Cys Glu Leu Leu Ile Ser Lys Glu Ser Trp Ser Tyr Ile
                85                  90                  95

Val Glu Ala Pro Asn Ser Asp Asn Gly Ala Cys Tyr Pro Gly Gln Phe
            100                 105                 110

Ala Asp Tyr Glu Glu Leu Arg Glu His Leu Ser Ser Val Ser Ser Phe
        115                 120                 125

Glu Lys Phe Glu Ile Phe Pro Lys Ala Ser Ser Trp Pro Asn His Asp
    130                 135                 140

Ser Asn Lys Gly Val Thr Ala Ala Cys Pro Tyr Ala Gly Ala Asn Ser
145                 150                 155                 160

Phe Tyr Arg Asn Leu Leu Trp Ile Val Lys Lys Gly Asn Ser Tyr Pro
                165                 170                 175
```

Lys Ile Asn Lys Ser Tyr Ile Asn Asn Lys Gly Lys Glu Val Leu Val
            180                 185                 190

Leu Trp Gly Ile His His Pro Pro Thr Ser Thr Asp Gln Gln Ser Leu
            195                 200                 205

Tyr Lys Asn Ala Asp Ala Tyr Val Phe Val Gly Thr Ser Arg Tyr Ser
210                 215                 220

Lys Lys Phe Lys Pro Glu Ile Ala Ile Arg Pro Lys Val Arg Asp Gln
225                 230                 235                 240

Glu Gly Arg Met Asn Tyr Tyr Trp Thr Leu Leu Asp Gln Gly Asp Thr
                245                 250                 255

Ile Thr Phe Glu Ala Thr Gly Asn Leu Val Ala Pro Arg Tyr Ala Phe
                260                 265                 270

Ala Met Glu Arg Asn Ala Gly Ser Gly Ile Ile Ile Ser Asp Thr Pro
                275                 280                 285

Val His Asp Cys Asn Thr Thr Cys Gln Thr Pro Lys Gly Ala Ile Asn
            290                 295                 300

Ser Asn Leu Pro Phe Gln Asn Val His Pro Ile Thr Ile Gly Glu Cys
305                 310                 315                 320

Pro Lys Tyr Val Arg Ser Thr Lys Leu Arg Met Val Thr Gly Leu Arg
                325                 330                 335

Asn Ile Pro Ser Val Gln Ser Arg Gly Leu Phe Gly Ala Ile Ala Gly
            340                 345                 350

Phe Leu Glu Gly Gly Trp Thr Gly Met Val Asn Gly Trp Tyr Gly Tyr
            355                 360                 365

His His Gln Asn Asp Gln Gly Ser Gly Tyr Ala Ala Asp Gln Lys Ser
        370                 375                 380

Thr Gln Ile Ala Ile Asp Gly Ile Ser Asn Lys Val Asn Ser Val Ile
385                 390                 395                 400

Glu Lys Met Asn Ile Gln Phe Thr Ala Val Gly Lys Glu Phe Ser His
                405                 410                 415

Leu Glu Arg Arg Ile Glu Asn Leu Asn Lys Lys Val Asp Asp Gly Leu
            420                 425                 430

Leu Asp Val Trp Thr Tyr Asn Ala Glu Met Leu Val Leu Leu Glu Asn
            435                 440                 445

Glu Arg Thr Leu Asp Phe His Asp Phe Asn Val Lys Asn Leu Tyr Glu
        450                 455                 460

Lys Val Lys Ser Gln Leu Arg Asn Asn Ala Lys Glu Ile Gly Asn Gly
465                 470                 475                 480

Cys Phe Glu Phe Tyr His Lys Cys Asp Asn Thr Cys Met Glu Ser Val
                485                 490                 495

Arg Asn Gly Thr Tyr Asp Tyr Pro Lys Tyr Tyr Glu Gly Ser Lys Leu
            500                 505                 510

Asn Arg Glu Glu Ile Asp Gly Val Lys Leu Glu Ser Met Gly Val Tyr
        515                 520                 525

Gln Ile Leu Ala Ile Tyr Ser Thr Ala Ala Ser Ser Leu Val Leu Leu
            530                 535                 540

Val Ser Leu Gly Ala Val Ser Phe Trp Met Cys Ser Asn Gly Ser Leu
545                 550                 555                 560

Gln Cys Lys Ile Cys Ile
                565

<210> SEQ ID NO 82
<211> LENGTH: 571

<212> TYPE: PRT
<213> ORGANISM: Artificial
<220> FEATURE:
<223> OTHER INFORMATION: synthetically-generated protein

<400> SEQUENCE: 82

```
Met Lys Thr Ile Ile Ala Phe Ser Cys Ile Leu Cys Leu Ile Phe Ala
1               5                   10                  15

Gln Lys Leu Pro Gly Ser Asp Asn Asn Ser Met Ala Thr Leu Cys Leu
            20                  25                  30

Gly His His Ala Val Pro Asn Gly Thr Leu Val Lys Thr Ile Thr Asp
        35                  40                  45

Asp Gln Ile Glu Val Thr Asn Ala Thr Glu Leu Val Gln Ser Ser Ser
    50                  55                  60

Thr Gly Arg Ile Cys Asn Ser Pro Gly His Gln Ile Leu Asp Gly Lys
65                  70                  75                  80

Asn Cys Thr Leu Ile Asp Ala Leu Leu Gly Asp Pro His Cys Asp Asp
                85                  90                  95

Phe Gln Asn Lys Trp Asp Leu Phe Val Glu Arg Ser Thr Ala Tyr Ser
            100                 105                 110

Gly Asn Cys Tyr Pro Tyr Tyr Val Pro Asp Tyr Ala Ser Leu Arg Glu
        115                 120                 125

Gln Leu Ser Leu Val Ala Ser Ser Gly Thr Leu Glu Phe Thr Gln Glu
    130                 135                 140

Ser Phe Asn Trp Thr Gly Val Ala Gln Asp Gly Ser Ser Tyr Ala Cys
145                 150                 155                 160

Arg Arg Gly Ser Val Asn Asn Ser Phe Phe Ser Arg Leu Asn Trp Leu
                165                 170                 175

Tyr Leu Asn Tyr Lys Tyr Pro Ala Leu Asn Val Thr Met Pro Asn Asn
            180                 185                 190

Asp Lys Phe Asp Lys Leu Tyr Ile Trp Gly Val His His Pro Gly Thr
        195                 200                 205

Asp Lys Asp Gln Thr Asn Leu Tyr Val Gln Ala Ser Gly Arg Val Val
    210                 215                 220

Ser Thr Lys Arg Ser Gln Gln Thr Val Ile Pro Asn Ile Gly Ser Arg
225                 230                 235                 240

Pro Trp Val Arg Gly Val Ser Ser Ile Ile Ser Ile Tyr Trp Thr Ile
                245                 250                 255

Val Lys Pro Gly Asp Ile Leu Leu Ile Asn Ser Thr Gly Asn Leu Ile
            260                 265                 270

Ala Pro Arg Gly Tyr Phe Lys Ile Gln Ser Gly Lys Ser Ser Gly Ile
        275                 280                 285

Met Arg Ser Asp Ala Pro Ile Asp Cys Asn Ser Glu Cys Ile Thr Pro
    290                 295                 300

Asn Gly Ser Ile Pro Asn Asp Lys Pro Phe Gln Asn Val Asn Arg Ile
305                 310                 315                 320

Thr Tyr Gly Ala Cys Pro Arg Tyr Val Lys Gln Asn Thr Leu Lys Leu
                325                 330                 335

Ala Thr Gly Met Arg Asn Val Pro Glu Lys Gln Thr Arg Gly Ile Phe
            340                 345                 350

Gly Ala Ile Ala Gly Phe Ile Glu Asn Gly Trp Glu Gly Met Val Asp
        355                 360                 365

Gly Trp Tyr Gly Phe Arg His Gln Asn Ser Glu Gly Thr Gly Gln Ala
    370                 375                 380
```

```
Ala Asp Leu Lys Ser Thr Gln Ala Ala Ile Asn Gln Ile Thr Gly Lys
385                 390                 395                 400

Leu Asn Arg Val Ile Lys Lys Thr Asn Glu Lys Phe His Gln Ile Glu
            405                 410                 415

Lys Glu Phe Ser Glu Val Glu Gly Arg Ile Gln Asp Leu Glu Lys Tyr
                420                 425                 430

Val Glu Asp Thr Lys Ile Asp Leu Trp Ser Tyr Asn Ala Glu Leu Leu
            435                 440                 445

Val Ala Leu Glu Asn Gln His Thr Ile Asp Leu Thr Asp Ser Glu Met
    450                 455                 460

Asn Lys Leu Phe Glu Arg Thr Arg Lys Gln Leu Arg Glu Asn Ala Glu
465                 470                 475                 480

Asp Met Gly Asn Gly Cys Phe Lys Ile Tyr His Lys Cys Asp Asn Ala
                485                 490                 495

Cys Ile Gly Ser Ile Arg Asn Gly Thr Tyr Asp His Asp Val Tyr Arg
                500                 505                 510

Asp Glu Ala Leu Asn Asn Arg Phe Gln Ile Lys Gly Val Gln Leu Lys
                515                 520                 525

Ser Gly Tyr Lys Asp Trp Ile Leu Trp Ile Ser Phe Ala Ile Ser Cys
    530                 535                 540

Phe Leu Leu Cys Val Val Leu Leu Gly Phe Ile Ser Met Trp Ala Cys
545                 550                 555                 560

Gln Lys Gly Asn Ile Arg Cys Asn Ile Cys Ile
                565                 570

<210> SEQ ID NO 83
<211> LENGTH: 566
<212> TYPE: PRT
<213> ORGANISM: Artificial
<220> FEATURE:
<223> OTHER INFORMATION: synthetically-generated protein

<400> SEQUENCE: 83

Met Lys Thr Ile Ile Ala Phe Ser Cys Ile Leu Cys Leu Ile Phe Ala
1               5                   10                  15

Gln Lys Leu Pro Gly Ser Asp Asn Ser Thr Ala Thr Leu Cys Leu Gly
            20                  25                  30

His His Ala Val Pro Asn Gly Thr Met Val Lys Thr Ile Thr Asp Asp
        35                  40                  45

Gln Val Glu Val Thr Asn Ala Thr Glu Leu Val Gln Ser Ser Ser Thr
    50                  55                  60

Gly Arg Ile Cys Asn Ser Pro His Gln Ile Leu Asp Gly Lys Asn Cys
65                  70                  75                  80

Thr Leu Ile Asp Ser Leu Leu Gly Asp Pro His Cys Asp Asp Phe Gln
                85                  90                  95

Asn Lys Glu Trp Asp Leu Phe Val Glu Arg Ser Lys Ala Tyr Ser Asn
            100                 105                 110

Cys Tyr Pro Tyr Tyr Val Pro Asp Tyr Ala Thr Leu Arg Ser Leu Val
        115                 120                 125

Ala Ser Ser Gly Asn Leu Glu Phe Thr Gln Glu Ser Phe Asn Trp Thr
    130                 135                 140

Gly Val Ala Gln Asp Gly Ser Ser Tyr Ala Cys Arg Arg Gly Ser Val
145                 150                 155                 160

Asn Ser Phe Phe Ser Arg Leu Asn Trp Leu Tyr Asn Leu Asn Tyr Lys
                165                 170                 175
```

Tyr Pro Glu Gln Asn Val Thr Met Pro Asn Asn Asp Lys Phe Asp Lys
            180                 185                 190

Leu Tyr Ile Trp Gly Val His His Pro Gly Thr Asp Lys Asp Gln Thr
        195                 200                 205

Asn Leu Tyr Val Gln Ala Ser Gly Arg Val Ile Val Ser Thr Lys Arg
    210                 215                 220

Ser Gln Gln Thr Ile Ile Pro Asn Ile Gly Ser Arg Pro Trp Val Arg
225                 230                 235                 240

Gly Val Ser Ser Ile Ser Ile His Trp Thr Ile Val Lys Pro Gly
                245                 250                 255

Asp Ile Leu Leu Ile Asn Ser Thr Gly Asn Leu Ile Ala Pro Arg Gly
            260                 265                 270

Tyr Phe Lys Ile Gln Asn Gly Lys Ser Ser Ile Met Arg Ser Asp Ala
        275                 280                 285

His Ile Asp Glu Cys Asn Ser Glu Cys Ile Thr Pro Asn Gly Ser Ile
    290                 295                 300

Ser Asn Asp Lys Pro Phe Gln Asn Val Asn Lys Ile Thr Tyr Gly Ala
305                 310                 315                 320

Cys Pro Arg Tyr Ile Lys Gln Asn Thr Leu Lys Leu Ala Thr Gly Met
                325                 330                 335

Arg Asn Ile Pro Glu Lys Gln Thr Arg Gly Ile Phe Gly Ala Ile Ala
            340                 345                 350

Gly Phe Ile Glu Asn Gly Trp Glu Gly Met Val Asn Gly Trp Tyr Gly
        355                 360                 365

Phe Arg His Gln Asn Ser Glu Gly Thr Gly Gln Ala Ala Asp Leu Lys
    370                 375                 380

Ser Thr Gln Ala Ala Ile Asn Gln Ile Thr Gly Lys Leu Asn Arg Val
385                 390                 395                 400

Ile Lys Lys Thr Asn Glu Lys Phe His Gln Ile Glu Lys Glu Phe Ser
                405                 410                 415

Glu Val Glu Gly Arg Ile Gln Asp Leu Glu Lys Tyr Val Glu Asp Thr
            420                 425                 430

Lys Ile Asp Ile Trp Ser Tyr Asn Ala Glu Leu Leu Val Ala Leu Glu
        435                 440                 445

Asn Gln His Thr Ile Asp Leu Thr Asp Ser Glu Met Ser Lys Leu Phe
    450                 455                 460

Glu Arg Thr Arg Arg Gln Leu Arg Glu Asn Ala Glu Asp Ile Gly Asn
465                 470                 475                 480

Gly Cys Phe Lys Ile Tyr His Lys Cys Asp Asn Ser Cys Met Glu Ser
                485                 490                 495

Ile Arg Asn Gly Thr Tyr Asp His Asp Ile Tyr Arg Asn Glu Ala Leu
            500                 505                 510

Asn Asn Arg Phe Gln Ile Lys Gly Val Gln Leu Lys Ser Gly Tyr Lys
        515                 520                 525

Asp Trp Ile Leu Trp Ile Ser Phe Ala Ile Ser Cys Phe Leu Leu Cys
    530                 535                 540

Val Val Leu Leu Gly Phe Ile Met Trp Ala Cys Gln Arg Gly Asn Ile
545                 550                 555                 560

Arg Cys Asn Ile Cys Val
                565

<210> SEQ ID NO 84
<211> LENGTH: 566
<212> TYPE: PRT

<213> ORGANISM: Artificial
<220> FEATURE:
<223> OTHER INFORMATION: synthetically-generated protein

<400> SEQUENCE: 84

| | | | | | | | | | | | | | | |
|---|---|---|---|---|---|---|---|---|---|---|---|---|---|---|
| Met | Lys | Thr | Ile | Ile | Ala | Leu | Ser | Tyr | Ile | Cys | Leu | Val | Phe | Ala |
| 1 | | | | 5 | | | | | 10 | | | | | 15 |
| Gln | Lys | Leu | Pro | Gly | Asn | Asp | Asn | Met | Ala | Thr | Leu | Cys | Leu | Gly |
| | | | 20 | | | | | 25 | | | | | 30 | |
| His | His | Ala | Val | Pro | Asn | Gly | Thr | Ile | Val | Lys | Thr | Ile | Thr | Asn | Asp |
| | | 35 | | | | | 40 | | | | | 45 | | |
| Gln | Ile | Glu | Val | Thr | Asn | Ala | Thr | Glu | Leu | Val | Gln | Ser | Phe | Ser | Thr |
| | 50 | | | | | 55 | | | | | 60 | | | | |
| Gly | Glu | Ile | Cys | Asn | Ser | Pro | His | Gln | Ile | Leu | Asp | Gly | Glu | Asn | Cys |
| 65 | | | | | 70 | | | | | 75 | | | | | 80 |
| Thr | Leu | Ile | Asp | Ala | Leu | Leu | Gly | Asp | Pro | Gln | Cys | Asp | Gly | Phe | Gln |
| | | | | 85 | | | | | 90 | | | | | 95 | |
| Asn | Asn | Lys | Trp | Asp | Leu | Phe | Val | Glu | Arg | Ser | Lys | Ala | His | Ser | Asn |
| | | | 100 | | | | | 105 | | | | | 110 | | |
| Cys | Tyr | Pro | Tyr | Asp | Val | Pro | Asp | Tyr | Ala | Ser | Leu | Arg | Ser | Leu | Val |
| | | 115 | | | | | 120 | | | | | 125 | | | |
| Ala | Ser | Ser | Gly | Thr | Leu | Glu | Phe | Asn | Asn | Glu | Ser | Phe | Asn | Trp | Thr |
| | 130 | | | | | 135 | | | | | 140 | | | | |
| Gly | Val | Thr | Gln | Asn | Gly | Gly | Ser | Ser | Ala | Cys | Lys | Arg | Gly | Pro | Asn |
| 145 | | | | | 150 | | | | | 155 | | | | | 160 |
| Asn | Ser | Phe | Phe | Ser | Arg | Leu | Asn | Trp | Leu | Thr | His | Leu | Asn | Phe | Lys |
| | | | | 165 | | | | | 170 | | | | | 175 | |
| Tyr | Pro | Ala | Leu | Glu | Val | Thr | Met | Pro | Asn | Asn | Glu | Gln | Phe | Asp | Lys |
| | | | 180 | | | | | 185 | | | | | 190 | | |
| Leu | Tyr | Ile | Trp | Gly | Val | His | His | Pro | Ala | Thr | Asp | Lys | Asp | Gln | Ile |
| | | 195 | | | | | 200 | | | | | 205 | | | |
| Ser | Leu | Tyr | Ala | Gln | Ala | Ala | Gly | Arg | Ile | Ile | Val | Ser | Thr | Lys | Arg |
| | 210 | | | | | 215 | | | | | 220 | | | | |
| Ser | Gln | Gln | Ala | Val | Ile | Pro | Asn | Ile | Gly | Ser | Arg | Pro | Arg | Val | Arg |
| 225 | | | | | 230 | | | | | 235 | | | | | 240 |
| Asp | Ile | Pro | Ser | Arg | Ile | Ser | Ile | Tyr | Trp | Thr | Ile | Val | Arg | Pro | Gly |
| | | | | 245 | | | | | 250 | | | | | 255 | |
| Asp | Ile | Leu | Leu | Ile | Lys | Ser | Thr | Gly | Asn | Leu | Ile | Ala | Pro | Arg | Gly |
| | | | 260 | | | | | 265 | | | | | 270 | | |
| Tyr | Phe | Lys | Ile | Arg | Ser | Gly | Lys | Ser | Ser | Ile | Met | Arg | Ser | Asp | Ala |
| | | 275 | | | | | 280 | | | | | 285 | | | |
| Pro | Ile | Gly | Lys | Cys | Asn | Ser | Ala | Cys | Ile | Thr | Pro | Asn | Gly | Ser | Ile |
| | 290 | | | | | 295 | | | | | 300 | | | | |
| Pro | Asn | Asp | Lys | Pro | Phe | Gln | Asn | Val | Asn | Arg | Ile | Thr | Tyr | Gly | Ala |
| 305 | | | | | 310 | | | | | 315 | | | | | 320 |
| Cys | Pro | Lys | Tyr | Val | Lys | Gln | Asn | Thr | Leu | Lys | Leu | Ala | Thr | Gly | Met |
| | | | | 325 | | | | | 330 | | | | | 335 | |
| Arg | Asn | Ile | Pro | Glu | Arg | Gln | Thr | Arg | Gly | Ile | Phe | Gly | Ala | Lys | Ala |
| | | | 340 | | | | | 345 | | | | | 350 | | |
| Gly | Phe | Ile | Glu | Asn | Gly | Trp | Glu | Gly | Met | Val | Asp | Gly | Trp | Tyr | Gly |
| | | 355 | | | | | 360 | | | | | 365 | | | |
| Phe | Arg | His | Gln | Asn | Ser | Glu | Gly | Arg | Gly | Gln | Ala | Ala | Asp | Leu | Lys |
| | 370 | | | | | 375 | | | | | 380 | | | | |
| Ser | Thr | Gln | Ala | Ala | Ile | Asp | Gln | Ile | Asn | Gly | Lys | Leu | Asn | Arg | Leu |

```
                385                 390                 395                 400
        Ile Gly Lys Thr Asn Glu Lys Phe His Gln Ile Glu Lys Glu Phe Ser
                        405                 410                 415

Glu Ile Glu Gly Arg Ile Gln Asp Leu Glu Lys Tyr Ile Glu Asp Thr
                        420                 425                 430

Lys Ile Asp Leu Trp Ser Tyr Asn Ala Glu Leu Leu Ile Ala Leu Glu
                        435                 440                 445

Asn Gln His Thr Ile Asp Leu Ala Asp Ser Glu Met Asn Lys Leu Phe
                        450                 455                 460

Glu Lys Thr Lys Lys Gln Leu Arg Glu Asn Ala Glu Asp Met Gly Asn
        465                 470                 475                 480

Gly Cys Leu Lys Ile Tyr His Lys Cys Asp Asn Ala Cys Ile Gly Ser
                        485                 490                 495

Ile Arg Asn Gly Thr Tyr Asp His Asp Val Tyr Arg Asp Glu Ala Leu
                        500                 505                 510

Asn Asn Arg Phe Gln Ile Lys Gly Val Glu Leu Lys Ser Glu Tyr Lys
                        515                 520                 525

Asp Trp Ile Leu Trp Ile Ser Phe Ala Met Ser Cys Phe Leu Leu Cys
                        530                 535                 540

Val Ala Leu Leu Gly Phe Ile Met Trp Ala Cys Gln Lys Gly Asn Ile
        545                 550                 555                 560

Lys Cys Asn Ile Cys Ile
                        565

<210> SEQ ID NO 85
<211> LENGTH: 566
<212> TYPE: PRT
<213> ORGANISM: Artificial
<220> FEATURE:
<223> OTHER INFORMATION: synthetically-generated protein

<400> SEQUENCE: 85

Met Lys Ala Ile Ile Ala Phe Ser Cys Ile Leu Cys Gln Ile Ser Ala
1               5                   10                  15

Gln Lys Leu Pro Gly Ser Asp Asn Ser Met Ala Thr Leu Cys Leu Gly
                20                  25                  30

His His Ala Val Pro Asn Gly Thr Leu Val Lys Thr Ile Thr Asp Asp
            35                  40                  45

Gln Ile Glu Val Thr Asn Ala Thr Glu Leu Val Gln Ser Thr Ser Lys
        50                  55                  60

Gly Glu Ile Cys Ser Ser Pro His Gln Ile Leu Asp Gly Lys Asn Cys
65                  70                  75                  80

Thr Leu Ile Asp Ala Leu Leu Gly Asp Pro His Cys Asp Asp Phe Gln
                85                  90                  95

Asn Lys Lys Trp Asp Leu Phe Val Glu Arg Ser Thr Ala Tyr Ser Asn
                100                 105                 110

Cys Tyr Pro Tyr Tyr Val Pro Asp Tyr Ala Ser Leu Arg Ser Leu Ile
            115                 120                 125

Ala Ser Ser Gly Thr Leu Glu Phe Thr Gln Glu Ser Phe Asp Trp Thr
        130                 135                 140

Gly Val Ala Gln Asn Gly Ser Ser Tyr Ala Cys Arg Arg Gly Ser Val
145                 150                 155                 160

Lys Ser Phe Phe Ser Arg Leu Asn Trp Leu His Asn Leu Asn Tyr Lys
                165                 170                 175

Tyr Pro Ala Leu Asn Val Thr Met Pro Asn Asn Asp Asn Phe Asp Lys
```

```
                180             185             190
Leu Tyr Ile Trp Gly Val His His Pro Ser Thr Asp Ser Asp Gln Thr
            195             200             205
Ser Leu Tyr Val Gln Ala Ser Gly Arg Val Thr Val Ser Thr Lys Arg
            210             215             220
Ser Gln Gln Thr Val Ile Pro Asn Ile Gly Ser Arg Pro Trp Ile Arg
225             230             235             240
Gly Val Ser Ser Ile Ile Ser Ile Tyr Trp Thr Ile Val Lys Pro Gly
            245             250             255
Asp Ile Leu Ile Ile Asn Ser Asn Gly Asn Leu Ile Ala Pro Arg Gly
            260             265             270
Tyr Phe Lys Ile Gln Ser Gly Lys Ser Ser Ile Met Arg Ser Asp Ala
            275             280             285
Pro Ile Gly Asn Cys Asn Ser Glu Cys Ile Thr Pro Asn Gly Ser Ile
            290             295             300
Pro Asn Asp Arg Pro Phe Gln Asn Val Asn Arg Ile Thr Tyr Gly Ala
305             310             315             320
Cys Pro Arg Tyr Val Lys Gln Asn Thr Leu Lys Leu Ala Thr Gly Met
            325             330             335
Arg Asn Val Pro Glu Lys Gln Thr Arg Gly Ile Leu Gly Ala Ile Ala
            340             345             350
Gly Phe Ile Glu Asn Gly Trp Glu Gly Met Ile Asp Gly Trp Tyr Gly
            355             360             365
Phe Arg His His Asn Ser Glu Gly Thr Gly Gln Ala Ala Asp Ile Lys
            370             375             380
Ser Thr Gln Ala Ala Ile Asn Gln Ile Asn Gly Lys Leu Asn Arg Val
385             390             395             400
Ile Glu Lys Thr Asn Glu Lys Phe His Gln Ile Glu Lys Glu Phe Ser
            405             410             415
Gly Val Glu Gly Arg Ile Gln Asp Leu Glu Arg Tyr Val Glu Asp Thr
            420             425             430
Lys Ile Asp Leu Trp Ser Tyr Asn Ala Glu Leu Leu Val Ala Met Glu
            435             440             445
Asn Gln His Thr Ile Asp Leu Thr Asp Ser Glu Met Asn Lys Leu Phe
            450             455             460
Glu Arg Thr Arg Lys Gln Leu Arg Glu Asn Ala Glu Asp Met Gly Asn
465             470             475             480
Gly Cys Phe Lys Ile Tyr His Lys Cys Asp Asn Thr Cys Ile Gly Ser
            485             490             495
Ile Arg Asn Gly Thr Tyr Asn His Asp Val Tyr Arg Asp Glu Ala Val
            500             505             510
Asn Asn Arg Phe Gln Ile Lys Gly Val Gln Leu Lys Leu Gly Tyr Lys
            515             520             525
Asp Trp Ile Leu Trp Ile Ser Phe Ala Thr Ser Cys Phe Leu Leu Cys
            530             535             540
Ala Val Leu Leu Gly Phe Ile Met Trp Ala Cys Gln Lys Gly Asn Ile
545             550             555             560
Arg Cys Asn Ile Cys Ile
            565

<210> SEQ ID NO 86
<211> LENGTH: 566
<212> TYPE: PRT
<213> ORGANISM: Artificial
```

<220> FEATURE:
<223> OTHER INFORMATION: synthetically-generated protein

<400> SEQUENCE: 86

```
Met Lys Thr Ile Ile Ala Phe Ser Cys Ile Leu Cys Leu Ile Phe Ala
1               5                   10                  15

Gln Lys Leu Pro Gly Ser Asp Asn Ser Met Ala Thr Leu Cys Leu Gly
            20                  25                  30

His His Ala Val Pro Asn Gly Thr Leu Val Lys Thr Ile Thr Asp Asp
        35                  40                  45

Gln Ile Glu Val Thr Asn Ala Thr Glu Leu Val Gln Ser Ser Ser Thr
    50                  55                  60

Gly Arg Ile Cys Asn Ser Pro His Gln Ile Leu Asp Gly Lys Asn Cys
65                  70                  75                  80

Thr Leu Ile Asp Ala Leu Leu Gly Asp Pro His Cys Asp Asp Phe Gln
                85                  90                  95

Asn Lys Glu Trp Asp Leu Phe Val Glu Arg Ser Thr Ala Tyr Ser Asn
            100                 105                 110

Cys Tyr Pro Tyr Tyr Val Pro Asp Tyr Ala Ser Leu Arg Ser Leu Val
        115                 120                 125

Ala Ser Ser Gly Thr Leu Glu Phe Thr Gln Glu Ser Phe Asn Trp Thr
    130                 135                 140

Gly Val Ala Gln Asp Gly Ser Ser Tyr Ala Cys Arg Arg Gly Ser Val
145                 150                 155                 160

Asn Ser Phe Phe Ser Arg Leu Asn Trp Leu Tyr Asn Leu Asn Tyr Lys
                165                 170                 175

Tyr Pro Glu Gln Asn Val Thr Met Pro Asn Asn Asp Lys Phe Asp Lys
            180                 185                 190

Leu Tyr Ile Trp Gly Val His His Pro Gly Thr Asp Lys Asp Gln Thr
        195                 200                 205

Asn Leu Tyr Val Gln Ala Ser Gly Arg Val Ile Val Ser Thr Lys Arg
    210                 215                 220

Ser Gln Gln Thr Val Ile Pro Asn Ile Gly Ser Arg Pro Trp Val Arg
225                 230                 235                 240

Gly Val Ser Ser Ile Ile Ser Ile Tyr Trp Thr Ile Val Lys Pro Gly
                245                 250                 255

Asp Ile Leu Leu Ile Asn Ser Thr Gly Asn Leu Ile Ala Pro Arg Gly
            260                 265                 270

Tyr Phe Lys Ile Gln Ser Gly Lys Ser Ser Ile Met Arg Ser Asp Ala
        275                 280                 285

His Ile Asp Glu Cys Asn Ser Glu Cys Ile Thr Pro Asn Gly Ser Ile
    290                 295                 300

Pro Asn Asp Lys Pro Phe Gln Asn Val Asn Arg Ile Thr Tyr Gly Ala
305                 310                 315                 320

Cys Pro Arg Tyr Val Lys Gln Asn Thr Leu Lys Leu Ala Thr Gly Met
                325                 330                 335

Arg Asn Val Pro Glu Lys Gln Thr Arg Gly Ile Phe Gly Ala Ile Ala
            340                 345                 350

Gly Phe Ile Glu Asn Gly Trp Glu Gly Met Val Asp Gly Trp Tyr Gly
        355                 360                 365

Phe Arg His Gln Asn Ser Glu Gly Thr Gly Gln Ala Ala Asp Leu Lys
    370                 375                 380

Ser Thr Gln Ala Ala Ile Asn Gln Ile Thr Gly Lys Leu Asn Arg Val
385                 390                 395                 400
```

```
Ile Lys Lys Thr Asn Glu Lys Phe His Gln Ile Glu Lys Glu Phe Ser
            405                 410                 415

Glu Val Glu Gly Arg Ile Gln Asp Leu Glu Lys Tyr Val Glu Asp Thr
            420                 425                 430

Lys Ile Asp Leu Trp Ser Tyr Asn Ala Glu Leu Leu Val Ala Leu Glu
            435                 440                 445

Asn Gln His Thr Ile Asp Leu Thr Asp Ser Glu Met Asn Lys Leu Phe
450                 455                 460

Glu Arg Thr Arg Lys Gln Leu Arg Glu Asn Ala Glu Asp Met Gly Asn
465                 470                 475                 480

Gly Cys Phe Lys Ile Tyr His Lys Cys Asp Asn Ala Cys Ile Gly Ser
            485                 490                 495

Ile Arg Asn Gly Thr Tyr Asp His Asp Val Tyr Arg Asp Glu Ala Leu
            500                 505                 510

Asn Asn Arg Phe Gln Ile Lys Gly Val Gln Leu Lys Ser Gly Tyr Lys
            515                 520                 525

Asp Trp Ile Leu Trp Ile Ser Phe Ala Ile Ser Cys Phe Leu Leu Cys
            530                 535                 540

Val Val Leu Leu Gly Phe Ile Met Trp Ala Cys Gln Lys Gly Asn Ile
545                 550                 555                 560

Arg Cys Asn Ile Cys Ile
                565

<210> SEQ ID NO 87
<211> LENGTH: 566
<212> TYPE: PRT
<213> ORGANISM: Artificial
<220> FEATURE:
<223> OTHER INFORMATION: synthetically-generated protein

<400> SEQUENCE: 87

Met Lys Thr Ile Ile Ala Leu Ser Tyr Ile Leu Cys Leu Val Phe Ala
1               5                   10                  15

Gln Lys Leu Pro Gly Asn Asp Asn Met Ala Thr Leu Cys Leu Gly
            20                  25                  30

His His Ala Val Pro Asn Gly Thr Ile Val Lys Thr Ile Thr Asn Asp
            35                  40                  45

Gln Ile Glu Val Thr Asn Ala Thr Glu Leu Val Gln Ser Thr Ser Lys
            50                  55                  60

Gly Glu Ile Cys Ser Ser Pro His Gln Ile Leu Asp Gly Glu Asn Cys
65                  70                  75                  80

Thr Leu Ile Asp Ala Leu Leu Gly Asp Pro His Cys Asp Asp Phe Gln
            85                  90                  95

Asn Lys Lys Trp Asp Leu Phe Val Glu Arg Ser Lys Ala His Ser Asn
            100                 105                 110

Cys Tyr Pro Tyr Val Pro Asp Tyr Ala Thr Leu Arg Ser Leu Val
            115                 120                 125

Ala Ser Ser Gly Asn Leu Glu Phe Thr Gln Glu Ser Phe Asn Trp Thr
            130                 135                 140

Gly Val Thr Gln Asp Gly Ala Ser Ser Ala Cys Lys Arg Arg Ser Ser
145                 150                 155                 160

Lys Ser Phe Phe Ser Arg Leu Asn Trp Leu His Asn Leu Asn Tyr Lys
            165                 170                 175

Tyr Pro Ala Leu Asn Val Thr Met Pro Asn Asn Asp Asn Phe Asp Lys
            180                 185                 190
```

```
Leu Tyr Ile Trp Gly Val His His Pro Ser Thr Asp Lys Asp Gln Thr
            195                 200                 205

Ser Leu Tyr Ile Gln Ala Ser Gly Arg Val Thr Val Ser Thr Lys Arg
210                 215                 220

Ser Gln Gln Ala Val Ile Pro Asn Ile Gly Ser Arg Pro Arg Val Arg
225                 230                 235                 240

Asp Ile Pro Ser Arg Ile Ser Ile Tyr Trp Thr Ile Val Arg Pro Gly
                245                 250                 255

Asp Ile Leu Leu Ile Asn Ser Asn Gly Asn Leu Ile Ala Pro Arg Gly
                260                 265                 270

Tyr Phe Lys Ile Arg Ser Gly Lys Ser Ser Ile Met Arg Ser Asp Ala
            275                 280                 285

Pro Ile Gly Asn Cys Asn Ser Glu Cys Ile Thr Pro Asn Gly Ser Ile
290                 295                 300

Ser Asn Asp Lys Pro Phe Gln Asn Val Asn Lys Ile Thr Tyr Gly Ala
305                 310                 315                 320

Cys Pro Arg Tyr Ile Lys Gln Asn Thr Leu Lys Leu Ala Thr Gly Met
                325                 330                 335

Arg Asn Ile Pro Glu Lys Gln Thr Arg Gly Ile Phe Gly Ala Lys Ala
                340                 345                 350

Gly Phe Ile Glu Asn Gly Trp Glu Gly Met Val Asn Gly Trp Tyr Gly
            355                 360                 365

Phe Arg His Gln Asn Ser Glu Gly Arg Gly Gln Ala Ala Asp Leu Lys
370                 375                 380

Ser Thr Gln Ala Ala Ile Asp Gln Ile Asn Gly Lys Leu Asn Arg Leu
385                 390                 395                 400

Ile Gly Lys Thr Asn Glu Lys Phe His Gln Ile Glu Lys Glu Phe Ser
                405                 410                 415

Glu Ile Glu Gly Arg Ile Gln Asp Leu Glu Arg Tyr Val Glu Asp Thr
            420                 425                 430

Lys Ile Asp Ile Trp Ser Tyr Asn Ala Glu Leu Leu Val Ala Met Glu
            435                 440                 445

Asn Gln His Thr Ile Asp Leu Thr Asp Ser Glu Met Ser Lys Leu Phe
            450                 455                 460

Glu Arg Thr Arg Arg Gln Leu Arg Glu Asn Ala Glu Asp Met Gly Asn
465                 470                 475                 480

Gly Cys Leu Lys Ile Tyr His Lys Cys Asp Asn Ser Cys Met Glu Ser
                485                 490                 495

Ile Arg Asn Gly Thr Tyr Asp His Asp Ile Tyr Arg Asn Glu Ala Leu
            500                 505                 510

Asn Asn Arg Phe Gln Ile Lys Gly Val Glu Leu Lys Ser Glu Tyr Lys
            515                 520                 525

Asp Trp Ile Leu Trp Ile Ser Phe Ala Thr Ser Cys Phe Leu Leu Cys
530                 535                 540

Ala Val Leu Leu Gly Phe Ile Met Trp Ala Cys Gln Lys Gly Asn Ile
545                 550                 555                 560

Lys Cys Asn Ile Cys Ile
                565

<210> SEQ ID NO 88
<211> LENGTH: 566
<212> TYPE: PRT
<213> ORGANISM: Artificial
<220> FEATURE:
```

<223> OTHER INFORMATION: synthetically-generated protein

<400> SEQUENCE: 88

```
Met Lys Ala Ile Ile Ala Phe Ser Cys Ile Leu Cys Gln Ile Phe Ala
1               5                   10                  15

Gln Lys Leu Pro Gly Asn Asp Asn Ser Thr Ala Thr Leu Cys Leu Gly
            20                  25                  30

His His Ala Val Ser Asn Gly Thr Leu Val Lys Thr Ile Thr Asp Asp
        35                  40                  45

Gln Val Glu Val Thr Asn Ala Thr Glu Leu Val Gln Asn Phe Ser Met
    50                  55                  60

Gly Lys Ile Cys Lys Asn Pro His Arg Ile Leu Asp Gly Ala Asn Cys
65                  70                  75                  80

Thr Leu Ile Asp Ser Leu Leu Gly Asp Pro His Cys Asp Gly Phe Gln
                85                  90                  95

Asn Glu Lys Trp Asp Leu Phe Ile Glu Arg Ser Lys Ala Phe Ser Asn
            100                 105                 110

Cys Tyr Pro Tyr Asp Val Pro Asp Tyr Ala Ser Leu Arg Ser Leu Ile
        115                 120                 125

Ala Ser Ser Gly Thr Leu Glu Phe Asn Asn Glu Ser Phe Asn Trp Thr
    130                 135                 140

Gly Val Thr Gln Asn Gly Gly Ser Ser Ala Cys Lys Arg Gly Pro Asn
145                 150                 155                 160

Asn Ser Phe Phe Ser Arg Leu Asn Trp Leu Thr His Leu Asn Phe Lys
                165                 170                 175

Tyr Pro Ala Leu Glu Val Thr Met Pro Asn Asn Glu Gln Phe Asp Lys
            180                 185                 190

Leu Tyr Ile Trp Gly Val His His Pro Ala Thr Asp Lys Asp Gln Ile
        195                 200                 205

Ser Leu Tyr Ala Gln Ala Ala Gly Arg Ile Ile Val Ser Thr Lys Arg
    210                 215                 220

Ser Gln Gln Thr Ile Ile Pro Asn Ile Gly Ser Arg Pro Trp Ile Arg
225                 230                 235                 240

Gly Val Ser Ser Ile Ile Ser Ile His Trp Thr Ile Val Lys Pro Gly
                245                 250                 255

Asp Met Leu Leu Ile Asn Ser Thr Gly Asn Ile Ile Ala Pro Arg Gly
            260                 265                 270

Tyr Phe Lys Ile Gln Thr Gly Lys Ser Ser Val Met Arg Ser Asp Ala
        275                 280                 285

Pro Ile Gly Lys Cys Asn Ser Ala Cys Ile Thr Pro Asn Gly Ser Ile
    290                 295                 300

Pro Asn Asp Arg Pro Phe Gln Asn Val Asn Lys Ile Thr Tyr Gly Ala
305                 310                 315                 320

Cys Pro Lys Tyr Val Lys Gln Asn Thr Leu Lys Leu Ala Thr Gly Met
                325                 330                 335

Arg Asn Ile Pro Glu Arg Gln Thr Arg Gly Ile Phe Gly Ala Ile Ala
            340                 345                 350

Gly Phe Ile Glu Asn Gly Trp Glu Gly Met Ile Asp Gly Trp Tyr Gly
        355                 360                 365

Phe Arg His His Asn Ser Glu Gly Thr Gly Gln Ala Ala Asp Ile Lys
    370                 375                 380

Ser Thr Gln Ala Ala Ile Asn Gln Ile Asn Gly Lys Leu Asn Arg Val
385                 390                 395                 400
```

```
Ile Glu Lys Thr Asn Glu Lys Phe His Gln Ile Lys Glu Phe Leu
                405                 410                 415

Glu Val Glu Gly Arg Ile Gln Asp Ile Glu Lys Tyr Ile Glu Asp Thr
            420                 425                 430

Lys Ile Asp Leu Trp Ser Tyr Asn Ala Glu Leu Leu Ile Ala Leu Glu
        435                 440                 445

Asn Gln His Thr Ile Asp Leu Ala Asp Ser Glu Met Asn Lys Leu Phe
    450                 455                 460

Glu Lys Thr Lys Lys Gln Leu Arg Glu Asn Ala Glu Asp Ile Gly Asn
465                 470                 475                 480

Gly Cys Phe Lys Ile Tyr His Lys Cys Asp Asn Thr Cys Ile Gly Ser
                485                 490                 495

Ile Arg Asn Gly Thr Tyr Asn His Asp Val Tyr Arg Asp Glu Ala Val
            500                 505                 510

Asn Asn Arg Phe Gln Ile Lys Gly Val Gln Leu Lys Leu Gly Tyr Lys
        515                 520                 525

Asp Trp Ile Leu Trp Ile Ser Phe Ala Met Ser Cys Phe Leu Leu Cys
    530                 535                 540

Val Ala Leu Leu Gly Phe Ile Met Trp Ala Cys Gln Arg Gly Asn Ile
545                 550                 555                 560

Arg Cys Asn Ile Cys Val
                565

<210> SEQ ID NO 89
<211> LENGTH: 465
<212> TYPE: PRT
<213> ORGANISM: Artificial
<220> FEATURE:
<223> OTHER INFORMATION: synthetically-generated protein

<400> SEQUENCE: 89

Met Asn Thr Asn Gln Arg Ile Ile Thr Ile Gly Thr Val Cys Met Ile
1               5                   10                  15

Val Gly Ile Ile Ser Leu Leu Leu Gln Ile Gly Asn Ile Val Ser Leu
            20                  25                  30

Trp Ile Ser His Ser Ile Gln Thr Gly Asn Glu Asn His Thr His Glu
        35                  40                  45

Cys Asn Gln Ser Val Ile Thr Tyr Glu Asn Asn Thr Trp Val Asn Gln
    50                  55                  60

Thr Tyr Val Asn Ile Ser Asn Thr Asn Ile Ala Gln Val Thr Ser Val
65                  70                  75                  80

Thr Ser Ile Ile Leu Ala Gly Asn Ser Ser Leu Cys Pro Val Ser Gly
                85                  90                  95

Trp Ala Ile Tyr Ser Lys Asp Asn Ser Ile Arg Ile Gly Ser Lys Gly
            100                 105                 110

Asp Ile Phe Val Ile Arg Glu Pro Phe Ile Ser Cys Ser Leu Glu Cys
        115                 120                 125

Arg Thr Phe Phe Leu Thr Gln Gly Ala Leu Leu Asn Asp Lys His Ser
    130                 135                 140

Asn Gly Thr Val Lys Asp Arg Ser Pro Tyr Arg Thr Leu Met Ser Cys
145                 150                 155                 160

Pro Ile Gly Glu Ala Pro Ser Pro Tyr Asn Ser Arg Phe Glu Ser Val
                165                 170                 175

Ala Trp Ser Ala Ser Ala Cys His Asp Gly Met Gly Trp Leu Thr Ile
            180                 185                 190
```

```
Gly Ile Ser Gly Pro Asp Asn Gly Ala Val Ala Val Leu Lys Tyr Asn
            195                 200                 205

Gly Ile Ile Thr Asp Thr Ile Lys Ser Trp Arg Asn Ile Leu Arg Thr
            210                 215                 220

Gln Glu Ser Glu Cys Val Cys Asn Gly Ser Cys Phe Thr Val Met Thr
225                 230                 235                 240

Asp Gly Pro Ser Asn Gly Gln Ala Ser Tyr Lys Ile Phe Lys Glu Lys
                245                 250                 255

Gly Lys Ile Ile Lys Ser Val Glu Leu Asp Ala Pro Asn Tyr His Tyr
            260                 265                 270

Glu Glu Cys Ser Cys Tyr Pro Asp Thr Gly Lys Val Val Cys Val Cys
            275                 280                 285

Arg Asp Asn Trp His Ala Ser Asn Arg Pro Trp Val Ser Phe Asn Gln
            290                 295                 300

Asn Leu Asp Tyr Gln Ile Gly Tyr Ile Cys Ser Gly Val Phe Gly Asp
305                 310                 315                 320

Asn Pro Arg Ser Asn Asp Gly Lys Gly Asn Cys Gly Pro Val Leu Ser
                325                 330                 335

Asn Gly Ala Asn Gly Val Lys Gly Phe Ser Phe Arg Tyr Gly Asn Gly
            340                 345                 350

Val Trp Ile Gly Arg Thr Lys Ser Ile Ser Arg Ser Gly Phe Glu
            355                 360                 365

Met Ile Trp Asp Pro Asn Gly Trp Thr Glu Thr Asp Ser Ser Phe Ser
            370                 375                 380

Ile Lys Gln Asp Ile Ile Ala Leu Asn Asp Trp Ser Gly Tyr Ser Gly
385                 390                 395                 400

Ser Phe Val Gln His Pro Glu Leu Thr Gly Met Asn Cys Ile Arg Pro
                405                 410                 415

Cys Phe Trp Val Glu Leu Ile Arg Gly Gln Pro Lys Glu Asn Thr Ile
            420                 425                 430

Trp Thr Ser Gly Ser Ser Ile Ser Phe Cys Gly Val Asn Ser Glu Thr
            435                 440                 445

Ala Ser Trp Ser Trp Pro Asp Gly Ala Asp Leu Pro Phe Thr Ile Asp
450                 455                 460

Lys
465

<210> SEQ ID NO 90
<211> LENGTH: 469
<212> TYPE: PRT
<213> ORGANISM: Artificial
<220> FEATURE:
<223> OTHER INFORMATION: synthetically-generated protein

<400> SEQUENCE: 90

Met Asn Thr Asn Gln Arg Ile Ile Thr Ile Gly Thr Val Cys Met Ile
1               5                   10                  15

Val Gly Ile Ile Ser Leu Leu Leu Gln Ile Gly Asn Ile Val Ser Leu
            20                  25                  30

Trp Ile Ser His Ser Ile Gln Thr Gly Trp Glu Asn His Thr Glu Met
            35                  40                  45

Cys Asn Gln Ser Val Ile Thr Tyr Val Asn Asn Thr Trp Val Asn Arg
        50                  55                  60

Thr Tyr Val Asn Ile Ser Asn Ile Lys Ile Ala Thr Ile Gln Asp Val
65                  70                  75                  80
```

Thr Ser Ile Ile Leu Ala Gly Asn Ser Ser Leu Cys Pro Val Ser Gly
                85                  90                  95

Trp Ala Val Tyr Ser Lys Asp Asn Ser Ile Arg Ile Gly Ser Lys Gly
            100                 105                 110

Asp Val Phe Val Met Arg Glu Pro Phe Ile Ser Cys Ser Gln Leu Glu
        115                 120                 125

Cys Arg Thr Phe Phe Leu Thr Gln Gly Ala Leu Leu Asn Asp Lys His
    130                 135                 140

Ser Asn Gly Thr Val Lys Asp Arg Ser Pro His Arg Thr Leu Met Ser
145                 150                 155                 160

Cys Pro Val Gly Glu Val Pro Ser Pro Tyr Asn Ser Lys Phe Glu Ser
                165                 170                 175

Val Ala Trp Ser Ala Ser Ala Cys His Asp Gly Met Gly Trp Leu Thr
            180                 185                 190

Ile Gly Ile Ser Gly Pro Asp Asp Gly Ala Val Ala Val Leu Lys Tyr
        195                 200                 205

Asn Gly Ile Ile Thr Asp Thr Ile Lys Ser Trp Arg Asn Lys Ile Leu
    210                 215                 220

Arg Thr Gln Glu Ser Glu Cys Val Cys Met Asn Gly Ser Cys Phe Thr
225                 230                 235                 240

Val Leu Thr Asp Gly Pro Ser Asn Gly Gln Ala Ser Tyr Lys Ile Phe
                245                 250                 255

Lys Val Glu Lys Gly Lys Ile Ile Lys Ser Ile Glu Leu Asp Ala Pro
            260                 265                 270

Asn Tyr His Tyr Glu Glu Cys Ser Cys Tyr Pro Asp Thr Gly Lys Val
        275                 280                 285

Met Cys Val Cys Arg Asp Asn Trp His Ala Ser Asn Arg Pro Trp Val
    290                 295                 300

Ser Phe Asn Gln Asn Leu Asp Tyr Gln Ile Gly Tyr Ile Cys Ser Gly
305                 310                 315                 320

Val Phe Gly Asp Asn Pro Arg Ser Asn Asp Gly Lys Gly Asn Cys Gly
                325                 330                 335

Pro Val Leu Ser Asn Gly Ala Asn Gly Val Lys Gly Phe Ser Tyr Arg
            340                 345                 350

Tyr Gly Asn Gly Val Trp Ile Gly Arg Thr Lys Ser Ile Asn Ser Arg
        355                 360                 365

Ser Gly Phe Glu Met Ile Trp Asp Pro Asn Gly Trp Thr Glu Thr Asp
    370                 375                 380

Ser Ser Phe Ser Met Lys Gln Asp Ile Ile Ala Leu Asn Asp Trp Ser
385                 390                 395                 400

Gly Tyr Ser Gly Ser Phe Val Gln His Pro Glu Leu Thr Gly Met Asn
                405                 410                 415

Cys Ile Arg Pro Cys Phe Trp Val Glu Leu Ile Arg Gly Gln Pro Lys
            420                 425                 430

Glu Ser Thr Ile Trp Ala Ser Gly Ser Ser Ile Ser Phe Cys Gly Val
        435                 440                 445

Asn Ser Glu Thr Ala Ser Trp Ser Trp Pro Asp Gly Ala Asn Leu Pro
    450                 455                 460

Phe Thr Ile Asp Lys
465

<210> SEQ ID NO 91
<211> LENGTH: 469
<212> TYPE: PRT

<213> ORGANISM: Artificial
<220> FEATURE:
<223> OTHER INFORMATION: synthetically-generated protein

<400> SEQUENCE: 91

```
Met Asn Thr Asn Gln Lys Ile Ile Thr Ile Gly Ser Val Cys Met Thr
1               5                   10                  15

Ile Gly Met Ala Asn Leu Ile Leu Gln Ile Gly Asn Ile Ile Ser Ile
            20                  25                  30

Trp Ile Ser His Ser Ile Gln Leu Gly Asn Gln Asn Gln Ile Glu Thr
        35                  40                  45

Cys Asn Gln Ser Val Ile Thr Tyr Glu Asn Asn Thr Trp Val Asn Gln
50                  55                  60

Thr Tyr Val Asn Ile Ser Asn Thr Asn Phe Ala Ala Gly Gln Ser Val
65                  70                  75                  80

Val Ser Val Lys Leu Ala Gly Asn Ser Ser Leu Cys Pro Val Ser Gly
                85                  90                  95

Trp Ala Ile Tyr Ser Lys Asp Asn Ser Val Arg Ile Gly Ser Lys Gly
            100                 105                 110

Asp Val Phe Val Ile Arg Glu Pro Phe Ile Ser Cys Ser Pro Leu Glu
        115                 120                 125

Cys Arg Thr Phe Phe Leu Thr Gln Gly Thr Leu Leu Asn Asp Lys His
130                 135                 140

Ser Asn Gly Thr Ile Lys Asp Arg Ser Pro Tyr Arg Thr Leu Met Ser
145                 150                 155                 160

Cys Pro Ile Gly Glu Val Pro Ser Pro Tyr Asn Ser Arg Phe Glu Ser
                165                 170                 175

Val Ala Trp Ser Ala Ser Ala Cys His Asp Gly Ile Asn Trp Leu Thr
            180                 185                 190

Ile Gly Ile Ser Gly Pro Asp Ser Gly Ala Val Ala Val Leu Lys Tyr
        195                 200                 205

Asn Gly Val Ile Thr Asp Thr Ile Lys Ser Trp Arg Asn Asn Ile Leu
210                 215                 220

Arg Thr Gln Glu Ser Glu Cys Val Cys Ile Asn Gly Ser Cys Phe Thr
225                 230                 235                 240

Ile Met Thr Asp Gly Pro Ser Asp Gly Gln Ala Ser Tyr Lys Ile Phe
                245                 250                 255

Arg Ile Glu Lys Gly Lys Ile Val Lys Ser Val Glu Met Asn Ala Pro
            260                 265                 270

Asn Tyr His Tyr Glu Glu Cys Ser Cys Tyr Pro Asp Ser Ser Glu Ile
        275                 280                 285

Thr Cys Val Cys Arg Asp Asn Trp His Ala Ser Asn Arg Pro Trp Val
290                 295                 300

Ser Phe Asp Gln Asn Leu Asp Tyr Gln Ile Gly Tyr Ile Cys Ser Gly
305                 310                 315                 320

Ile Phe Gly Asp Asn Pro Arg Pro Asn Asp Lys Thr Gly Ser Cys Gly
                325                 330                 335

Pro Val Ser Ser Asn Gly Ala Asn Gly Val Lys Gly Phe Ser Phe Arg
            340                 345                 350

Tyr Gly Asn Gly Val Trp Ile Gly Arg Thr Lys Ser Ile Ser Ser Arg
        355                 360                 365

Asn Gly Phe Glu Met Ile Trp Asp Pro Asn Gly Trp Thr Gly Thr Asp
370                 375                 380

Asn Asn Phe Ser Ile Lys Gln Asp Ile Val Gly Ile Asn Glu Trp Ser
```

```
385                 390                 395                 400
Gly Tyr Ser Gly Ser Phe Val Gln His Pro Glu Leu Thr Gly Leu Asp
                405                 410                 415

Cys Ile Arg Pro Cys Phe Trp Val Glu Leu Ile Arg Gly Arg Pro Lys
                420                 425                 430

Glu Asn Thr Ile Trp Thr Ser Gly Ser Ile Ser Phe Cys Gly Val
                435                 440                 445

Asn Ser Asp Thr Val Gly Trp Ser Trp Pro Asp Gly Ala Glu Leu Pro
450                 455                 460

Phe Thr Ile Asp Lys
465

<210> SEQ ID NO 92
<211> LENGTH: 469
<212> TYPE: PRT
<213> ORGANISM: Artificial
<220> FEATURE:
<223> OTHER INFORMATION: synthetically-generated protein

<400> SEQUENCE: 92

Met Asn Pro Asn Gln Lys Ile Ile Thr Ile Gly Ser Ile Cys Met Thr
1               5                   10                  15

Ile Gly Ile Ala Ser Leu Ile Leu Gln Ile Gly Asn Ile Val Ser Leu
                20                  25                  30

Trp Val Ser His Ser Ile Gln Thr Arg Trp Glu Asn His Thr Glu Val
                35                  40                  45

Cys Asn Gln Asn Val Ile Thr Tyr Val Asn Asn Thr Leu Val Asn Arg
50                  55                  60

Thr Tyr Val Asn Ile Ser Asn Thr Asn Ile Ala Thr Ile Gln Asp Val
65                  70                  75                  80

Thr Ser Ile Met Leu Ala Gly Asn Ser Ser Leu Cys Pro Ile Ser Gly
                85                  90                  95

Trp Ala Ile Tyr Ser Lys Asp Asn Ser Ile Arg Ile Gly Ser Lys Gly
                100                 105                 110

Asp Ile Phe Val Ile Arg Glu Pro Phe Ile Ser Cys Ser His Leu Glu
                115                 120                 125

Cys Arg Thr Phe Phe Leu Thr Gln Gly Ala Leu Leu Asn Asp Arg His
                130                 135                 140

Ser Asn Gly Thr Val Lys Asp Arg Ser Pro Tyr Arg Thr Leu Met Ser
145                 150                 155                 160

Cys Pro Ile Gly Glu Ala Pro Ser Pro Tyr Asn Ser Arg Phe Glu Ser
                165                 170                 175

Val Ala Trp Ser Ala Ser Ala Cys His Asp Gly Thr Ser Trp Leu Thr
                180                 185                 190

Ile Gly Ile Ser Gly Pro Asp Asn Gly Ala Val Ala Val Leu Lys Tyr
                195                 200                 205

Asn Asp Ile Ile Thr Asp Thr Ile Lys Ser Trp Arg Lys Asn Ile Leu
                210                 215                 220

Arg Thr Gln Glu Ser Glu Cys Ala Cys Val Asn Gly Ser Cys Phe Thr
225                 230                 235                 240

Val Met Thr Asp Gly Pro Ser Asn Gly Gln Ala Ser Tyr Lys Ile Phe
                245                 250                 255

Lys Ile Glu Lys Gly Lys Val Val Lys Ser Val Glu Leu Asn Ala Pro
                260                 265                 270

Asn Tyr His Tyr Glu Glu Cys Ser Cys Tyr Pro Asp Thr Gly Lys Val
```

```
                275                 280                 285
Val Cys Val Cys Arg Asp Asn Trp His Gly Ser Asn Arg Pro Trp Val
290                 295                 300

Ser Phe Asn Gln Asn Leu Glu Tyr Gln Ile Gly Tyr Ile Cys Ser Gly
305                 310                 315                 320

Val Leu Gly Asp Asn Pro Arg Pro Asn Asp Arg Thr Gly Ser Cys Gly
                325                 330                 335

Pro Val Phe Ser Asn Gly Ala Asn Gly Val Lys Gly Phe Ser Phe Lys
                340                 345                 350

Tyr Gly Asn Gly Val Trp Ile Gly Arg Thr Lys Ser Thr Ser Ser Arg
                355                 360                 365

Ser Gly Phe Glu Met Ile Trp Asp Pro Asp Gly Trp Thr Arg Thr Asp
                370                 375                 380

Asp Lys Phe Ser Val Lys Gln Asp Ile Ile Ala Leu Thr Asp Trp Ser
385                 390                 395                 400

Gly Tyr Ser Gly Ser Phe Val Gln His Pro Glu Leu Thr Gly Leu Asp
                405                 410                 415

Cys Met Arg Pro Cys Phe Trp Val Glu Leu Ile Arg Gly Gln Pro Lys
                420                 425                 430

Glu Asn Thr Ile Trp Ala Ser Gly Ser Ser Ile Ser Phe Cys Gly Val
                435                 440                 445

Asp Ser Glu Thr Ala Ser Trp Ser Trp Pro Asp Gly Ala Asp Leu Pro
450                 455                 460

Phe Thr Ile Asp Lys
465

<210> SEQ ID NO 93
<211> LENGTH: 469
<212> TYPE: PRT
<213> ORGANISM: Artificial
<220> FEATURE:
<223> OTHER INFORMATION: synthetically-generated protein

<400> SEQUENCE: 93

Met Asn Thr Asn Gln Arg Ile Ile Thr Ile Gly Thr Val Cys Met Ile
1               5                   10                  15

Val Gly Ile Ile Ser Leu Leu Gln Ile Gly Asn Ile Val Ser Leu
                20                  25                  30

Trp Ile Ser His Ser Ile Gln Thr Gly Trp Glu Asn His Thr Glu Met
                35                  40                  45

Cys Asn Gln Ser Val Ile Thr Tyr Glu Asn Asn Thr Trp Val Asn Gln
50                  55                  60

Thr Tyr Val Asn Ile Ser Asn Ile Lys Ile Ala Thr Ile Gln Asp Val
65                  70                  75                  80

Thr Ser Ile Ile Leu Ala Gly Asn Ser Ser Leu Cys Pro Val Ser Gly
                85                  90                  95

Trp Ala Ile Tyr Ser Lys Asp Asn Ser Ile Arg Ile Gly Ser Lys Gly
                100                 105                 110

Asp Ile Phe Val Ile Arg Glu Pro Phe Ile Ser Cys Ser Gln Leu Glu
                115                 120                 125

Cys Arg Thr Phe Phe Leu Thr Gln Gly Ala Leu Leu Asn Asp Lys His
                130                 135                 140

Ser Asn Gly Thr Val Lys Asp Arg Ser Pro Tyr Arg Thr Leu Met Ser
145                 150                 155                 160

Cys Pro Ile Gly Glu Ala Pro Ser Pro Tyr Asn Ser Arg Phe Glu Ser
```

-continued

```
                165                 170                 175
Val Ala Trp Ser Ala Ser Ala Cys His Asp Gly Met Gly Trp Leu Thr
            180                 185                 190
Ile Gly Ile Ser Gly Pro Asp Asn Gly Ala Val Ala Val Leu Lys Tyr
        195                 200                 205
Asn Gly Ile Ile Thr Asp Thr Ile Lys Ser Trp Arg Asn Lys Ile Leu
    210                 215                 220
Arg Thr Gln Glu Ser Glu Cys Val Cys Met Asn Gly Ser Cys Phe Thr
225                 230                 235                 240
Val Leu Thr Asp Gly Pro Ser Asn Gly Gln Ala Ser Tyr Lys Ile Phe
                245                 250                 255
Lys Val Glu Lys Gly Lys Ile Ile Lys Ser Ile Glu Leu Asp Ala Pro
            260                 265                 270
Asn Tyr His Tyr Glu Glu Cys Ser Cys Tyr Pro Asp Thr Gly Lys Val
        275                 280                 285
Met Cys Val Cys Arg Asp Asn Trp His Ala Ser Asn Arg Pro Trp Val
    290                 295                 300
Ser Phe Asn Gln Asn Leu Asp Tyr Gln Ile Gly Tyr Ile Cys Ser Gly
305                 310                 315                 320
Val Phe Gly Asp Asn Pro Arg Ser Asn Asp Gly Lys Gly Asn Cys Gly
                325                 330                 335
Pro Val Leu Ser Asn Gly Ala Asn Gly Val Lys Gly Phe Ser Tyr Arg
            340                 345                 350
Tyr Gly Asn Gly Val Trp Ile Gly Arg Thr Lys Ser Ile Asn Ser Arg
        355                 360                 365
Ser Gly Phe Glu Met Ile Trp Asp Pro Asn Gly Trp Thr Glu Thr Asp
    370                 375                 380
Ser Ser Phe Ser Met Lys Gln Asp Ile Ile Ala Leu Thr Asp Trp Ser
385                 390                 395                 400
Gly Tyr Ser Gly Ser Phe Val Gln His Pro Glu Leu Thr Gly Met Asn
                405                 410                 415
Cys Ile Arg Pro Cys Phe Trp Val Glu Leu Ile Arg Gly Gln Pro Lys
            420                 425                 430
Glu Ser Thr Ile Trp Ala Ser Gly Ser Ser Ile Ser Phe Cys Gly Val
        435                 440                 445
Asn Ser Glu Thr Ala Ser Trp Ser Trp Pro Asp Gly Ala Asp Leu Pro
    450                 455                 460
Phe Thr Ile Asp Lys
465

<210> SEQ ID NO 94
<211> LENGTH: 469
<212> TYPE: PRT
<213> ORGANISM: Artificial
<220> FEATURE:
<223> OTHER INFORMATION: synthetically-generated protein

<400> SEQUENCE: 94

Met Asn Pro Asn Gln Lys Ile Ile Thr Ile Gly Ser Val Cys Met Thr
1               5                   10                  15
Ile Gly Met Ala Asn Leu Ile Leu Gln Ile Gly Asn Ile Ile Ser Ile
                20                  25                  30
Trp Ile Ser His Ser Ile Gln Leu Gly Asn Gln Asn Gln Ile Glu Thr
            35                  40                  45
Cys Asn Gln Ser Val Ile Thr Tyr Val Asn Asn Thr Trp Val Asn Arg
```

```
            50                  55                  60
Thr Tyr Val Asn Ile Ser Asn Thr Asn Phe Ala Ala Gly Gln Ser Val
 65                  70                  75                  80

Val Ser Val Lys Leu Ala Gly Asn Ser Ser Leu Cys Pro Ile Ser Gly
                 85                  90                  95

Trp Ala Ile Tyr Ser Lys Asp Asn Ser Val Arg Ile Gly Ser Lys Gly
                100                 105                 110

Asp Val Phe Val Ile Arg Glu Pro Phe Ile Ser Cys Ser His Leu Glu
                115                 120                 125

Cys Arg Thr Phe Phe Leu Thr Gln Gly Ser Leu Leu Asn Asp Lys His
                130                 135                 140

Ser Asn Gly Thr Ile Lys Asp Arg Ser Pro Tyr Arg Thr Leu Met Ser
145                 150                 155                 160

Cys Pro Ile Gly Glu Val Pro Ser Pro Tyr Asn Ser Arg Phe Glu Thr
                165                 170                 175

Val Ala Trp Ser Ala Ser Ala Cys His Asp Gly Ile Asn Trp Leu Thr
                180                 185                 190

Ile Gly Ile Ser Gly Pro Asp Ser Gly Ala Val Ala Val Leu Lys Tyr
                195                 200                 205

Asn Asp Ile Ile Thr Asp Thr Ile Lys Ser Trp Arg Asn Asn Ile Leu
210                 215                 220

Arg Thr Gln Glu Ser Glu Cys Ala Cys Val Asn Gly Ser Cys Phe Thr
225                 230                 235                 240

Val Met Thr Asp Gly Pro Ser Asp Gly Gln Ala Ser Tyr Lys Ile Phe
                245                 250                 255

Arg Ile Glu Lys Gly Lys Ile Val Lys Ser Val Glu Met Asn Ala Pro
                260                 265                 270

Asn Tyr His Tyr Glu Glu Cys Ser Cys Tyr Pro Asp Ser Ser Glu Ile
                275                 280                 285

Thr Cys Val Cys Arg Asp Asn Trp His Gly Ser Asn Arg Pro Trp Val
                290                 295                 300

Ser Phe Asn Gln Asn Leu Glu Tyr Gln Ile Gly Tyr Ile Cys Ser Gly
305                 310                 315                 320

Ile Phe Gly Asp Asn Pro Arg Pro Asn Asp Lys Thr Gly Ser Cys Gly
                325                 330                 335

Pro Val Ser Ser Asn Gly Ala Asn Gly Val Lys Gly Phe Ser Phe Lys
                340                 345                 350

Tyr Gly Asn Gly Val Trp Ile Gly Arg Thr Lys Ser Ile Ser Ser Arg
                355                 360                 365

Asn Gly Phe Glu Met Ile Trp Asp Pro Asn Gly Trp Thr Gly Thr Asp
370                 375                 380

Asn Asn Phe Ser Ile Lys Gln Asp Ile Ile Ala Leu Asn Asp Trp Ser
385                 390                 395                 400

Gly Tyr Ser Gly Ser Phe Val Gln His Pro Glu Leu Thr Gly Leu Asp
                405                 410                 415

Cys Ile Arg Pro Cys Phe Trp Val Glu Leu Ile Arg Gly Arg Pro Lys
                420                 425                 430

Glu Asn Thr Ile Trp Thr Ser Gly Ser Ser Ile Ser Phe Cys Gly Val
                435                 440                 445

Asn Ser Asp Thr Val Gly Trp Ser Trp Pro Asp Gly Ala Glu Leu Pro
450                 455                 460

Phe Thr Ile Asp Lys
465
```

<210> SEQ ID NO 95
<211> LENGTH: 469
<212> TYPE: PRT
<213> ORGANISM: Artificial
<220> FEATURE:
<223> OTHER INFORMATION: synthetically-generated protein

<400> SEQUENCE: 95

Met Asn Thr Asn Gln Lys Ile Ile Thr Ile Gly Ser Ile Cys Met Thr
1               5                   10                  15

Ile Gly Ile Ala Ser Leu Ile Leu Gln Ile Gly Asn Ile Ile Ser Ile
                20                  25                  30

Trp Val Ser His Ser Ile Gln Thr Arg Trp Glu Asn His Thr Glu Val
            35                  40                  45

Cys Asn Gln Asn Val Ile Thr Tyr Val Asn Asn Thr Trp Val Asn Gln
        50                  55                  60

Thr Tyr Val Asn Ile Ser Asn Thr Asn Ile Ala Thr Ile Gln Asp Val
65                  70                  75                  80

Thr Pro Ile Ile Leu Ala Gly Asn Ser Pro Leu Cys Pro Val Ser Gly
                85                  90                  95

Trp Ala Val Tyr Ser Lys Asp Asn Ser Ile Arg Ile Gly Ser Lys Gly
            100                 105                 110

Asp Ile Phe Val Met Arg Glu Pro Phe Ile Ser Cys Ser Pro Leu Glu
        115                 120                 125

Cys Arg Thr Phe Phe Leu Thr Gln Gly Ala Leu Leu Asn Asp Arg His
    130                 135                 140

Ser Asn Gly Thr Val Lys Asp Arg Ser Pro His Arg Thr Leu Met Ser
145                 150                 155                 160

Cys Pro Val Gly Glu Val Pro Ser Pro Tyr Asn Ser Lys Phe Glu Ser
                165                 170                 175

Val Ala Trp Ser Ala Ser Ala Cys His Asp Gly Thr Ser Trp Leu Thr
            180                 185                 190

Ile Gly Ile Ser Gly Pro Asp Asp Gly Ala Val Ala Val Leu Lys Tyr
        195                 200                 205

Asn Gly Val Ile Thr Asp Thr Ile Lys Ser Trp Arg Lys Asn Ile Leu
210                 215                 220

Arg Thr Gln Glu Ser Glu Cys Val Cys Ile Asn Gly Ser Cys Phe Thr
225                 230                 235                 240

Ile Met Thr Asp Gly Pro Ser Asn Gly Gln Ala Ser Tyr Lys Ile Phe
                245                 250                 255

Lys Ile Glu Lys Gly Lys Val Val Lys Ser Val Glu Leu Asn Ala Pro
            260                 265                 270

Asn Tyr His Tyr Glu Glu Cys Ser Cys Tyr Pro Asp Thr Gly Lys Val
        275                 280                 285

Val Cys Val Cys Arg Asp Asn Trp His Ala Ser Asn Arg Pro Trp Val
    290                 295                 300

Ser Phe Asp Gln Asn Leu Asp Tyr Gln Ile Gly Tyr Ile Cys Ser Gly
305                 310                 315                 320

Val Leu Gly Asp Asn Pro Arg Pro Asn Asp Arg Thr Gly Ser Cys Gly
                325                 330                 335

Pro Val Phe Ser Asn Gly Ala Asn Gly Val Lys Gly Phe Ser Phe Arg
            340                 345                 350

Tyr Gly Asn Gly Val Trp Ile Gly Arg Thr Lys Ser Thr Ser Ser Arg
        355                 360                 365

```
Ser Gly Phe Glu Met Ile Trp Asp Pro Asp Gly Trp Thr Arg Thr Asp
    370                 375                 380

Asp Lys Phe Ser Val Lys Gln Asp Ile Val Gly Ile Asn Glu Trp Ser
385                 390                 395                 400

Gly Tyr Ser Gly Ser Phe Ile Gln His Pro Glu Leu Thr Gly Leu Asp
                405                 410                 415

Cys Met Arg Pro Cys Phe Trp Val Glu Leu Ile Arg Gly Gln Pro Lys
            420                 425                 430

Glu Asn Thr Ile Trp Ala Ser Gly Ser Ser Ile Ser Phe Cys Gly Val
                435                 440                 445

Asp Ser Glu Thr Ala Ser Trp Ser Trp Pro Asp Gly Ala Asn Leu Pro
        450                 455                 460

Phe Thr Ile Asp Lys
465

<210> SEQ ID NO 96
<211> LENGTH: 466
<212> TYPE: PRT
<213> ORGANISM: Artificial
<220> FEATURE:
<223> OTHER INFORMATION: synthetically-generated protein

<400> SEQUENCE: 96

Met Asn Pro Asn Gln Lys Ile Ile Thr Ile Gly Ser Val Ser Leu Ile
1               5                   10                  15

Ile Ala Thr Ile Cys Phe Leu Met Gln Ile Ala Ile Leu Val Thr Thr
                20                  25                  30

Val Thr Leu His Phe Lys Gln His Asp Cys Asn Ser Pro Pro Asn Asn
            35                  40                  45

Gln Val Met Leu Cys Glu Pro Pro Thr Ile Ile Glu Arg Asn Thr Glu
    50                  55                  60

Ile Val Tyr Leu Thr Asn Thr Thr Ile Glu Lys Glu Ile Cys Pro Lys
65                  70                  75                  80

Leu Ala Glu Tyr Arg Asn Trp Ser Lys Pro Gln Cys Asn Ile Thr Gly
                85                  90                  95

Phe Ala Pro Phe Ser Lys Asp Asn Ser Ile Arg Leu Ser Ala Gly Gly
            100                 105                 110

Asp Ile Trp Val Thr Arg Glu Pro Tyr Val Ser Cys Asp Pro Asp Lys
        115                 120                 125

Cys Tyr Gln Phe Ala Leu Gly Gln Gly Thr Thr Leu Asn Asn Gly His
    130                 135                 140

Ser Asn Asp Thr Val His Asp Arg Thr Pro Tyr Arg Thr Leu Leu Met
145                 150                 155                 160

Asn Glu Leu Gly Val Pro Phe His Leu Gly Thr Arg Gln Val Cys Ile
                165                 170                 175

Ala Trp Ser Ser Ser Ser Cys His Asp Gly Lys Ala Trp Leu His Val
            180                 185                 190

Cys Ile Thr Gly Asp Asp Glu Asn Ala Thr Ala Ser Phe Ile Tyr Asn
        195                 200                 205

Gly Arg Leu Val Asp Ser Ile Gly Ser Trp Ser Lys Asn Ile Leu Arg
    210                 215                 220

Thr Gln Glu Ser Glu Cys Val Cys Ile Asn Gly Thr Cys Thr Val Val
225                 230                 235                 240

Met Thr Asp Gly Ser Ala Ser Gly Lys Ala Asp Thr Lys Ile Leu Phe
                245                 250                 255
```

```
Ile Glu Glu Gly Lys Ile Ile His Ile Ser Thr Leu Ser Gly Ser Ala
            260                 265                 270

Gln His Val Glu Glu Cys Ser Cys Tyr Pro Arg Tyr Pro Gly Val Arg
            275                 280                 285

Cys Val Cys Arg Asp Asn Trp Lys Gly Ser Asn Arg Pro Ile Val Asp
            290                 295                 300

Ile Asn Val Lys Asp Tyr Ser Ile Val Ser Ser Tyr Val Cys Ser Gly
305                 310                 315                 320

Leu Val Gly Asp Thr Pro Arg Lys Asn Asp Ser Ser Ser Cys Leu
                325                 330                 335

Asp Pro Asn Asn Glu Glu Gly Gly His Gly Val Lys Gly Trp Ala Phe
            340                 345                 350

Asp Asp Gly Asn Asp Val Trp Met Gly Arg Thr Ile Ser Glu Glu Leu
            355                 360                 365

Arg Leu Gly Tyr Glu Thr Phe Lys Val Ile Gly Trp Ser Lys Pro Asn
            370                 375                 380

Ser Lys Leu Gln Thr Asn Arg Gln Val Ile Val Glu Arg Gly Asn Arg
385                 390                 395                 400

Ser Gly Tyr Ser Gly Ile Phe Ser Val Glu Gly Lys Ser Cys Ile Asn
                405                 410                 415

Arg Cys Phe Tyr Val Glu Leu Ile Arg Gly Arg Lys Glu Thr Lys
            420                 425                 430

Val Trp Trp Thr Ser Asn Ser Ile Val Val Phe Cys Gly Thr Ser Gly
            435                 440                 445

Thr Tyr Gly Thr Gly Ser Trp Pro Asp Gly Ala Asp Ile Asn Leu Met
    450                 455                 460

Pro Ile
465

<210> SEQ ID NO 97
<211> LENGTH: 469
<212> TYPE: PRT
<213> ORGANISM: Artificial
<220> FEATURE:
<223> OTHER INFORMATION: synthetically-generated protein

<400> SEQUENCE: 97

Met Asn Pro Asn Gln Lys Ile Ile Thr Ile Gly Ser Val Ser Leu Thr
1               5                   10                  15

Ile Ala Thr Ile Cys Phe Leu Met Gln Ile Ala Ile Leu Val Thr Thr
            20                  25                  30

Val Thr Leu His Phe Lys Gln His Asp Tyr Asn Ser Pro Pro Asn Asn
            35                  40                  45

Gln Ala Met Leu Cys Glu Pro Thr Ile Ile Glu Arg Asn Thr Thr Glu
    50                  55                  60

Ile Val Tyr Leu Thr Asn Thr Thr Ile Glu Lys Glu Ile Cys Pro Lys
65                  70                  75                  80

Leu Ala Glu Tyr Arg Ser Trp Ser Lys Pro Gln Cys Asn Ile Thr Gly
                85                  90                  95

Phe Ala Pro Phe Ser Arg Asp Asn Ser Ile Arg Leu Ser Ala Gly Gly
            100                 105                 110

Asp Ile Trp Val Thr Arg Glu Pro Tyr Val Ser Cys Asp His Asp Lys
            115                 120                 125

Cys Tyr Gln Phe Ala Leu Gly Gln Gly Thr Thr Leu Asn Asn Gly His
    130                 135                 140
```

```
Ser Asn Asn Thr Val His Asp Arg Thr Pro Tyr Arg Thr Leu Leu Met
145                 150                 155                 160

Asn Glu Leu Gly Val Pro Phe His Leu Gly Thr Arg Gln Val Cys Met
            165                 170                 175

Ala Trp Ser Ser Ser Cys His Asp Gly Arg Ala Trp Leu His Val
        180                 185                 190

Cys Ile Thr Gly Asn Asp Asn Ala Thr Ala Ser Phe Ile Tyr Asp
        195                 200                 205

Gly Arg Leu Val Asp Ser Ile Gly Ser Trp Ser Lys Lys Ile Leu Arg
            210                 215                 220

Thr Gln Glu Ser Glu Cys Val Cys Ile Asn Gly Ile Cys Thr Val Val
225                 230                 235                 240

Met Thr Asp Gly Ser Ala Ser Glu Lys Ala Asp Thr Lys Ile Leu Phe
            245                 250                 255

Val Glu Glu Gly Lys Ile Val His Ile Ser Thr Leu Ser Gly Ser Ala
            260                 265                 270

Gln His Val Glu Glu Cys Ser Cys Tyr Pro Arg Phe Pro Gly Val Arg
        275                 280                 285

Cys Val Cys Arg Asp Asn Trp Lys Gly Ser Asn Arg Pro Ile Val Asp
290                 295                 300

Ile Asn Val Lys Asn Tyr Ser Ile Val Ser Ser Tyr Val Cys Ser Gly
305                 310                 315                 320

Leu Val Gly Asp Thr Pro Arg Lys Ser Asp Ser Val Ser Ser Ser Tyr
            325                 330                 335

Cys Leu Asp Pro Asn Asn Glu Lys Gly Gly His Gly Val Lys Gly Trp
            340                 345                 350

Ala Phe Asp Asp Gly Asn Asp Val Trp Met Gly Arg Thr Ile Asn Glu
            355                 360                 365

Thr Leu Arg Leu Gly Tyr Glu Thr Phe Lys Val Ile Glu Gly Trp Ser
370                 375                 380

Lys Ala Asn Ser Lys Leu Gln Thr Asn Arg Gln Val Ile Val Glu Lys
385                 390                 395                 400

Gly Asp Arg Ser Gly Tyr Ser Gly Ile Phe Ser Ile Glu Gly Lys Asn
            405                 410                 415

Cys Ile Asn Arg Cys Phe Tyr Val Glu Leu Ile Arg Gly Arg Lys Gln
            420                 425                 430

Glu Thr Glu Val Trp Trp Thr Ser Asn Ser Ile Val Val Phe Cys Gly
            435                 440                 445

Thr Ser Gly Thr Tyr Gly Ala Gly Ser Trp Pro Asp Gly Ala Asp Ile
            450                 455                 460

Ser Leu Met Pro Ile
465

<210> SEQ ID NO 98
<211> LENGTH: 469
<212> TYPE: PRT
<213> ORGANISM: Artificial
<220> FEATURE:
<223> OTHER INFORMATION: synthetically-generated protein

<400> SEQUENCE: 98

Met Asn Pro Asn Gln Lys Ile Ile Thr Ile Gly Ser Ile Ser Leu Thr
1               5                   10                  15

Leu Ala Ala Met Cys Phe Leu Met Gln Ile Ala Ile Leu Val Thr Asn
                20                  25                  30
```

-continued

```
Val Thr Leu His Phe Lys Gln His Asn Cys Asp Ser Ser Pro Asn Asn
         35                  40                  45
His Val Met Phe Cys Glu Pro Thr Ile Ile Glu Arg Asn Ile Thr Glu
 50                  55                  60
Ile Val Tyr Leu Thr Asn Ile Thr Ile Glu Lys Glu Lys Cys Pro Lys
 65                  70                  75                  80
Leu Ala Glu Tyr Arg Asn Trp Ser Lys Pro Gln Cys Lys Ile Thr Gly
                 85                  90                  95
Phe Ala Pro Phe Ser Lys Asp Asn Ser Ile Arg Leu Ser Ala Gly Gly
                100                 105                 110
Ala Ile Trp Val Thr Arg Glu Pro Tyr Val Ser Cys Asp Pro Asp Lys
            115                 120                 125
Cys Tyr Gln Phe Ala Leu Gly Gln Gly Thr Thr Leu Asn Asn Arg His
130                 135                 140
Ser Asn Asp Thr Ile His Asp Arg Thr Pro Tyr Arg Thr Leu Leu Met
145                 150                 155                 160
Ser Glu Leu Gly Val Pro Phe His Leu Gly Thr Arg Gln Val Cys Ile
                165                 170                 175
Ala Trp Ser Ser Ser Cys Tyr Asp Gly Lys Ala Trp Leu His Val
            180                 185                 190
Cys Ile Thr Gly Asp Asp Lys Asn Ala Thr Ala Ser Phe Ile Tyr Asn
            195                 200                 205
Gly Arg Leu Val Asp Ser Ile Gly Ser Trp Ser Lys Asn Ile Leu Arg
210                 215                 220
Thr Gln Glu Ser Glu Cys Val Cys Ile Asn Gly Thr Cys Ala Val Val
225                 230                 235                 240
Met Thr Asp Gly Ser Ala Ser Gly Lys Ala Asp Thr Lys Ile Leu Phe
                245                 250                 255
Ile Glu Glu Gly Lys Ile Val His Ile Ser Pro Leu Leu Gly Ser Ala
                260                 265                 270
Gln His Val Glu Glu Cys Ser Cys Tyr Pro Arg Tyr Pro Gly Val Arg
            275                 280                 285
Cys Val Cys Arg Asp Asn Trp Arg Gly Ser Asn Arg Pro Ile Val Asp
290                 295                 300
Ile Asn Val Lys Asp Tyr Ser Ile Val Ser Ser Tyr Val Cys Ser Gly
305                 310                 315                 320
Leu Val Gly Asp Thr Pro Arg Lys Asp Asp Lys Ser Ser Ser Ser Asn
                325                 330                 335
Cys Leu Asn Pro Asn Asn Glu Glu Gly Gly His Gly Val Lys Gly Trp
                340                 345                 350
Ala Phe Asp Asp Gly Asp Asp Val Trp Met Gly Arg Thr Ile Ser Glu
            355                 360                 365
Lys Leu Arg Ser Gly Tyr Glu Thr Phe Lys Val Ile Glu Gly Trp Ser
370                 375                 380
Lys Pro Asn Ser Lys Leu Gln Ile Asn Arg Gln Val Ile Val Asp Arg
385                 390                 395                 400
Gly Asn Arg Ser Gly Tyr Ser Gly Ile Phe Ser Val Glu Gly Lys Ser
                405                 410                 415
Cys Ile Asn Arg Cys Phe Tyr Val Glu Leu Ile Arg Gly Arg Gln
                420                 425                 430
Glu Thr Arg Val Trp Trp Thr Ser Asn Ser Ile Ile Val Phe Cys Gly
            435                 440                 445
```

```
Thr Ser Gly Thr Tyr Gly Ser Gly Ser Trp Pro Asp Gly Ala Asp Ile
    450                 455                 460

Asn Phe Met Pro Ile
465

<210> SEQ ID NO 99
<211> LENGTH: 469
<212> TYPE: PRT
<213> ORGANISM: Artificial
<220> FEATURE:
<223> OTHER INFORMATION: synthetically-generated protein

<400> SEQUENCE: 99

Met Asn Pro Asn Gln Arg Ile Ile Thr Ile Gly Ser Val Ser Leu Ile
1               5                   10                  15

Ile Ala Thr Ile Cys Phe Leu Met Gln Val Ala Ile Leu Val Thr Thr
            20                  25                  30

Val Thr Leu His Phe Lys Gln His Asp Cys Asn Ser Ser Pro Asn Asn
        35                  40                  45

Gln Val Met Leu Cys Glu Pro Thr Ile Ile Glu Arg Asn Lys Thr Glu
    50                  55                  60

Ile Val Tyr Leu Thr Asn Thr Thr Val Glu Lys Glu Ile Cys Pro Lys
65                  70                  75                  80

Pro Ala Glu Tyr Arg Asn Trp Ser Lys Pro Gln Cys Asn Ile Ala Gly
                85                  90                  95

Phe Ala Pro Phe Ser Lys Asp Asn Ser Val Arg Leu Ser Ala Gly Gly
            100                 105                 110

Asp Ile Trp Ile Thr Arg Glu Pro Tyr Val Ser Cys Asp Leu Asp Lys
        115                 120                 125

Cys Tyr Gln Phe Ala Leu Gly His Gly Thr Thr Leu Asn Asn Gly His
130                 135                 140

Ser Asn Asp Thr Val His Asp Arg Thr Pro Tyr Arg Thr Leu Leu Met
145                 150                 155                 160

Asn Glu Leu Gly Ile Pro Phe His Leu Gly Thr Lys Gln Val Cys Ile
                165                 170                 175

Ala Trp Ser Ser Ser Ser Cys His Asp Gly Lys Ala Trp Leu His Val
            180                 185                 190

Cys Val Thr Gly His Asp Glu Asn Ala Thr Ala Ser Ile Ile Tyr Asn
        195                 200                 205

Gly Arg Leu Val Asp Ser Ile Gly Ser Trp Ser Gln Asn Ile Leu Arg
    210                 215                 220

Thr Gln Glu Ser Glu Cys Val Cys Ile Asn Gly Thr Cys Thr Val Val
225                 230                 235                 240

Met Thr Asp Gly Ser Ala Ser Gly Arg Ala Asp Thr Lys Ile Leu Phe
                245                 250                 255

Ile Glu Glu Gly Lys Ile Ile His Ile Ser Thr Leu Ser Gly Ser Ala
            260                 265                 270

Lys His Val Glu Glu Cys Ser Cys Tyr Pro Arg Tyr Pro Gly Val Arg
        275                 280                 285

Cys Ile Cys Arg Asp Asn Trp Lys Gly Ser Asn Arg Pro Val Val Asp
    290                 295                 300

Ile Asn Val Lys Asp Tyr Ser Thr Val Ser Ser Tyr Val Cys Ser Gly
305                 310                 315                 320

Leu Val Gly Asp Thr Pro Arg Lys Asn Asp Ser Phe Ser Ser Ser His
                325                 330                 335
```

```
Cys Leu Asp Pro Asn Asn Glu Glu Gly Gly His Gly Val Lys Gly Trp
            340                 345                 350

Ala Phe Asp Asp Gly Asn Asp Leu Trp Met Gly Arg Thr Ile Ser Glu
        355                 360                 365

Lys Ser Arg Leu Gly Tyr Glu Thr Phe Lys Val Ile Lys Gly Trp Ser
370                 375                 380

Lys Pro Asn Ser Lys Leu Gln Thr Asn Arg Gln Val Ile Val Gly Arg
385                 390                 395                 400

Gly Asn Arg Ser Gly Tyr Ser Gly Ile Phe Ser Val Glu Gly Lys Asn
                405                 410                 415

Cys Ile Asn Arg Cys Phe Tyr Val Glu Leu Ile Arg Gly Arg Lys Glu
            420                 425                 430

Glu Thr Lys Val Trp Trp Thr Ser Asn Ser Ile Leu Val Phe Cys Gly
            435                 440                 445

Thr Ser Gly Thr Tyr Gly Thr Gly Ser Trp Pro Asp Gly Ala Asp Ile
    450                 455                 460

Asn Leu Met Pro Ile
465

<210> SEQ ID NO 100
<211> LENGTH: 469
<212> TYPE: PRT
<213> ORGANISM: Artificial
<220> FEATURE:
<223> OTHER INFORMATION: synthetically-generated protein

<400> SEQUENCE: 100

Met Asn Pro Asn Gln Lys Ile Ile Thr Ile Gly Ser Val Ser Leu Ile
1               5                   10                  15

Ile Ala Thr Ile Cys Phe Leu Met Gln Ile Ala Ile Leu Val Thr Thr
            20                  25                  30

Val Thr Leu His Phe Lys Gln His Asp Tyr Asn Ser Pro Pro Asn Asn
        35                  40                  45

Gln Val Met Leu Cys Glu Pro Thr Ile Ile Glu Arg Asn Lys Thr Glu
    50                  55                  60

Ile Val Tyr Leu Thr Asn Thr Thr Ile Glu Lys Glu Ile Cys Pro Lys
65                  70                  75                  80

Leu Ala Glu Tyr Arg Asn Trp Ser Lys Pro Gln Cys Asn Ile Thr Gly
                85                  90                  95

Phe Ala Pro Phe Ser Lys Asp Asn Ser Ile Arg Leu Ser Ala Gly Gly
            100                 105                 110

Asp Ile Trp Val Thr Arg Glu Pro Tyr Val Ser Cys Asp Pro Asp Lys
        115                 120                 125

Cys Tyr Gln Phe Ala Leu Gly Gln Gly Thr Thr Leu Asn Asn Gly His
    130                 135                 140

Ser Asn Asp Thr Val His Asp Arg Thr Pro Tyr Arg Thr Leu Leu Met
145                 150                 155                 160

Asn Glu Leu Gly Val Pro Phe His Leu Gly Thr Arg Gln Val Cys Ile
                165                 170                 175

Ala Trp Ser Ser Ser Ser Cys His Asp Gly Lys Ala Trp Leu His Val
            180                 185                 190

Cys Ile Thr Gly Asp Asp Lys Asn Ala Thr Ala Ser Phe Ile Tyr Asn
        195                 200                 205

Gly Arg Leu Val Asp Ser Ile Gly Ser Trp Ser Lys Asn Ile Leu Arg
    210                 215                 220
```

```
Thr Gln Glu Ser Glu Cys Val Cys Ile Asn Gly Thr Cys Thr Val Val
225                 230                 235                 240

Met Thr Asp Gly Ser Ala Ser Gly Lys Ala Asp Thr Lys Ile Leu Phe
            245                 250                 255

Ile Glu Glu Gly Lys Ile Ile His Ile Ser Thr Leu Ser Gly Ser Ala
            260                 265                 270

Gln His Val Glu Glu Cys Ser Cys Tyr Pro Arg Tyr Pro Gly Val Arg
        275                 280                 285

Cys Val Cys Arg Asp Asn Trp Lys Gly Ser Asn Arg Pro Ile Val Asp
        290                 295                 300

Ile Asn Val Lys Asp Tyr Ser Ile Val Ser Ser Tyr Val Cys Ser Gly
305                 310                 315                 320

Leu Val Gly Asp Thr Pro Arg Lys Asn Asp Ser Phe Ser Ser His
            325                 330                 335

Cys Leu Asp Pro Asn Asn Glu Glu Gly Gly His Gly Val Lys Gly Trp
            340                 345                 350

Ala Phe Asp Asp Gly Asn Asp Val Trp Met Gly Arg Thr Ile Asn Glu
            355                 360                 365

Thr Leu Arg Leu Gly Tyr Glu Thr Phe Lys Val Ile Glu Gly Trp Ser
370                 375                 380

Lys Pro Asn Ser Lys Leu Gln Thr Asn Arg Gln Val Ile Val Glu Lys
385                 390                 395                 400

Gly Asp Arg Ser Gly Tyr Ser Gly Ile Phe Ser Val Glu Gly Lys Ser
            405                 410                 415

Cys Ile Asn Arg Cys Phe Tyr Val Glu Leu Ile Arg Gly Arg Lys Glu
            420                 425                 430

Glu Thr Lys Val Trp Trp Thr Ser Asn Ser Ile Val Val Phe Cys Gly
            435                 440                 445

Thr Ser Gly Thr Tyr Gly Thr Gly Ser Trp Pro Asp Gly Ala Asp Ile
    450                 455                 460

Asn Leu Met Pro Ile
465

<210> SEQ ID NO 101
<211> LENGTH: 469
<212> TYPE: PRT
<213> ORGANISM: Artificial
<220> FEATURE:
<223> OTHER INFORMATION: synthetically-generated protein

<400> SEQUENCE: 101

Met Asn Pro Asn Gln Arg Ile Ile Thr Ile Gly Ser Val Ser Leu Thr
1               5                   10                  15

Ile Ala Thr Ile Cys Phe Leu Met Gln Val Ala Ile Leu Val Thr Thr
            20                  25                  30

Val Thr Leu His Phe Lys Gln His Asp Cys Asn Ser Pro Asn Asn
        35                  40                  45

Gln Val Met Phe Cys Glu Pro Thr Ile Ile Glu Arg Asn Thr Thr Glu
    50                  55                  60

Ile Val Tyr Leu Thr Asn Thr Thr Val Glu Lys Glu Ile Cys Pro Lys
65              70                  75                  80

Pro Ala Glu Tyr Arg Asn Trp Ser Lys Pro Gln Cys Lys Ile Thr Gly
                85                  90                  95

Phe Ala Pro Phe Ser Arg Asp Asn Ser Ile Arg Leu Ser Ala Gly Gly
            100                 105                 110
```

```
Ala Ile Trp Val Thr Arg Glu Pro Tyr Val Ser Cys Asp Leu Asp Lys
            115                 120                 125

Cys Tyr Gln Phe Ala Leu Gly Gln Gly Thr Thr Leu Asn Asn Arg His
130                 135                 140

Ser Asn Asp Thr Ile His Asp Arg Thr Pro Tyr Arg Thr Leu Leu Met
145                 150                 155                 160

Asn Glu Leu Gly Ile Pro Phe His Leu Gly Thr Lys Gln Val Cys Ile
            165                 170                 175

Ala Trp Ser Ser Ser Cys Tyr Asp Gly Lys Ala Trp Leu His Val
            180                 185                 190

Cys Ile Thr Gly Asn Asp Asn Ala Thr Ala Ser Phe Ile Tyr Asp
            195                 200                 205

Gly Arg Leu Val Asp Ser Ile Gly Ser Trp Ser Lys Lys Ile Leu Arg
            210                 215                 220

Thr Gln Glu Ser Glu Cys Val Cys Ile Asn Gly Ile Cys Thr Val Val
225                 230                 235                 240

Met Thr Asp Gly Ser Ala Ser Gly Arg Ala Asp Thr Lys Ile Leu Phe
            245                 250                 255

Val Glu Glu Gly Lys Ile Val His Ile Ser Thr Leu Ser Gly Ser Ala
            260                 265                 270

Lys His Val Glu Glu Cys Ser Cys Tyr Pro Arg Tyr Pro Gly Val Arg
            275                 280                 285

Cys Ile Cys Arg Asp Asn Trp Lys Gly Ser Asn Arg Pro Val Val Asp
            290                 295                 300

Ile Asn Val Lys Asn Tyr Ser Ile Val Ser Ser Tyr Val Cys Ser Gly
305                 310                 315                 320

Leu Val Gly Asp Thr Pro Arg Lys Ser Asp Ser Val Ser Ser Ser Tyr
            325                 330                 335

Cys Leu Asp Pro Asn Asn Glu Lys Gly Gly His Gly Val Lys Gly Trp
            340                 345                 350

Ala Phe Asp Asp Gly Asp Asp Val Trp Met Gly Arg Thr Ile Ser Glu
            355                 360                 365

Lys Ser Arg Leu Gly Tyr Glu Thr Phe Lys Val Ile Lys Gly Trp Ser
370                 375                 380

Lys Pro Asn Ser Lys Leu Gln Ile Asn Arg Gln Val Ile Val Asp Arg
385                 390                 395                 400

Gly Asn Arg Ser Gly Tyr Ser Gly Ile Phe Ser Val Glu Gly Lys Asn
            405                 410                 415

Cys Ile Asn Arg Cys Phe Tyr Val Glu Leu Ile Arg Gly Arg Lys Gln
            420                 425                 430

Glu Thr Glu Val Trp Trp Thr Ser Asn Ser Ile Ile Val Phe Cys Gly
            435                 440                 445

Thr Ser Gly Thr Tyr Gly Ser Gly Ser Trp Pro Asp Gly Ala Asp Ile
            450                 455                 460

Asn Phe Met Pro Ile
465

<210> SEQ ID NO 102
<211> LENGTH: 469
<212> TYPE: PRT
<213> ORGANISM: Artificial
<220> FEATURE:
<223> OTHER INFORMATION: synthetically-generated protein

<400> SEQUENCE: 102
```

-continued

```
Met Asn Ser Asn Gln Lys Ile Ile Thr Ile Gly Ser Ile Ser Leu Thr
1               5                   10                  15

Leu Ala Ala Met Cys Phe Leu Met Gln Ile Ala Ile Leu Val Thr Asn
            20                  25                  30

Val Thr Leu His Phe Asn Gln Cys Glu Cys His Tyr Pro Pro Asn Asn
        35                  40                  45

Gln Val Ile Leu Cys Glu Pro Thr Ile Glu Arg Asn Ile Thr Glu
    50                  55                  60

Ile Val Tyr Leu Thr Asn Ile Thr Ile Glu Lys Glu Lys Cys Pro Lys
65                  70                  75                  80

Leu Ala Glu Tyr Arg Ser Trp Ser Lys Pro Gln Cys Asn Ile Ala Gly
                85                  90                  95

Phe Ala Pro Phe Ser Lys Asp Asn Ser Val Arg Leu Ser Ala Gly Gly
            100                 105                 110

Asp Ile Trp Ile Thr Arg Glu Pro Tyr Val Ser Cys Asp His Asp Lys
        115                 120                 125

Cys Tyr Gln Phe Ala Leu Gly His Gly Thr Thr Leu Asn Asn Gly His
    130                 135                 140

Ser Asn Asn Thr Val His Asp Arg Thr Pro Tyr Arg Thr Leu Leu Met
145                 150                 155                 160

Ser Glu Leu Gly Val Pro Phe His Leu Gly Thr Arg Gln Val Cys Met
                165                 170                 175

Ala Trp Ser Ser Ser Cys His Asp Gly Lys Ala Trp Leu His Val
            180                 185                 190

Cys Val Thr Gly His Asp Glu Asn Ala Thr Ala Ser Ile Ile Tyr Asn
        195                 200                 205

Gly Arg Leu Val Asp Ser Ile Gly Ser Trp Ser Gln Asn Ile Leu Arg
    210                 215                 220

Thr Gln Glu Ser Glu Cys Val Cys Ile Asn Gly Thr Cys Ala Val Val
225                 230                 235                 240

Met Thr Asp Gly Ser Ala Ser Gly Lys Ala Asp Thr Arg Ile Leu Phe
                245                 250                 255

Ile Glu Glu Gly Lys Ile Val His Ile Ser Pro Leu Leu Gly Ser Ala
            260                 265                 270

Gln His Val Glu Glu Cys Ser Cys Tyr Pro Arg Phe Pro Gly Val Arg
        275                 280                 285

Cys Val Cys Arg Asp Asn Trp Arg Gly Ser Asn Arg Pro Val Val Asp
    290                 295                 300

Ile Asn Val Lys Asp Tyr Ser Thr Val Ser Ser Tyr Val Cys Ser Gly
305                 310                 315                 320

Leu Val Gly Asp Thr Pro Arg Lys Asp Asp Lys Ser Ser Ser Ser Asn
                325                 330                 335

Cys Leu Asn Pro Asn Asn Glu Glu Gly Gly His Gly Val Lys Gly Trp
            340                 345                 350

Ala Phe Asp Asp Gly Asn Asp Leu Trp Met Gly Arg Thr Ile Ser Glu
        355                 360                 365

Lys Leu Arg Ser Gly Tyr Glu Thr Phe Lys Val Ile Glu Gly Trp Ser
    370                 375                 380

Lys Ala Asn Ser Lys Leu Gln Thr Asn Arg Gln Val Ile Val Gly Arg
385                 390                 395                 400

Gly Asn Arg Ser Gly Tyr Ser Gly Ile Phe Ser Ile Glu Gly Lys Asn
                405                 410                 415

Cys Ile Asn Arg Cys Phe Tyr Val Glu Leu Ile Arg Gly Arg Arg Gln
```

```
             420                 425                 430
Glu Thr Arg Val Trp Trp Thr Ser Asn Ser Ile Leu Val Phe Cys Gly
        435                 440                 445

Thr Ser Gly Thr Tyr Gly Ala Gly Ser Trp Pro Asp Gly Ala Asp Ile
    450                 455                 460

Ser Leu Met Pro Ile
465

<210> SEQ ID NO 103
<211> LENGTH: 1680
<212> TYPE: DNA
<213> ORGANISM: Artificial
<220> FEATURE:
<223> OTHER INFORMATION: synthetically-generated coding sequence

<400> SEQUENCE: 103
atgaaggtga agctgctggt gctgctgtgc acctttacag ccacctacgc cgacacaatc      60
tgtatcggct atcacgccaa caattccaca gacaccgtgg ataccgtgct ggagaagaac     120
gtgacagtga cccactccgt gaacctgctg gaggattctc acaatggcaa gctgtgcctg     180
ctgaagggca tcgccccact gcagctgggc aactgtctg tggccggctg gatcctgggc      240
aatcccgagt gtgagctgct gatcagcaag gagtcttgga gctacatcgt ggagacacca     300
aaccccgaga tggcacctg ctaccccggc tttgccgact atgaggagct gagggagcag      360
ctgagcagcg tgagcagctt cgagcggttc gagatcttcc ctaaggagtc ctcttggcca     420
aaccacacag tgaccaaggg cgtgtccgcc tcttgtagcc acaacggcag ctccttctac     480
cggaatctgc tgtggctgac cggcaagaac ggcctgtacc ctaatctgtc caagtcttat     540
gccaacaata ggagaaagga ggtgctggtg ctgtggggag tgcaccaccc acctaacatc     600
ggcgatcagc tgtaccacac agagaatgcc tatgtgagcg tggtgtctag ccactactcc     660
cggtttaccc ccgagatcgc caagaggcct aaggtgcgcg accaggaggg cagaatcaac     720
tactattgga cactgctgga gcccggcgat accatcatct tcgaggccaa cggcaatctg     780 atcgcccta gatatgcctt tgccctgtcc aggggattcg aagcggaat catctccaat      840 gcccctatgg acgagtgcga tgccaagtgt cagacaccac agggcgccat caactcctct     900
ctgccatttc agaatgtgca ccccgtgaca atcggcgagt gtcctaagta cgtgcggagc     960
gccaagctga gaatggtgac cggcctgcgg aacatcccaa gcatccagtc cagaggcctg    1020
tttggagcaa tcgcaggctt catcgaggga ggatggaccg aatggtgga cggctggtac     1080 ggctatcacc accagaatga gcagggctct ggctatgccg ccgatcagaa gagcacacag    1140
aacgccatca tggcatcac caacaaggtc aattccgtga tcgagaagat gaacacacag     1200
tttaccgccg tgggcaagga gttcaataag ctggagcgga aatgagaa cctgaataag      1260 aaggtggacg atggctttct ggacatctgg acatacaacg ccgagctgct ggtgctgctg    1320
gagaatgaga ggaccctgga cttccacgat ccaacgtga gaatctgta tgagaaggtg     1380 aagtctcagc tgaagaacaa tgccaaggag atcggcaacg gctgcttcga gttttaccac    1440
aagtgcaacg acgagtgtat ggagagcgtg aagaatggca catacgatta tcccaagtat    1500
tctgaggaga gcaagctgaa tagggagaag atcgatggcg tgaagctgga gagcatgggc    1560
gtgtaccaga tcctggccat ctattccacc gtggcaagct ccctggtgct gctggtgtct    1620
ctgggcgcca tcagcttctg gatgtgctcc aacggctctc tgcagtgccg catctgtatc    1680

<210> SEQ ID NO 104
```

<211> LENGTH: 1695
<212> TYPE: DNA
<213> ORGANISM: Artificial
<220> FEATURE:
<223> OTHER INFORMATION: synthetically-generated coding sequence

<400> SEQUENCE: 104

| | |
|---|---|
| atgaaggtga agctgctggt gctgctgtgc accttcacag ccacctacgc cgacacaatc | 60 |
| tgtatcggct atcacgccaa caatagcaca gacaccgtgg ataccgtgct ggagaagaac | 120 |
| gtgacagtga cccactctgt gaatctgctg gagaacagcc acaatggcaa gctgtgcctg | 180 |
| ctgaagggca tcgccccact gcagctggga actgcagcg tggcaggatg gatcctggga | 240 |
| aatccagagt gtgagctgct gatctccaag gagtcttgga gctacatcgt ggagaagcca | 300 |
| aaccccgaga tggcacatg ctaccccggc cacttcgccg actatgagga gctgagggag | 360 |
| cagctgagct ccgtgtctag cctggagcgg ttcgagatct ttcctaagga gtcctcttgg | 420 |
| ccaaaccaca cagtgaccgg cgtgtccgcc tcttgtagcc acaacggcga gagctccttt | 480 |
| tacaggaatc tgctgtggct gaccggcaag aacggcctgt accctaatct gtccaagtct | 540 |
| tatgccaaca taaggagaa ggaggtgctg gtgctgtggg agtgcacca cccacctaac | 600 |
| atcggcgatc agcgcgccct gtaccacaca gagaatgcct acgtgagcgt ggtgtctagc | 660 |
| cactactctc ggaagttcac ccccgagatc gccaagaggc ctaaggtgcg cgaccaggag | 720 |
| ggcagaatca actactattg gacactgctg gagcccggcg ataccatcat ctttgaggcc | 780 |
| aacggcaatc tgatcgcccc tagatatgcc ttcgccctga gcaggggatt tggatccggc | 840 |
| atcatcaact ctaatgcccc tatggacaag tgcgatgcca agtgtcagac cccacagggc | 900 |
| gccatcaact cctctctgcc attccagaat gtgcaccccg tgacaatcgg cgagtgtcct | 960 |
| aagtacgtgc ggagcgccaa gctgagaatg gtgaccggcc tgcggaacat cccaagcgtg | 1020 |
| cagtccagag gactgttcgg agcaatcgca ggctttatcg agggaggctg gacaggcatg | 1080 |
| atcgacggct ggtacggcta tcaccaccag aatgagcagg gcagcggcta tgccgccgat | 1140 |
| cagaagtcca cacagaacgc catcaatggc atcaccaaca aggtcaattc cgtgatcgag | 1200 |
| aagatgaaca tccagttcac cgccgtgggc aaggagtta taagctgga gcggagaatg | 1260 |
| gagaacctga ataagaaggt ggacgatggc ttcatcgata tctggacata caacgccgag | 1320 |
| ctgctggtgc tgctggagaa tgagcggacc ctggactttc acgattctaa cgtgaagaat | 1380 |
| ctgtatgaga aggtgaagag ccagctgaag aacaatgcca aggaagtggg caacggctgc | 1440 |
| ttcgagtttt accacaagtg caacgacgag tgtatggagt ccgtgaagaa tgagacctac | 1500 |
| gattatccca gtattctga ggagagcaag ctgaataggg agaagatcga cggcgtgaag | 1560 |
| ctggattcca gggcgtgta ccagatcctg acaatctatt ctaccgtggc cagctccctg | 1620 |
| gtgctgctgg tgagcctggg agccatctcc ttttggatgt gctccaacgg ctctctgcag | 1680 |
| tgcaagatct gtatc | 1695 |

<210> SEQ ID NO 105
<211> LENGTH: 1698
<212> TYPE: DNA
<213> ORGANISM: Artificial
<220> FEATURE:
<223> OTHER INFORMATION: synthetically-generated coding sequence

<400> SEQUENCE: 105

| | |
|---|---|
| atgaaggcca tcctggtggt gctgctgtac acctttgcca cagccaacgc cgacaccctg | 60 |
| tgcatcggct atcacgccaa caatagcacc gacacagtgg atacagtgct ggagaagaat | 120 |

```
gtgaccgtga cacactccgt gaacctgctg gaggataagc acaatggcaa gctgtgcaag      180
ctgaggggag tggcacctct gcacctgggc aagtgcaaca tcgccggctg gatcctgggc      240
aatccagagt gtgagtccct gtctaccgcc agctcctggt cctacatcgt ggagacctct      300
agctccgaca acggcacatg ctaccctggc gactttatcg attatgagga gctgagggag      360
cagctgtcta gcgtgagcag cttcgagcgg ttcgagatct tccccaagac cagctcctgg      420
cctaaccacg atagcaataa gggagtgaca gcagcatgtc cacacgcagg cgccaagtcc      480
ttctacaaga acctgatctg gctggtgaag aagggcaatt cttaccccaa gctgagcaag      540
tcctatatca cgacaagggg caaggaggtg ctggtgctgt ggggcatcca ccacccatct      600
accagcgccg accagcagtc cctgtaccag aatgccgatg cctacgtgtt cgtgggcaca      660
tcccggtact ctaagaagtt caagccagag atcgccatcc ggcccaaggt gagagaccag      720
gagggcagaa tgaactacta ttggaccctg gtggagccag gcgataagat caccttttgag     780 gcaacaggaa acctggtggt gcccagatat gccttcgcca tggagagaaa tgccggctcc      840
ggcatcatca tctctgacac ccccgtgcac gattgcaaca ccacatgtca gacccctaag      900
ggcgccatca cacatctct gccttttccag aatatccacc caatcacaat cggcaagtgc      960
cccaagtacg tgaagagcac caagctgagg ctggccacag gcctgcgcaa tgtgcctagc     1020
atccagtcca ggggactgtt tggagcaatc gcaggcttca tcgagggagg atggaccgga     1080
atggtggatg gatggtacgg ctatcaccac cagaacgagc agggctctgg ctatgccgcc     1140
gacctgaaga gcacccagaa tgccatcgat aagatcacaa acaaggtcaa tagcgtgatc     1200
gagaagatga acacccagtt tacagccgtg ggcaaggagt tcaatcaccc tggagaagcgc    1260 atcgagaacc tgaataagaa ggtggacgat ggctttctgg acatctggac ctacaacgcc     1320
gagctgctgg tgctgctgga gaatgagagg acactggact accacgattc caacgtgaag     1380
aatctgtatg agaaggtgcg ctctcagctg aagaacaatg ccaaggagat cggcaacggc     1440
tgcttcgagt tttaccacaa gtgcgacaac acctgtatgg agtctgtgaa gaatggcaca     1500
tacgattatc ccaagtatag cgaggaggcc aagctgaatc gggaggagat cgatggcgtg     1560
aagctggaga gcaccagaat ctaccagatc ctggccatct attccacagt ggcctctagc     1620
ctggtgctgg tggtgagcct gggagcaatc tccttctgga tgtgctctaa cggcagcctg     1680
cagtgcagga tctgtatc                                                   1698
```

<210> SEQ ID NO 106
<211> LENGTH: 1689
<212> TYPE: DNA
<213> ORGANISM: Artificial
<220> FEATURE:
<223> OTHER INFORMATION: synthetically-generated coding sequence

<400> SEQUENCE: 106

```
atgaaggtga agctgctggt gctgctgtgc accttcacag ccacctacgc cgacacaatc       60
tgtatcggct atcacgccaa caatagcaca gacaccgtgg ataccatcct ggagaagaac      120
gtgacagtga cccactctgt gaatctgctg gagaacagcc acaatggcaa gctgtgcctg      180
ctgaagggca tcgcccccact gcagctggga aactgctccg tggcaggatg gatcctggga      240
aatccagagt gtgagctgct gatctctaag gagtcttgga gctacatcgt ggagaagcca      300
aaccccgaga tggcacatg ctaccccggc gacttcatca actatgagga gctgagggag      360
cagctgagct ccgtgtctag cctggagcgg ttcgagatct ttcctaagga gtcctcttgg      420
```

| | |
|---|---|
| ccaaatcaca cagtgaccgg cgtgtccgcc tcttgtagcc acaacggcga gagctccttt | 480 |
| taccggaatc tgctgtggct gaccggcaag aacggcctgt accctaatct gtccaagtct | 540 |
| tatgccaaca ataaggagaa ggaggtgctg gtgctgtggg gagtgcacca cccacctaac | 600 |
| atcggcgatc agagagccct gtaccacaca gagaatgcct acgtgagcgt ggtgtctagc | 660 |
| cactactcta ggaagttcac ccccgagatc gccaagaggc ctaaggtgcg cgaccaggag | 720 |
| ggacgcatca actactattg gacactgctg gagcccggcg ataccatcat ctttgaggcc | 780 |
| aacggcaatc tgatcgcccc tagatatgcc ttcgccctga gcaggggatt tggatccggc | 840 |
| atcatcaact ctaatgcccc tatggacaag tgcgatgcca agtgtcagac cccacagggc | 900 |
| gccatcaact cctctctgcc attccagaat gtgcacccccg tgacaatcgg cgagtgtcct | 960 |
| aagtacgtgc ggagcgccaa gctgagaatg gtgaccggcc tgcggaacat cccaagcatc | 1020 |
| cagtccagag gactgctggg agcaatcgca ggctttatcg agggaggctg gacaggcatg | 1080 |
| atcgacggct ggtacggcta tcaccaccag aacgcacagg aagcggata tgcagcagac | 1140 |
| cagaagtcca cacagaatgc catcgatgag atcaccaaca aggtcaattc cgtgatcgag | 1200 |
| aagatgaaca tccagttcac cgccgtgggc aaggagttta ataagctgga gcggagaatg | 1260 |
| gagaacctga ataagaaggt ggacgatggc ttcatcgata tctggacata caacgccgag | 1320 |
| ctgctgatcc tgctggagaa tgagcggacc ctggactttc acgatagcaa cgtgaagaat | 1380 |
| ctgtatgaga aggtgagaaa ccagctgaag aacaatgcca aggaagtggg caatggctgc | 1440 |
| ttcgagtttt accacaagtg caacgacgag tgtatggagt ccgtgaagaa tggcatctac | 1500 |
| gattatccca gtattctga ggagagcaag ctgaacaggg agaagatcga tggcgtgaag | 1560 |
| ctggagtcta tgggcgtgta ccagatcctg gccatctata gcaccgtggc aagctccctg | 1620 |
| gtgctgctgg tgagcctggg agccatctcc ttttggatgt gctccggcca ctcttgcaga | 1680 |
| atctgtatc | 1689 |

<210> SEQ ID NO 107
<211> LENGTH: 1698
<212> TYPE: DNA
<213> ORGANISM: Artificial
<220> FEATURE:
<223> OTHER INFORMATION: synthetically-generated coding sequence

<400> SEQUENCE: 107

| | |
|---|---|
| atggaggcca tcctggtggt gctgctgtac acctttacca gccaacgc cgacacactg | 60 |
| tgcgtgggct atcacgccaa caatagcacc gacacagtgg ataccgtgct ggagcggaat | 120 |
| gtgaccgtga cacactccgt gaacctgctg gaggattctc acaatggcaa gctgtgcaga | 180 |
| ctgaaggca tcgcccctct gcagctgggc aagtgcaaca tcgccggctg gctgctgggc | 240 |
| aatccagagt gtgagtccct gttttctaag agagctggt cctacatcgt ggagaccccc | 300 |
| aaccctgaga tggcacatg ctaccctggc cacttcgccg actatgagga gctgagggag | 360 |
| cagctgaaca gcgtgagcag cttcgagcgg ttcgagatgt tcccaaagac ctctagctgg | 420 |
| cccgaccacg attccaataa gggagtgacc acagcatgtc cacacgcagg agcaaagggc | 480 |
| ttttacaaga acctgatctg gctgacaaag aagggcaata gctacccccaa gctgtctcag | 540 |
| agctatatca acgataaggg caaggagatc ctggtgctgt ggggcatcca ccacccaagc | 600 |
| accacagccg accagcagtc cctgtaccag aatgccgata cctacgtgtt cgtgggcaca | 660 |
| agcaagtact ccaagaagtt caagcctgag atcgccaccc ggccaaaggt gagagaccag | 720 |
| gagcggagaa tgaactacta ttggaccctg atcgagccag gcgataagat cacatttgag | 780 |

```
gccaacggca atctggtggt gccccggtat gccttcacca tggagagaaa cgccggctcc    840
ggcatcatca tctctgacac aagcgtgcac gattgcaata ccacatgtca gaccccgag     900 ggcgccatca acacatccct gcccttccac aatatccacc ctatcaccat cggcgagtgc    960
cccaagtacg tgaggtctac caagctgcgc atggtgacag gcctgaggaa cgtgccttcc   1020
gtgcagtcta ggggactgtt tggagcaatc gcaggcttca tcgagggagg atggaccgga   1080
atgatggacg gatggtacgg ctatcaccac cagaatggcc agggctctgg ctatgccgcc   1140
gatcagaaga gcacccagaa cgccatcaat ggcatcacaa acaaggtcaa ttccgtgatc   1200
gacaagatga cacccagtt tacagccgtg ggcaaggagt tcaataagct ggagaagagg   1260
atggagaacc tgaataagaa ggtggacgat ggctttatcg acgtgtggac ctacaacgcc   1320
gagctgctga tcctgctgga gaatgagcgc acactggact accacgattc caaggtgaag   1380
aacctgtatg agaaggtgaa gtctcagctg aagaacaatg ccaaggagac cggcaatggc   1440
tgcttcgagt tttaccacaa gtgcaacaat gagtgtatgg agtctgtgaa gaacggcaca   1500
tacgactatc ctcggtatag cgaggaggcc aagctgaata gagagaagat cgatggcgtg   1560
aagctggaga gcacccgggt gtaccagatc ctggccatct attccacagc cgcctcctct   1620
ctggtgctgg tggtgtctct gggcgagatc agcttctgga tgtgcagcaa cggctccctg   1680
aggtgccgca tctgtatc                                                  1698

<210> SEQ ID NO 108
<211> LENGTH: 1692
<212> TYPE: DNA
<213> ORGANISM: Artificial
<220> FEATURE:
<223> OTHER INFORMATION: synthetically-generated coding sequence

<400> SEQUENCE: 108
atgaagacca tcatcgccct gtcttatatc ctgtgcctgg tgttcgccca gaagctgcca     60
ggcaatgaca acaatagcac cgccacactg tgcctgggac accacgccgt gcccaacggc    120
acaatcgtga agaccatcac aaatgatcag atcgaggtga ccaacgccac agagctggtg    180
cagagctcca ccggcgagat ctgcgacagc cctcaccaga tcctggatgg cgagaactgt    240
acactgatcg acgcactgct gggcgaccca cagtgcgatg gcttccagaa taagaagtgg    300
gatctgtttg tggagcggtc taaggcctac agcaactgtt accccatga cgtgcctgat    360 tatgcctccc tgagatctct ggtggcctct agcggcaccc tggagttcaa caatgagtct    420
tttaattgga ccggcgtgac acagaacggc acatcctctg cctgcatccg agatctaat    480 agcttcttta gcaggctgaa ttggctgact cacctgaact tcaagtaccc cgccctgaac    540
gtgacaatgc ctaacaatga gcagtttgac aagctgtata tctggggagt gcaccaccca    600
ggcaccgaca aggatcagat cttcctgtac gcacagtccg aaggatcac cgtgtccaca    660 aagagatctc agcaggccgt gatccctaat atcggatcta ggccaaggag gatcccaagc    720
cgcatctcca tctattggac catcgtgaag cctggcgaca tcctgctgat caacagcaca    780
ggcaatctga tcgcccccaa gggctacttc aagatccgct ctggcaagag ctccatcatg    840
cggagcgacg cccaatcgg caagtgctcc gagtgtatca ccccaatgg ctctatccct    900 aacgataagc catttcagaa cgtgaatcgg atcacatacg gcgcctgtcc cagatatgtg    960
aagcagaccc tgaagctggc cacaggcatg aggaacgtgc ctgagaagca gaccagggga   1020
atcttcggag caatcgcagg ctttatcgag aatggctggg agggcatggt ggacggctgg   1080
```

| | |
|---|---|
| tacggctttc ggcaccagaa cagcgaggga agaggacagg cagcagacct gaagtccacc | 1140 |
| caggcagcca tcgatcagat caacggcaag ctgaataggc tgatcggcaa gacaaatgag | 1200 |
| aagttccacc agatcgagaa ggagttttcc gaggtggagg ccgcatcca ggatctggag | 1260 |
| aagtacgtgg aggacaccaa gatcgatctg tggagctata atgccgagct gctggtggcc | 1320 |
| ctggagaacc agcacaccat cgacctgaca gattccgaga tgaacaagct gttcgagaag | 1380 |
| accaagaagc agctgcggga gaatgccgag gacatgggca acggctgctt taagatctat | 1440 |
| cacaagtgcg ataatgcctg tatcggctcc atcagaaacg gcacatacga ccacgacgtg | 1500 |
| tacagggacg aggccctgaa caatcgcttc cagatcaagg gcgtggagct gaagtctggc | 1560 |
| tacaaggatt ggatcctgtg gatcagcttc gccatctcct gctttctgct gtgcgtggcc | 1620 |
| ctgctgggct ttatcatgtg ggcctgccag aagggcaaca tccggtgtaa tatcagatgc | 1680 |
| aacatctgta tc | 1692 |

<210> SEQ ID NO 109
<211> LENGTH: 1698
<212> TYPE: DNA
<213> ORGANISM: Artificial
<220> FEATURE:
<223> OTHER INFORMATION: synthetically-generated coding sequence

<400> SEQUENCE: 109

| | |
|---|---|
| atgaagacca tcatcgccct gtctcacatc ctgtgcctgg tgttcgccca gaagatccca | 60 |
| ggcaacgaca atagcaccgc cacactgtgc atcggacacc acgccgtgcc caacggcatg | 120 |
| atcgtgaaga ccatcacaaa tgatagaatc gaggtgacca acgccacaga gctggtgcag | 180 |
| aatagctcca tcggcgagat ctgcgacagc ccccaccaga tcctggatgg cgagaattgt | 240 |
| acactgatcg acgcactgct gggcgaccct cactgcgatg gctttcagaa cgagaagtgg | 300 |
| gatctgttcg tggagagatc taaggccttt agcaattgtt accccctatga cgtgcctgat | 360 |
| tacgcctccc tgaggtctct ggtggcctct agcggcaccc tggagttcaa gaatgagtcc | 420 |
| tttaactgga ccggcgtggc ccagaacggc acatcctctg cctgcatccg agaagctcc | 480 |
| tctagcttct tttctaggct gaattggctg acccacctga actacacata tccagccctg | 540 |
| aatgtgacaa tgcccaacaa ggagcagttc gacaagctgt acatctgggg agtgcaccac | 600 |
| ccaggcaccg acaaggatca gatctttctg tatgcccagt cctctggccg catcaccgtg | 660 |
| tccacaaagc ggtctcagca gacagccatc ccaaatatcg gaagcaggcc aaggatcagg | 720 |
| gacatcccta gccgcatctc catctactgg accatcgtga agcccggcga cgtgctggtc | 780 |
| atcaactcca atggcaacct gatcgcccct cgcggctatt tcaagatcca gtccggcaag | 840 |
| agctccatca tgcggtctga cgccccatc ggcaagtgca agagcgagtg tatcacacct | 900 |
| aatggctcta tcagcaacga taagccattt cagaatgtga acaagatcac ctacggcgcc | 960 |
| tgtcctagat atgtgaagca ctccacctg aagctggcca caggcatgag aaacgtgcca | 1020 |
| gagaagcaga ccaggggact gttcggagca atcgcaggct ttatcgagaa cggctgggag | 1080 |
| ggcatgaagg acggctggta cggcttcaga caccagaata gcgagggaag gggacaggca | 1140 |
| gcagatctga gtccacaca ggccgccatc aatcagatca cggcaagct gaaccgcctg | 1200 |
| atcggcaaga ccaatgagaa gttccaccag atcgagaagg agtttagcga ggtggaggga | 1260 |
| agggtgcagg acctggagaa gtacgtggag gactctaaga tcgatctgtg gagctataac | 1320 |
| gccgcctgc tggtggccct ggagaatcag cacaccatcg acctgacaga ttccgagatg | 1380 |
| aacaagctgt tcgagagaac caggaagcag ctgagagaga atgccgagga catgggcaac | 1440 |

```
ggctgtttta caatctacca caagtgcgat aacgcctgta tcggctctat caggaatggc     1500
acctacgacc acaacgtgta tcgcgatgag gccctgaata agcggttcca gatcaagggc     1560
atcgagctga agtccggcta taaggattgg atcctgtgga tcagcttcgc catctcctgc     1620
tttctgctgt gcgtggccct gctgggcttt atcatgtggg cctgccagaa gggcaatatc     1680
cggtgcaaca tctgtatc                                                  1698
```

<210> SEQ ID NO 110
<211> LENGTH: 1698
<212> TYPE: DNA
<213> ORGANISM: Artificial
<220> FEATURE:
<223> OTHER INFORMATION: synthetically-generated coding sequence

<400> SEQUENCE: 110

```
atgaagacca tcatcgccct gtcttatatc ctgtgcctgg tgttcgccca gaagctgcct      60
ggcaacgaca atagcaccgc cacactgtgc ctgggacacc acgccgtgcc aaatggcaca     120
atcgtgaaga ccatcacaaa cgatcagatc gaggtgacca atgccacaga gctggtgcag     180
aacagctcca tcgcgagat ctgcgactcc ccacaccaga tcctggatgg cgagaactgt     240
accctgatcg acgcactgct gggcgaccca cagtgcgatg gcttccagaa taagaagtgg     300
gatctgtttg tggagagatc taaggcctac agcaactgtt accctatga cgtgcctgat     360 tatgcctccc tgaggtctct ggtggcctct agcggcaccc tggagttcaa caatgagagc     420
tttaattgga cggcgtgac acagaacggc acatcctctg cctgcatccg agaagcaac     480 aattccttct tttctagact gaactggctg actcacctga atttcaagta ccctgccctg     540
aatgtgacaa tgccaaacaa tgagcagttt gacaagctgt atatctgggg agtgcaccac     600
cctggcaccg acaaggatca gatcttcctg tacgcacaga gctccggaag gatcaccgtg     660
tccacaaagc ggtctcagca ggccgtgatc cctaacatcg aagcaggcc aaggatcagg     720 gacatcccaa gccgcatctc catctattgg accatcgtga agccaggcga tatcctgctg     780
atcaactcca caggcaatct gatcgccccc agaggctact tcaagatcag gtctggcaag     840
tctagcatca tgcggagcga cgccccatc ggcaagtgca agtccgagtg tatcaccct     900 aacggctcta tcccaaatga taagcccttt cagaacgtga atagaatcac atacggcgcc     960
tgtcccagat atgtgaagca gaataccctg aagctggcca caggcatgcg caacgtgcct    1020
gagaagcaga ccagggaat cttcggagca atcgcaggct ttatcgagaa tggctgggag    1080
ggcatggtgg acggctggta cggctttaga caccagaaca gcgagggaag gggacaggca    1140
gcagacctga gtccaccca ggccgccatc gatcagatca cggcaagct gaatcgcctg    1200 atcggcaaga caaacgagaa gttccaccag atcgagaagg agttttccga ggtggaggc    1260 cggatccagg atctggagaa gtacgtggag gacaccaaga tcgatctgtg gtcctataat    1320
gccgagctgc tggtggccct ggagaaccag cacaccatcg acctgacaga ttctgagatg    1380
aacaagctgt tcgagaagac caagaagcag ctgagagaga acgccgagga catgggcaat    1440
ggctgtttta agatctatca caagtgcgat aatgcctgta tcggctctat caggaacggc    1500
acatacgacc acgacgtgta ccgcgacgag gccctgaaca tcggttcca gatcaagggc    1560 gtggagctga gagcggcta caaggattgg atcctgtgga tcagcttcgc catctcctgc    1620
tttctgctgt gcgtggccct gctgggcttt atcatgtggg cctgccagaa gggcaacatc    1680
aggtgcaata tctgtatc                                                 1698
```

<210> SEQ ID NO 111
<211> LENGTH: 1698
<212> TYPE: DNA
<213> ORGANISM: Artificial
<220> FEATURE:
<223> OTHER INFORMATION: synthetically-generated coding sequence

<400> SEQUENCE: 111

| | | | | | |
|---|---|---|---|---|---|
| atgaagacca | tcatcgccct | gtcccacatc | ctgtgcctgg | tgttcgccca | gaagatcccc | 60 |
| ggcaacgaca | attccaccgc | aatgctgtgc | ctgggacacc | acgccgtgtc | taatggcaca | 120 |
| atcgtgaaga | ccatcacaaa | tgatcgcatc | gaggtgacca | acgccacaga | gctggtgcag | 180 |
| agctcctcta | ccggcgagat | ctgcgacagc | cctcaccgga | tcctggatgg | caagaactgt | 240 |
| acactgatcg | acgcactgct | gggcgaccca | cactgcgatg | gcttccagaa | taaggagtgg | 300 |
| gatctgtttg | tggagcggag | caaggcccac | tctaactgtt | accctatga | cgtgcctgat | 360 |
| tacgtgagcc | tgcggtccct | ggtggcaagc | tccggcaccc | tggagttcaa | gaatgagtct | 420 |
| tttaactgga | ccggcgtggc | ccagaacggc | acatctagcg | cctgcatccg | agatcctct | 480 |
| agctccttct | ttagcagact | gaattggctg | acccacctga | actacacata | tccagccctg | 540 |
| aatgtgacaa | tgcccaacaa | tgagaagttc | gacaagctgt | acatctgggg | agtgcaccac | 600 |
| ccaggcaccg | acaacgatca | gatctttctg | tatgcacagg | ccagcggaag | gatcaccgtg | 660 |
| agcacaaagc | ggtcccagca | gacagtgatc | ccaaatatcg | gatccaggcc | acgcgtgcgg | 720 |
| aacatcccttt | ctaggatcag | catctactgg | accatcgtga | agcccggcga | cgtgctggtc | 780 |
| atcaacagca | tggcaaccct | gatcgcccct | cgcggctatt | tcaagatcca | gagcggcaag | 840 |
| tctagcatca | tgcggtccga | cgcccctatc | ggcaagtgca | attccgagtg | tatcacacct | 900 |
| aatggctcca | tctctaacga | taagccattt | cagaatgtga | acaagatcac | ctacggcgcc | 960 |
| tgtccaagat | atgtgaagca | ctccaccctg | aagctggcca | caggcatgag | gaacgtgccc | 1020 |
| gagagacaga | caaggggcat | cttcggcgcc | atcgccgtgt | ttatcgagaa | tggctgggag | 1080 |
| ggcatgatgg | acggctggta | cggcttccgc | caccagaact | ctgagggcac | cggacaggca | 1140 |
| gcagatctga | agagcacaca | ggccgccatc | aatcagatca | acggcaagct | gaatagactg | 1200 |
| atcgagaaga | ccaacgagaa | gttccaccag | atcgagaagg | agttttctga | ggtggagggc | 1260 |
| agggtgcagg | acctggagaa | gtacgtggag | gactccaaga | tcgatctgtg | gtcttataat | 1320 |
| gcaggactgc | tggtggccct | ggagaaccag | cacaccatcc | acctgacaga | tagcgagatg | 1380 |
| aacaagctgt | tcgagagaac | caagaagcag | ctgagggaga | tgccgagga | catgggcaac | 1440 |
| ggctgtttta | caatctacca | caagtgcgat | aatgcctgta | tcgagtccat | cagaaatggc | 1500 |
| acctacgacc | acaacgtgta | tagagatgag | gccctgaaca | agaggttcca | gatcaagggc | 1560 |
| atcgagctga | agtctggcta | taaggactgg | gtgctgtgga | tctcttttcgc | catcagctgc | 1620 |
| tttctgctgt | gcgtggtgct | gctgggcttt | atcatgtggg | cctgccagcg | cggcaatatc | 1680 |
| cggtgcaaca | tctgtatc | | | | | 1698 |

<210> SEQ ID NO 112
<211> LENGTH: 1698
<212> TYPE: DNA
<213> ORGANISM: Artificial
<220> FEATURE:
<223> OTHER INFORMATION: synthetically-generated coding sequence

<400> SEQUENCE: 112

| | | | | | |
|---|---|---|---|---|---|
| atgagaacca | tcatcgccct | gagctatatc | ttctgtctgg | tgtttgccca | gaagctgcca | 60 |

```
gagaacgaca attccaccgc cacactgtgc atcggacacc acgccgtgcc caacggcaca    120
ctggtgaaga ccatcacaaa cgatcaggtg gaggtgacca tgccacaga gctggtgcag    180 agctcctcta ccggaggaat ctgcgactcc ccacaccaga tcctggatgg caagaattgt    240
acactggtgg acgcactgct gggcgaccct cactgcgatg gcttccagaa cgagaagtgg    300
gatctgttcg tggagagatc taaggccttt agcaattgtt acccatatga cgtgcaggat    360
tacgcctctc tgaggagcct gatcgcaagc tccggcaccc tggagttcaa caatgagagc    420
tttaactggg ccggcgtgac ccagaatggc acatctagcg cctgcaagcg agatctaac     480 tcctcttttct ttagcaggct gaattggctg acccacctga agttcaagta cccagccctg    540
aacgtgacaa tgcccaataa ggagcagttt gacaagctgt atatctgggg agtgcaccac    600
ccatccaccg actctgatca gatctccctg tacgcccagg cctctggcag agtgaccgtg    660
tccacaaaga ggtctcagca gacagccatc ccaaacatcg gctccaggcc ccgcatccgg    720
aatatcccta gccgcgtgtc catctattgg accatcgtga gcccggcga tatcctgctg    780 atcaactgta caggcaatct gatcgccct cgcggctact tcaagatccg gaacggcaag    840
agctccatca tgcggtccaa cgccctatc ggcaagtgca atagcgcctg tatcacccca    900
aacggctcca tccccaatgg caagcctttt cagaacgtga atagagtgac atacggcgcc    960
tgccctagat atgtgaagca gtctaccctg aagctggcca caggcatgcg caacgtgcca   1020
gagaagcaga ccagggact gttcggagca atcgcaggct ttatcgagaa cggctgggag   1080
ggcatgaagg acggctggta cggcttccgg caccagaatt ccgagggaat cggacaggca   1140
gcagacctga gtctacaca ggccgccgtg gatcagatca acggcaagct gaatcgcgtg   1200
atcgagaaga ccaacgagaa gttccaccag atcgagaagg agttacaga ggtggagggc   1260 cggatccagg acatcgagaa gtacgtggag gacaccaagg tggatctgtg gtcttataac   1320
gccgagctgc tggtgagcct ggagaatcag cacaccatcg acatgacaga tagcgagatg   1380
aataagctgt tcgagagaac caggaagcag ctgagagaga acgccgagga tatcggcaat   1440 ggctgttta agatctatca caagtgcaac aatgcctgta tcggctctat caggaacgag   1500
acatacgacc acaacgtgta ccgcgatgag gccctgaaca atcggttcca catcaagggc   1560
gtggagctga gagcggcta caagaactgg atcctgtgga tcagcttcgc cacctcctgc   1620 ttttctgctgt gcatcgtgct gctgggcttt atcatgtggg cctgccagaa gggcaacatc   1680
aagtgcaata tctgtatc                                                 1698

<210> SEQ ID NO 113
<211> LENGTH: 1713
<212> TYPE: DNA
<213> ORGANISM: Artificial
<220> FEATURE:
<223> OTHER INFORMATION: synthetically-generated coding sequence

<400> SEQUENCE: 113
atgaagacca tcatcgcctt ctcttgcatc ctgtgcctga tctttgccca gaagctgccc      60
ggctccgaca caattctat ggccacccctg tgcctgggac accacgcagt gcctaatggc     120
acactggtga gaccatcac agacgatcag atcgaggtga ccaacgccac agagctggtg     180
cagagctcct ctaccggcag gatctgtaat tcccctggcc accagatcct ggatggcaag    240
aactgcacac tgatcgacgc cctgctgggc gatccacact gtgacgattt ccagaataag    300
tgggacctgt tgtggagcg gagcaccgcc tactccggca actgctatcc ctactatgtg     360
```

| | |
|---|---|
| cctgattacg ccagcctgag agagcagctg tccctggtgg ccagctccgg caccctggag | 420 |
| ttcacacagg agtctttaa ttggaccgga gtggcacagg acggctctag ctacgcctgt | 480 |
| cggagaggca gcgtgaacaa ttctttcttt agccgcctga actggctgta tctgaattac | 540 |
| aagtatcccg ccctgaacgt gacaatgcct aacaatgaca agttcgataa gctgtacatc | 600 |
| tggggagtgc accacccagg aaccgacaag gatcagacaa atctgtatgt gcaggccagc | 660 |
| ggcagggtgt tgtctaccaa cgcagccag cagacagtga tccctaacat cggctcccgg | 720 |
| ccatgggtga gaggcgtgtc ctctatcatc tctatctact ggaccatcgt gaagcctggc | 780 |
| gacatcctgc tgatcaacag cacaggcaat ctgatcgccc caaggggcta tttcaagatc | 840 |
| cagtccggca agagctccgg catcatgcgc tctgacgccc caatcgattg caacagcgag | 900 |
| tgtatcaccc ccaacggctc catcccaaat gataagccct ttcagaacgt gaataggatc | 960 |
| acatacggcg cctgcccacg ctatgtgaag cagaataccc tgaagctggc cacaggcatg | 1020 |
| cggaacgtgc ccgagaagca gaccagaggc atcttcggcg ccatcgccgg ctttatcgag | 1080 |
| aatggctggg agggcatggt ggacggctgg tacggcttcc ggcaccagaa ctctgaggga | 1140 |
| accggacagg cagcagatct gaagagcacc caggcagcca tcaaccagat cacaggcaag | 1200 |
| ctgaatagag tgatcaagaa gaccaacgag aagttccacc agatcgagaa ggagtttagc | 1260 |
| gaggtggagg gaaggatcca ggacctggag aagtacgtgg aggacaccaa gatcgatctg | 1320 |
| tggtcctata atgccgagct gctggtggcc ctggagaacc agcacaccat cgacctgaca | 1380 |
| gattctgaga tgaacaagct gttcgagagg accaggaagc agctgaggga gaacgcagag | 1440 |
| gacatgggca atggctgctt taagatctac acaagtgcg ataatgcctg tatcggctcc | 1500 |
| atcagaaacg gcacatacga ccacgacgtg taccggacg aggccctgaa caatagattc | 1560 |
| cagatcaagg gcgtgcagct gaagagcggc tataaggatt ggatcctgtg gatctccttc | 1620 |
| gccatctctt gctttctgct gtgcgtggtg ctgctgggct ttatctccat gtgggcctgt | 1680 |
| cagaagggca acatcagatg caatatctgt atc | 1713 |

<210> SEQ ID NO 114
<211> LENGTH: 1698
<212> TYPE: DNA
<213> ORGANISM: Artificial
<220> FEATURE:
<223> OTHER INFORMATION: synthetically-generated coding sequence

<400> SEQUENCE: 114

| | |
|---|---|
| atgaagacca tcatcgcctt cagctgcatc ctgtgcctga tctttgccca gaagctgcct | 60 |
| ggctccgaca attctaccgc caccctgtgc ctgggacacc acgcagtgcc aaacggcaca | 120 |
| atggtgaaga ccatcacaga cgatcaggtg gaggtgacca atgccacaga gctggtgcag | 180 |
| agctcctcta ccggccggat ctgcaatagc ccacaccaga tcctggatgg caagaactgt | 240 |
| acactgatcg actccctgct gggcgatccc cactgcgacg atttccagaa taaggagtgg | 300 |
| gacctgtttg tggagaggtc taaggcctac agcaactgtt atccctacta tgtgcctgat | 360 |
| tacgccaccc tgcgctccct ggtggccagc tccggcaatc tggagttcac ccaggagtct | 420 |
| tttaactgga caggagtggc acaggacggc tctagctacg catgccggag aggcagcgtg | 480 |
| aactccttct tttctagact gaattggctg tataacctga attacaagta tcctgagcag | 540 |
| aacgtgacca tgccaaacaa tgacaagttc gataagctgt acatctgggg agtgcaccac | 600 |
| cctggaaccc acaaggatca gacaaatctg tatgtgcagg ccagcggcag agtgatcgtg | 660 |
| agcaccaagc ggagccagca gacaatcatc ccaaacatcg gctctcggcc ctgggtgaga | 720 |

```
ggcgtgtcct ctatcatcag catccactgg accatcgtga agccaggcga catcctgctg      780
atcaactcca caggcaatct gatcgccccc agaggctact tcaagatcca gaatggcaag      840
agctccatca tgagatccga cgcccacatc gatgagtgca actctgagtg tatcaccccc      900
aacggctcta tcagcaatga taagccttt cagaacgtga taagatcac atacggcgcc       960 tgccccaggt atatcaagca gaataccctg aagctggcca caggcatgag gaacatccct     1020
gagaagcaga cccgcggcat cttcggagca atcgcaggct ttatcgagaa cggctgggag     1080
ggcatggtga atggctggta tggcttccgc caccagaaca gcgagggaac cggacaggca     1140
gcagacctga agtccaccca ggccgccatc aaccagatca caggcaagct gaatagagtg     1200
atcaagaaga ccaacgagaa gttccaccag atcgagaagg agttttctga ggtggagggc     1260
agaatccagg atctggagaa gtacgtggag gacaccaaga tcgatatctg gtcctataat     1320
gccgagctgc tggtggccct ggagaaccag cacaccatcg acctgacaga tagcgagatg     1380
tccaagctgt tcgagcggac caggcgccag ctgagagaga cgccgagga catcggcaat      1440 ggctgtttta agatctacca caagtgcgat aatagctgta tggagtccat caggaacggc     1500
acatacgacc acgatatcta tcggaacgag gccctgaaca atagattcca gatcaagggc     1560
gtgcagctga agagcggcta taaggactgg atcctgtgga tctctttcgc catcagctgc     1620
tttctgctgt gcgtggtgct gctgggcttt atcatgtggg cctgccagag gggcaacatc     1680
cgctgcaata tctgcgtg                                                   1698

<210> SEQ ID NO 115
<211> LENGTH: 1698
<212> TYPE: DNA
<213> ORGANISM: Artificial
<220> FEATURE:
<223> OTHER INFORMATION: synthetically-generated coding sequence

<400> SEQUENCE: 115
atgaaggcca tcctggtggt gctgctgtac acctttacca cagccaacgc cgacacactg       60
tgcatcggct atcacgccaa caatagcacc gacacagtgg ataccgtgct ggagaagaat      120
gtgaccgtga cacacagcgt gaacctgctg gaggattccc acaatggcaa gctgtgcaag      180
ctgaggggag tggcaccact gcacctgggc aagtgcaaca tcgcaggatg gctgctggga      240
aatccagagt gtgagagcct gtccaccgcc agctcctggt cctacatcgt ggagacctct      300
aacagcgaca atggcacatg ctacccaggc gacttcatca actatgagga gctgagggag      360
cagctgagca gcgtgagcag cttcgagcgg ttcgagatct tccccaagac cagctcctgg      420
cctaaccacg acaccaatag gggagtgaca gcagcatgtc cacacgcagg aacaaactcc      480
ttctaccgca atctgatctg gctggtgaag aagggcaatt cttaccctaa gctgtccaag      540
tcttatatca acaataagga gaaggagtg ctggtgctgt gggcaatcca ccacccagc        600 acctccgccg accagcagag cctgtaccag aacgccgatg cctacgtgtt cgtgggctct      660
agcaggtact cccgcaagtt cgagccagag atcgcaacca ggccaaaggt gagagaccag      720
gccggcagga tgaattacta ttggacactg gtggagcccg gcgataagat cacctttgag      780
gccacaggca acctggtggt gcctcggtat gccttcgccc tgaagagaaa ttctggcagc     840
ggcatcatca tctccgatac ctctgtgcac gactgcgata ccacatgtca gacccctaac     900
ggcgccatca atacaagcct gccttttccag aacatccacc cagtgacaat cggcgagtgc     960
cctaagtacg tgaagtccac caagctgagg atggccacag gcctgcgcaa tatcccaagc    1020
```

| | |
|---|---|
| atccagtccc gcggcctgtt tggagcaatc gcaggcttca tcgagggagg atggaccgga | 1080 |
| atgatcgacg gatggtacgg ctatcaccac cagaacgagc agggctctgg ctatgccgcc | 1140 |
| gacctgaaga gcacccagaa tgccatcgat ggcatcacaa acaaggtcaa tagcgtgatc | 1200 |
| gagaagatga acacccagtt tacagccgtg gcaaggagt tcaataagct ggagcggaga | 1260 |
| atggagaacc tgaataagaa ggtggacgat ggctttctgg atatctggac ctacaacgcc | 1320 |
| gagctgctgg tgctgctgga gaatgagcgg acactggact accacgattc caacgtgaag | 1380 |
| aatctgtatg agaaggtgag atctcagctg aagaacaatg ccaaggagat cggcaacggc | 1440 |
| tgcttcgagt tttaccacaa gtgcaacaat gagtgtatgg agtctgtgaa gaacggcacc | 1500 |
| tacgactatc ccaagtatag cgaggaggcc aagctgaatg ggaggagat cgatggcgtg | 1560 |
| aagctggaga gcaccagaat ctaccagatc ctggccatct attccacagt ggcctcctct | 1620 |
| ctggtgctgc tggtgtccct gggcgccatc tctttctgga tgtgctctaa cggcagcctg | 1680 |
| cagtgccgga tctgtatc | 1698 |

<210> SEQ ID NO 116
<211> LENGTH: 1695
<212> TYPE: DNA
<213> ORGANISM: Artificial
<220> FEATURE:
<223> OTHER INFORMATION: synthetically-generated coding sequence

<400> SEQUENCE: 116

| | |
|---|---|
| atgaaggtga agctgctgat cctgctgtgc acctttacag ccacctacgc cgacacaatc | 60 |
| tgtatcggct atcacgccaa caattccaca gacaccgtgg ataccatcct ggagaagaac | 120 |
| gtgacagtga cccactctgt gaatctgctg gagaacaggc acaatggcaa gctgtgcctg | 180 |
| ctgaaggaa tcgcaccact gcagctggga aactgcagcg tggcaggatg gatcctgggc | 240 |
| aatcctgagt gtgagtctct gatcagcaag aagtcctggt cttacatcgt ggagacaccc | 300 |
| aaccctgaga atggcgcctg ctaccccggc gagtttgccg attatgagga gctgagggag | 360 |
| cagctgagca ccgtgagcag cttcgagcgg ttcgagatct tcccaaagga gtctagctgg | 420 |
| cccaaccaca cagtgaccgg cgtgagcgcc tcctgttctc acaacggcga gaggtccttc | 480 |
| taccgcaatc tgatctggct gaccgtgaag aacggcctgt accctaatct gagcaagtcc | 540 |
| tatgagaatg acaagggcaa ggaggtgctg atcctgtggg gcgtgcacca cccatccaac | 600 |
| atcggcgatc agcgcacact gtaccacacc gagaatgcct acgtgagcgt ggtgtcctct | 660 |
| cactacagcc ggagattcac acctgagatc accaagcggc caaaggtgag agaccaggag | 720 |
| ggccggatca actactattg gacactgctg gagcctggcg ataccatcat ctttgaggcc | 780 |
| aacggcaatc tgatcgcccc atggtatgcc ttcgccctga gcagaggcct gggatccggc | 840 |
| atcatcacat ctaatgcccc aatggacgag tgcgatgcca agtgtcagac cccacaggga | 900 |
| gccatcaaca gctccctgcc ctttcagaat gtgcacctg tgacaatcgg cgagtgtcca | 960 |
| aagtacgtga ggagcgccaa gctgaggatg gtgaccggac tgaggaacgt gcctccatc | 1020 |
| cagtctagag gcctgctggg agcaatcgca ggcttcatcg agggaggatg acaggaatg | 1080 |
| gtggacggat ggtacggcta tcaccaccag aatggacagg gatccggata tgcagcagat | 1140 |
| caggagtcta cacagaacgc catcaatggc atcaccaaca aggtcaatag catcatcgag | 1200 |
| aagatgaaca tccagtttac ctccgtgggc aaggagttca atcacctgga gaagaggatc | 1260 |
| gagaacctga ataagaaggt ggacgatggc tttctggacg tgtggacata caacgccgag | 1320 |
| ctgctgatcc tgctggagaa tgagcgcacc ctggacttcc acgattccaa cgtgaagtct | 1380 |

```
ctgtatgaga aggtgaagag ccagctgaag aacaatgcca aggaagtggg caatggctgc   1440
ttcgagtttt accacaagtg cgacgataca tgtatggagt ccgtgaagaa cggcacctac   1500
aattatccta agtatagcga ggagtccaag ctgaaccggg agaagatcga cggcgtgaag   1560
ctggattcta tgggcgtgta cagaatcctg gccatctata gcaccgtggc ctctagcctg   1620
gtgctggtgg tgagcctggg agcaatctcc ttttggatgt gctctaacgg cagcctgcag   1680
tgccgggtgt gcatc                                                    1695
```

<210> SEQ ID NO 117
<211> LENGTH: 1698
<212> TYPE: DNA
<213> ORGANISM: Artificial
<220> FEATURE:
<223> OTHER INFORMATION: synthetically-generated coding sequence

<400> SEQUENCE: 117

```
atggaggcca agctgttcgt gctgttttgc gccttcaccg ccctgaaggc cgacacaatc     60
tgcgtgggct accacgccaa caatagcacc gagacagtgg ataccgtgct ggagaagaac    120
gtggccgtga cacactccgt gaacctgctg gaggacaagc acaatggcaa gctgtgcaag    180
ctgggaggaa tcgcaccact gcacctgggc aagtgcaaca tcgccggctg gatcctgggc    240
aatcctgagt gtgagctgct gatcagcaag gagtcttgga gctacatcgt ggaggcccca    300
aactccgaca atggagcatg ctacccagga cagttcgcag attatgagga gctgcgggag    360
cacctgagct ccgtgtctag cttttgagaag ttcgagatct ttccaaaggc ctcctcttgg    420
cccaaccacg attctaataa gggagtgacc gcagcatgtc cttacgcagg cgccaacagc    480
ttttatagga atctgctgtg gatcgtgaag aagggcaaca gctacccaaa gatcaataag    540
tcctacatca acaataaggg caaggaggtg ctggtgctgt ggggaatcca ccacccacct    600
acctccacag accagcagtc tctgtacaag aacgccgatg cctacgtgtt cgtgggcacc    660
tcccggtact ctaagaagtt taagcctgag atcgccatca ggccaaaggt gcgcgaccag    720
gagggcagaa tgaattacta ttggaccctg ctggaccagg gcgataccat cacattcgag    780
gcaacaggaa acctggtggc caagatatg cctttgcca tggagcgcaa tgccggcagc    840
ggcatcatca tctccgacac ccctgtgcac gattgcaaca ccacatgtca gacaccaaag    900
ggcgccatca acagcaatct gccctttcag aatgtgcacc ctatcaccat cggcgagtgt    960
ccaaagtacg tgcggtccac caagctgaga atggtgacag gcctgcggaa catccccagc   1020
gtgcagtcca gaggcctgtt cggagcaatc gcaggcttttc tggagggagg atggacaggc   1080
atggtgaacg gctggtacgg ctatcaccac cagaatgacc agggctctgg ctatgccgcc   1140
gatcagaaga gcacccagat cgccatcgac ggcatctcta caaggtcaa tagcgtgatc   1200 gagaagatga atatccagtt cacagccgtg ggcaaggagt ttagccacct ggagcggaga   1260
atcgagaacc tgaataagaa ggtggacgat ggcctgctgg acgtgtggac ctacaacgcc   1320
gagatgctgg tgctgctgga gaatgagagg acactggact tccacgactt caacgtgaag   1380
aatctgtacg agaaggtgaa gtcccagctg cgcaacaatg ccaaggagat cggcaacggc   1440
tgcttcgagt tttatcacaa gtgcgacaac acctgtatga gtccgtgag gaatggcaca   1500 tacgattatc ctaagtacta tgaggagtct aagctgaatc gcgaggagat cgatggcgtg   1560
aagctggagt ccatgggcgt gtaccagatc ctggccatct attctaccgc agccagctcc   1620
ctggtgctgc tggtgtccct gggagccgtg tctttctgga tgtgctctaa cggcagcctg   1680
```

```
cagtgcaaga tctgtatc                                                      1698

<210> SEQ ID NO 118
<211> LENGTH: 1713
<212> TYPE: DNA
<213> ORGANISM: Artificial
<220> FEATURE:
<223> OTHER INFORMATION: synthetically-generated coding sequence

<400> SEQUENCE: 118
atgaagacca tcatcgcctt ctcctgcatc ctgtgcctga tcttcgccca gaagctgccc          60
ggcagcgaca caactccat ggccaccctg tgcctgggac accacgccgt gccaaacggc          120
accctggtga agaccatcac cgacgaccag atcgaggtga ccaacgccac cgagctggtg         180
cagtccagct ccaccggaag gatctgcaac agcccaggac accagatcct ggacggcaag         240
aactgcaccc tgatcgacgc tctgctgggc gacccacact gcgacgactt ccagaacaag         300
tgggacctgt tcgtggagcg cagcaccgcc tactccggca actgctaccc ctactacgtg         360
ccagactacg ccagcctgag ggagcagctg tccctggtgg ctagctccgg caccctggag         420
ttcacccagg agtccttcaa ctggaccggc gtggcccagg acggaagctc ctacgcttgc         480
aggaggggaa gcgtgaacaa cagcttcttc tccagactga actggctgta cctgaactac         540
aagtaccccg ccctgaacgt gaccatgcca acaacgaca gttcgacaa gctgtacatc          600 tggggagtgc accacccagg caccgacaag gaccagacca acctgtacgt gcaggcctcc         660
ggaagggtgg tgagcaccaa gagatcccag cagaccgtga tccccaacat cggatccagg         720
ccatgggtgc ggggcgtgag ctccatcatc agcatctact ggaccatcgt gaagcccggc         780
gacatcctgc tgatcaactc caccggcaac ctgatcgccc aaggggcta cttcaagatc         840 cagagcggca gagctccgg catcatgaga gcgacgccc ccatcgactg caactccgag          900
tgcatcaccc caaacggcag catccccaac gacaagccat tccagaacgt gaacaggatc         960
acctacggcg cctgccccag atacgtgaag cagaacaccc tgaagctggc caccggcatg        1020
cgcaacgtgc cagagaagca gaccagggga atcttcggag ctatcgctgg cttcatcgag        1080
aacggctggg agggcatggt ggacggctgg tacggcttcc gccaccagaa ctccagggc         1140 accggacagg ctgctgacct gaagagcacc caggccgcca tcaaccagat caccggcaag        1200
ctgaaccgcg tgatcaagaa gaccaacgag aagttccacc agatcgagaa ggagttctcc        1260
gaggtggagg gcagaatcca ggacctggag aagtacgtgg aggacaccaa gatcgacctg        1320
tggtcctaca acgccgagct gctggtggcc ctggagaacc agcacaccat cgacctgacc        1380
gacagcgaga tgaacaagct gttcgagagg accagaaagc agctgcgcga aacgccgag         1440 gacatgggca acggctgctt caagatctac cacaagtgcg acaacgcctg catcggcagc        1500
atccggaacg gcacctacga ccacgacgtg taccgcgacg aggccctgaa caaccggttc        1560
cagatcaagg gcgtgcagct gaagtccggc tacaaggact ggatcctgtg gatcagcttc        1620
gccatctcct gcttcctgct gtgcgtggtg ctgctgggct tcatcagcat gtgggcctgc        1680
cagaagggca catccggtg caacatctgc atc                                      1713

<210> SEQ ID NO 119
<211> LENGTH: 1698
<212> TYPE: DNA
<213> ORGANISM: Artificial
<220> FEATURE:
<223> OTHER INFORMATION: synthetically-generated coding sequence

<400> SEQUENCE: 119
```

```
atgaagacca tcatcgcctt ctcctgcatc ctgtgcctga tcttcgccca gaagctgcca        60
ggaagcgaca actccaccgc caccctgtgc ctgggacacc acgccgtgcc aaacggcacc       120
atggtgaaga ccatcaccga cgaccaggtg gaggtgacca acgccaccga gctggtgcag       180
tccagctcca ccgaaggat ctgcaactcc ccacaccaga tcctggacgg caagaactgc        240
accctgatcg acagcctgct gggcgaccca cactgcgacg acttccagaa caaggagtgg       300
gacctgttcg tggagaggtc caaggcctac agcaactgct accctacta cgtgccagac       360 tacgccaccc tgagatccct ggtggccagc tccggcaacc tggagttcac ccaggagagc      420
ttcaactgga ccggcgtggc ccaggacgga agctcctacg cttgcaggag gggcagcgtg       480
aactccttct tcagccggct gaactggctg tacaacctga actacaagta ccccgagcag       540
aacgtgacca tgccaaacaa cgacaagttc gacaagctgt acatctgggg agtgcaccac       600
ccaggcaccg acaaggacca gaccaacctg tacgtgcagg cctccggacg cgtgatcgtg       660
tccaccaaga gaagccagca gaccatcatc cccaacatcg gatccaggcc atgggtgcgg       720
ggcgtgagct ccatcatcag catccactgg accatcgtga gcccggcga catcctgctg        780 atcaacagca ccgaaaacct gatcgctcca aggggctact tcaagatcca gaacggcaag       840
agctccatca tgcggtccga cgcccacatc gacgagtgca cagcgagtg catcaccccc        900 aacggcagca tctccaacga caagccattc cagaacgtga acaagatcac ctacggcgcc       960
tgccccaggt acatcaagca gaacaccctg aagctggcca ccggcatgag gaacatccca      1020
gagaagcaga ccagaggcat cttcggcgcc atcgccggct tcatcgagaa cggctgggag       1080
ggcatggtga acggctggta cggcttcaga caccagaact ccgagggcac cggacaggct       1140
gctgacctga agagcaccca ggccgccatc aaccagatca ccggcaagct gaaccgcgtg       1200
atcaagaaga ccaacgagaa gttccaccag atcgagaagg agttctccga ggtggaggga       1260
aggatccagg acctggagaa gtacgtggag gacaccaaga tcgacatctg gagctacaac       1320
gccgagctgc tggtggccct ggagaaccag cacaccatcg acctgaccga ctccgagatg       1380
agcaagctgt tcgagcgcac caggagacag ctgcgggaga acgccgagga catcggcaac       1440
ggctgcttca gatctacca caagtgcgac aactcctgca tggagagcat caggaacggc       1500
acctacgacc acgacatcta ccgcaacgag gccctgaaca accggttcca gatcaagggc       1560
gtgcagctga agagcggcta caaggactgg atcctgtgga tctccttcgc catcagctgc       1620
ttcctgctgt gcgtggtgct gctgggcttc atcatgtggg cctgccagag gggcaacatc       1680
agatgcaaca tctgcgtg                                                    1698
```

<210> SEQ ID NO 120
<211> LENGTH: 1698
<212> TYPE: DNA
<213> ORGANISM: Artificial
<220> FEATURE:
<223> OTHER INFORMATION: synthetically-generated coding sequence

<400> SEQUENCE: 120

```
atgaagacca tcatcgcctt ctcctgcatc ctgtgcctga tcttcgccca gaagctgccc        60
ggcagcgaca actccatggc caccctgtgc ctgggacacc acgccgtgcc aaacggcacc       120
ctggtgaaga ccatcaccga cgaccagatc gaggtgacca acgccaccga gctggtgcag       180
tccagctcca ccggcaggat ctgcaacagc cccaccagat cctggacgg caagaactgc        240 accctgatcg acgctctgct gggcgaccca cactgcgacg acttccagaa caaggagtgg       300
```

```
gacctgttcg tggagcgcag caccgcctac agcaactgct accCctacta cgtgccagac    360
tacgccagcc tgcggtccct ggtggctagc tccggcaccc tggagttcac ccaggagtcc    420
ttcaactgga ccggcgtggc ccaggacgga agctcctacg cttgcaggag gggcagcgtg    480
aactccttct tcagcagact gaactggctg tacaacctga actacaagta ccccgagcag    540
aacgtgacca tgccaaacaa cgacaagttc gacaagctgt acatctgggg agtgcaccac    600
ccaggcaccg acaaggacca gaccaacctg tacgtgcagg cctccggacg cgtgatcgtg    660
tccaccaaga gaagccagca gaccgtgatc cccaacatcg atccaggcc atgggtgcgg    720 ggcgtgagct ccatcatcag catctactgg accatcgtga agcccggcga catcctgctg    780
atcaacagca ccggcaacct gatcgcccca aggggctact caagatcca gtccggcaag    840 agctccatca tgagaagcga cgcccacatc gacgagtgca actccgagtg catcacccCc    900
aacggcagca tccccaacga caagccattc cagaacgtga acaggatcac ctacggcgcc    960
tgccccagat acgtgaagca gaacaccctg aagctggcca ccggcatgcg caacgtgcca   1020
gagaagcaga ccaggggaat cttcggagct atcgctggct tcatcgagaa cggctgggag   1080
ggcatggtgg acggctggta cggcttccgc caccagaact ccgagggcac cggacaggct   1140
gctgacctga gagcaccca ggccgccatc aaccagatca ccggcaagct gaaccgcgtg   1200
atcaagaaga ccaacgagaa gttccaccag atcgagaagg agttcagcga ggtggagggc   1260
agaatccagg acctggagaa gtacgtggag gacaccaaga tcgacctgtg gtcctacaac   1320
gccgagctgc tggtggccct ggagaaccag cacaccatcg acctgaccga cagcgagatg   1380
aacaagctgt tcgagaggac cagaaagcag ctgcgcgaga cgccgagga catgggcaac   1440 ggctgcttca agatctacca caagtgcgac aacgcctgca tcggctccat ccggaacggc   1500
acctacgacc acgacgtgta ccgcgacgag gccctgaaca ccggttcca gatcaagggc   1560 gtgcagctga agagcggcta caaggactgg atcctgtgga tctccttcgc catcagctgc   1620
ttcctgctgt gcgtggtgct gctgggcttc atcatgtggg cctgccagaa gggcaacatc   1680
cggtgcaaca tctgcatc                                                 1698
```

<210> SEQ ID NO 121
<211> LENGTH: 1698
<212> TYPE: DNA
<213> ORGANISM: Artificial
<220> FEATURE:
<223> OTHER INFORMATION: synthetically-generated coding sequence

<400> SEQUENCE: 121

```
atgaagacca tcatcgccct gtcctacatc ctgtgcctgg tgttcgccca gaagctgcca    60
ggaaacgaca caacatggc caccctgtgc ctgggacacc acgccgtgcc caacggcacc    120
atcgtgaaga ccatcaccaa cgaccagatc gaggtgacca acgccaccga gctggtgcag    180
tccaccagca agggcgagat ctgctccagc ccacaccaga tcctggacgg cgagaactgc    240
accctgatcg acgtctgct gggcgaccca cactgcgacg acttccagaa caagaagtgg    300
gacctgttcg tggagagatc caaggcccac agcaactgct accCctacta cgtgccagac    360
tacgccaccc tgcgctccct ggtggcttcc agcggcaacc tggagttcac ccaggagagc    420
ttcaactgga ccggagtgac ccaggacgga gcttccagcg cctgcaagcg ccggtccagc    480
aagtccttct tcagccgcct gaactggctg cacaacctga actacaagta cccagccctg    540
aacgtgacca tgcccaacaa cgacaacttc gacaagctgt acatctgggg cgtgcaccac    600
ccatccaccg acaaggacca gacctccctg tacatccagg ccagcggaag ggtgaccgtg    660
```

```
tccaccaaga ggagccagca ggccgtgatc ccaaacatcg gatccaggcc acgggtgagg      720
gacatcccct cccggatcag catctactgg accatcgtga ggccaggcga catcctgctg      780
atcaacagca acggcaacct gatcgccccc agaggctact tcaagatccg ctccggcaag      840
tccagcatca tgcggagcga cgcccccatc ggcaactgca cagcgagtg catcaccccca     900 aacggctcca tcagcaacga caagcccttc cagaacgtga acaagatcac ctacggcgcc      960
tgcccaaggt acatcaagca gaacaccctg aagctggcca ccggcatgag aaacatcccc     1020
gagaagcaga ccagggaat cttcggagct aaggctggct tcatcgagaa cggctgggag     1080
ggcatggtga acggctggta cggcttcaga caccagaact ccgagggaag gggacaggct     1140
gctgacctga gagcaccca ggccgccatc gaccagatca cggcaagct gaacagactg      1200 atcggcaaga ccaacgagaa gttccaccag atcgagaagg agttctccga gatcgagggc     1260
cggatccagg acctggagag gtacgtggag gacaccaaga tcgacatctg gagctacaac     1320
gccgagctgc tggtggccat ggagaaccag cacaccatcg acctgaccga ctccgagatg     1380
agcaagctgt tcgagagaac caggagacag ctgcgcgaga cgccgagga catgggcaac     1440 ggctgcctga gatctacca caagtgcgac aactcctgca tggagagcat ccggaacggc     1500
acctacgacc acgacatcta ccggaacgag gccctgaaca caggttcca gatcaagggc     1560 gtggagctga gagcgagta caaggactgg atcctgtgga tctccttcgc caccagctgc     1620
ttcctgctgt gcgccgtgct gctgggcttc atcatgtggg cctgccagaa gggcaacatc     1680
aagtgcaaca tctgcatc                                                   1698
```

<210> SEQ ID NO 122
<211> LENGTH: 1698
<212> TYPE: DNA
<213> ORGANISM: Artificial
<220> FEATURE:
<223> OTHER INFORMATION: synthetically-generated coding sequence

<400> SEQUENCE: 122

```
atgaaggcca tcatcgcctt ctcctgcatc ctgtgccaga tcttcgccca gaagctgccc       60
ggcaacgaca actccaccgc caccctgtgc ctgggacacc acgccgtgag caacggcacc      120
ctggtgaaga ccatcaccga cgaccaggtg gaggtgacca acgccaccga gctggtgcag      180
aacttctcca tgggcaagat ctgcaagaac ccccacagga tcctggacgg cgccaactgc      240
accctgatcg acagcctgct gggcgaccca cactgcgacg gcttccagaa cgagaagtgg      300
gacctgttca tcgagaggtc caaggccttc agcaactgct accccacga cgtgccagac      360 tacgcctccc tgagaagcct gatcgcctcc agcggcaccc tggagttcaa caacgagtcc      420
ttcaactgga ccggagtgac ccagaacgga ggatccagcg cctgcaagag gggacccaac      480
aactccttct tcagcagact gaactggctg acccacctga acttcaagta ccccgccctg      540
gaggtgacca tgccaaacaa cgagcagttc gacaagctgt acatctgggg agtgcaccac      600
ccagctaccg acaaggacca gatcagcctg tacgctcagg ctgctggaag gatcatcgtg      660
tccaccaaga gaagccagca gaccatcatc cccaacatcg gctccaggcc atggatcaga      720
ggcgtgtcca gcatcatcag catccactgg accatcgtga gcccggcga catgctgctg      780 atcaactcca ccggcaacat catcgcccca cgcggctact tcaagatcca gaccggcaag      840
tccagcgtga tgcggagcga cgctccaatc ggcaagtgca actccgcctg catcaccccca      900 aacggaagca tccccaacga ccgcccattc cagaacgtga acaagatcac ctacggcgcc      960
```

-continued

```
tgccccaagt acgtgaagca gaacaccctg aagctggcca ccggcatgag gaacatccca    1020
gagaggcaga ccaggggaat cttcggagct atcgccggct tcatcgagaa cggctgggag    1080
ggcatgatcg acggctggta cggcttccgc caccacaact ccgagggcac cggacaggct    1140
gctgacatca agagcaccca ggctgccatc aaccagatca acggcaagct gaaccgcgtg    1200
atcgagaaga ccaacgagaa gttccaccag atcgagaagg agttcctgga ggtggagggc    1260
cggatccagg acatcgagaa gtacatcgag gacaccaaga tcgacctgtg gtcctacaac    1320
gccgagctgc tgatcgccct ggagaaccag cacaccatcg acctggccga cagcgagatg    1380
aacaagctgt tcgagaagac caagaagcag ctgagggaga cgccgagga catcggcaac    1440 ggctgcttca agatctacca caagtgcgac aacacctgca tcggcagcat cagaaacggc    1500
acctacaacc acgacgtgta ccgcgacgag gccgtgaaca accggttcca gatcaagggc    1560
gtgcagctga agctgggcta caaggactgg atcctgtgga tctccttcgc catgagctgc    1620
ttcctgctgt gcgtggccct gctgggcttc atcatgtggg cttgccagag gggaaacatc    1680
aggtgcaaca tctgcgtg                                                  1698
```

METHODS OF MAKING AND USING UNIVERSAL CENTRALIZED INFLUENZA VACCINE GENES

CROSS REFERENCE TO RELATED APPLICATIONS

This application is a National Stage Application under 35 U.S.C. § 371 and claims the benefit of priority to International Application No. PCT/US2019/052137, filed Sep. 20, 2019, which claims the benefit of U.S. Application No. 62/734,791, filed on Sep. 21, 2018. The contents of such applications are incorporated by reference in their entireties.

TECHNICAL FIELD

This disclosure generally relates to vaccines and, specifically, influenza vaccines.

BACKGROUND

Influenza virus was identified as the causative agent for febrile illness in swine in 1931. Influenza virus in humans was discovered two years later in 1933.

Annually, 5-15% of the world's population is affected by epidemics and have upper respiratory tract infections, 3 to 5 million have severe illness, and 250,000 to 500,000 cases result in death (WHO 2009). In the U.S., seasonal influenza affects up to 20% of the population, results in 200,000 hospitalizations and approximately 37,000 deaths each year. The World Health Organization (WHO) states, "influenza rapidly spreads around the world in seasonal epidemics and imposes a considerable economic burden in the form of hospital and other health care costs and lost productivity. In the United States of America, it is estimated that influenza epidemics cost up to $167 billion per year."

While these seasonal infections are certainly of concern, pandemic influenza outbreaks and intentional releases of pathogenic influenza are of substantially higher concern. During the past century, there have been several severe pandemics (WHO 2009). In 1918-1919, an H1N1 known as the Spanish Flu caused the world's largest influenza pandemic, killing 20-40 million people. In 1957, the Asian flu caused by an H2N2 virus resulted in ~1.5 million deaths, and in 1968, the Hong Kong flu caused by an H3N2 influenza resulted in ~1 million deaths.

Prior to the mid-1990s, the primary circulating virus strains in pigs was classical swine influenza A H1N1. Since 1997, several new strains of swine influenza virus have emerged, including H1N1, H3N2 and H1N2. The emerging triple reassortants were combinations of avian, human and swine influenza genes. In March of 2009, swine influenza emerged in Mexico and in both California and Texas in the United States. This novel swine flu circulated the globe and infected 24% of the world's human population.

Since swine are susceptible to human, avian and swine influenza, they act as a mixing vessel to create new reassorted influenza viruses. Not only is there a risk of zoonosis from influenza infected swine, Influenza A virus of swine (IAV-S) is one of the most important pathogens of swine. The virus is widespread worldwide, causing tremendous economic loss to swine producers. Clinically, pigs infected with IAV-S often display signs of an acute respiratory disease, which is rapidly resolved after 7-10 days. However, when associated with other pathogens of the porcine respiratory disease complex, IAV-S infection in pigs often leads to severe pneumonia and even to death. One study estimated the losses due to swine influenza resulted in approximately $700,000,000 in losses for the United States swine industry.

Thus, there is a significant need for an influenza vaccine that is effective against divergent influenza virus strains. This disclosure provides for methods of making and using universal centralized influenza vaccine genes.

SUMMARY

The universal vaccine genes described herein were created using several unique strategies that are described herein, and were computationally optimized to provide the greatest possible vaccine efficacy. These unique sequences can allow for the production of a universal vaccine for the prevention of influenza virus infections that provides near-complete protection against all divergent influenza virus strains.

In one aspect, a vaccine polypeptide having at least 90% sequence identity (e.g., at least 95% sequence identity; at least 99% sequence identity; or 100% sequence identity) to an amino acid sequence selected from the group consisting of any of SEQ ID NOs: 1-102 is provided.

In some embodiments, the vaccine polypeptide has at least 90% sequence identity (e.g., at least 95% sequence identity; at least 99% sequence identity; or 100% sequence identity) to an amino acid sequence selected from the group consisting of SEQ ID NOs: 6-8, 13-15, 20-22, 27-29, 34-36, 41-43, 49-52, 57-60, 65-67, 72-74, 79-81, 86-88, 93-95, and 100-102.

In some embodiments, the vaccine polypeptide has at least 90% sequence identity (e.g., at least 95% sequence identity; at least 99% sequence identity; or 100% sequence identity) to an amino acid sequence selected from the group consisting of SEQ ID NOs: 3, 6, 17, 20, 46, 49, 54, and 57.

In some embodiments, the polypeptide is encoded by a nucleic acid sequence having at least 90% sequence identity (e.g., at least 95% sequence identity; at least 99% sequence identity; or 100% sequence identity) to a nucleic acid sequence selected from the group consisting of SEQ ID NO:103-122.

In another aspect, a vaccine composition comprising at least one of the vaccine polypeptides described herein is provided along with a delivery vehicle. In some embodiments, the delivery vehicle is a virus. Representative viruses include, without limitation, an adenovirus, an adeno-associated virus, a retrovirus, an alphavirus, a paramyxovirus, or a rhabdovirus. In some embodiments, the delivery vehicle is a pharmaceutically acceptable carrier. A representative pharmaceutically acceptable carrier is saline. In some embodiments, the delivery vehicle is a nanoparticle (e.g., a lipid nanoparticle). In some embodiments, a vaccine composition includes at least two vaccine polypeptides, at least three vaccine polypeptides, at least four vaccine polypeptides, at least eight vaccine polypeptides, or at least twelve vaccine polypeptides.

In yet another aspect, a method of vaccinating a subject is provided. Such a method typically includes administering a centralized vaccine polypeptide as described herein or a vaccine composition as described herein to a subject in need of vaccination. Representative subjects include a human and a swine. In some embodiments, the administering step is repeated more than once.

In some embodiments, a vaccine polypeptide as described herein is a universal vaccine against at least about 3 different viral sub-types. In some embodiments, a vaccine polypeptide as described herein is a universal vaccine against at least about 12 viral sub-types.

Definitions

Antigen and immunogen are used interchangeably throughout this disclosure. Both refer to antigenic proteins that induce immune responses.

A universal vaccine refers to a vaccine that can provide protection against most variants within an influenza subtype and subtypes within both group 1 and 2 influenza viruses. A universal vaccine can provide protection using multiple immunogens.

A centralized sequence refers to a sequence that mimics an ancestor of influenza infections during past years. Centralized sequences (e.g., polypeptides) are designed to localize to the center of a phylogenetic tree of a subtype of influenza virus. The centralized sequences described herein were created using individual wild type sequences that represent the major branches of the representative phylogenetic tree. The rationale for this approach was to produce an immunogen that is centrally located with respect to all other variants. Such a protein then has lower sequence divergence with all of the variants than any two randomly selected genes.

Unless otherwise defined, all technical and scientific terms used herein have the same meaning as commonly understood by one of ordinary skill in the art to which the methods and compositions of matter belong. Although methods and materials similar or equivalent to those described herein can be used in the practice or testing of the methods and compositions of matter, suitable methods and materials are described below. In addition, the materials, methods, and examples are illustrative only and not intended to be limiting. All publications, patent applications, patents, and other references mentioned herein are incorporated by reference in their entirety.

**p<0.01, *p<0.05, n.s. not significant; one-way ANOVA with Bonferroni multiple comparisons).

FIG. 28A-28D are graphs showing the total T cell response after single shot vaccination with A/California/07/09 (28A), A/Puerto Rico/8/34 (28B), A/New Caledonia/20/99 (28C), or A/Brisbane/59/07 (28D) strains. Data is expressed as the number of mean spot forming cells (SFC) per million splenocytes with standard error (SEM) (**p<0.0001, *p<0.001, **p<0.01, *p<0.05; one-way ANOVA with Bonferroni multiple comparisons).

Figure 29:
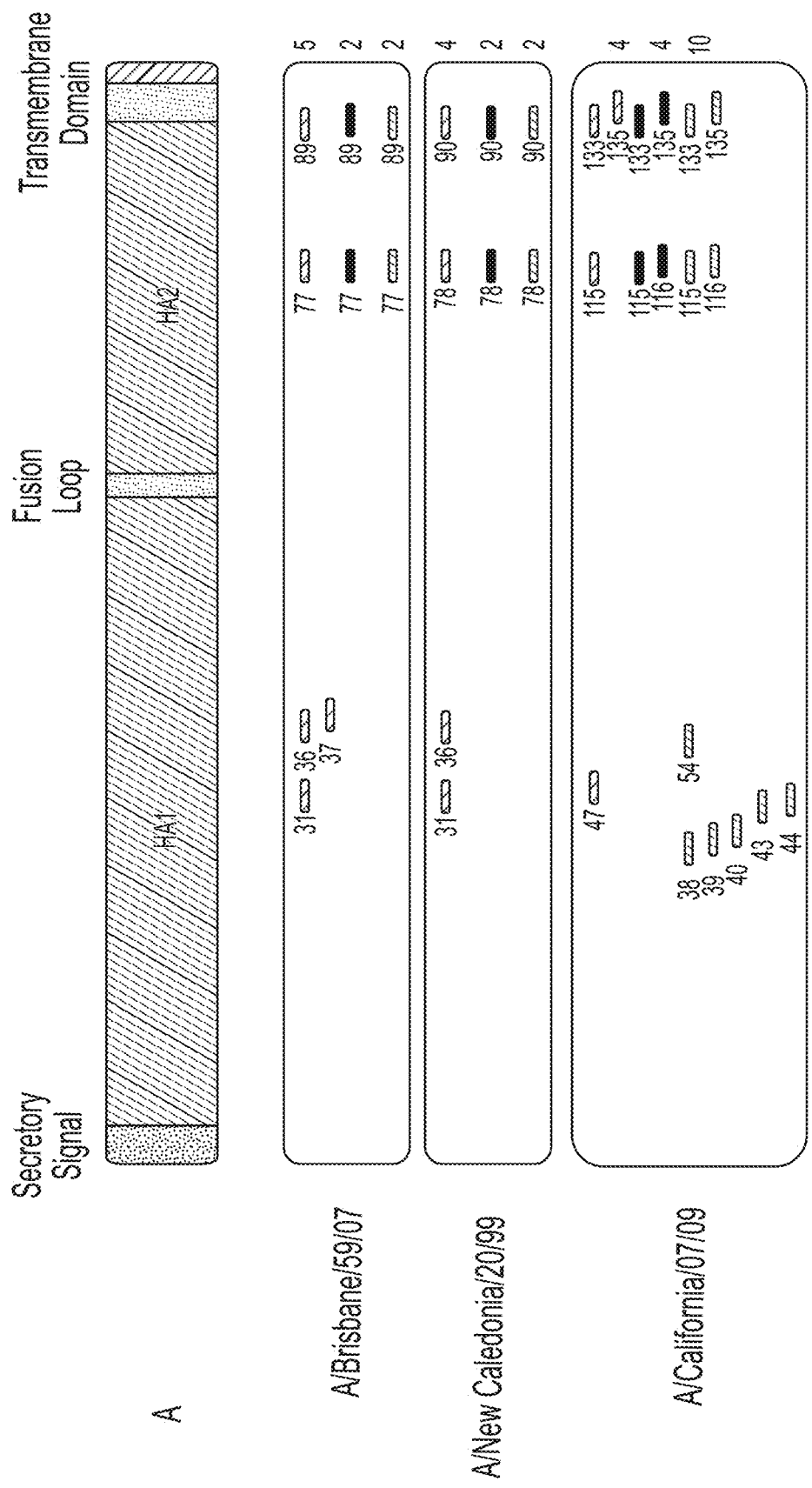
Figure 29:
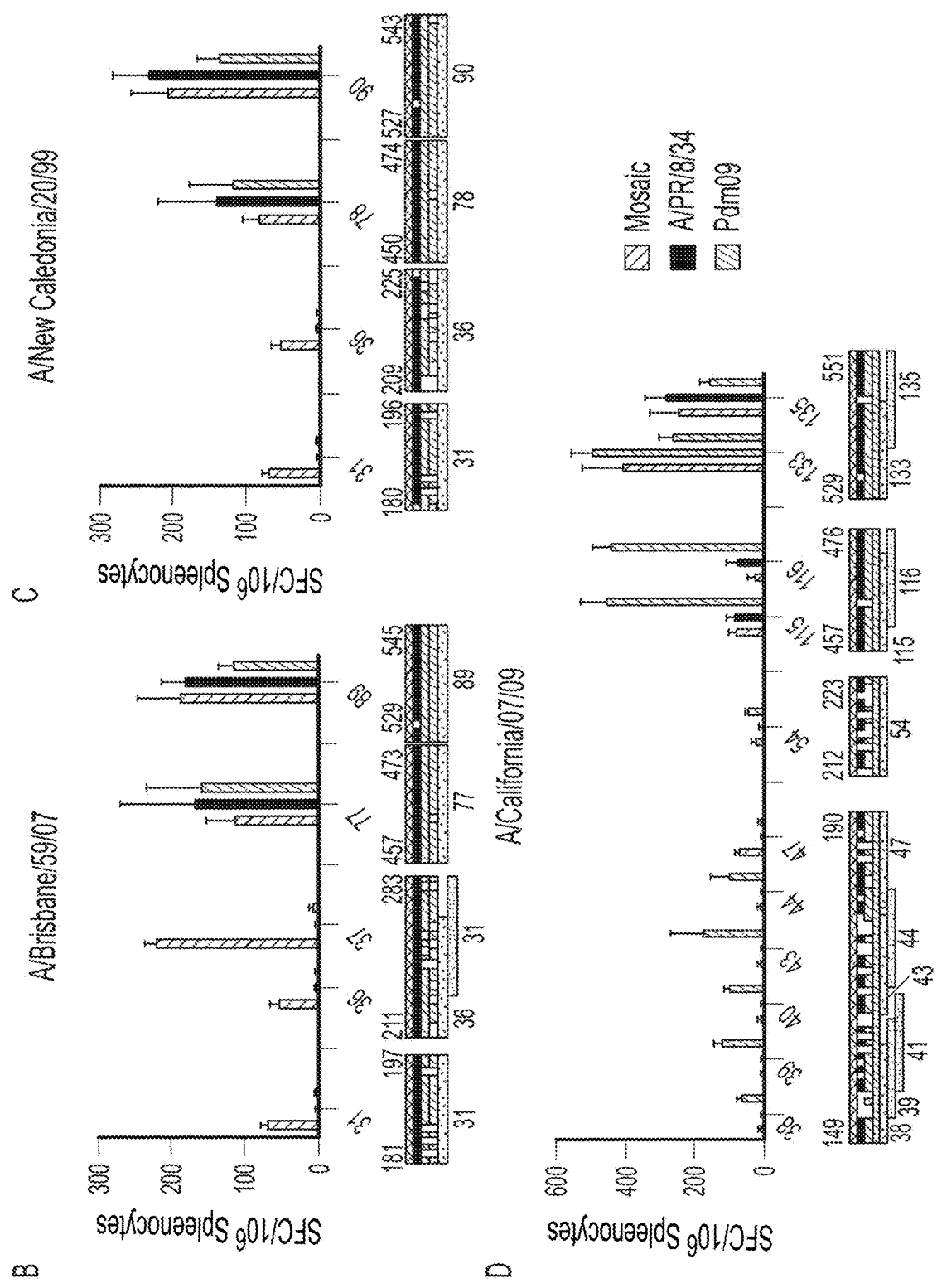

FIG. 29A is a schematic of positive responses (i.e., greater than 50 spot forming cells (SFC) per million splenocytes) shown in relation to the HA gene location.

FIG. 29B-29D are graphs showing the quantification of positive peptides for A/Brisbane/59/07 (29B), A/New Caledonia/20/99 (29C), and A/California/07/09 (29D) shown schematically above the HA sequence to indicate the positions of possible epitopes. Data is expressed as the mean spot forming cells (SFC) per million splenocytes with standard error (SEM).

Figure 30:
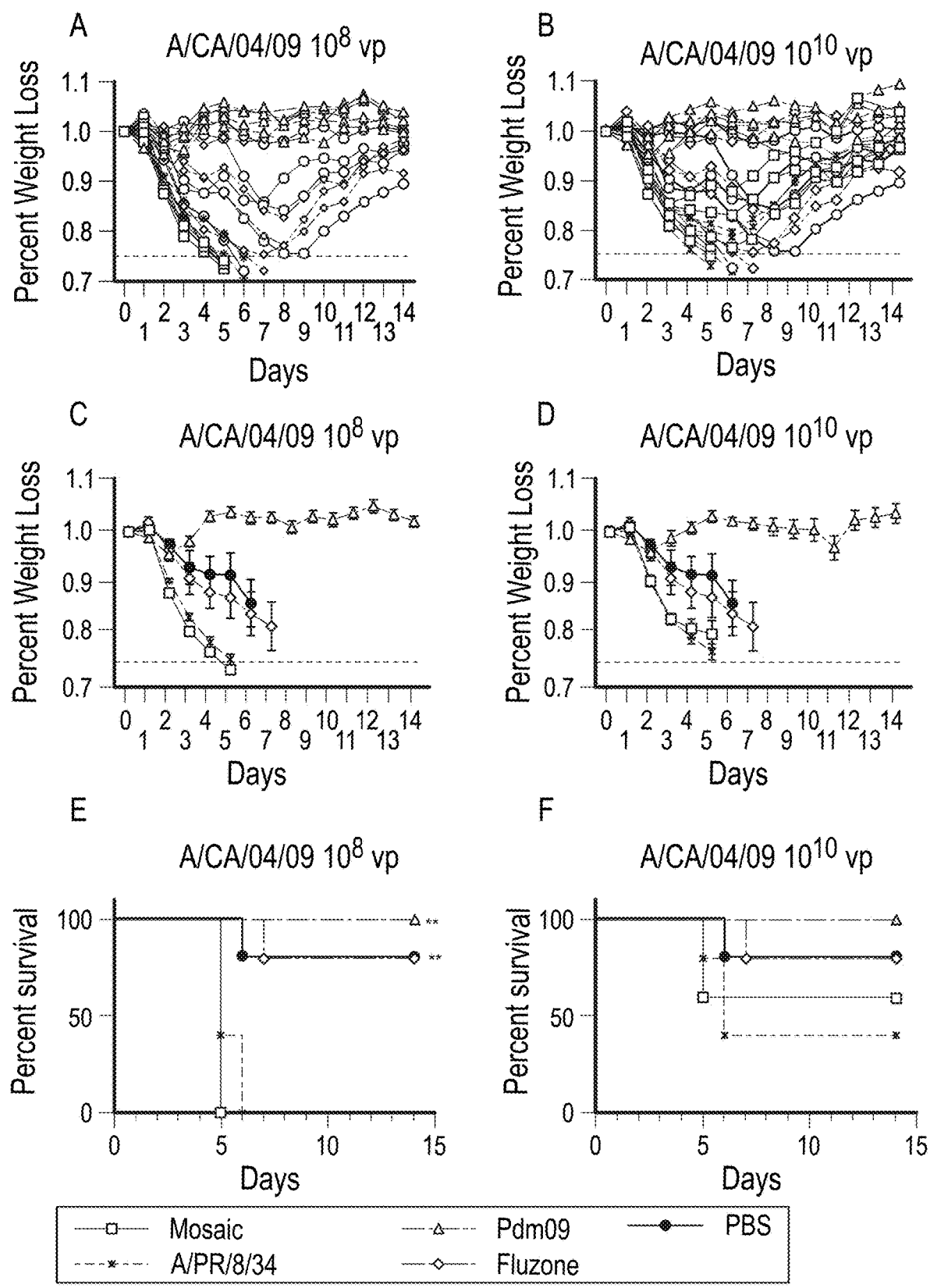

FIG. 30 are graphs that show the protection against A/California/04/09 lethal challenge. Weight loss for individual mice is shown in (30A, 30B), average weight loss is shown in (30C, 30D), and percent survival is shown in (30E, 30F). (Survival data was analyzed with log rank test compared to the PBS control; **p<0.0001, *p<0.001, **p<0.01, *p<0.05).

Figure 31:
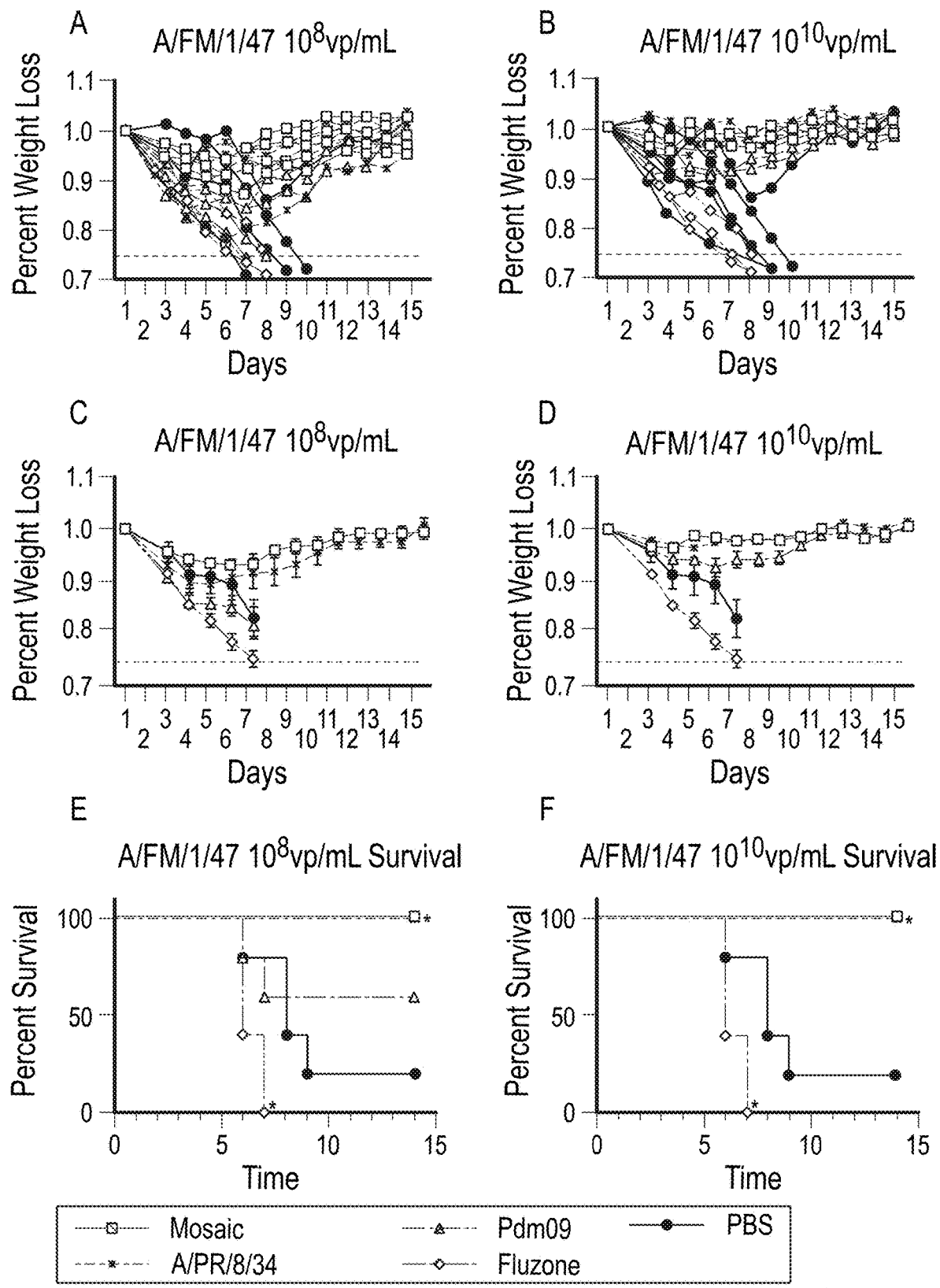

FIG. 31 are graphs showing weight loss for individual mice (31A, 31B), average weight loss (31C, 31D), and percent survival (31E, 31F) for mice immunized with either 10e8 or 10e10 virus particles, respectively, of recombinant Ad5-H1-Mosaic-HA, Ad5-A/PR/8/34-HA, Ad5-A/TX/05/09-HA (pdm09), 150 ng of Fluzone HA, or PBS and challenged with 100MLD50 3 weeks later. Survival data was analyzed with log rank test compared to the PBS control; *p<0.05.

Figure 32:
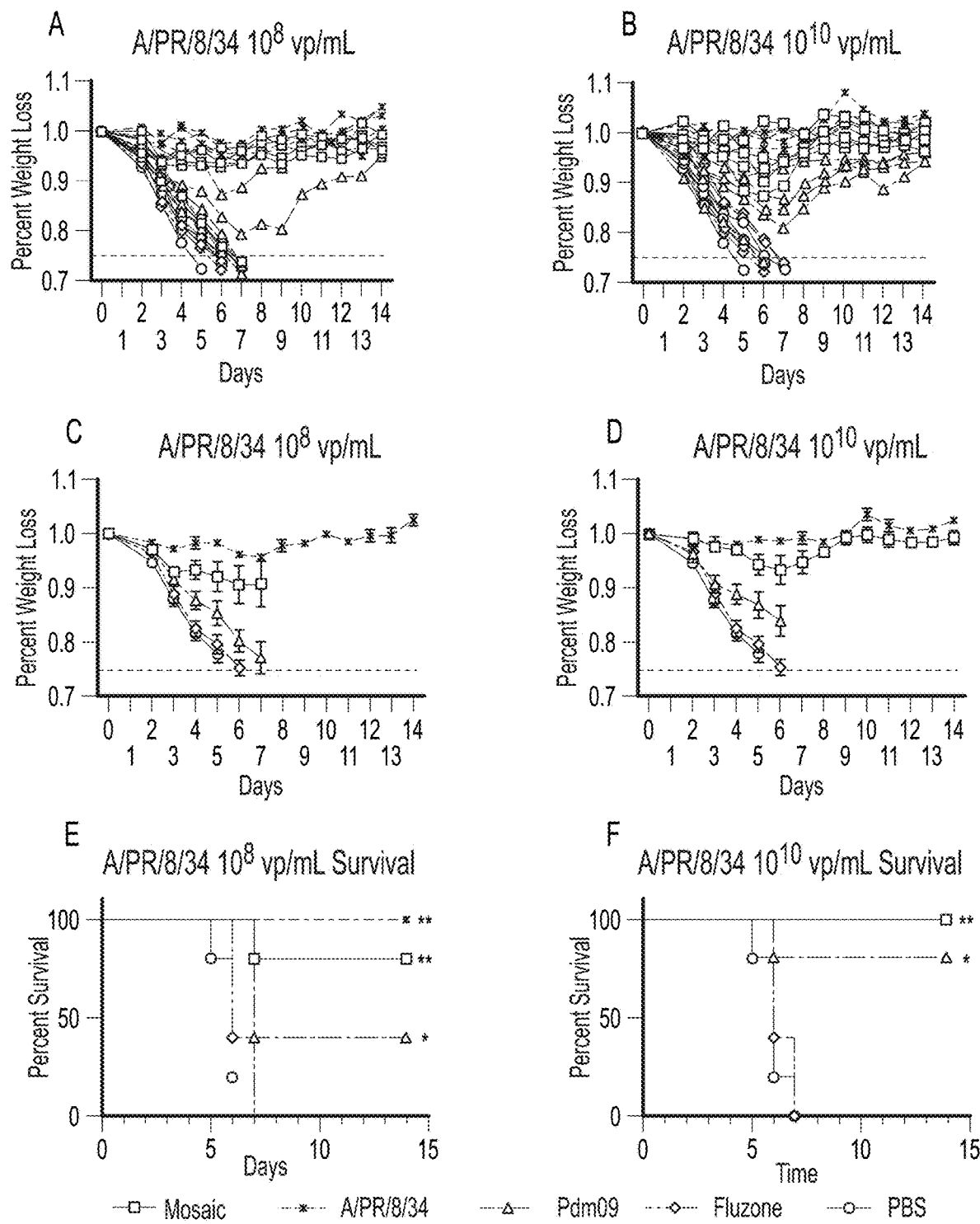

FIG. 32 are graphs showing weight loss for individual mice (32A, 32B), average weight loss (32C, 32D), and percent survival (32E, 32F) for mice immunized with either 10e8 or 10e10 virus particles, respectively, of recombinant Ad5-H1-Mosaic-HA, Ad5-A/PR/8/34-HA, Ad5-A/TX/05/09-HA (pdm09), 150 ng of Fluzone HA, or PBS and challenged with 100MLD50 3 weeks later. Survival data was analyzed with log rank test compared to the PBS control (**p<0.01, *p<0.05).

Figure 33:
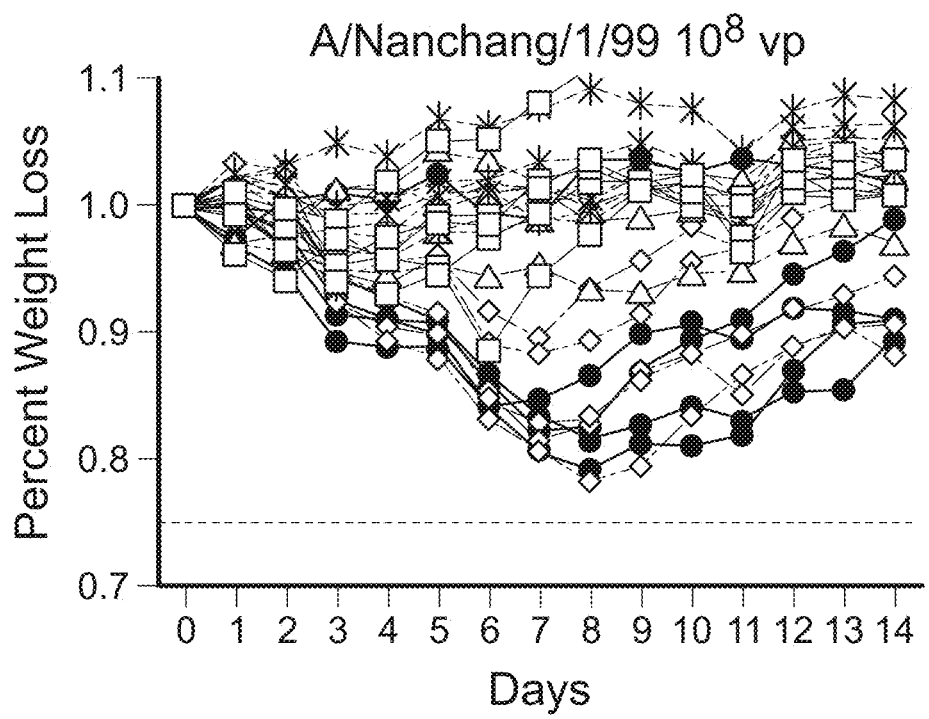
Figure 33:
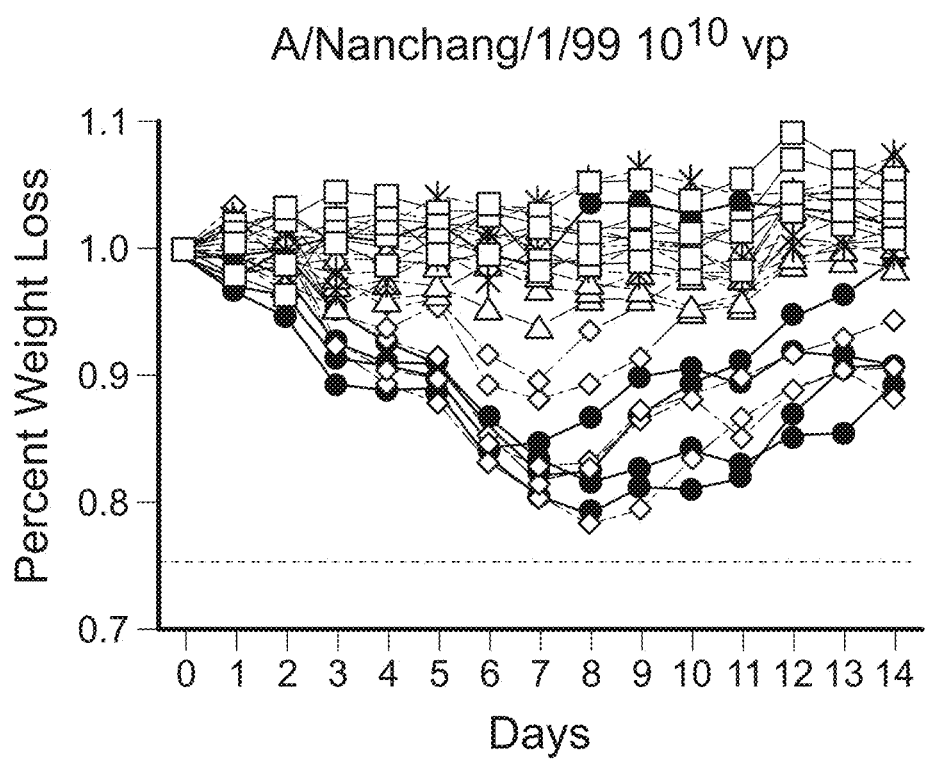
Figure 33:
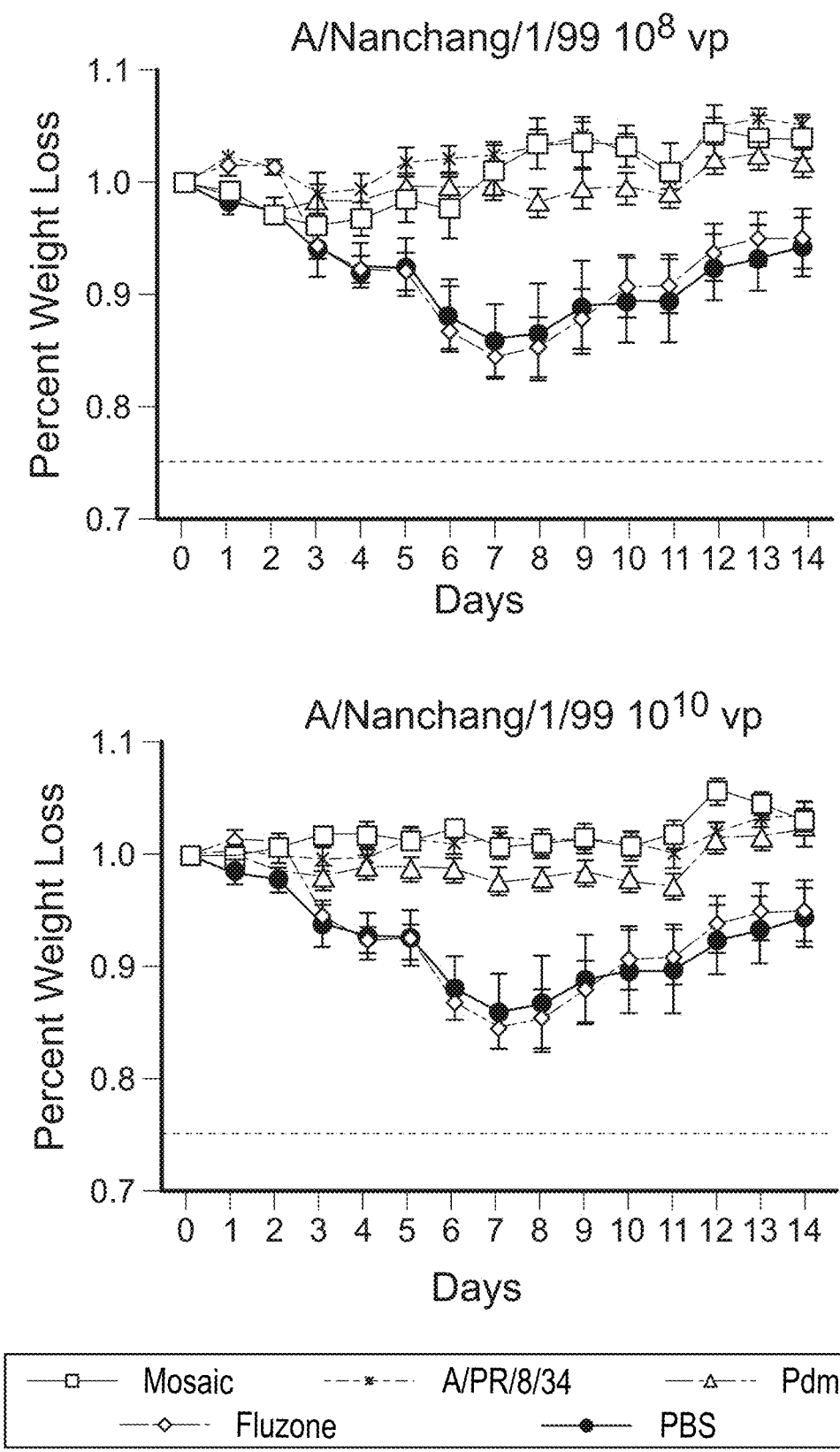

FIG. 33 are graphs that demonstrate protection against A/Nanchang/1/99 lethal challenge. Weight loss for individual mice is shown in (33A, 33B), average weight loss is shown in (33C, 33D), and percent survival is shown in (33E, 33F). (Survival data was analyzed with log rank test compared to the PBS control; **p<0.0001, *p<0.001, **p<0.01, *p<0.05).

Figure 34A:
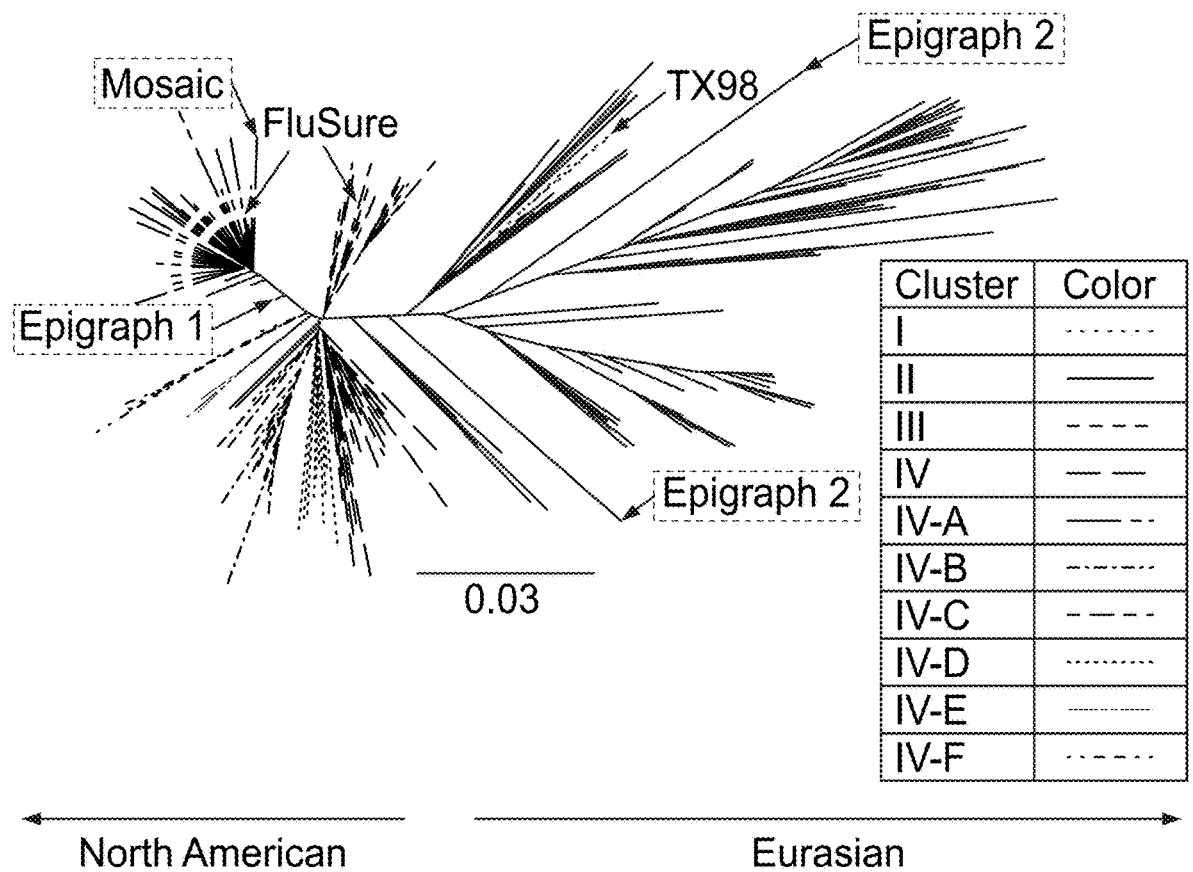

FIG. 34A shows a Jukes-Cantor neighbor joining tree constructed from an alignment of the Mosaic and three Epigraph immunogens described herein and the original sequence population.

Figure 34B:
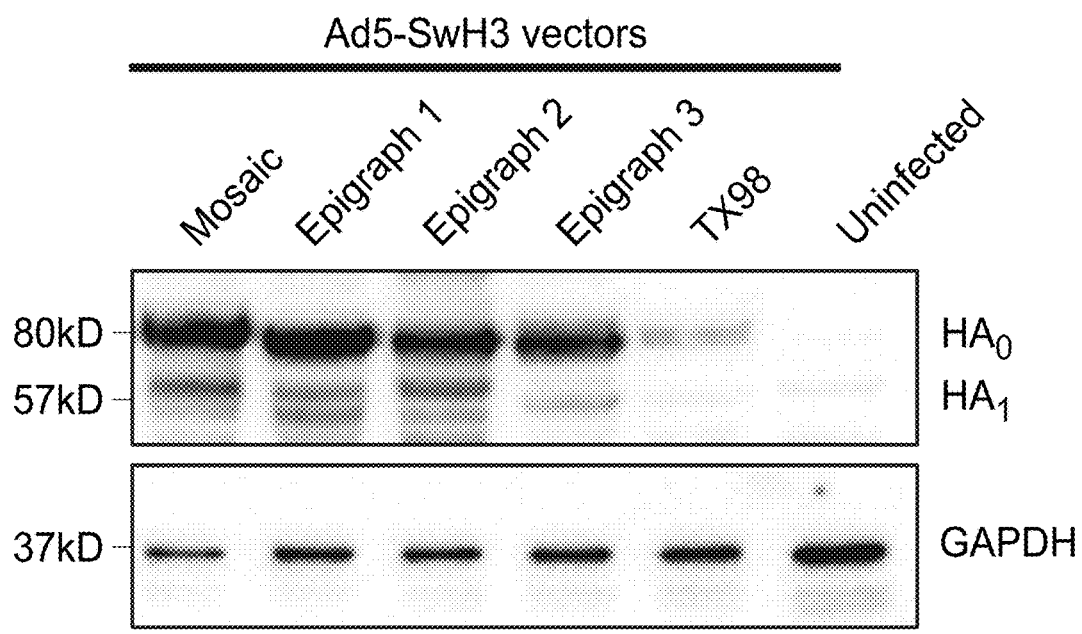

FIG. 34B is a Western blot of Hemagglutinin expression from each vector. A wild type comparator HA gene (A/swine/Texas/4199-2/1998 [TX98]) was used as a control.

Figure 35A:
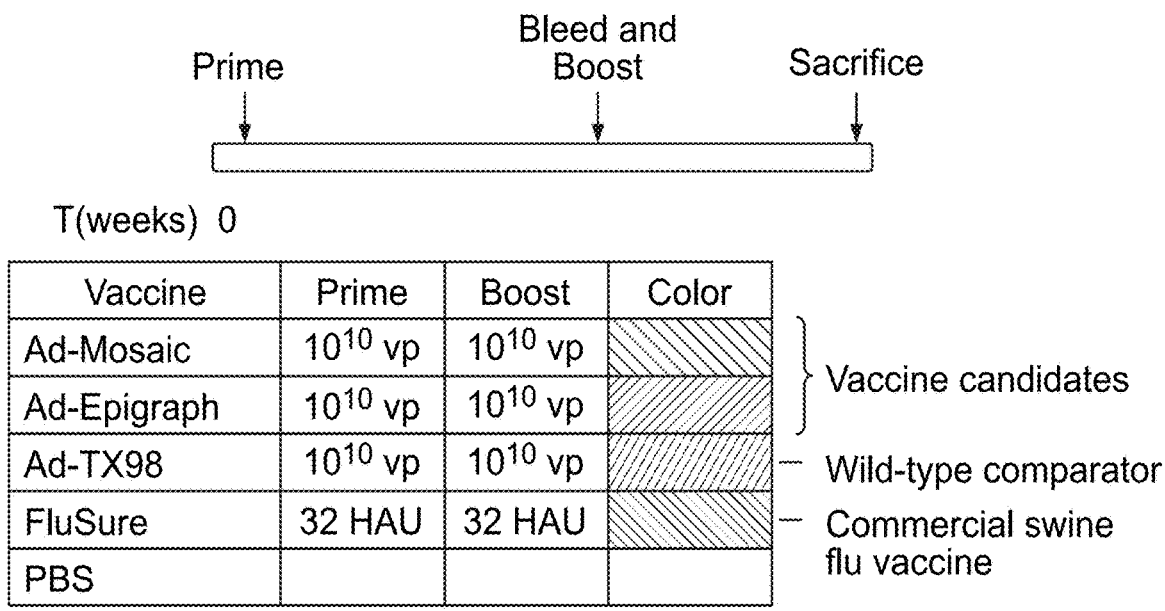

FIG. 35A shows the experimental time line for vaccination and boost.

Figure 35B:
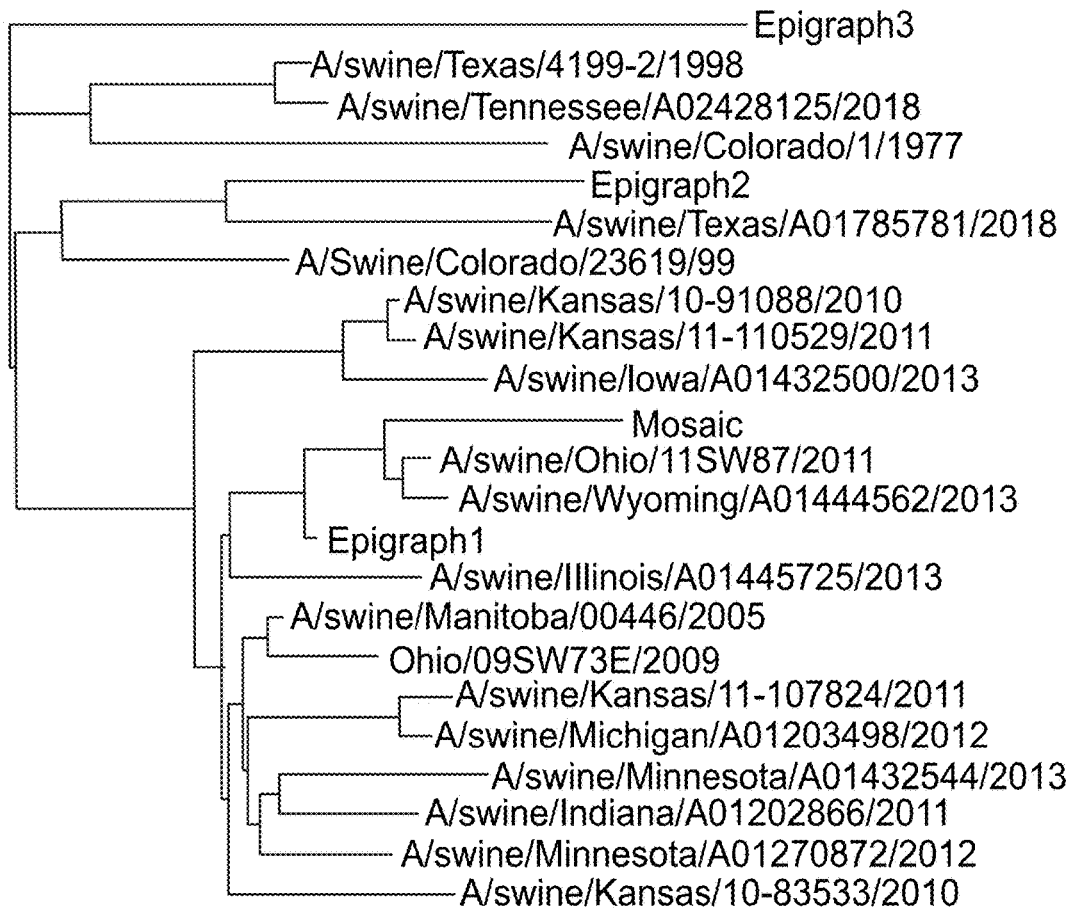

FIG. 35B shows the representative divergent H3 swine influenza viruses that were chosen for analysis of antibody development.

Figure 35C:
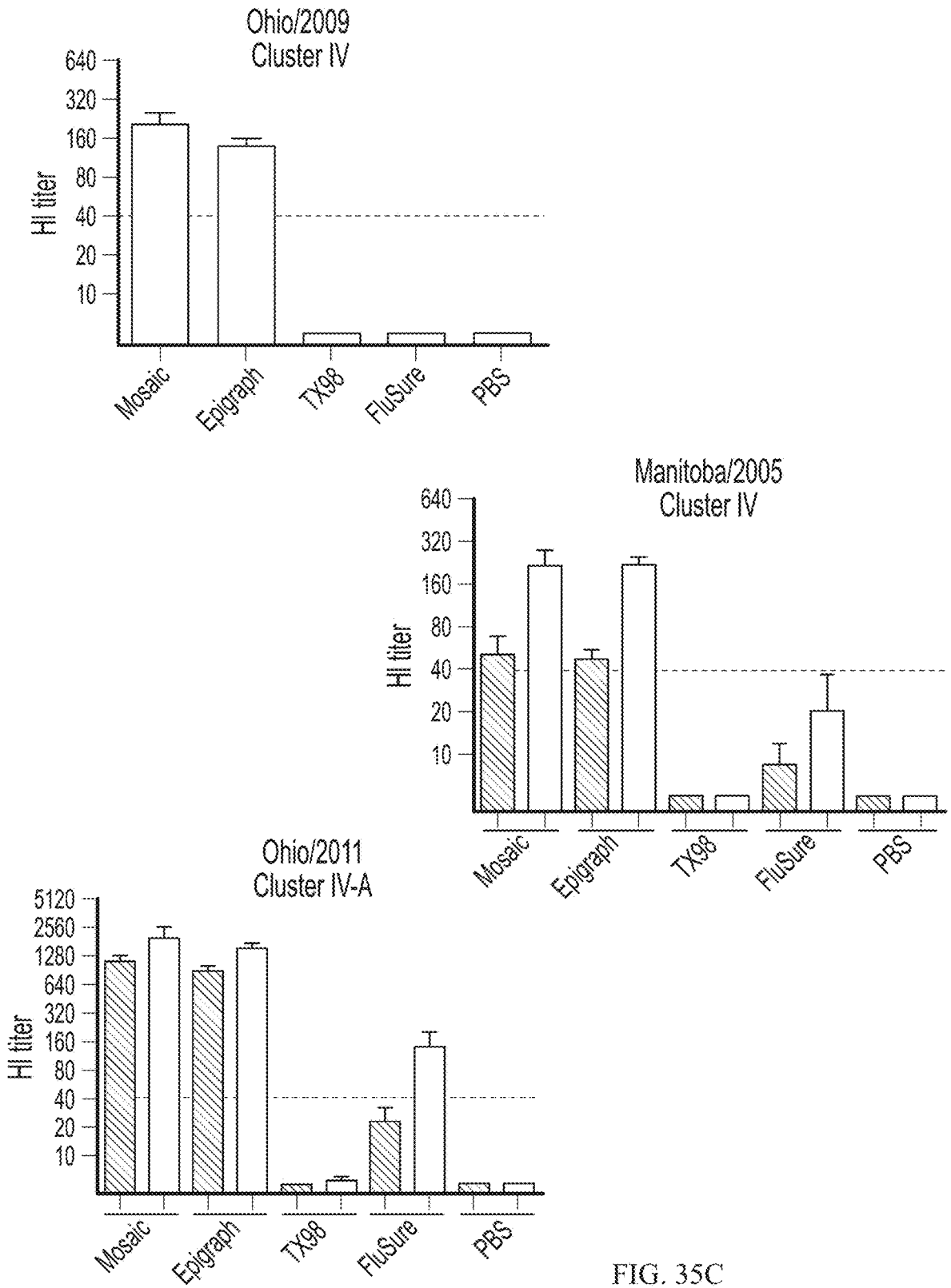

FIG. 35C are graphs of hemmaglutination inhibition (HI) were performed as described by the World Health Organization standard protocols. HI titers are reported as geometric mean titers f standard error. The dotted line represents the standard titer or 40 considered to confer protection against challenge.

Figure 36A:
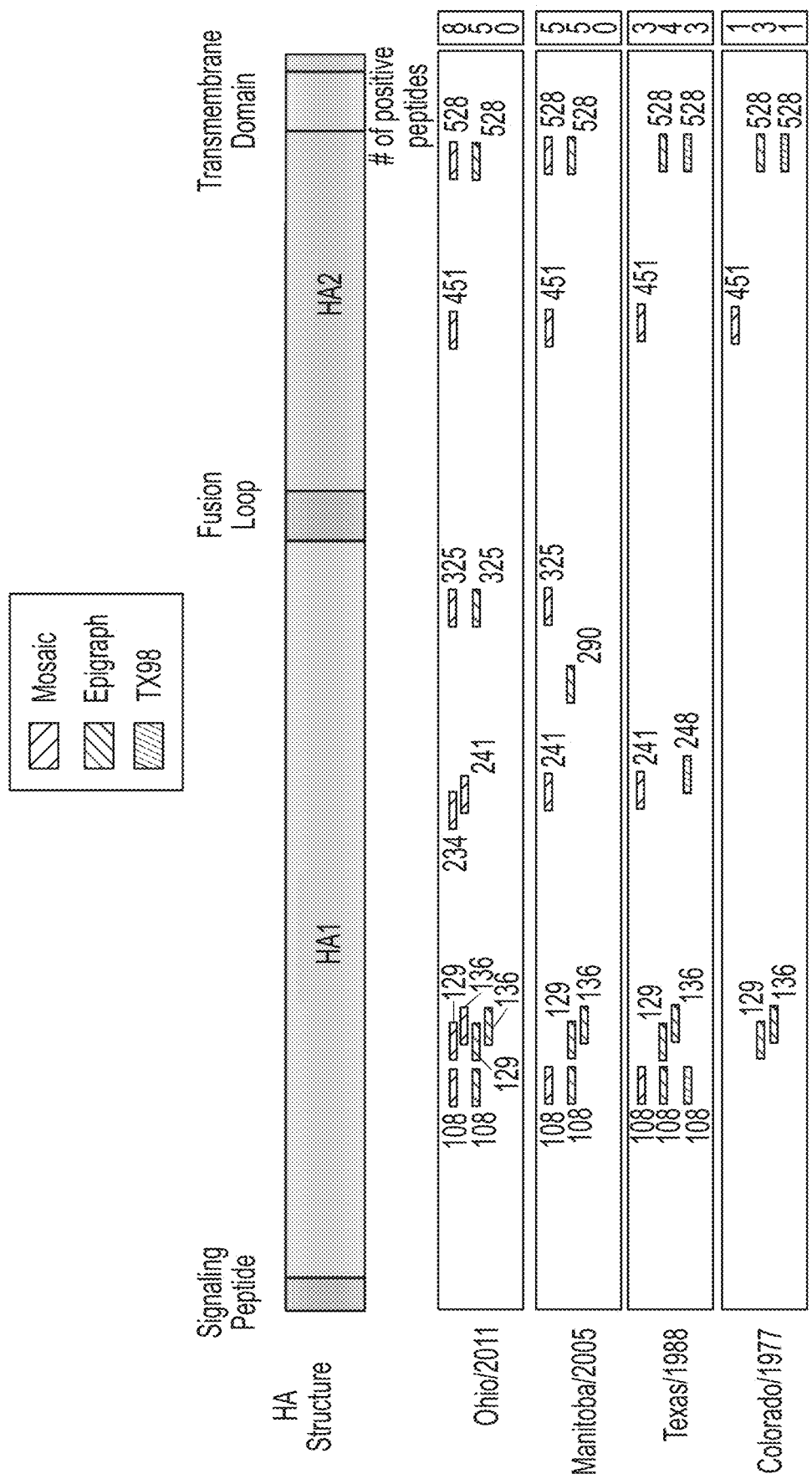

FIG. 36A is a schematic showing the T cell epitopes induced by the vaccine immunogens to four representative divergent swH3 viruses. A peptide was considered positive if the spot-forming cells (SFC) per million was greater than 50.

Figure 36B:
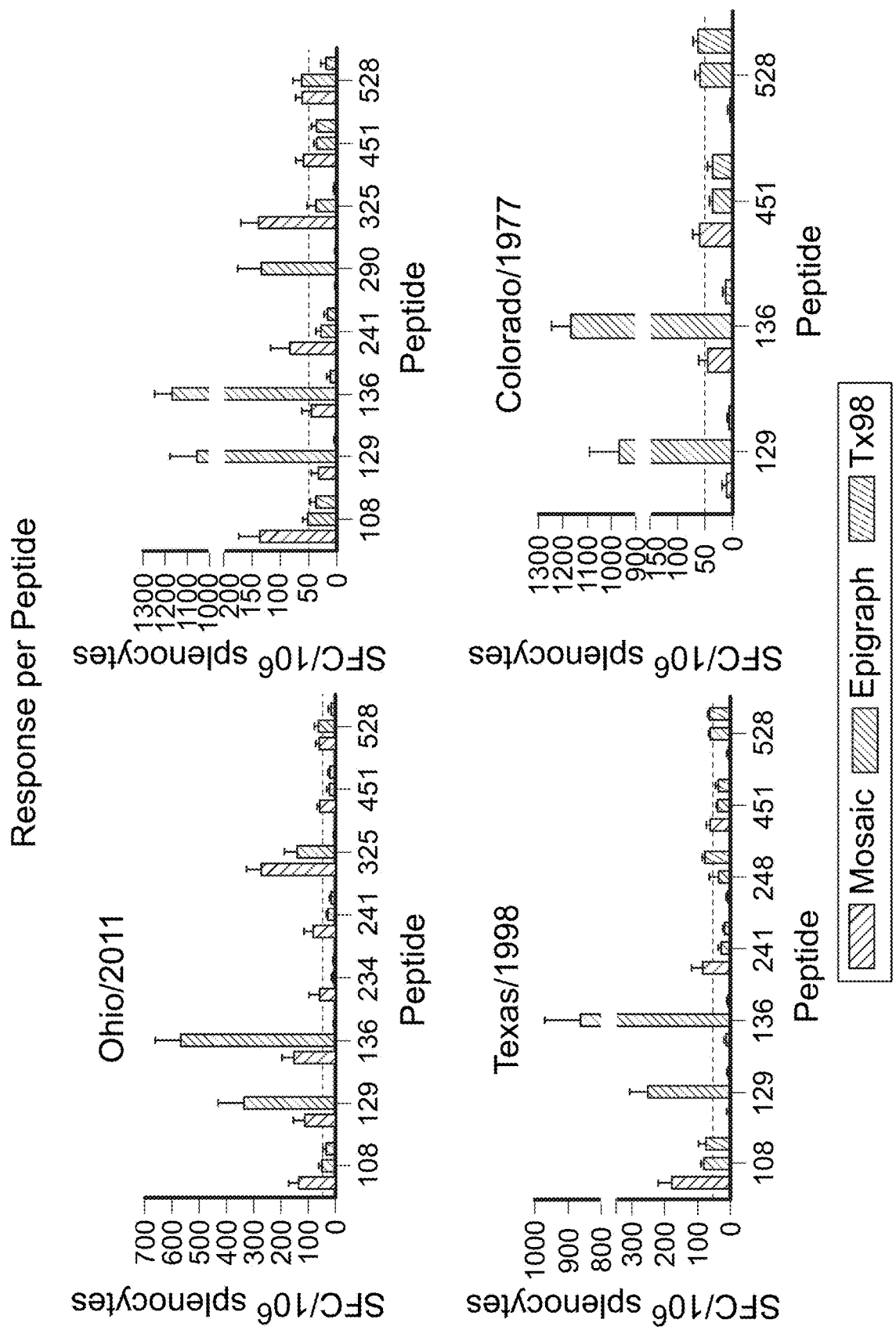

FIG. 36B are graphs showing individual responses to positive peptides.

Figure 36C:
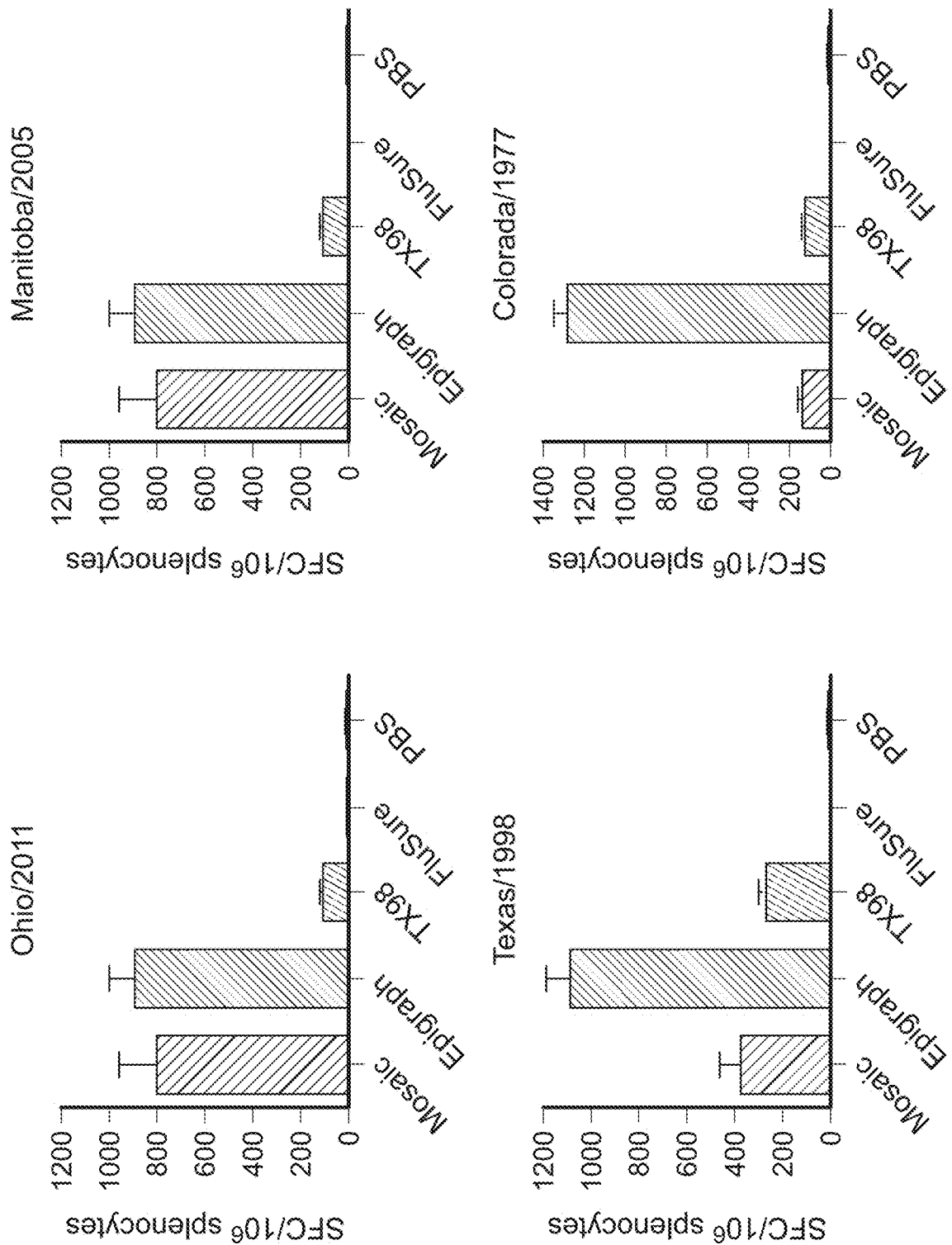

FIG. 36C are graphs showing total T-cell responses.

Figure 37A:
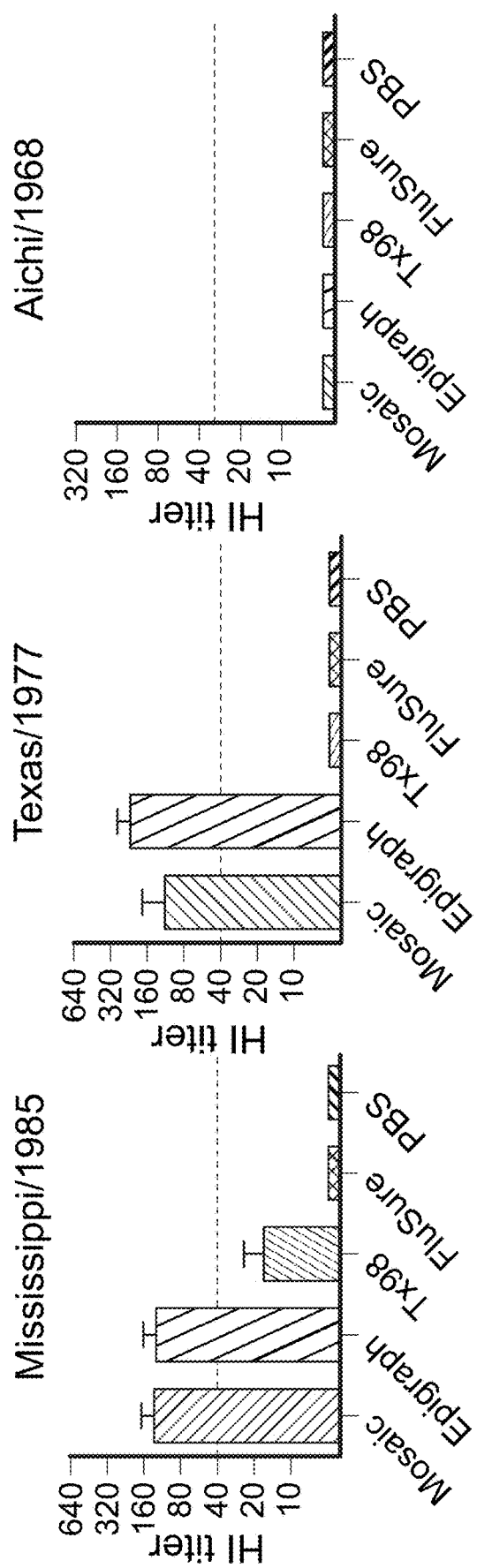

FIG. 37A are graphs showing the geometric mean HI titer was determined ±standard error with representative human H3N2 virus isolates.

Figure 37B:
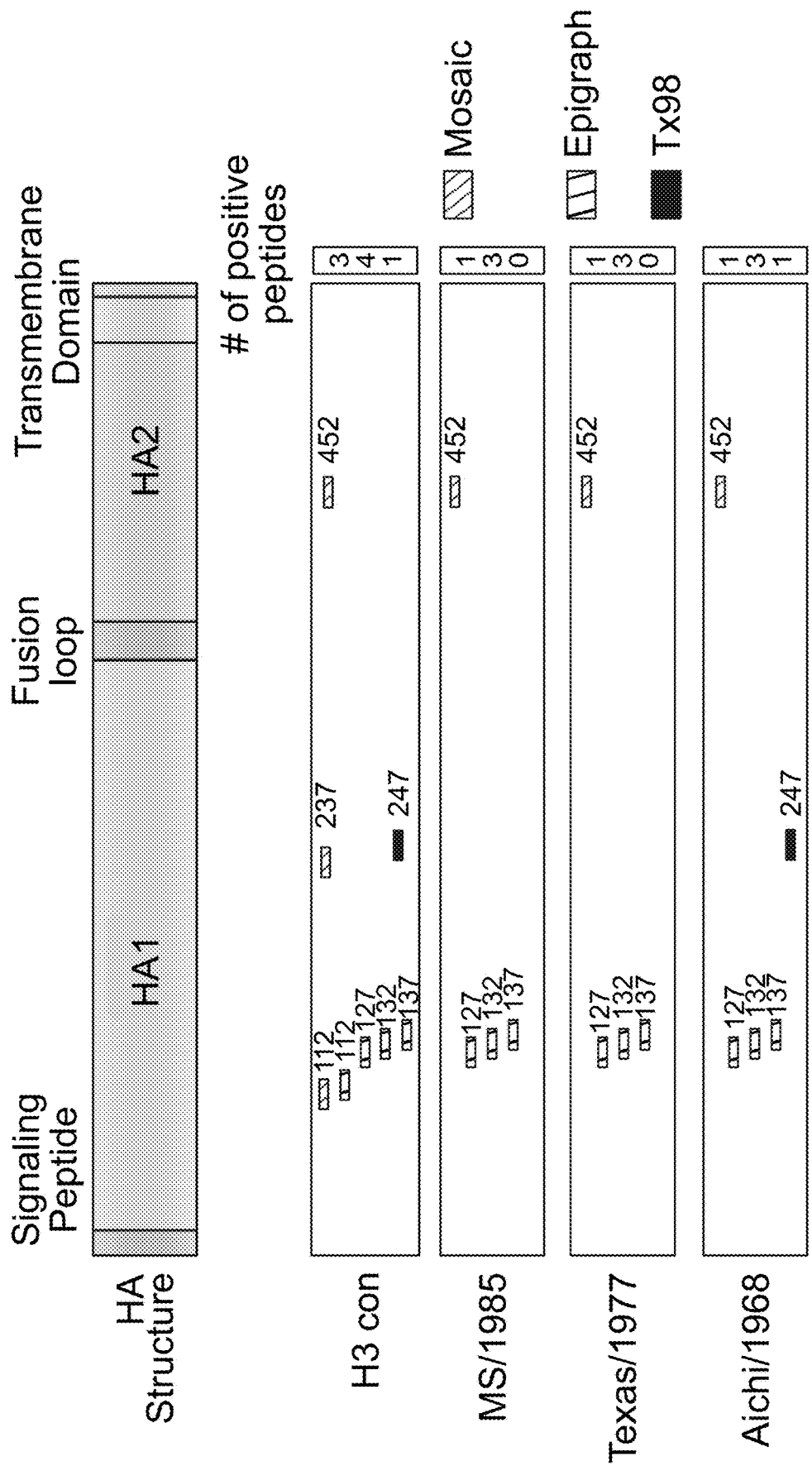

FIG. 37B is a schematic showing peptides considered positive for a cross-reactive T-cell immune responses against any of four representative human influenza strains.

Figure 37C:
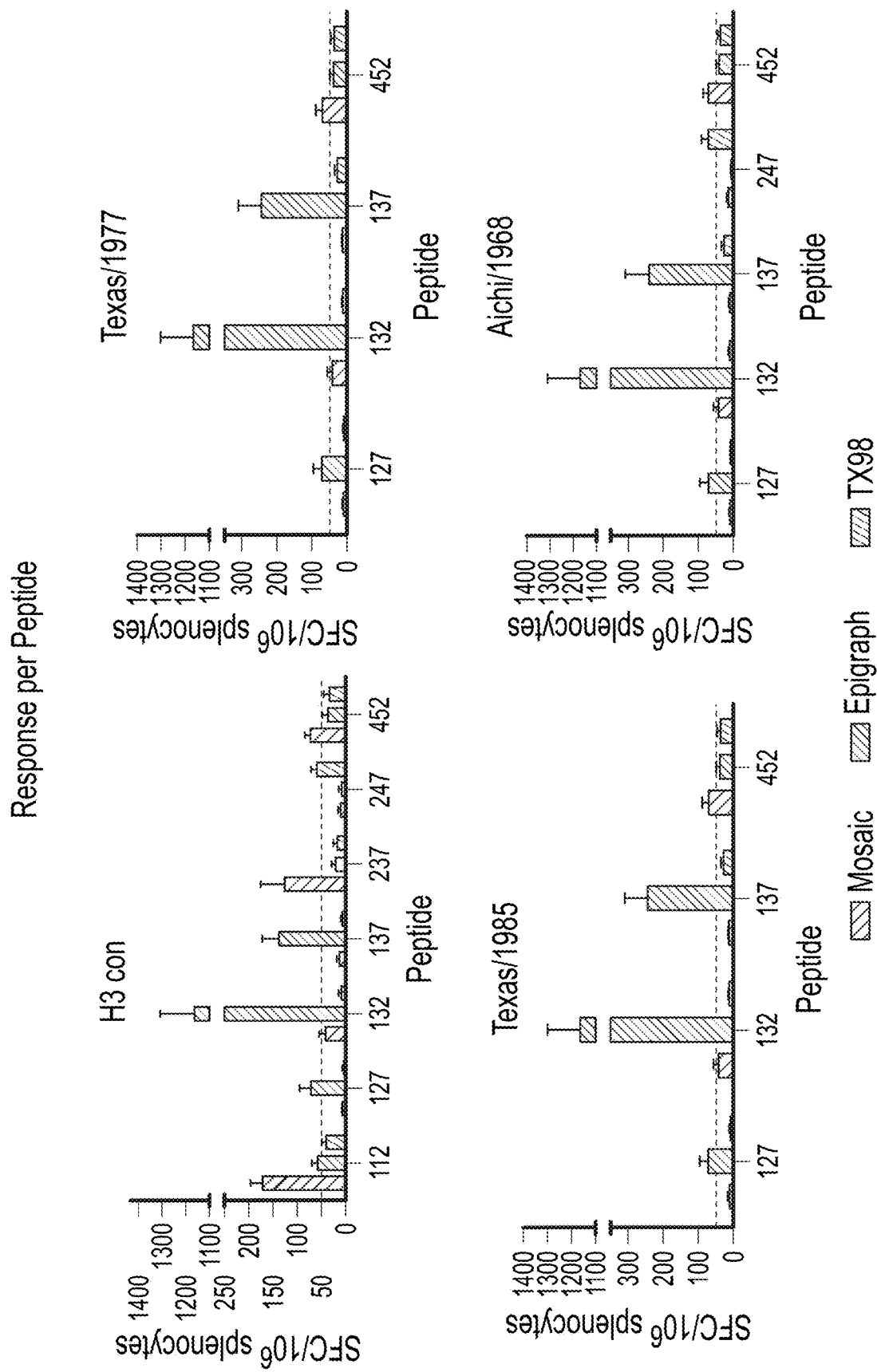

FIG. 37C are graphs showing individual responses to positive peptides.

Figure 37D:
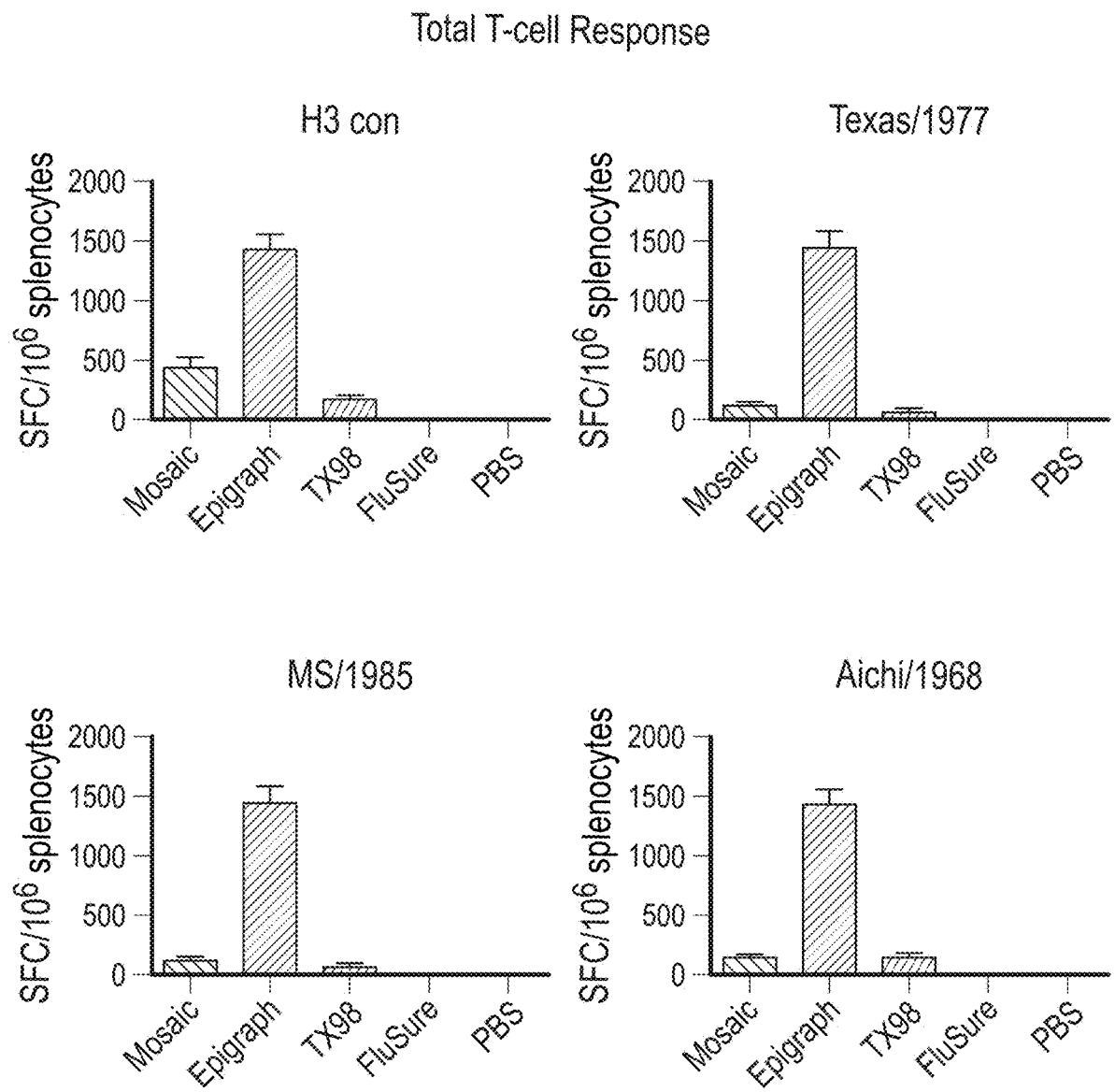

FIG. 37D are graphs showing total T-cell responses.

FIG. 38A are graphs showing weight loss in mice after challenge with Manitoba/2005.

FIG. 38B are graphs showing weight loss in mice after challenge with Colorado/1977.

LIST OF SEQUENCES

SEQ ID NO:1 is the amino acid sequence of a universal HA vaccine from human H1 influenza A serotypes generated using consensus of unique sequence (COUS).

SEQ ID NO:2 is the amino acid sequence of a universal HA vaccine from human H1 (pH1N1) influenza A serotypes generated using a consensus of unique sequence (COUS).

SEQ ID NO:3 is the amino acid sequence of a universal HA vaccine from human H1 influenza A serotypes generated using Mosaic1.

SEQ ID NO:4 is the amino acid sequence of a universal HA vaccine from human H1 influenza A serotypes generated using Mosaic 2.

SEQ ID NO:5 is the amino acid sequence of a universal HA vaccine from human H1 influenza A serotypes generated using Mosaic 3.

SEQ ID NO:6 is the amino acid sequence of a universal HA vaccine from human H1 influenza A serotypes generated using Epigraph1.

SEQ ID NO:7 is the amino acid sequence of a universal HA vaccine from human H1 influenza A serotypes generated using Epigraph2.

SEQ ID NO:8 is the amino acid sequence of a universal HA vaccine from human H1 influenza A serotypes generated using Epigraph3.

SEQ ID NO:9 is the amino acid sequence of a universal HA vaccine from human H2 influenza A serotypes generated using COUS.

SEQ ID NO:10 is the amino acid sequence of a universal HA vaccine from human H2 influenza A serotypes generated using Mosaic1.

SEQ ID NO:11 is the amino acid sequence of a universal HA vaccine from human H2 influenza A serotypes generated using Mosaic2.

SEQ ID NO:12 is the amino acid sequence of a universal HA vaccine from human H2 influenza A serotypes generated using Mosaic3.

SEQ ID NO:13 is the amino acid sequence of a universal HA vaccine from human H2 influenza A serotypes generated using Epigraph1.

SEQ ID NO:14 is the amino acid sequence of a universal HA vaccine from human H2 influenza A serotypes generated using Epigraph2.

SEQ ID NO:15 is the amino acid sequence of a universal HA vaccine from human H2 influenza A serotypes generated using Epigraph3.

SEQ ID NO:16 is the amino acid sequence of a universal HA vaccine from human H3 influenza A serotypes generated using COUS.

SEQ ID NO:17 is the amino acid sequence of a universal HA vaccine from human H3 influenza A serotypes generated using Mosaic1.

SEQ ID NO:18 is the amino acid sequence of a universal HA vaccine from human H3 influenza A serotypes generated using Mosaic2.

SEQ ID NO:19 is the amino acid sequence of a universal HA vaccine from human H3 influenza A serotypes generated using Mosaic3.

SEQ ID NO:20 is the amino acid sequence of a universal HA vaccine from human H3 influenza A serotypes generated using Epigraph1.

SEQ ID NO:21 is the amino acid sequence of a universal HA vaccine from human H3 influenza A serotypes generated using Epigraph2.

SEQ ID NO:22 is the amino acid sequence of a universal HA vaccine from human H3 influenza A serotypes generated using Epigraph3.

SEQ ID NO:23 is the amino acid sequence of a universal HA vaccine from human H5 influenza A serotypes generated using COUS.

SEQ ID NO:24 is the amino acid sequence of a universal HA vaccine from human H5 influenza A serotypes generated using Mosaic1.

SEQ ID NO:25 is the amino acid sequence of a universal HA vaccine from human H5 influenza A serotypes generated using Mosaic2.

SEQ ID NO:26 is the amino acid sequence of a universal HA vaccine from human H5 influenza A serotypes generated using Mosaic3.

SEQ ID NO:27 is the amino acid sequence of a universal HA vaccine from human H5 influenza A serotypes generated using Epigraph1.

SEQ ID NO:28 is the amino acid sequence of a universal HA vaccine from human H5 influenza A serotypes generated using Epigraph2.

SEQ ID NO:29 is the amino acid sequence of a universal HA vaccine from human H5 influenza A serotypes generated using Epigraph3.

SEQ ID NO:30 is the amino acid sequence of a universal NA vaccine from human N1 influenza A serotypes generated using COUS.

SEQ ID NO:31 is the amino acid sequence of a universal NA vaccine from human N1 influenza A serotypes generated using Mosaic1.

SEQ ID NO:32 is the amino acid sequence of a universal NA vaccine from human N1 influenza A serotypes generated using Mosaic2.

SEQ ID NO:33 is the amino acid sequence of a universal NA vaccine from human N1 influenza A serotypes generated using Mosaic3.

SEQ ID NO:34 is the amino acid sequence of a universal NA vaccine from human N1 influenza A serotypes generated using Epigraph1.

SEQ ID NO:35 is the amino acid sequence of a universal NA vaccine from human N1 influenza A serotypes generated using Epigraph2.

SEQ ID NO:36 is the amino acid sequence of a universal NA vaccine from human N1 influenza A serotypes generated using Epigraph3.

SEQ ID NO:37 is the amino acid sequence of a universal NA vaccine from human N2 influenza A serotypes generated using COUS.

SEQ ID NO:38 is the amino acid sequence of a universal NA vaccine from human N2 influenza A serotypes generated using Mosaic1.

SEQ ID NO:39 is the amino acid sequence of a universal NA vaccine from human N2 influenza A serotypes generated using Mosaic2.

SEQ ID NO:40 is the amino acid sequence of a universal NA vaccine from human N2 influenza A serotypes generated using Mosaic3.

SEQ ID NO:41 is the amino acid sequence of a universal NA vaccine from human N2 influenza A serotypes generated using Epigraph1.

SEQ ID NO:42 is the amino acid sequence of a universal NA vaccine from human N2 influenza A serotypes generated using Epigraph2.

SEQ ID NO:43 is the amino acid sequence of a universal NA vaccine from human N2 influenza A serotypes generated using Epigraph3.

SEQ ID NO:44 is the amino acid sequence of a universal HA vaccine from human Victoria-like influenza B serotypes generated using COUS.

SEQ ID NO:45 is the amino acid sequence of a universal HA vaccine from human Victoria-like influenza B serotypes generated using Centered Consensus (CC).

SEQ ID NO:46 is the amino acid sequence of a universal HA vaccine from human Victoria-like influenza B serotypes generated using Mosaic1.

SEQ ID NO:47 is the amino acid sequence of a universal HA vaccine from human Victoria-like influenza B serotypes generated using Mosaic2.

SEQ ID NO:48 is the amino acid sequence of a universal HA vaccine from human Victoria-like influenza B serotypes generated using Mosaic3.

SEQ ID NO:49 is the amino acid sequence of a universal HA vaccine from human Victoria-like influenza B serotypes generated using Epigraph1.

SEQ ID NO:50 is the amino acid sequence of a universal HA vaccine from human Victoria-like influenza B serotypes generated using Epigraph2.

SEQ ID NO:51 is the amino acid sequence of a universal HA vaccine from human Victoria-like influenza B serotypes generated using Epigraph3.

SEQ ID NO:52 is the amino acid sequence of a universal HA vaccine from human Victoria-like influenza B serotypes generated using Epigraph4.

SEQ ID NO:53 is the amino acid sequence of a universal HA vaccine from human Yamagata-like influenza B serotypes generated using COUS.

SEQ ID NO:54 is the amino acid sequence of a universal HA vaccine from human Yamagata-like influenza B serotypes generated using Mosaic1.

SEQ ID NO:55 is the amino acid sequence of a universal HA vaccine from human Yamagata-like influenza B serotypes generated using Mosaic2.

SEQ ID NO:56 is the amino acid sequence of a universal HA vaccine from human Yamagata-like influenza B serotypes generated using Mosaic3.

SEQ ID NO:57 is the amino acid sequence of a universal HA vaccine from human Yamagata-like influenza B serotypes generated using Epigraph1.

SEQ ID NO:58 is the amino acid sequence of a universal HA vaccine from human Yamagata-like influenza B serotypes generated using Epigraph2.

SEQ ID NO:59 is the amino acid sequence of a universal HA vaccine from human Yamagata-like influenza B serotypes generated using Epigraph3.

SEQ ID NO:60 is the amino acid sequence of a universal HA vaccine from human Yamagata-like influenza B serotypes generated using Epigraph4.

SEQ ID NO:61 is the amino acid sequence of a universal NA vaccine from human Victoria-like influenza B serotypes generated using COUS.

SEQ ID NO:62 is the amino acid sequence of a universal NA vaccine from human Victoria-like influenza B serotypes generated using Mosaic1.

SEQ ID NO:63 is the amino acid sequence of a universal NA vaccine from human Victoria-like influenza B serotypes generated using Mosaic2.

SEQ ID NO:64 is the amino acid sequence of a universal NA vaccine from human Victoria-like influenza B serotypes generated using Mosaic3.

SEQ ID NO:65 is the amino acid sequence of a universal NA vaccine from human Victoria-like influenza B serotypes generated using Epigraph1.

SEQ ID NO:66 is the amino acid sequence of a universal NA vaccine from human Victoria-like influenza B serotypes generated using Epigraph2.

SEQ ID NO:67 is the amino acid sequence of a universal NA vaccine from human Victoria-like influenza B serotypes generated using Epigraph3.

SEQ ID NO:68 is the amino acid sequence of a universal NA vaccine from human Yamagata-like influenza B serotypes generated using COUS.

SEQ ID NO:69 is the amino acid sequence of a universal NA vaccine from human Yamagata-like influenza B serotypes generated using Mosaic1.

SEQ ID NO:70 is the amino acid sequence of a universal NA vaccine from human Yamagata-like influenza B serotypes generated using Mosaic2.

SEQ ID NO:71 is the amino acid sequence of a universal NA vaccine from human Yamagata-like influenza B serotypes generated using Mosaic3.

SEQ ID NO:72 is the amino acid sequence of a universal NA vaccine from human Yamagata-like influenza B serotypes generated using Epigraph1.

SEQ ID NO:73 is the amino acid sequence of a universal NA vaccine from human Yamagata-like influenza B serotypes generated using Epigraph2.

SEQ ID NO:74 is the amino acid sequence of a universal NA vaccine from human Yamagata-like influenza B serotypes generated using Epigraph3.

SEQ ID NO:75 is the amino acid sequence of a universal HA vaccine from swine H1 influenza A serotypes using COUS.

SEQ ID NO:76 is the amino acid sequence of a universal HA vaccine from swine H1 influenza A serotypes using Mosaic1.

SEQ ID NO:77 is the amino acid sequence of a universal HA vaccine from swine H1 influenza A serotypes using Mosaic2.

SEQ ID NO:78 is the amino acid sequence of a universal HA vaccine from swine H1 influenza A serotypes using Mosaic3.

SEQ ID NO:79 is the amino acid sequence of a universal HA vaccine from swine H1 influenza A serotypes using Epigraph1.

SEQ ID NO:80 is the amino acid sequence of a universal HA vaccine from swine H1 influenza A serotypes using Epigraph2.

SEQ ID NO:81 is the amino acid sequence of a universal HA vaccine from swine H1 influenza A serotypes using Epigraph3.

SEQ ID NO:82 is the amino acid sequence of a universal HA vaccine from swine H3 influenza A serotypes using COUS.

SEQ ID NO:83 is the amino acid sequence of a universal HA vaccine from swine H3 influenza A serotypes using Mosaic1.

SEQ ID NO:84 is the amino acid sequence of a universal HA vaccine from swine H3 influenza A serotypes using Mosaic2.

SEQ ID NO:85 is the amino acid sequence of a universal HA vaccine from swine H3 influenza A serotypes using Mosaic3.

SEQ ID NO:86 is the amino acid sequence of a universal HA vaccine from swine H3 influenza A serotypes using Epigraph1.

SEQ ID NO:87 is the amino acid sequence of a universal HA vaccine from swine H3 influenza A serotypes using Epigraph2.

SEQ ID NO:88 is the amino acid sequence of a universal HA vaccine from swine H3 influenza A serotypes using Epigraph3.

SEQ ID NO:89 is the amino acid sequence of a universal NA vaccine from swine N1 influenza A serotypes using COUS.

SEQ ID NO:90 is the amino acid sequence of a universal NA vaccine from swine N1 influenza A serotypes using Mosaic1.

SEQ ID NO:91 is the amino acid sequence of a universal NA vaccine from swine N1 influenza A serotypes using Mosaic2.

SEQ ID NO:92 is the amino acid sequence of a universal NA vaccine from swine N1 influenza A serotypes using Mosaic3.

SEQ ID NO:93 is the amino acid sequence of a universal NA vaccine from swine N1 influenza A serotypes using Epigraph1.

SEQ ID NO:94 is the amino acid sequence of a universal NA vaccine from swine N1 influenza A serotypes using Epigraph2.

SEQ ID NO:95 is the amino acid sequence of a universal NA vaccine from swine N1 influenza A serotypes using Epigraph3.

SEQ ID NO:96 is the amino acid sequence of a universal NA vaccine from swine N2 influenza A serotypes using COUS.

SEQ ID NO:97 is the amino acid sequence of a universal NA vaccine from swine N2 influenza A serotypes using Mosaic1.

SEQ ID NO:98 is the amino acid sequence of a universal NA vaccine from swine N2 influenza A serotypes using Mosaic2.

SEQ ID NO:99 is the amino acid sequence of a universal NA vaccine from swine N2 influenza A serotypes using Mosaic3.

SEQ ID NO:100 is the amino acid sequence of a universal NA vaccine from swine N2 influenza A serotypes using Epigraph1.

SEQ ID NO:101 is the amino acid sequence of a universal NA vaccine from swine N2 influenza A serotypes using Epigraph2.

SEQ ID NO:102 is the amino acid sequence of a universal NA vaccine from swine N2 influenza A serotypes using Epigraph3.

SEQ ID NO:103 is a nucleic acid sequence encoding a universal HA vaccine from human H1 influenza A using Consensus (Cons).

SEQ ID NO:104 is a nucleic acid sequence encoding a universal HA vaccine from human H1 influenza A using Mosaic1.

SEQ ID NO:105 is a nucleic acid sequence encoding a universal HA vaccine from human H1 influenza A using Epigraph1.

SEQ ID NO:106 is a nucleic acid sequence encoding a universal HA vaccine from human H1 influenza A using Epigraph2.

SEQ ID NO:107 is a nucleic acid sequence encoding a universal HA vaccine from human H1 influenza A using Epigraph3.

SEQ ID NO:108 is a nucleic acid sequence encoding a universal HA vaccine from human H3 influenza A using Consensus (Cons).

SEQ ID NO:109 is a nucleic acid sequence encoding a universal HA vaccine from human H3 influenza A using Mosaic1.

SEQ ID NO:110 is a nucleic acid sequence encoding a universal HA vaccine from human H3 influenza A using Epigraph1.

SEQ ID NO:111 is a nucleic acid sequence encoding a universal HA vaccine from human H3 influenza A using Epigraph2.

SEQ ID NO:112 is a nucleic acid sequence encoding a universal HA vaccine from human H3 influenza A using Epigraph3.

SEQ ID NO:113 is a nucleic acid sequence encoding a universal HA vaccine from swine H1 influenza A using Consensus.

SEQ ID NO:114 is a nucleic acid sequence encoding a universal HA vaccine from swine H1 influenza A using Mosaic1.

SEQ ID NO:115 is a nucleic acid sequence encoding a universal HA vaccine from swine H1 influenza A using Epigraph1.

SEQ ID NO: 116 is a nucleic acid sequence encoding a universal HA vaccine from swine H1 influenza A using Epigraph2.

SEQ ID NO:117 is a nucleic acid sequence encoding a universal HA vaccine from swine H1 influenza A using Epigraph3.

SEQ ID NO:118 is a nucleic acid sequence encoding a universal NA vaccine from swine H3 influenza A using Consensus.

SEQ ID NO:119 is a nucleic acid sequence encoding a universal NA vaccine from swine H3 influenza A using Mosaic1.

SEQ ID NO:120 is a nucleic acid sequence encoding a universal NA vaccine from swine H3 influenza A using Epigraph1.

SEQ ID NO:121 is the nucleic acid sequence encoding a universal HA vaccine from swine H3 influenza A using Epigraph2.

SEQ ID NO:122 is the nucleic acid sequence encoding a universal HA vaccine from swine H3 influenza A using Epigraph3.

DETAILED DESCRIPTION

A universal vaccine for influenza has become a high priority and there are several efforts being pursued to achieve this goal, since prevention of influenza in humans would have a very significant impact on healthcare costs and burden. Here, a solution is proposed to create universal virus vaccines using several strategies that have not been previously employed. Therefore, the approach described herein is unique because it utilized all known strains infecting humans and swine, and thus, the genes described herein are unique and do not exist in nature.

Trivalent Inactivated Vaccine (TIV) (e.g., FluZone) is the workhorse of modern influenza vaccination and has protected millions of humans from influenza morbidity and mortality. While effective, TIV has limitations that support the development of alternate vaccine platforms. For example, production of the vaccine in embryonated eggs is one fundamental problem with this vaccine platform. A large fraction of humans are allergic to egg ovalbumin and cannot take this vaccine. Generating influenza vaccines in eggs is time consuming, labor intensive, and relies on the availability of embryonated eggs. TIV only provides short-term immunity and this immunity is highly strain specific. Intramuscular delivery does not stimulate high levels of the secretory IgA that is thought to be more reactive against heterologous viruses, and TIV also importantly fails to induce cross-protective T cell immunity.

Live-Attenuated Cold-Adapted Vaccines (e.g., FluMist) is a cold-adapted influenza virus platform that can abortively replicate when introduced intranasally where the temperature is below 37° C. For this reason, FluMist can be superior to TIV because it can drive a combination of antibody and T cell responses. Cold adaptation has the advantage of faster vaccine production, induces protection, and has the ability to generate both mucosal and humoral immune responses that include secretory IgA, serum IgG, cytokine stimulation and the priming of CTL responses. The platform is limited by short duration of immunity, strain specificity, and contraindicated use in the very young, elderly, or immunocompromised.

Influenza surveillance in Asia and Australia is used to predict which influenza strains might spread in the United States in the following year. This generally effective strategy can fail. In fact, the concordance of WHO recommended strains and those strains causing outbreaks was only 50% between 1997 and 2005. Put another way, during those influenza seasons the strain predictions failed 50% of the time, leaving humans unprotected against seasonal and potentially pandemic influenza. The degree of vaccine mismatch with the 2009 pandemic Swine flu, based on HA amino acid divergence (20.5%), approached the maximal ~21% HA amino acid divergence between all H1 strains. As a result of this mismatch, the 2009 pandemic infected 24% of the global population. In contrast, the HA1-COT immunogen is only 7.6% divergent from the pandemic strain and provides protection in mouse challenge models.

The vaccine strategies described herein will be important to the prevention of influenza, and will significantly reduce or eliminate the probability of emergent zoonotic re-assorted influenza viruses from swine.

Centralized vaccine genes have been shown to induce broader cross-reactive immunity against divergent virus strains as compared to wild type genes and may be very useful as universal vaccines. These centralized vaccine genes can be constructed by several different methods. Vaccine genes designed using the Consensus, Mosaic and Epigraph methods were evaluated herein for their ability to induce protection against divergent H1N1 and H3N2 Swine Influenza A Virus as universal vaccine genes.

The following methodologies were used to create the universal vaccine immunogens described herein:

Centralized Consensus (CC) Genes—A CC gene is constructed using the most common amino acid at each position in a protein using an alignment of representative wild type gene sequences. This strategy creates a vaccine gene that localizes to the center of the phylogenetic tree and is equidistant to all known wild type virus strains. See FIG. 4B. Since functional elements, such as cleavage sites, transmembrane domains, localization signals, and fusion domains are critical to natural proteins, they are preserved within the CC genes. This technique has been shown to induce greater cross-reactive immunity to divergent HIV and Influenza viruses compared to wild type genes.

Consensus of Unique Sequences (COUS) Genes—A COUS gene is similar to a CC gene in that it is also uses the most common amino acid at each position. However, the alignment used to create the COUS gene consists of all known unique sequences for the given gene. This technique accounts for all of the known variants in the database and is biased towards the majority. FIG. 4C. The greatest advantage of this technique is that it selects a vaccine gene that is most closely related to the predominant circulating strains and, therefore, more likely to be protective against a randomly selected wild type challenge strain.

Mosaic Genes—In silico recombination is used to generate Mosaic genes. Full-length natural sequences are repetitively recombined with preference given to 9-mers duplicated in the sequences. This strategy uses a genetic algorithm to select for the highest possible potential T cell epitopes (PTE). FIG. 4D. Mosaic genes have shown to be promising vaccine candidates for HIV and other pathogens including HCV, Ebola and Influenza. Fischer et al., 2007, Nature Med., 13:100-6.

Epigraph Genes—Mosaic and Epigraph genes are designed to offer the same optimization of PTEs, however Epigraph genes provide substantially greater advantages over the Mosaic and consensus approaches. Unlike Mosaic approaches that use an algorithm, Epigraphs are designed using a faster graph-based design. A major element to the Epigraph approach is the ability to design multiple Epigraph genes that maximize vaccine coverage. FIG. 4E. The multiple Epigraph genes can localize to the major phylogenetic clusters of natural proteins or can span coverage across multiple clusters using recombinant Epigraph genes. This approach has been used to develop personalized therapeutic HIV vaccine candidates and a Pan-Filovirus Vaccine. Theiler and Korber, 2018, Stat. Med., 37:181-94.

It is proposed that centralized antigens will induce the greatest degree of cross-protective immune responses against mismatched influenza challenge, and, if so, they will impart a large impact on the field of influenza vaccine research. Examples of changes to the clinical practice of influenza vaccination may include the use of centralized antigens in the annual trivalent injection vaccine (TIV) or the stockpiling of centralized vaccines for use in the case of vaccine mismatch. Repeated exposure to a centralized vaccine, if used, for example, in an annual formulation, may induce enhanced cross-protective responses due to repeated boosting and affinity maturation to conserved epitopes in the centralized antigens.

Our approach to creating Centralized Consensus influenza genes is unique. For the consensus HA antigens, unique sequences were identified in the database. This eliminates repetitive sequences that may bias the consensus antigens towards more common strains and allows the reconstruction of a centralized sequence that represents all of the evolved sequences equally. Based on preliminary data in mice, the inclusion of a centralized gene in a swine influenza vaccine would reduce the risk of complete vaccine mismatch. Additionally, the centralized gene may boost responses against conserved elements that are common to all strains of influenza within that subtype.

The COUS genes that are described herein also are unique in that they are created using a dataset that consists of all known and unique influenza genes. This strategy biases these genes toward the predominant circulating strains. Therefore, the genetic relationship of the COUS genes and the circulating viruses is optimized. This strategy increases the probability of vaccine efficacy.

In order to create the Mosaic swine influenza vaccine antigens, the Mosaic Vaccine Designer program from the Los Alamos National Laboratories Tool Suite was used. Again, unique swine influenza HA protein sequences were obtained from the Influenza Research Database and were computationally analyzed for optimal potential T cell epitope coverage.

Lastly, the same HA data set was submitted to the Epigraph software suite where a three HA antigen cocktail was created. The Epigraph software selects for the immunogen that best represents the most common B and T cell epitopes in the dataset. This immunogen is designated Epigraph1. A second immunogen is designed to represent the second most common B and T cell epitopes, referred to as Epigraph2. Finally, a third immunogen representing the third most common B and T cell epitopes is designed and designated Epigraph3.

Figure 4:
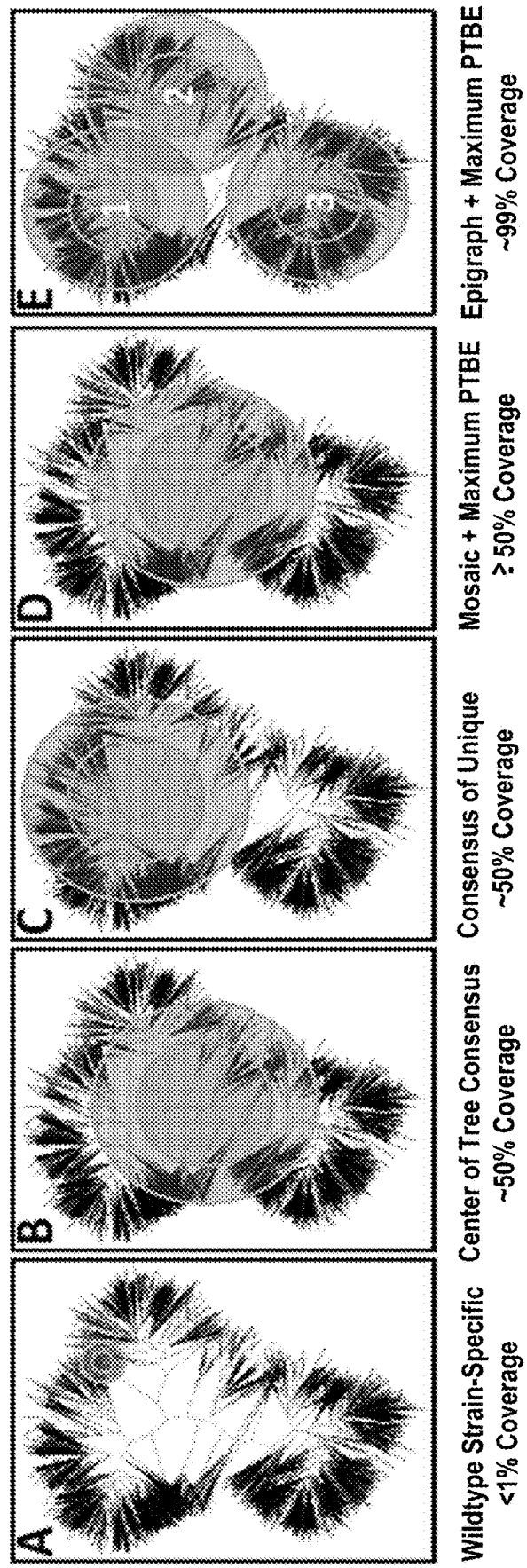
FIG. 4 shows the vaccine coverage of five different vaccine immunogen approaches. The blue circles represent predicted coverage for vaccine protection and the red circles represent the predicted coverage for complete sterilizing immunity induced by each of the vaccine immunogens. Vaccines based on wild type immunogens are very strain-specific and produce little, if any, cross-protective immunity (A). A centralized consensus vaccine is designed to localize to the center of the phylogenetic tree and represent all wild type strains equally (B). We have found that, indeed, these vaccine immunogens provide greater cross-protective immunity as compared to wild type genes when the vaccines are mismatched. A second consensus approach is to create a consensus of unique sequences (COUS), which gives equal weight to all unique influenza variants and gives bias towards more contemporary strains (C). Another immunogen approach is shown as a mosaic immunogen. The mosaic vaccine approach uses computational recombination over millions of generations to select for the single best vaccine immunogen with the greatest ≥9-mer coverage as compared to the average of all wild type sequences. Single mosaic immunogens also localize near the center of the tree as they are designed to be represent all known wild type sequences (D). The epigraph immunogens are designed in the same way as the mosaic immunogens with the exception that this is a multi-immunogen approach. The epigraph-designed immunogens focus on clusters of protein sequences to create a cocktail of immunogens that produce the greatest level of coverage across the designated number of immunogens requested in the cocktail. The design described herein focused on the use of a three-immunogen cocktail to give the greatest level of coverage without the burden of too many sequences (E).
Figure 5:
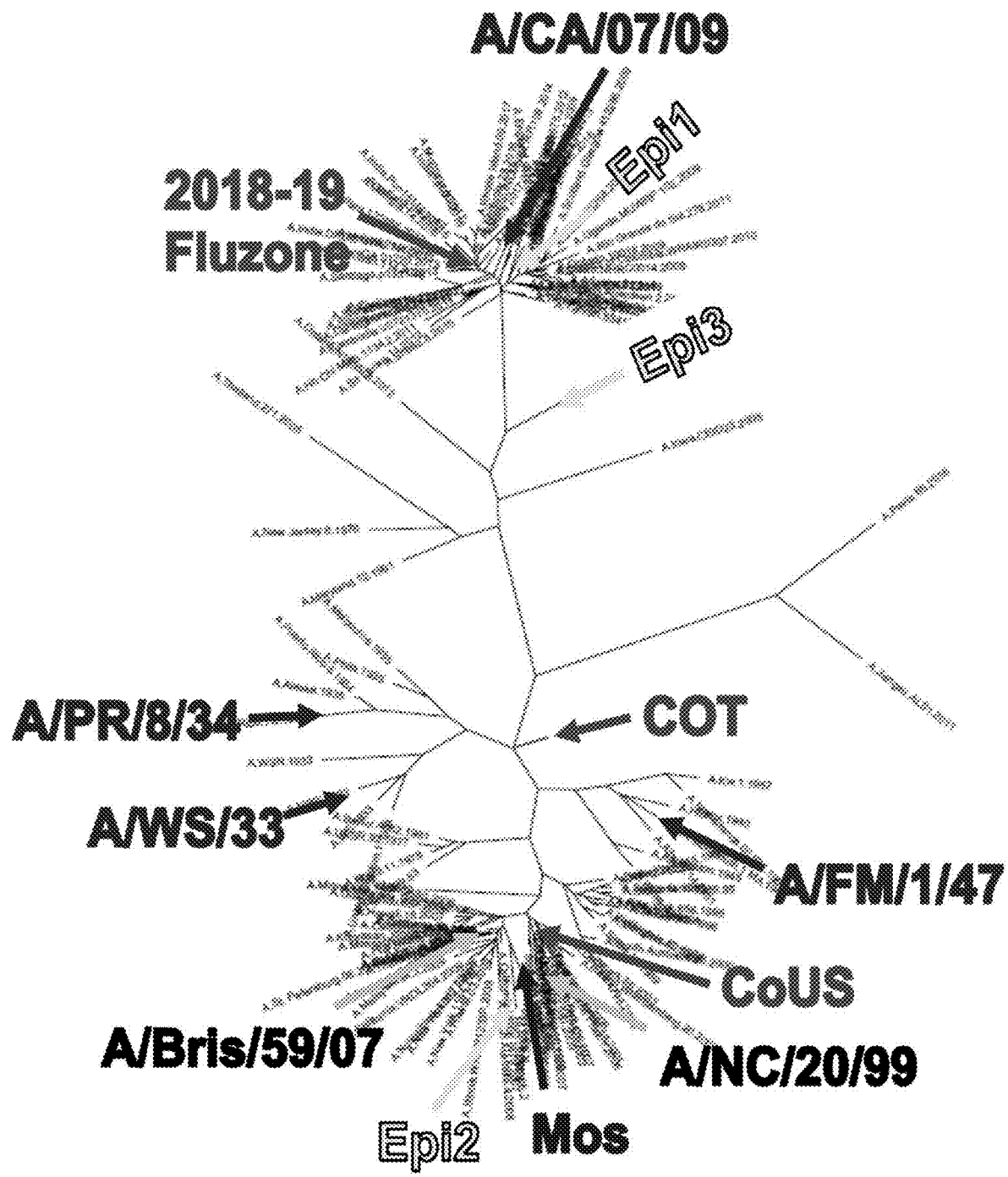
FIG. 5 shows a phylogenetic analysis of H1 HA proteins created by Consensus centralized Center of Tree (COT), Consensus of Unique Sequences (CoUS), Mosaic (Mos) and Epigraph (Epi) computational approaches. 7313 unique human H1 Influenza virus proteins were downloaded and laboratory strains and duplicate sequences were excluded. In order to show where the sequences localize on the phylogenetic tree, only representative sequences were chosen that show sequence evolution from years 1918 to 2018. The Mosaic Vaccine Design and Epigraph programs that are available through the HIV database tools suite were used to create the Mosaic and Epigraph candidate vaccine proteins, respectively. The consensus COT vaccine protein was designed to localize to the center of the tree. The Consensus CoUS candidate vaccine protein was computationally derived using the Consensus Maker Software. Both the CoUS and Mosaic proteins localize to the center of the main Influenza H1 cluster, which represents the majority of H1 diversity. These two candidate vaccine immunogens represent the average or ancestral protein from which all future influenza strains would evolve. The two major exceptions to the approaches is that the Consensus protein simply represents the most conserved amino acid sequence at each position, while the mosaic also seeks to represent the most commonly repeated sequences and it is also biased towards ≥9-mer motifs that maximally optimize the potential T and B cell epitopes (PTBE). The epigraph software is also designed to maximize the PTBEs within the final vaccine candidates, however, it is also designed to identify multiple Epigraph protein sequences that maximally cover the widest range of diversity within the influenza cluster. Indeed, the Epigraph 2 protein also localizes to the main cluster of all human Influenza H1N1 viruses analyzed, whereas the Epigraph 1 protein localizes to the central region of the pd09. In order to maximize coverage of sequences in between clusters, a third Epigraph 3 protein was created. This third protein is a unique recombinant of proteins in which short segments are synthetically recombined to make a montage protein sequence that represents viruses of classical and pd09 ancestry. The Consensus, Mosaic, and Epigraph proteins are shown in green, blue and yellow, respectively. The FluZone protein is shown in red. The challenge viruses and viruses for immune correlates are shown in purple and black, respectively.

All the vaccine antigens were analyzed phylogenetically and found to localize either to the center of the phylogenetic tree, in the case of Centralized Consensus and Mosaic proteins, or to the two main influenza clusters with a recombinant covering the minor cluster, in the case of the Epigraph vaccines (FIG. 4).

The methodologies described herein can be applied to other viruses with high levels of genetic diversity (e.g., human immunodeficiency virus (HIV), Newcastle disease virus (NDV), porcine reproductive and respiratory syndrome (PRRS), or human papillomavirus (HPV)). Although the centralized influenza genes described herein can be used as human vaccines, these same strategies can be applied to vaccinate reservoir animals (e.g., swine, poultry, horses) against influenza infections and significantly reduce or eliminate the probability of the emergence of re-assorted swine influenza viruses. Thus, the vaccination of reservoir animals at the source of virus evolution could intervene at this primary step and result in the elimination of potential future zoonotic influenza outbreaks that result in pandemics.

A number of different vaccine polypeptides were generated; the amino acid sequences of such polypeptides are shown in SEQ ID NO:1-102 and representative nucleic acid sequences are shown in SEQ ID NO:103-122. Those skilled in the art would appreciate that a nucleic acid sequence encoding each amino acid sequence can readily be determined.

In addition to the vaccine polypeptides having the sequences shown in SEQ ID NOs:1-102 and encoded by the nucleic acids shown in SEQ ID NOs:103-122, polypeptides and nucleic acids are provided that have at least 90% sequence identity (e.g., at least 91%, at least 92%, at least 93%, at least 94%, at least 95%, at least 96%, at least 97%, at least 98%, at least 99% or 100% sequence identity) to the vaccine polypeptides having the sequences shown in SEQ ID NOs:1-102 or to the nucleic acids shown in SEQ ID NOs:103-122.

In calculating percent sequence identity, two sequences are aligned and the number of identical matches of nucleotides or amino acid residues between the two sequences is determined. The number of identical matches is divided by the length of the aligned region (i.e., the number of aligned nucleotides or amino acid residues) and multiplied by 100 to arrive at a percent sequence identity value. It will be appreciated that the length of the aligned region can be a portion of one or both sequences up to the full-length size of the shortest sequence. It also will be appreciated that a single sequence can align with more than one other sequence and hence, can have different percent sequence identity values over each aligned region.

The alignment of two or more sequences to determine percent sequence identity can be performed using the algorithm described by Altschul et al. (1997, Nucleic Acids Res., 25:3389 3402) as incorporated into BLAST (basic local alignment search tool) programs, available at ncbi.nlm.nih.gov on the World Wide Web. BLAST searches can be performed to determine percent sequence identity between a sequence (nucleic acid or amino acid) and any other sequence or portion thereof aligned using the Altschul et al. algorithm. BLASTN is the program used to align and compare the identity between nucleic acid sequences, while BLASTP is the program used to align and compare the identity between amino acid sequences. When utilizing BLAST programs to calculate the percent identity between a sequence and another sequence, the default parameters of the respective programs generally are used.

Vectors containing nucleic acid molecules that encode polypeptides also are provided. Vectors, including expression vectors, are commercially available or can be produced by recombinant technology. A vector containing a nucleic acid molecule can have one or more elements for expression operably linked to such a nucleic acid molecule, and further can include sequences such as those encoding a selectable marker (e.g., an antibiotic resistance gene), and/or those that can be used in purification of a polypeptide (e.g., 6×His tag). Elements for expression include nucleic acid sequences that direct and regulate expression of nucleic acid coding sequences. One example of an expression element is a promoter sequence. Expression elements also can include one or more of introns, enhancer sequences, response elements, or inducible elements that modulate expression of a nucleic acid molecule. Expression elements can be of bacterial, yeast, insect, mammalian, or viral origin and vectors can contain a combination of expression elements from different origins. As used herein, operably linked means that elements for expression are positioned in a vector relative to a coding sequence in such a way as to direct or regulate expression of the coding sequence.

A nucleic acid molecule, e.g., a nucleic acid molecule in a vector (e.g., an expression vector, a viral vector) can be introduced into a host cell. The term "host cell" refers not only to the particular cell(s) into which the nucleic acid molecule has been introduced, but also to the progeny or potential progeny of such a cell. Many suitable host cells are known to those skilled in the art; host cells can be prokaryotic cells (e.g., E. coli) or eukaryotic cells (e.g., yeast cells, insect cells, plant cells, mammalian cells). Representative host cells can include, without limitation, A549, WEHI, 3T3, 10T1/2, BHK, MDCK, COS 1, COS 7, BSC 1, BSC 40, BMT 10, VERO, WI38, HeLa, 293 cells, Saos, C2C12, L cells, HT1080, HepG2 and primary fibroblast, hepatocyte and myoblast cells derived from mammals including human, monkey, mouse, rat, rabbit, and hamster. Methods for introducing nucleic acid molecules into host cells are well known in the art and include, without limitation, calcium phosphate precipitation, electroporation, heat shock, lipofection, microinjection, and viral-mediated nucleic acid transfer (e.g., transduction).

With respect to polypeptides, "purified" refers to a polypeptide (i.e., a peptide or a polypeptide) that has been separated or purified from cellular components that naturally accompany it. Typically, the polypeptide is considered "purified" when it is at least 70% (e.g., at least 75%, 80%, 85%, 90%, 95%, or 99%) by dry weight, free from the polypeptides and naturally occurring molecules with which it is naturally associated. Since a polypeptide that is chemically synthesized is, by nature, separated from the components that naturally accompany it, a synthetic polypeptide is considered "purified," but further can be removed from the components used to synthesize the polypeptide (e.g., amino acid residues). With respect to nucleic acid molecules, "isolated" refers to a nucleic acid molecule that is separated from other nucleic acid molecules that are usually associated with it in the genome. In addition, an isolated nucleic acid molecule can include an engineered nucleic acid molecule such as a recombinant or a synthetic nucleic acid molecule.

Polypeptides can be obtained (e.g., purified) from natural sources (e.g., a biological sample) by known methods such as DEAE ion exchange, gel filtration, and/or hydroxyapatite chromatography. A purified polypeptide also can be obtained, for example, by expressing a nucleic acid molecule in an expression vector or by chemical synthesis. The extent of purity of a polypeptide can be measured using any appropriate method, e.g., column chromatography, polyacrylamide gel electrophoresis, or HPLC analysis. Similarly, nucleic acid molecules can be obtained (e.g., isolated) using routine methods such as, without limitation, recombinant nucleic acid technology (e.g., restriction enzyme digestion and ligation) or the polymerase chain reaction (PCR; see, for example, PCR Primer: A Laboratory Manual, Dieffenbach & Dveksler, Eds., Cold Spring Harbor Laboratory Press, 1995). In addition, isolated nucleic acid molecules can be chemically synthesized.

In some embodiments, a vaccine as described herein can be multivalent (e.g., 4-valent, 12-valent, 16-valent). For example, a vaccine can include a plurality of polypeptides as described herein. For example, a vaccine can include one or more of the Mosaic1 vaccine polypeptides (e.g., SEQ ID NOs: 3, 10, 17, 24, 31, 38, 46, 54, 62, 69, 76, 83, 90, 97, 104, 109, 114, or 119), one or more of the Epigraph1 vaccine polypeptides (e.g., SEQ ID NOs: 6, 13, 20, 27, 34, 41, 49, 57, 65, 72, 79, 86, 93, 100, 105, 110, 115, or 120), one or more of the Mosaic2 vaccine polypeptides (e.g., SEQ ID NOs: 4, 11, 18, 25, 32, 39, 47, 55, 63, 70, 77, 84, 91, or 98), one or more of the Epigraph2 vaccine polypeptides (SEQ ID NOs: 7, 14, 21, 28, 35, 42, 50, 58, 66, 73, 80, 87, 94, 101, 106, 111, 116, or 121), or combinations thereof. In some embodiments, a vaccine can include one or more of the Epigraph vaccine polypeptides (e.g., Epigraph1, Epigraph2, Epigraph3; e.g., SEQ ID NOs: 6-8, 13-15, 20-22, 27-29, 34-36, 41-43, 49-52, 57-60, 65-67, 72-74, 79-81, 86-88, 93-95, or 100-102).

Typically, one or more of the human vaccine polypeptides described herein are administered to a human to provide protective immunity against influenza and one or more of the swine vaccine polypeptides described herein are administered to a swine to provide protective immunity against influenza. In some instances, however, one or more of the human vaccine polypeptides described herein can be administered to an animal (e.g., a bird, a pig, a horse, a dog, a cat) to provide protective immunity against influenza (e.g., avian influenza, swine influenza, equine influenza, canine influenza, feline influenza), and/or one or more of the swine vaccine polypeptides described herein can be administered to a human or a non-swine animal to provide protective immunity against influenza.

The vaccine polypeptides described herein can be suspended in a physiologically acceptable or compatible carrier and administered to a subject. Pharmaceutically acceptable carriers include saline, which may be formulated with a variety of buffering solutions (e.g., phosphate buffered saline), lactose, sucrose, calcium phosphate, gelatin, dextran, agar, pectin, and water. Conventional and pharmaceutically acceptable routes of administration include, but are not limited to, direct delivery to an organ such as, for example, the liver or lung, orally, intranasally, intratracheally, by inhalation, intravenously, intramuscularly, intraocularly, subcutaneously, intradermally, transmucosally, or by other routes of administration. The vaccine polypeptides described herein, or nucleic acids (e.g., DNA, RNA) encoding such viral polypeptides, can be delivered using a viral vector (e.g., an adenovirus, an adeno-associated virus, a retrovirus, an alphavirus, a paramyxovirus, or a rhabdovirus) or nanoparticles (e.g., lipid nanoparticles).

The vaccine polypeptides described herein can be administered in sufficient amounts to provide a therapeutic benefit without undue adverse effects. The dose of the vaccine polypeptide administered to a subject will depend primarily on factors such as the condition being treated, and the age, weight, and health of the subject. Simply by way of example, an effective dosage of a vaccine polypeptide to be administered to a human subject can be in the range of from about 15 micrograms (µg) to about 90 µg (e.g., about 20 µg to about 80 µg; about 25 µg to about 75 µg; about 30 µg to about 70 µg; about 40 µg to about 60 µg; about 45 µg to about 55 µg; about 50 µg). In some instances, a subject can be administered one or more of the vaccine polypeptides described herein seasonally or upon detection of influenza or antibodies against influenza; in some instances, a subject can be administered one or more of the vaccine polypeptides described herein in early childhood, thereby providing protective immunity in that subject for years or decades. Under certain circumstances, it may be desirable to re-administer one or more of the vaccine polypeptides described herein to the subject after a period of time following the first administration (e.g., weeks, months, years (e.g., decades)) in the form or a "booster" vaccine.

In accordance with the present invention, there may be employed conventional molecular biology, microbiology, biochemical, and recombinant DNA techniques within the skill of the art. Such techniques are explained fully in the literature. The invention will be further described in the following examples, which do not limit the scope of the methods and compositions of matter described in the claims.

EXAMPLES

Example 1—Viral Genes and the Generated Vaccine Sequences

The genetic relationships between the vaccine genes described herein and wild type circulating genes are shown in FIGS. 9-23. Since the vaccine genes described herein were made using all unique HA sequences, they are not like any genes that would be made using other strategies such as Consensus, COBRA, Mosaics, and COT.

The unique universal vaccine genes described herein are for use against Human Influenza A Virus (H1, H2, H3, H5, N1 and N2 (SEQ ID NOs:1-43)), Human Influenza B Virus (HA Yamagata-like, HA Victoria-like, NA Yamagata-like, NA Victoria-like (SEQ ID NOs:44-74)) and Swine Influenza A Virus (H1, H3, N1 and N2 (SEQ ID NOs:75-102)), and can be applied to the creation of a universal influenza vaccine that provides complete protection against all known influenza strains. Nucleic acid sequences encoding representative influenza vaccines are shown in SEQ ID NOs:103-122.

Example 2—Preliminary Results

IACUC. All animals were housed in the UNL Life Sciences Annex under the Association for Assessment and Accreditation of Laboratory Animal Care (AALAC) guidelines with animal use protocols approved by the corresponding the UNL IACUC protocol. All animal experiments were carried out according to the provisions of the Animal Welfare Act, PHS Animal Welfare Policy, the principles of the NIH Guide for the Care and Use of Laboratory Animals, and the policies and procedures of UNL.

Sex as a Biological Variable. Only female mice were used in the in vivo studies. However, all successful vaccine candidates were confirmed in studies using male mice.

Biohazard. All biohazard materials were subject to approval by the UNL Institutional Biosafety Committee (IBC). The UNL IBC was responsible for the safe use of infectious agents and recombinant DNA within UNL laboratories. This research did not use any reagents rated higher than BSL2.

Rigor and Transparency. In order to ensure statistical significance, groups of 5 mice and ferrets were used. In order to confirm reproducibility, all in vivo studies were repeated at least once. In addition, preliminary dose-dependent studies were performed that act as replicates within each experiment.

Production of Centralized COT H1, 2, 3, and 5 Genes. Comparison of select H1 HA proteins from 1933 to 2009 generated a phylogenetic tree with ~21.0% sequence divergence across the branches. Due to high levels of genetic diversity, selecting a single wild type HA protein as a broadly cross-reactive vaccine was not thought to be feasible. Rather than select one wild type gene as a vaccine, a centralized gene was generated that mimics an ancestor of influenza infections during the past 78 years. The rationale for this was to produce an immunogen that is centrally located with respect to all other variants. Such a protein practically has lower sequence divergence with all of the variants as compared to any two randomly selected proteins. The centralized genes have been found to induce very effective levels of protection against divergent strains of influenza in BALB/c mice.

Figure 1:
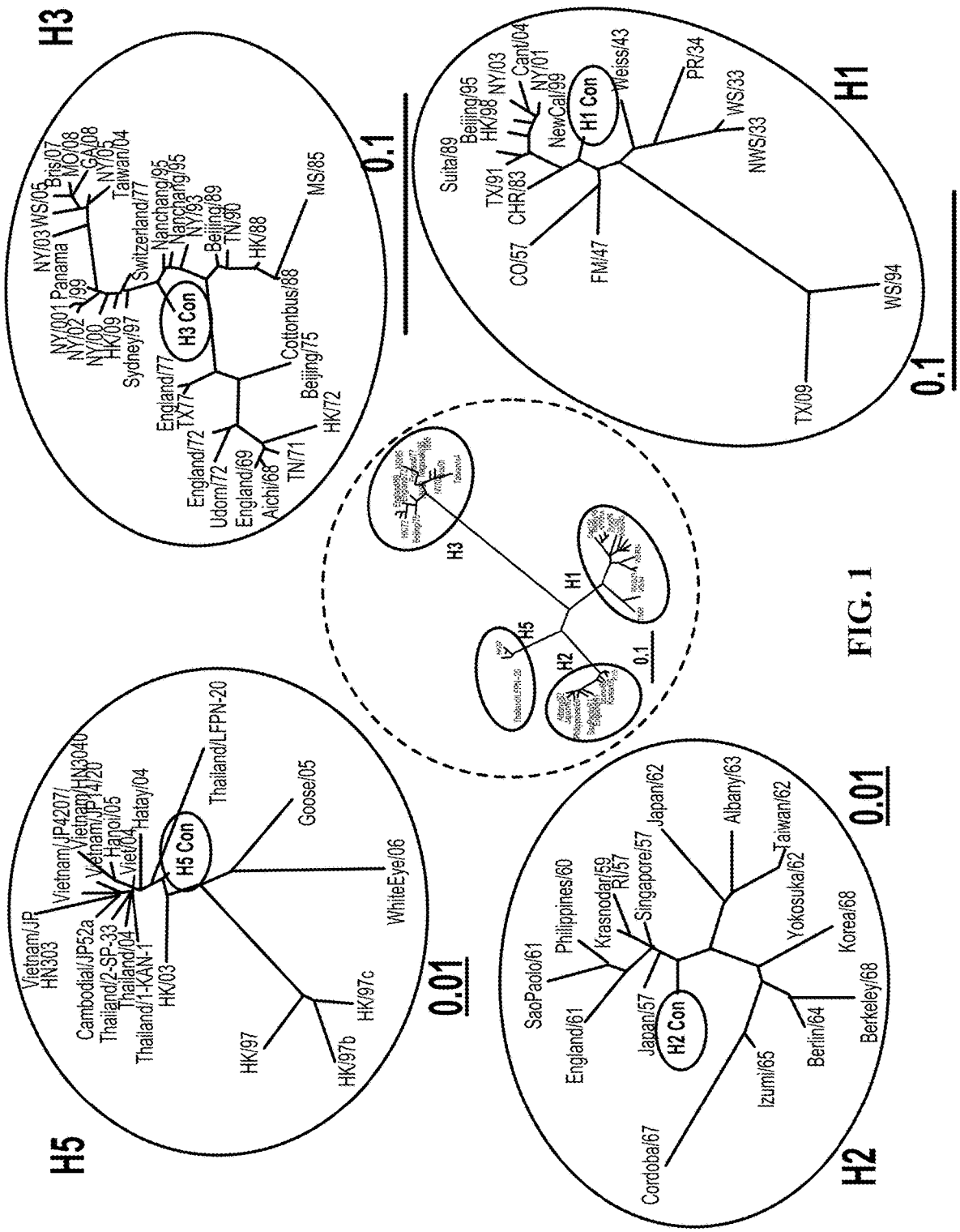
FIG. 1 is a schematic showing the phylogenetic analyses of centralized hemagglutinin genes. The genetic relationships between the consensus genes and wild type genes are shown in unrooted neighbor-joining phylogenetic trees. H1, H2, H3 and H5 consensus COT genes are shown localizing to the center of the tree. Black bars indicate the percent divergence of the HA amino acid sequences. The central tree (dotted line) illustrates the degree of genetic diversity between the HA subtypes.

Phylogenetic Analyses of Centralized HA Genes. The relationship of the consensus COT genes to other wild type genes are shown in FIG. 1. All of the consensus genes localize to the central region of each of the respective trees. The average genetic distance of the H1, H2, H3 and H5 consensus genes to the wild type genes was 7.04%, 2.86%, 5.44% and 1.65% respectively. However, the maximum genetic distance between wild type H1, H2, H3 and H5 genes was 20.7%, 7.9%, 14.7% and 5.1% respectively. The centralized COT immunogens act to reduce genetic diversity to mismatched genes by being equidistant to all analyzed wild type genes (FIG. 1). The center tree shows the significant divergence between the influenza HA subtypes. The evolution of influenza allows for extreme level of plasticity in the HA genes, and the HA subtypes can be up to 60% divergent and still have identical functionality (FIG. 1).

In the case of mismatch, H1-COT induced better protection as compared to wild type immunogens.

Figure 2:
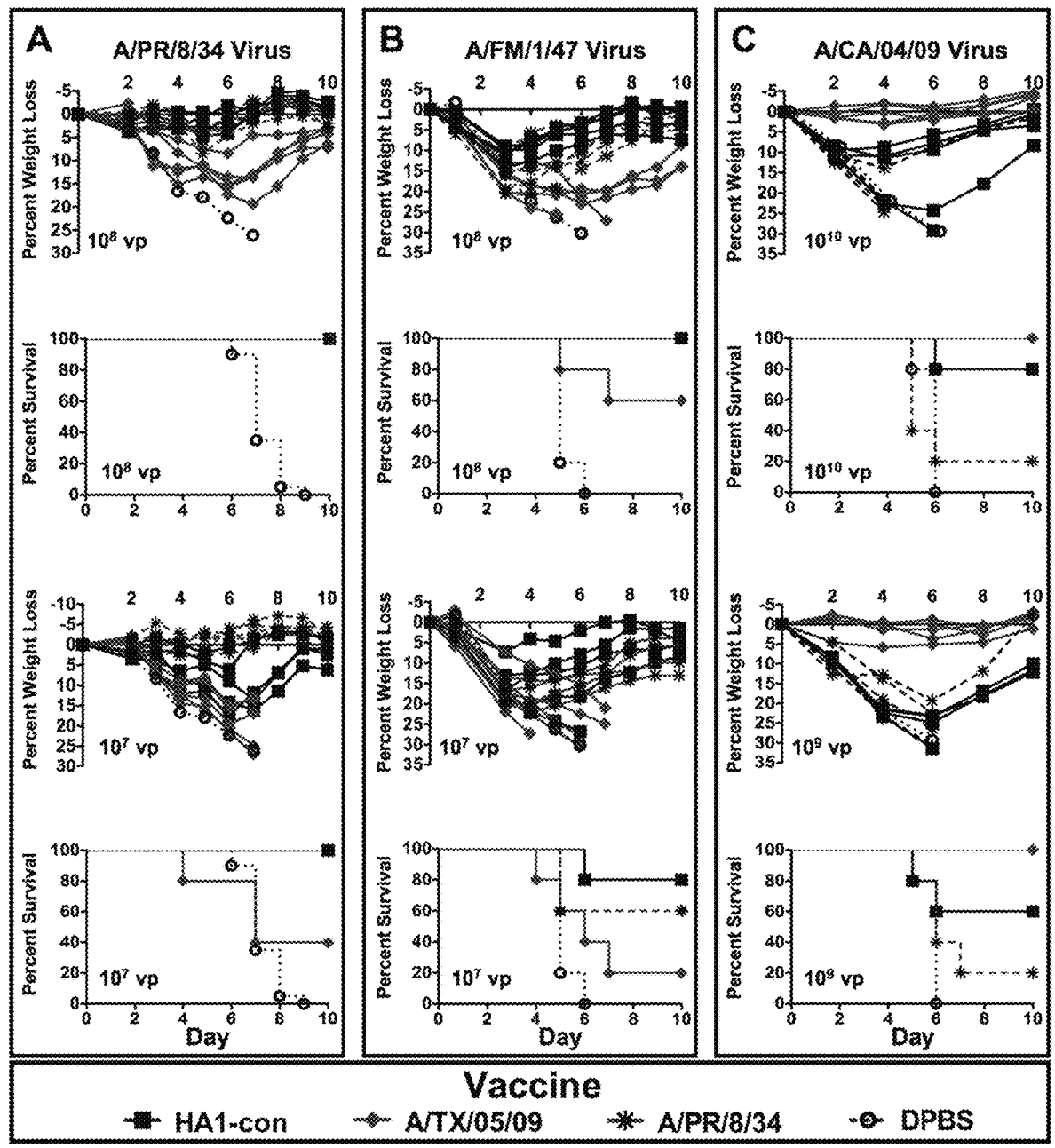
FIG. 2 is a graph showing protection against influenza virus infection by wild type and centralized HA immunogens. Mice were immunized intramuscularly with A/PR/8/34, H1-COT, and A/CA/04/09 HA expressing adenovirus. Three weeks after immunization, the mice were challenged intranasally with 100 $LD_{50}$ of influenza virus A/PR/8/34 (left), A/FM/1/47 (center) or 70 $LD_{50}$ of A/CA/04/09 (right). Individual mouse weights for the vaccinated mice and the mean and standard error of the control DPBS immunized mice are shown. Mice exhibiting profound signs of disease and less than 75% of baseline weights were humanely sacrificed.

Protection Against Lethal A/PR/8/34 Influenza. The homologous PR/8/34 vaccine was able to induce protective responses using the lowest dose of vaccine as compared to the mismatched vaccines, H1-COT and A/TX/05/09 (FIG. 2A). A/PR/8/34 immunized mice did not show any signs of disease or death with doses as low as 107 vp (FIG. 2A). However, mice vaccinated with H1-COT vaccine recovered and survived the challenge, whereas 60% of mice vaccinated with A/TX/05/09 at the same dose did not survive (FIG. 2A).

Protection Against Letha A/FM/1/47Influenza. In this challenge study, all of the vaccines were mismatched to the challenge strain. The mice vaccinated with the H1-COT vaccine showed the least weight loss and disease as well as the highest level of survival against the lethal challenge (FIG. 2B). The centralized H1-COT vaccine was superior to the two wild type vaccine immunogens.

Protection Against Lethal A/California/04/09. The matched CA/04/09 vaccine provided the best levels of protection against a lethal challenge with A/CA/04/09. However, when the vaccines were mismatched, the centralized H1-COT induced better protective immunity as compared to A/PR/8/34 (FIG. 2C). Importantly, 60% of H1-COT vaccinated mice survived, while only 20% of A/PR/8/34 vaccinated mice survived (FIG. 2C).

These data demonstrate that the centralized HA1-con immunogen is able to mediate cross-protection against a divergent influenza virus in three separate stringent challenge models, including 2009 H1N1.

This project will test the utility of centralized immunogens as foundation immunogens against other influenza strains.

Protection Against Divergent Lethal Challenge After Multivalent (H1+H2+H3+H5) COT HA Vaccination. The ultimate proof of vaccine efficacy is a challenge study. Groups of mice were vaccinated with a multivalent vaccine consisting of four distinct Consensus COT HA subtypes, H1, H2, H3 and H5. It was successfully shown that multiple HA immunogens could be delivered simultaneously and the centralized immunogens provided 100% survival against 8 of 9 divergent lethal influenza viruses representing H1N1, H3N1, H3N2 and H5N1 influenza (Table 1). This challenge model was extremely stringent, and seven challenges consisted of 100 mouse lethal dose 50% ($MLD_{50}$) and two challenges at 10 $MLD_{50}$. In addition, there were no signs of disease in 7 out of 9 lethal challenges. This was very much in contrast to mice immunized with the traditional influenza vaccines, FluMist and FluZone. Mice immunized with these vaccines induced robust HI titers against 7 of 7 influenza viruses tested, however, they failed to provide any protection against disease in death when challenged with lethal influenza virus (Table 1). Interestingly, the universal multivalent vaccine also induced significantly higher T cell immunity and neutralizing antibody as compared to the traditional vaccines. The improved cellular and humoral immunity of the HA-COT vaccines can be selected for during the design and production of these universal vaccine immunogens.

TABLE 1

Summary of Supporting Data

| | Universal Vaccine | FluMist | FluZone |
|---|---|---|---|
| Hemmaglutination Inhibition Titers | 9/11 (82%) | 7/7 (100%) | 7/7 (100%) |
| Neutralization Titers | 6/6 (100%) | 1/4 (25%) | 1/4 (25%) |
| Cellular Immunity | ++++ | + | + |
| Linear Antibody Binding | ++ | ++++ | ++++ |
| Linear Antibody Coverage | ++++ | ++++ | ++++ |
| Protection Against Disease | 7/9 (78%) | 0/5 (0%) | 0/5 (0%) |
| Survival | 8/9 (89%) | 0/5 (0%) | 0/5 (0%) |

Figure 3:
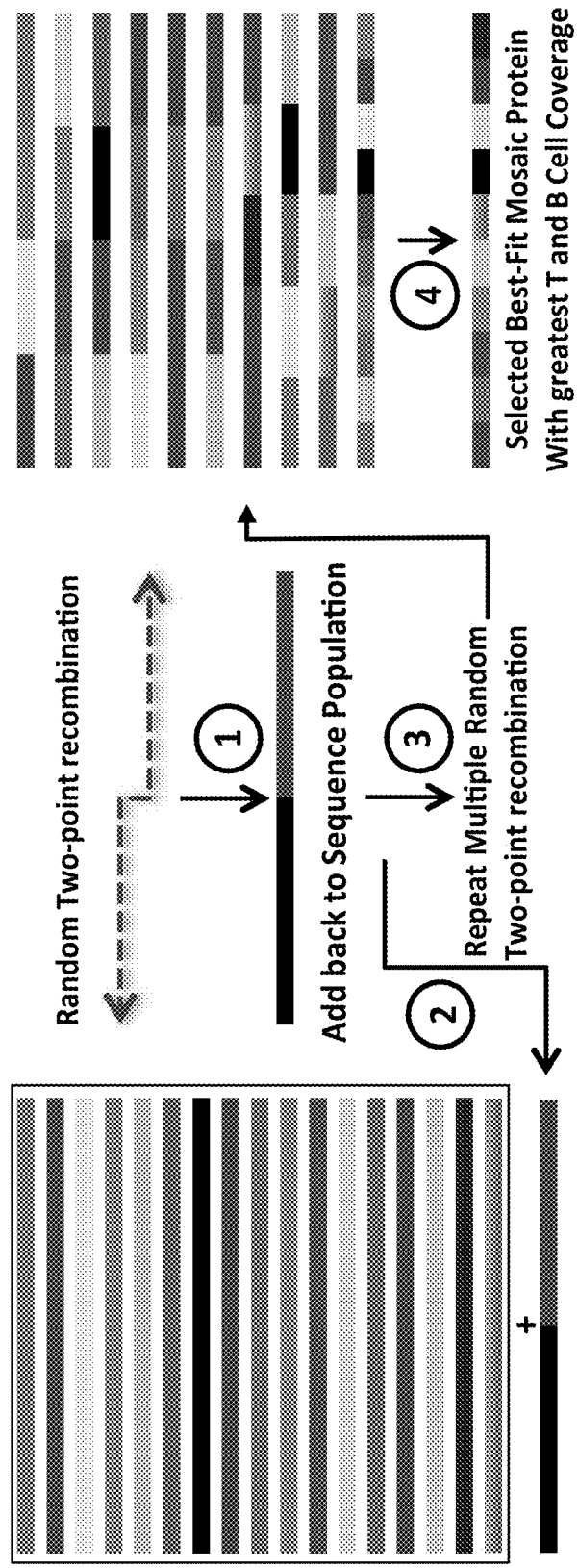
FIG. 3 is a schematic of mosaic and epigraph vaccine immunogen construction. This diagram shows how novel mosaic Influenza proteins are constructed. All of the intra-subtype hemagglutinin (HA) or neuraminidase (NA) proteins are aligned and used as natural sequences to create Mosaic sequences. Two sequences are randomly chosen and a two-point recombination is created (Step 1). The new recombinant is evaluated and if "fitness" has increased it is placed back into the protein pool (Step 2). This process is repeated for a defined number of generations, usually millions, in order to create a set of mosaic proteins that mimic naturally derived novel recombinants (Step 3). As the process continues the proteins that have the best coverage are chosen ultimately resulting in the Best-Fit Mosaic Protein (Step 4). Ultimately, the Mosaic vaccine immunogen is centralized to the phylogenetic tree and represents all of the wild type proteins equally, with a bias toward potential T and B cell epitopes (PTBEs).

Construction of Human H1 and H3 COT, CoUS, Mosaic and Epigraph Candidate Vaccine Immunogens. Wild type vaccine immunogens are poorly immunogenic and provide strain-specific immunity (FIG. 4A). Center of tree (COT) strategies have been evaluated in which the vaccine immunogen is located to the central node of the phylogenetic tree and is, therefore, equidistant to all analyzed variants. This is advantageous since, the COT immunogen is most likely to be more closely related to a vaccine mismatch than any random wild type gene (FIG. 4B). The major disadvantage to this approach was that it gave equal weight to all major branches of the tree, some of which have only one or two unique strains. A second approach used only unique sequences to create the consensus immunogen, a consensus of unique sequences (CoUS). This had the advantage of giving equal weight to all know flu variants and was biased toward more contemporary strains. This strategy worked to localize the vaccine immunogen to give the greatest protection against the greatest number of unique sequences (FIG. 4C). A third universal vaccine strategy used in silico recombination with an algorithm that selected for recombinants that represent the most common repeated motifs. This Mosaic strategy is described in FIG. 3 and had the advantage of selecting for a universal vaccine immunogen that had been optimized for the greatest number of T and B cell epitopes (FIG. 4D). The final strategy utilized the same optimization of T and B cell epitopes as the Mosaic strategy, but, in this case, selected for a cocktail of vaccine immunogens that maximize vaccine coverage (FIG. 4E).

Parameters for creating the Human H1 candidate vaccine immunogens. In order to create the centralized human Influenza H1 HA genes, 6908 unique human HA protein sequences (duplicates excluded) were downloaded from the Influenza Research Database. The sequences were full-length and represent global coverage from the years 1918 to 2018. The consensus COT sequence was created as previously described (Weaver et al., 2011, PLoS One, 6:e18314). In order to create the consensus CoUS gene, only unique sequences were submitted to the Consensus Maker software program. In order to produce the Mosaic gene, the FASTA formatted sequences were submitted to the Mosaic Vaccine Designer at the Los Alamos National Laboratories and a Mosaic sequence was created using the following parameters: Cocktail Size: 1, Epitope Length: 9, Rare Threshold: 1, Run Time: 10 hrs, Population size: 200, Cycle Time: 10, Stall Time: 10, Internal Crossover Probability: 0.5. Mosaic Vaccine Sequence Coverage: 0.730394. The Epigraph sequences were created using the Epigraph vaccine design software with the following parameters: Algorithm: Unaligned sequence, Epitope Length: 9, Cocktail Size: 3. The consensus COT and CoUS, and optimized genes were introduced back into the original protein sequence file, realigned in ClustalW and the nexus output file was used to generate a neighbor-joining tree using PAUP 4.0a. The phylogenetic relationship of the centralized proteins to the natural proteins was identified.

Parameters for creating the Human H3 candidate vaccine immunogens. In order to create the consensus and optimized genes, 7313 unique human Influenza H3 HA protein sequences were downloaded from the Influenza Research Database. The sequences were full-length and represent global coverage from the years 1918 to 2018. The consensus COT was created as previously described (Weaver et al., 2011, PLoS One, 6:e18314). The unique H3 HA protein sequences were used to create the CoUS sequence using the Consensus Maker Software. The FASTA formatted sequences were submitted to the Mosaic Vaccine Designer at the Los Alamos National Laboratories and a mosaic sequence was created using the following parameters: Cocktail Size: 1, Epitope Length: 9, Rare Threshold: 1, Run Time: 10 hrs, Population size: 200, Cycle Time: 10, Stall Time: 10, Internal Crossover Probability: 0.5. Mosaic Vaccine Sequence Coverage: 0.827791. The Epigraph sequences were created using the Epigraph Software with the following parameters: Algorithm: Unaligned sequence, Epitope Length: 9, Cocktail Size: 3. The centralized genes were introduced back into the original protein sequence file, realigned in ClustalW and the nexus output file was used to generate a neighbor-joining tree using PAUP 4.0a. The phylogenetic relationship of the centralized proteins to the natural proteins was identified.

Figure 6:
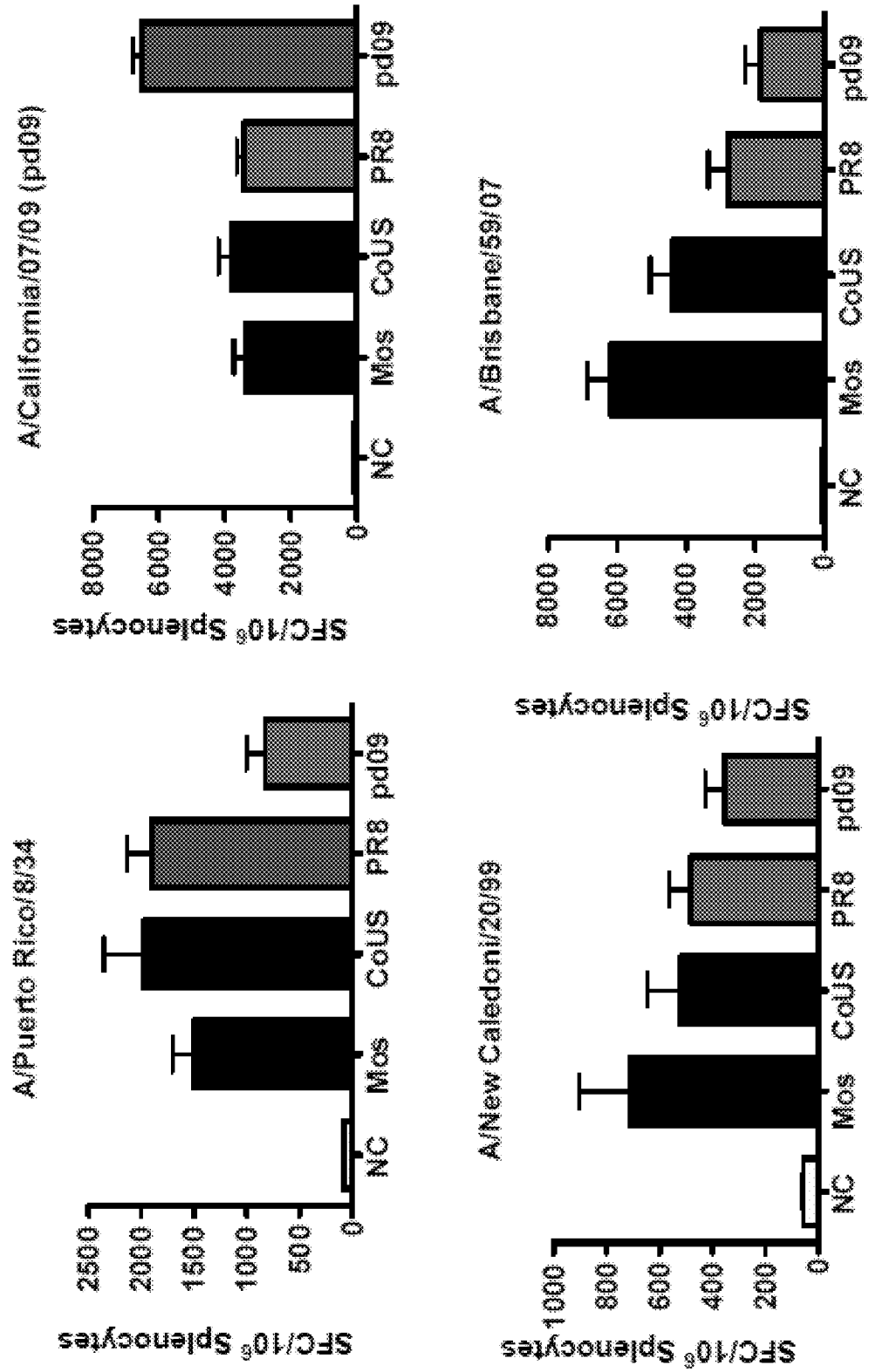
FIG. 6 are graphs showing sum T cell responses to several HA vaccine candidates. In order to determine if the proposed strategies would induce greater levels of T cell responses, the ability of the consensus CoUS and Mosaic vaccine strategies compared to two wild type HA vaccines. All four HA vaccine immunogens were cloned into an Adenovirus expression system and groups of five mice were immunized with $10^8$ vp/mouse. Three weeks after immunization, the splenocytes were harvested and the total T cells responses to four divergent influenza viruses was determined using an overlapping peptide library. Interferon-gamma secreting cells were detected using an ELISpot assay. The green bars indicate that the vaccine and the peptide pools are matched.

Improved Cellular Immune Responses In Novel HA Vaccine Immunogens. Mice were immunized with adenoviruses expressing novel human H1 Mosaic and CoUS genes and their ability to drive cellular immunity was compared against four divergent influenza viruses. When screened using an overlapping peptide library and ELISpot assay, it was found that in all cases of mismatch, the new Mosaic and CoUS genes induced greater levels of overall cellular immunity (FIG. 6). Interestingly, the Mosaic and CoUS genes induced T cell immunity against A/Puerto Rico/8/34 peptides equivalent to that of the vaccine expressing the homologous PR8 HA immunogen. In the case of the pd09 immune responses, the homologous HA vaccine induced the most robust immunity against the homologous peptides. However, in the case of vaccine mismatch, the Mosaic and CoUS HA vaccines induced equivalent or superior cellular immunity as compared to the wildtype PR8 and pd09 comparator vaccines (FIG. 6).

Figure 7:
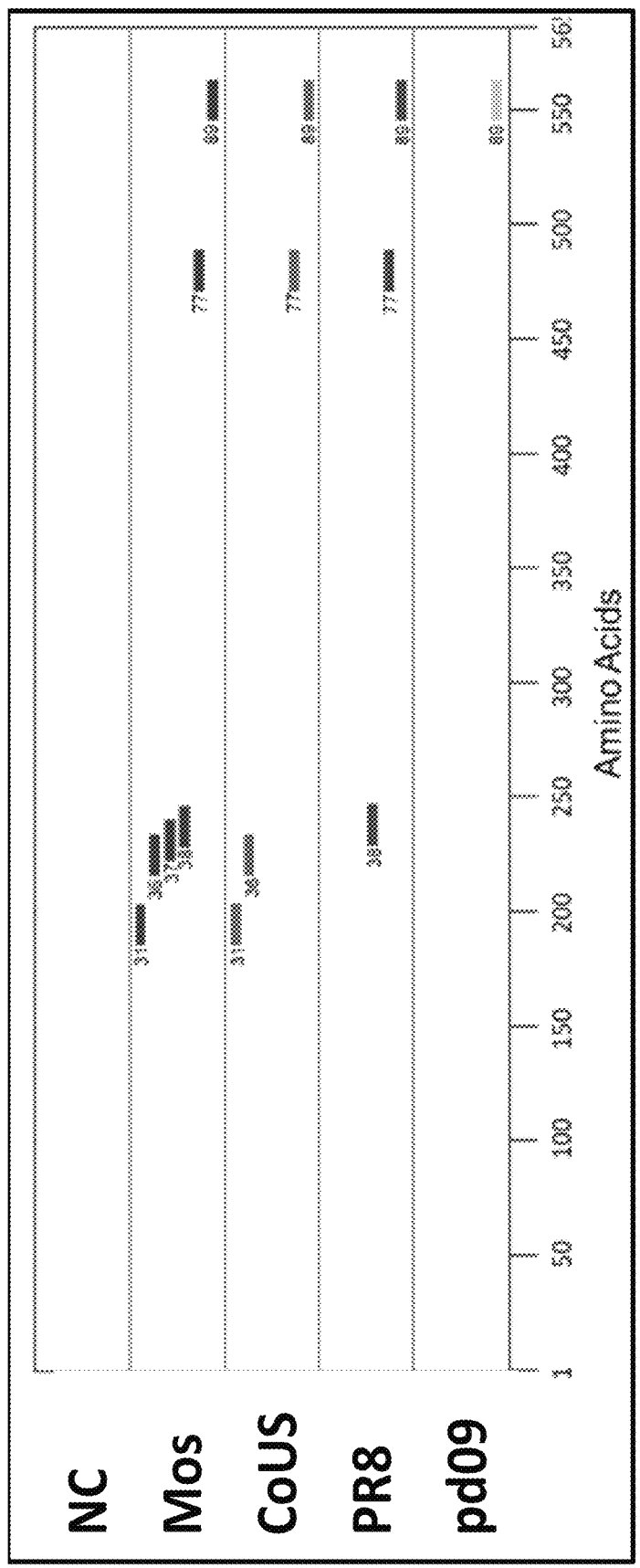
FIG. 7 is a schematic showing the epitope mapping of vaccines. The splenocytes from Mosaic, CoUS, PR8 and pd09 HA vaccinated mice were screened for induced T cell epitopes using a Brisbane/59/07 peptide library and the positive peptides were represented by red, green, purple and yellow bars, respectively.

In addition, the T cell epitopes were mapped against the Brisbane peptide library. The Mosaic vaccine generated the greatest level of recognized peptides, followed by the CoUS vaccine immunogen with 6 and 4 peptides, respectively (FIG. 7). This was compared to the wild type responses to 3 and 1 peptides, respectively. The Mosaic, CoUS, PR8 and pd09 HA vaccines induced T cell responses against 5, 4, 3 and 1 epitopes, respectively (FIG. 7). This empirical data showed that the Mosaic vaccine strategy does indeed select for greatest T cell coverage, and likely B cell coverage, of all of the vaccine strategies.

Figure 8:
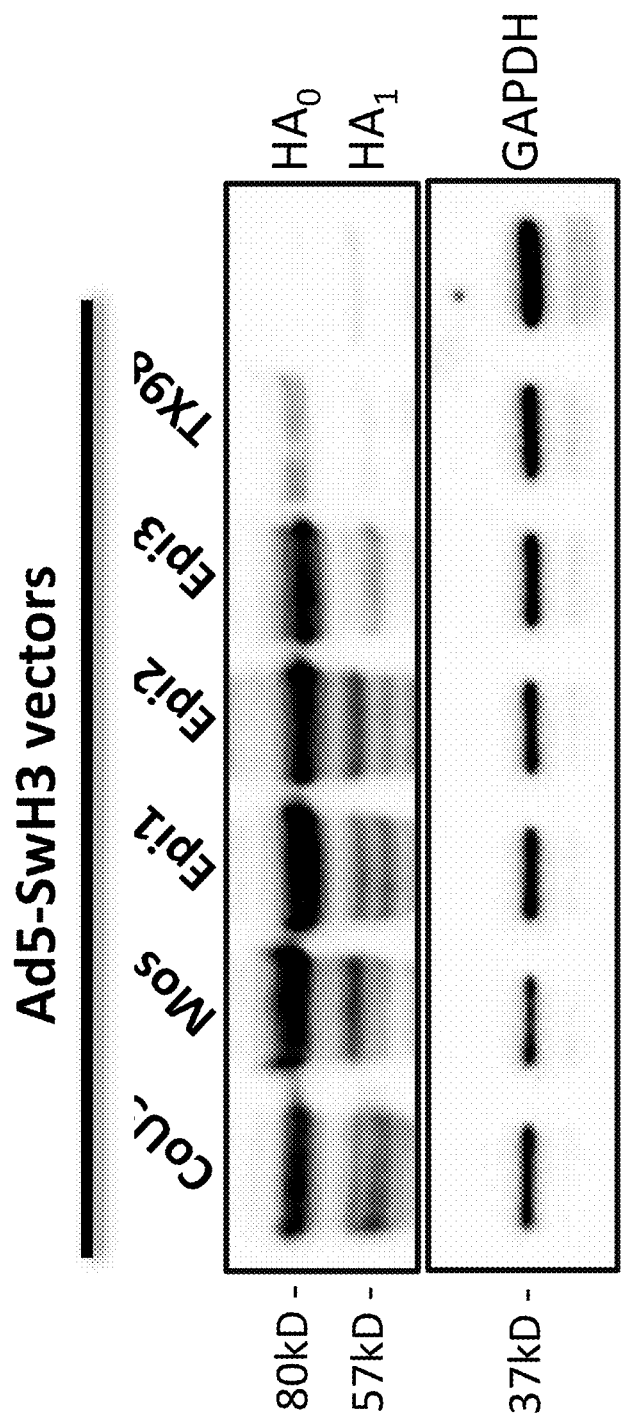
FIG. 8 is a Western blot analysis of vaccine vectors. The adenovirus vaccine vectors were analyzed for protein expression. 293 cells were infected with equivalent infectious units and protein was detected by probing the blots with polyclonal Goat anti-A/swine/Indiana/0392/2011 serum.
Figure 9:
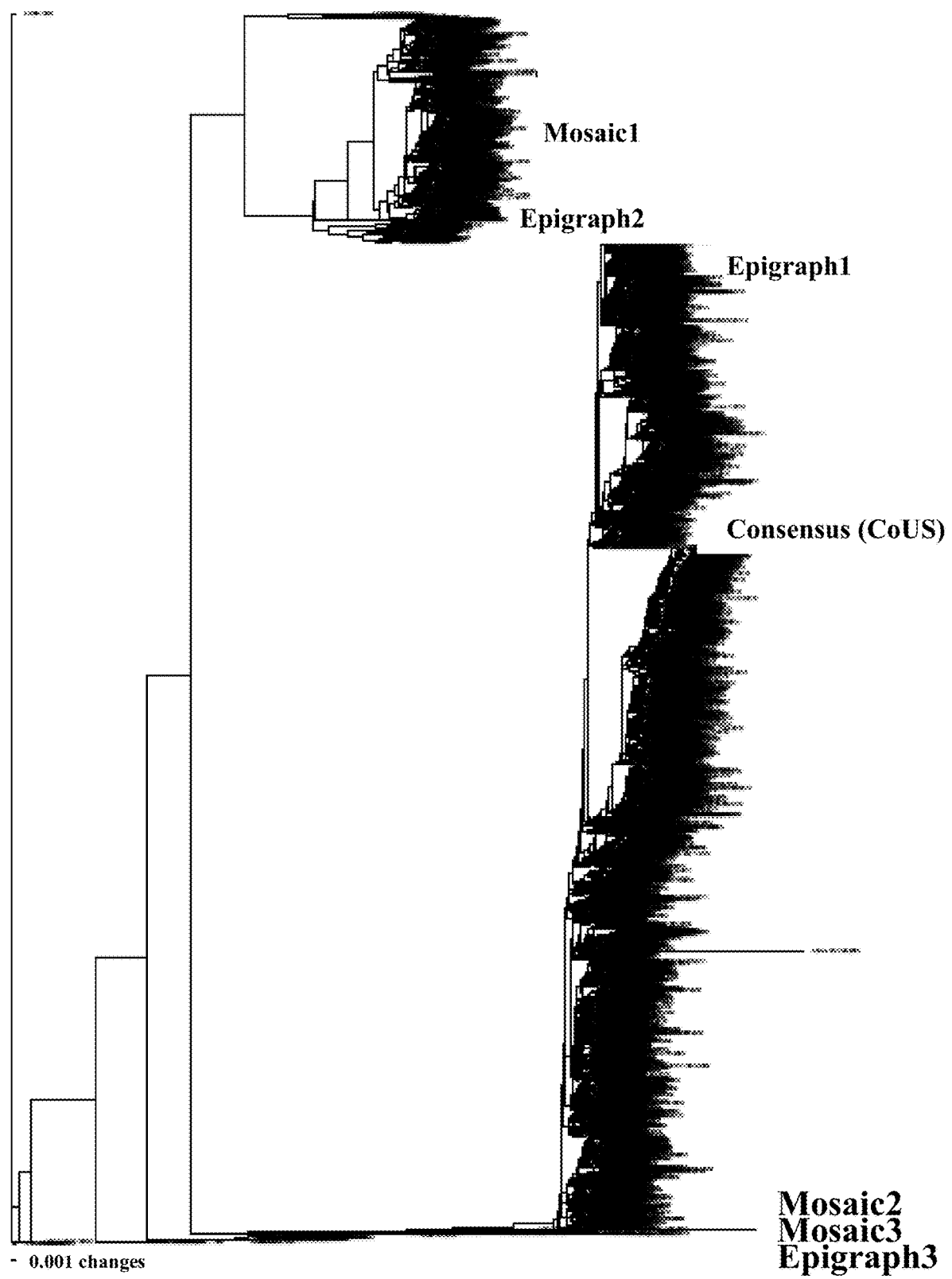
FIG. 9 shows the phylogenetic relationship between the vaccine genes described herein and various strains of human influenza A H1.
Figure 10:
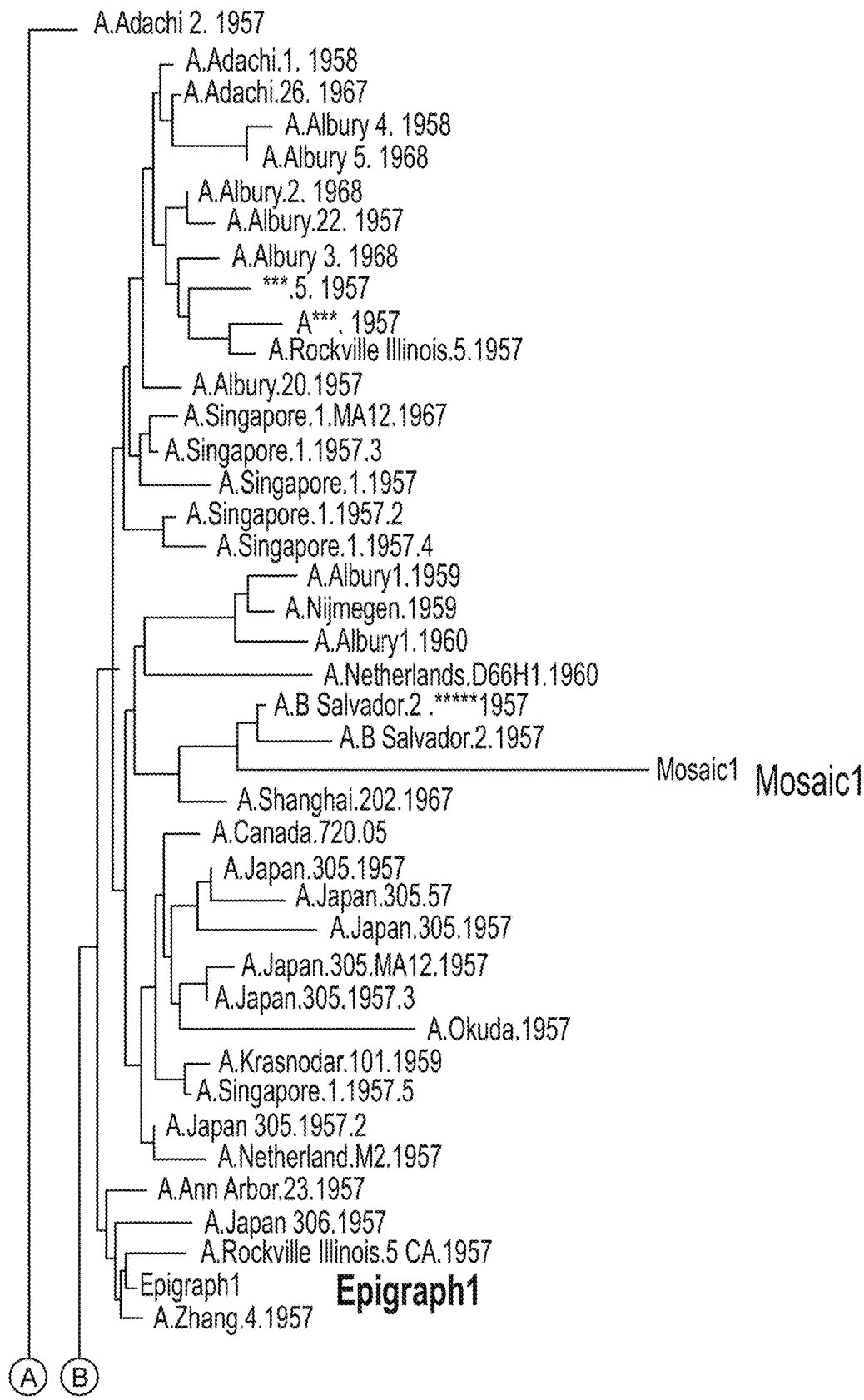
FIG. 10 shows the phylogenetic relationship between the vaccine genes described herein and various strains of human influenza A H2.
Figure 10:
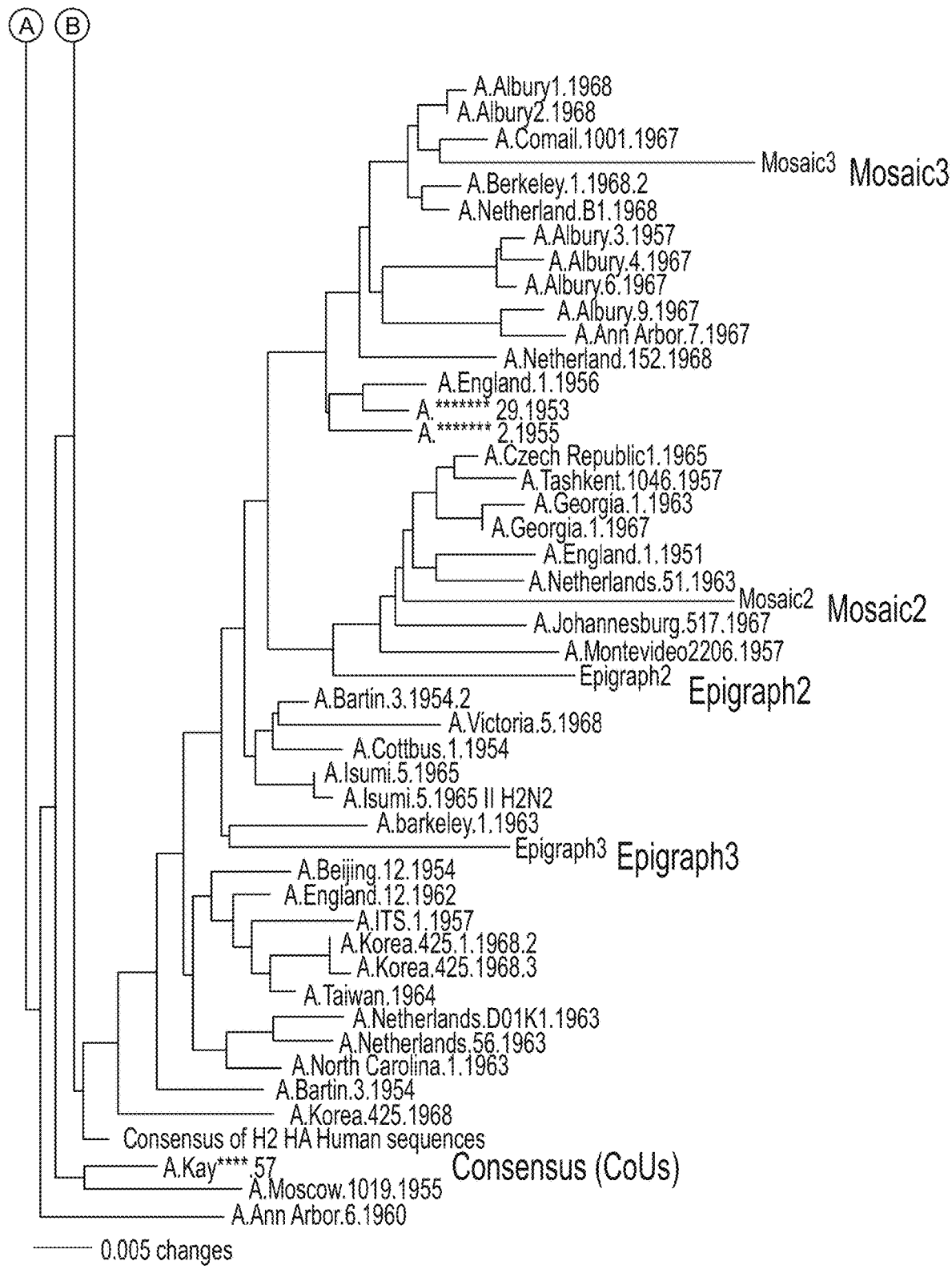
Figure 11:
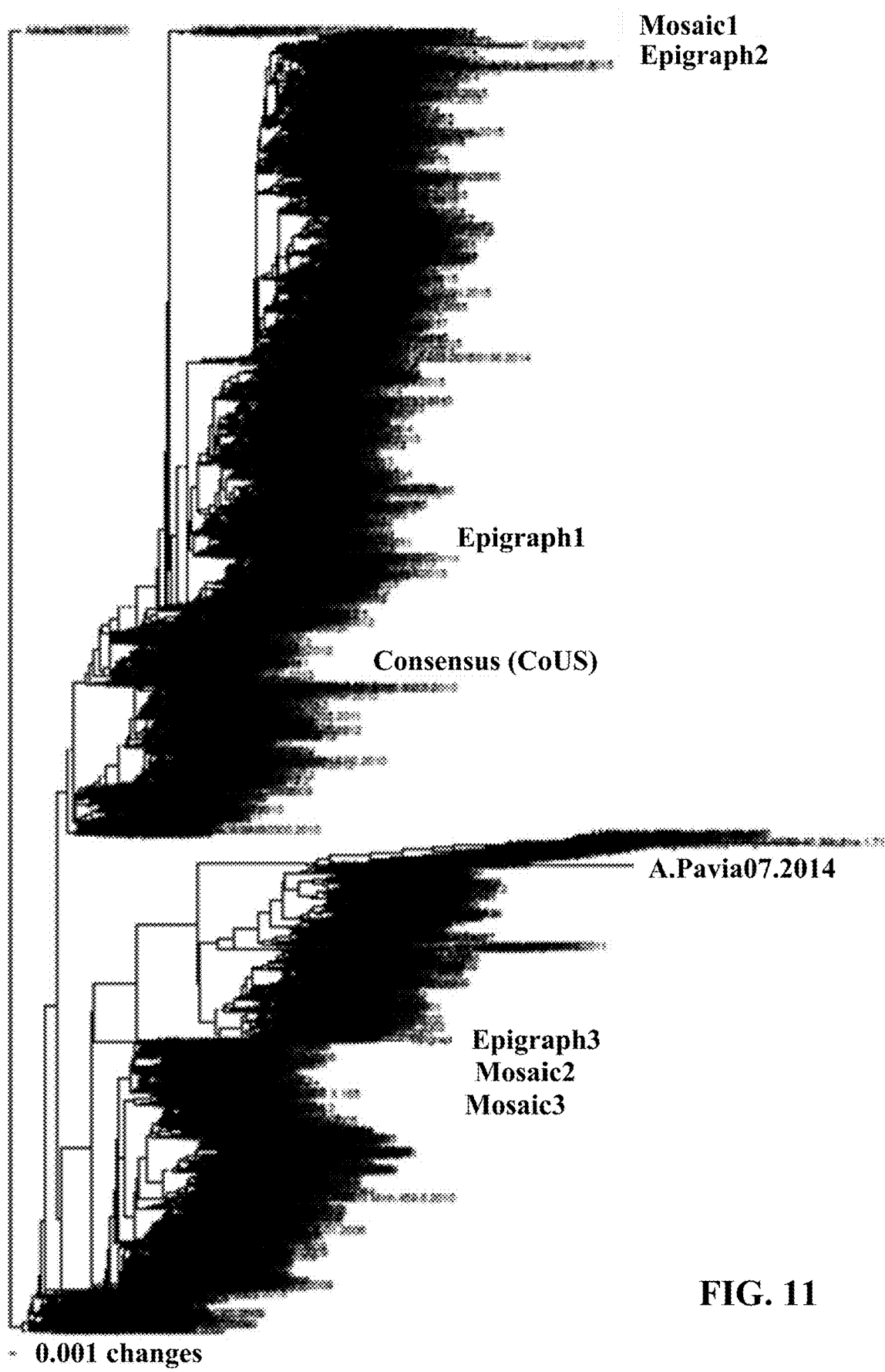
FIG. 11 shows the phylogenetic relationship between the vaccine genes described herein and various strains of human influenza A H3.
Figure 12:
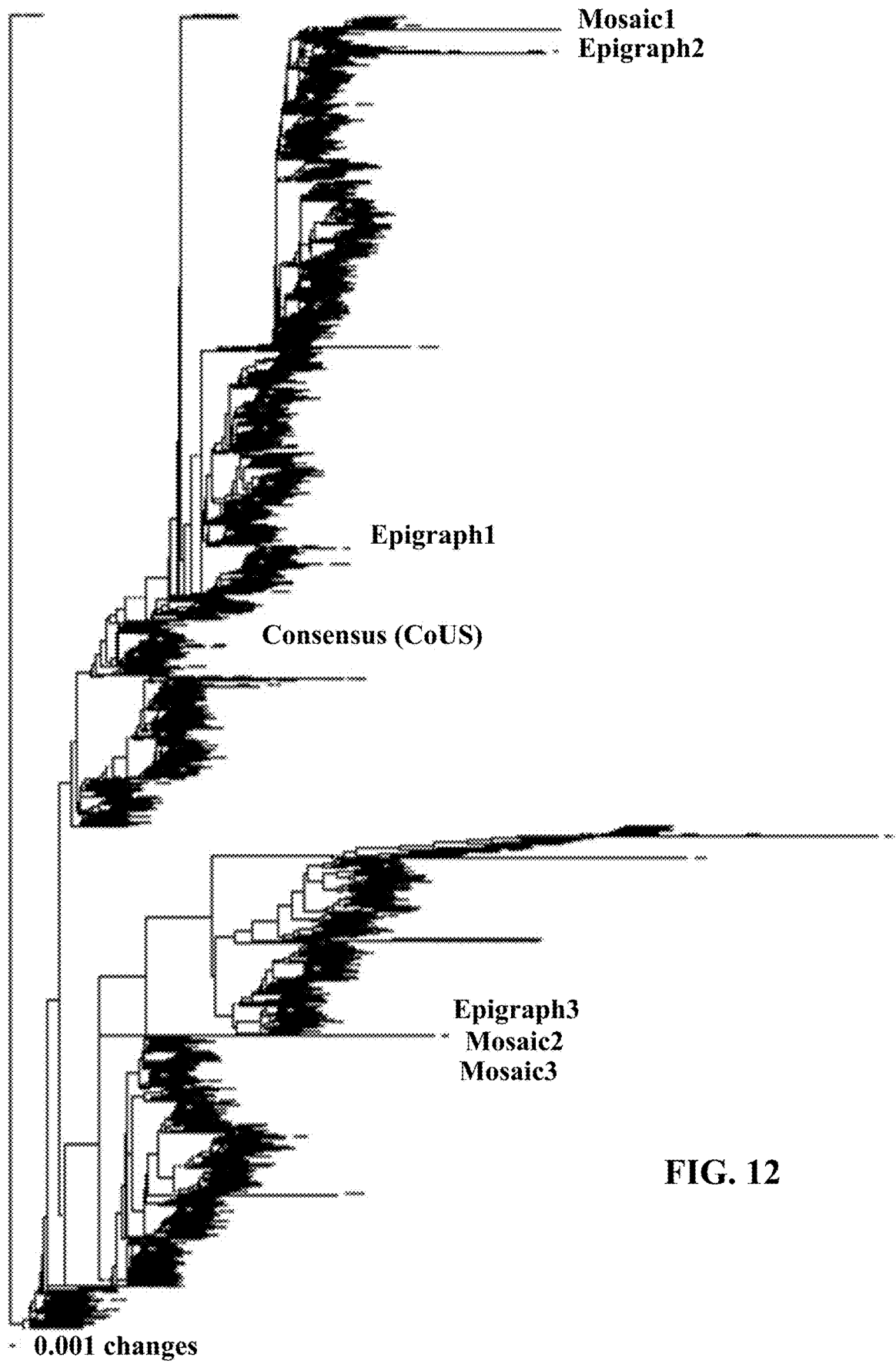
FIG. 12 shows the phylogenetic relationship between the vaccine genes described herein and various strains of human influenza A H3.
Figure 13:
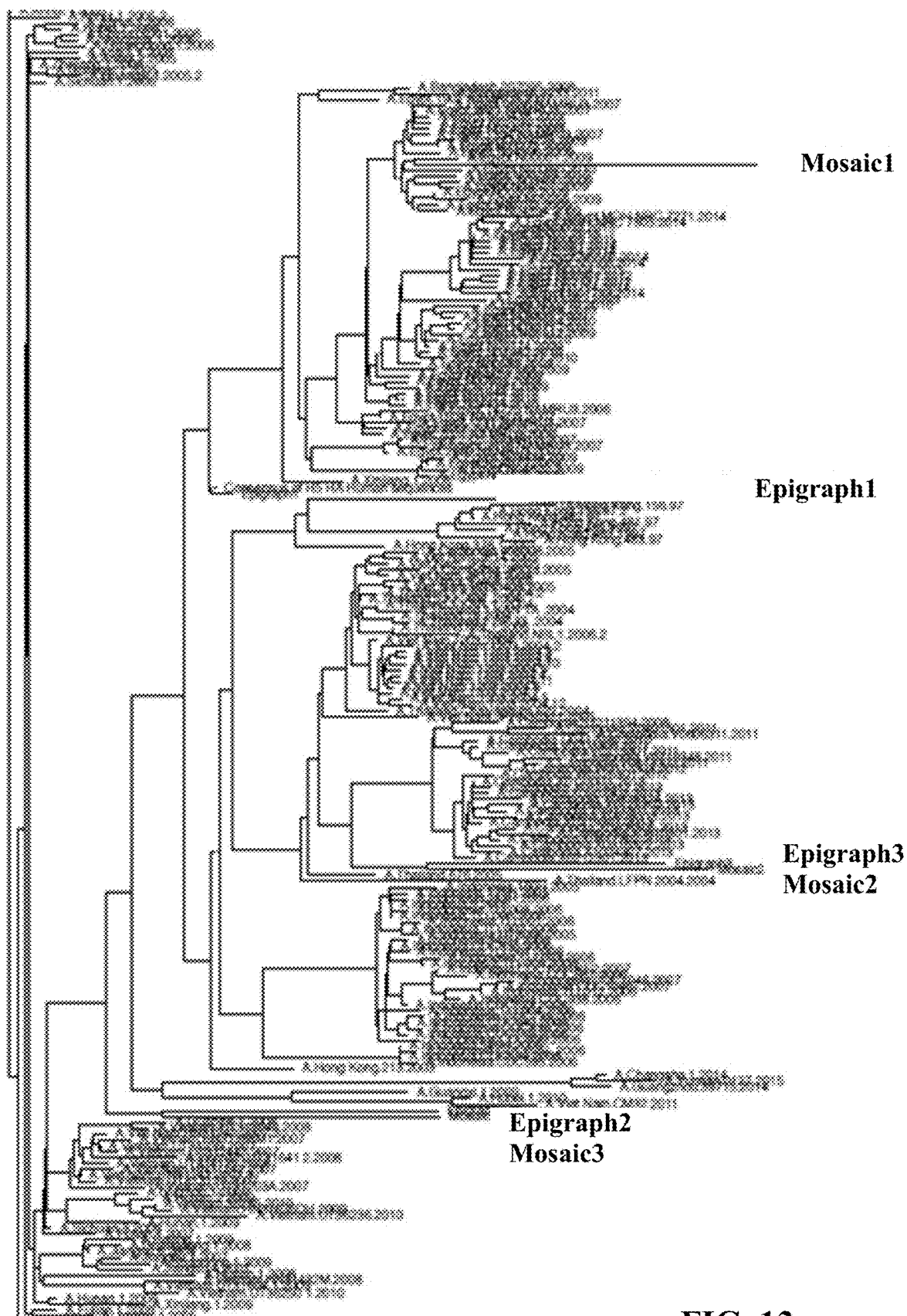
FIG. 13 shows the phylogenetic relationship between the vaccine genes described herein and various strains of human influenza A H5.
Figure 14:
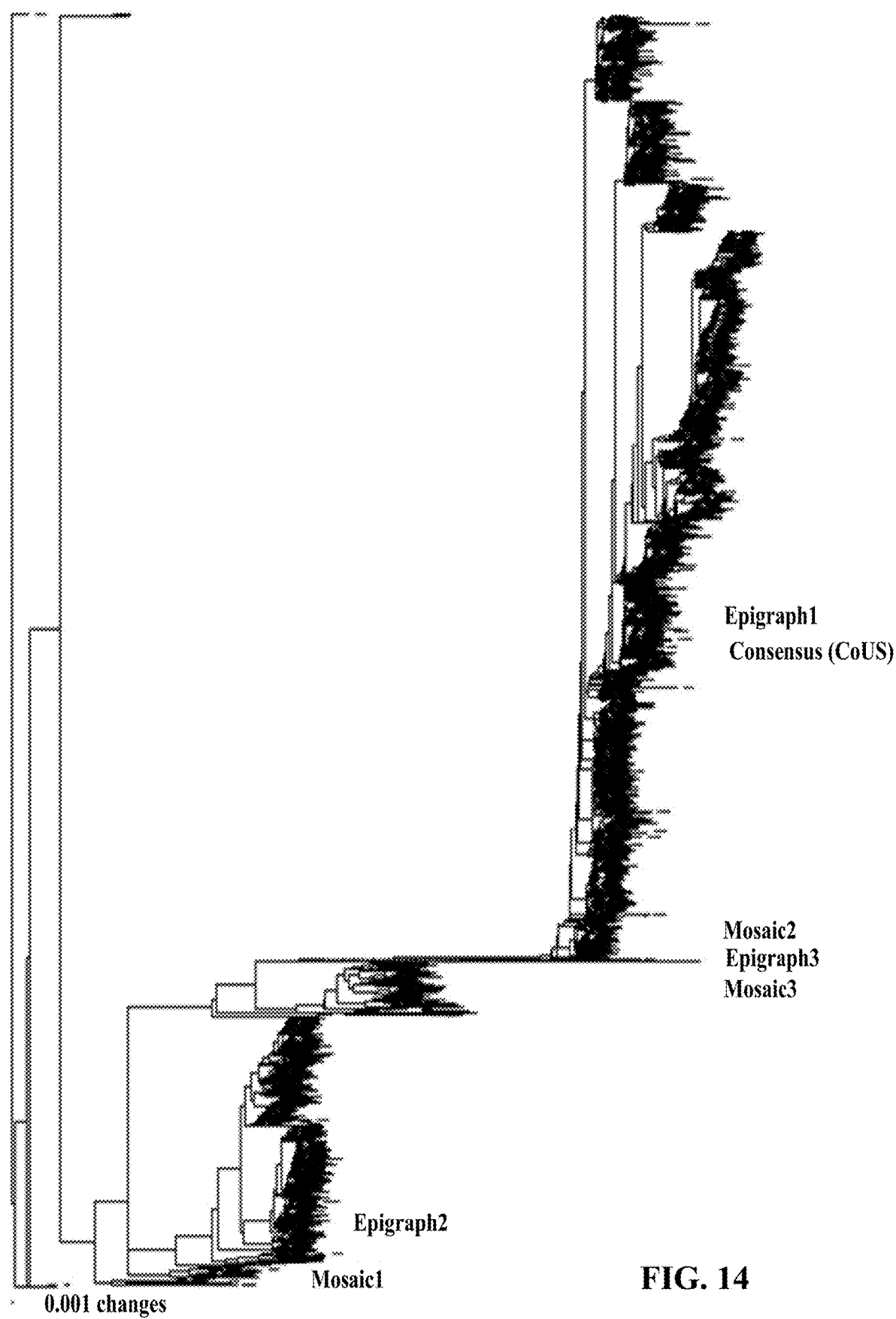
FIG. 14 shows the phylogenetic relationship between the vaccine genes described herein and various strains of human influenza A N1.
Figure 15:
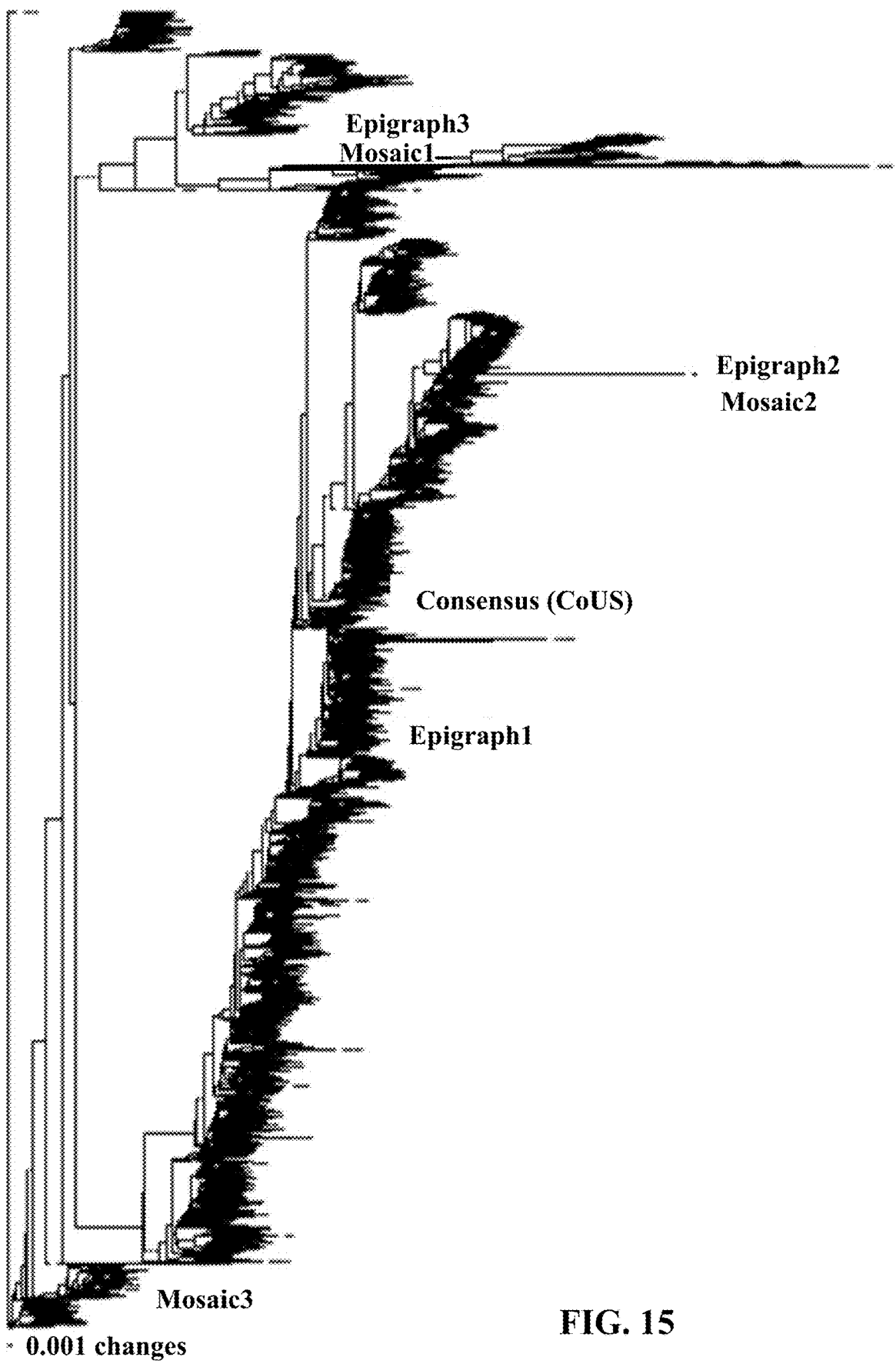
FIG. 15 shows the phylogenetic relationship between the vaccine genes described herein and various strains of human influenza A N2.
Figure 16:
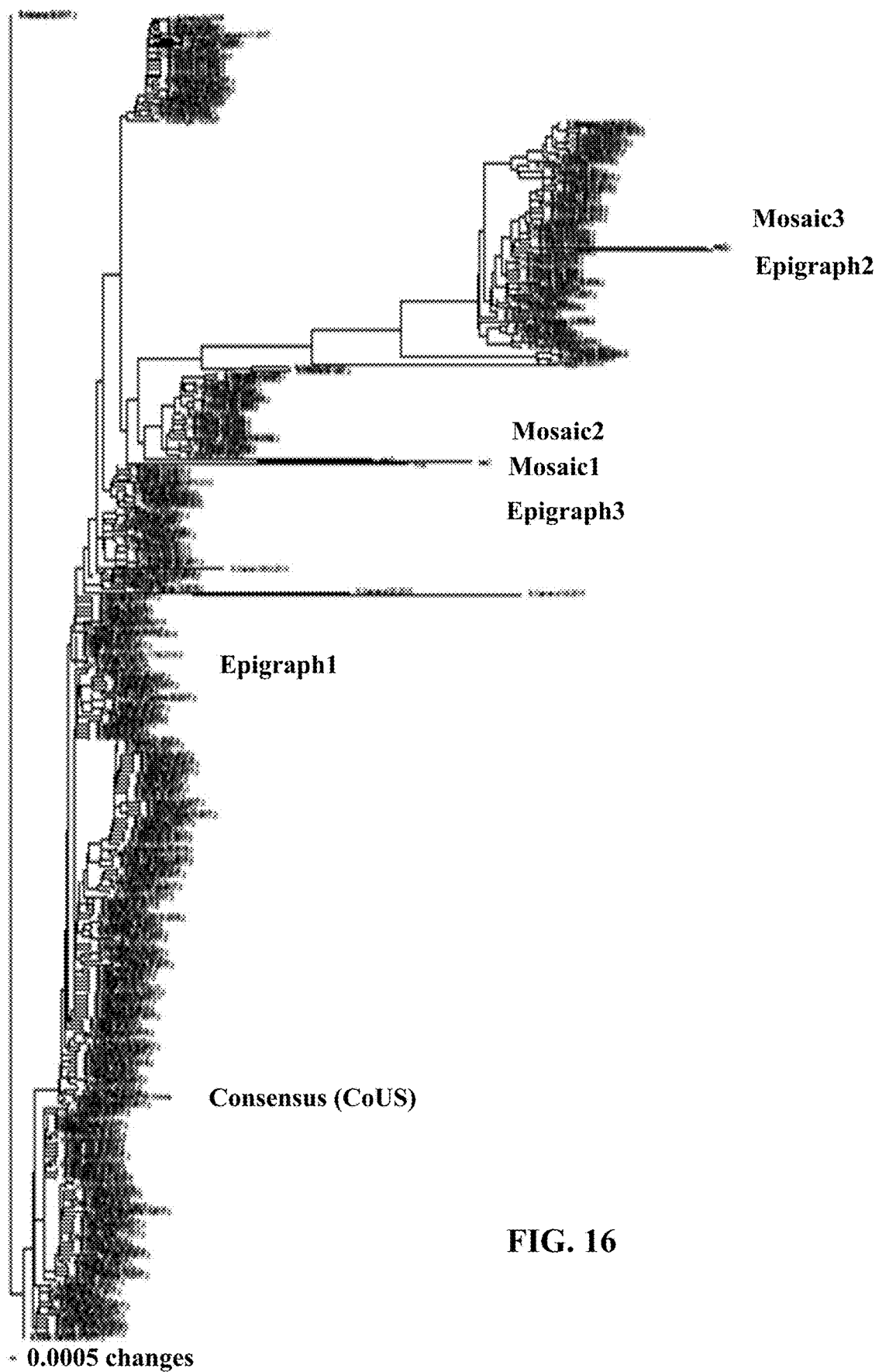
FIG. 16 shows the phylogenetic relationship between the vaccine genes described herein and various strains of human influenza B HA Victoria.
Figure 17:
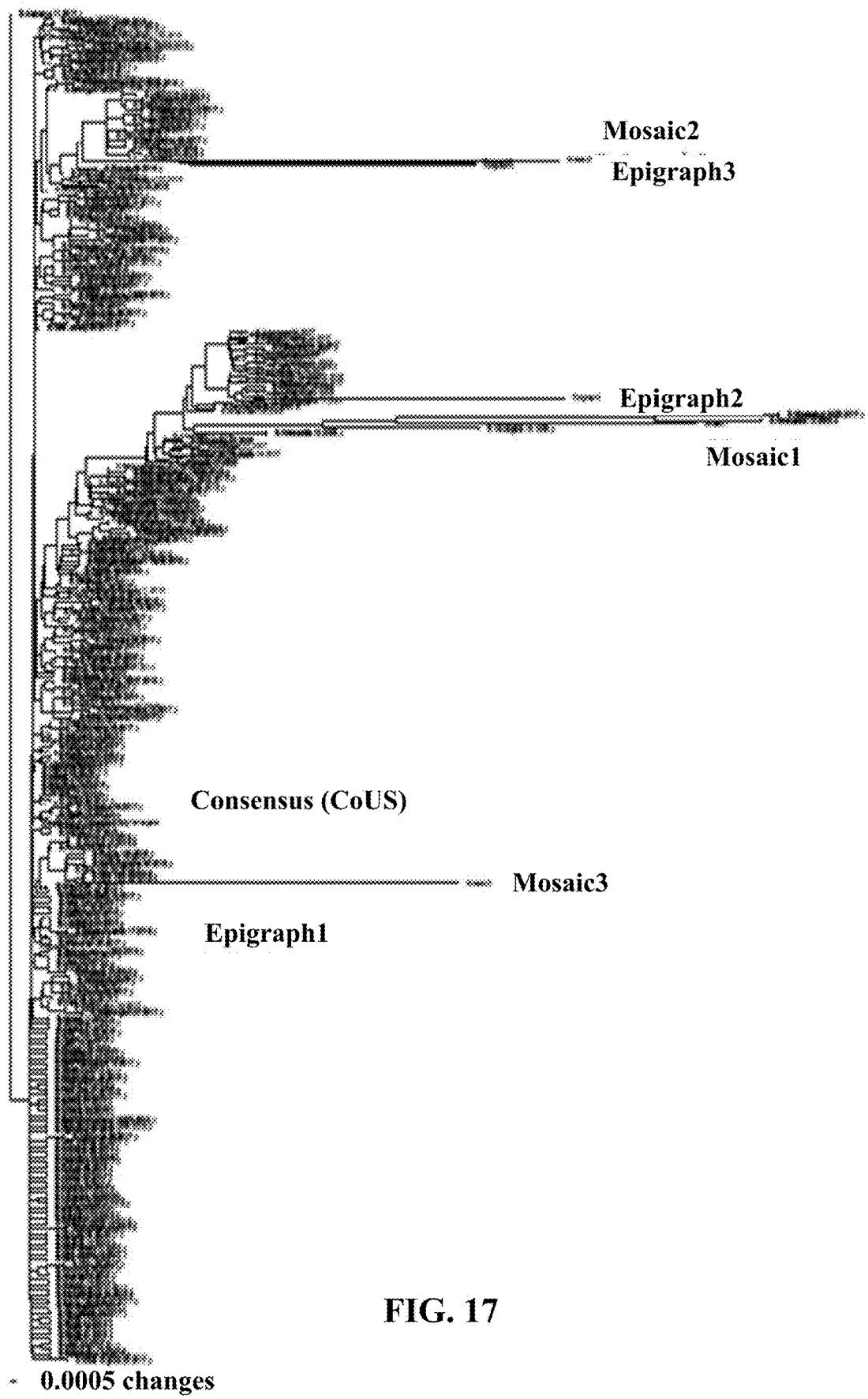
FIG. 17 shows the phylogenetic relationship between the vaccine genes described herein and various strains of human influenza B HA Yamagata.
Figure 18:
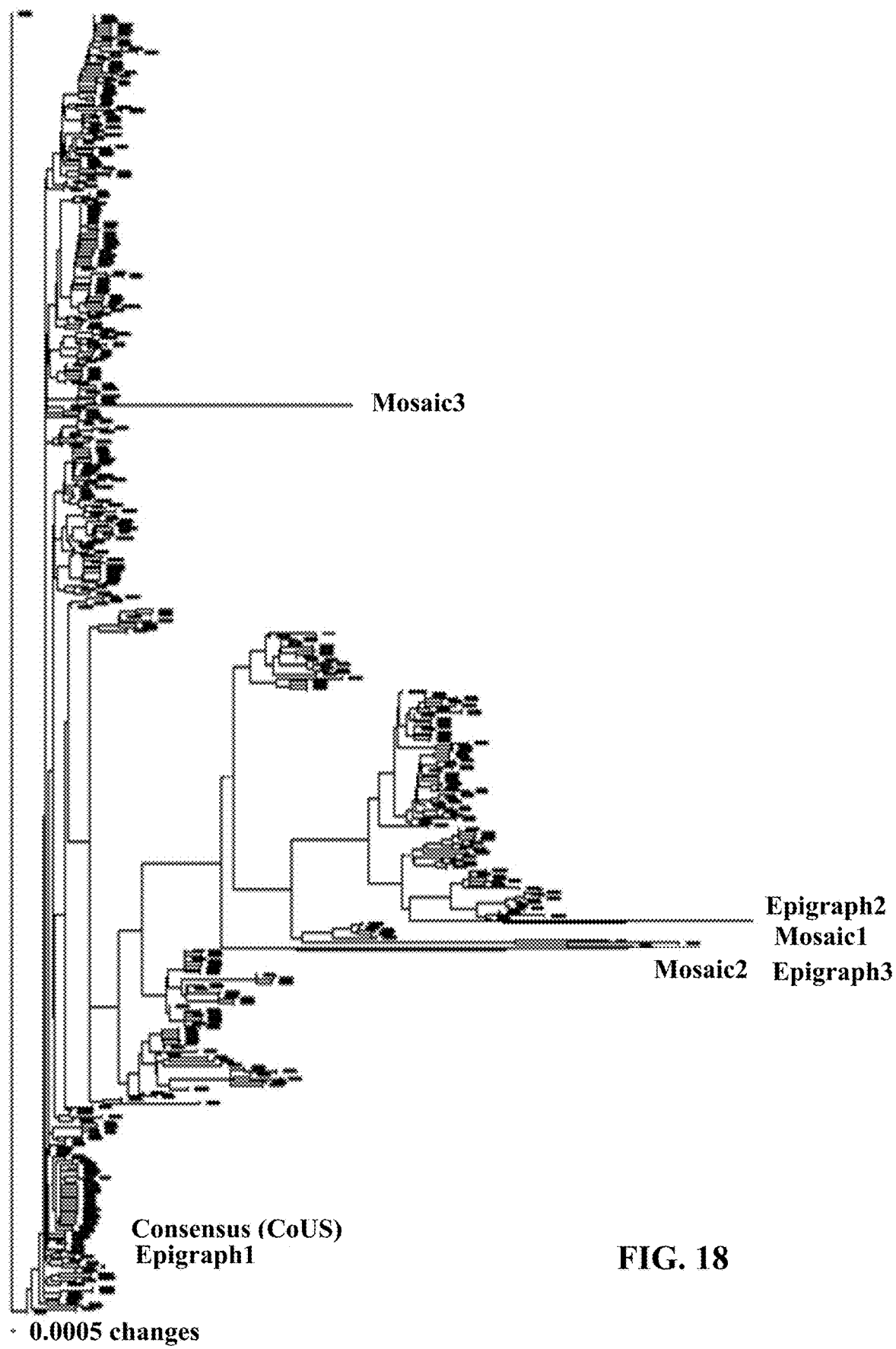
FIG. 18 shows the phylogenetic relationship between the vaccine genes described herein and various strains of human influenza B NA Victoria.
Figure 19:
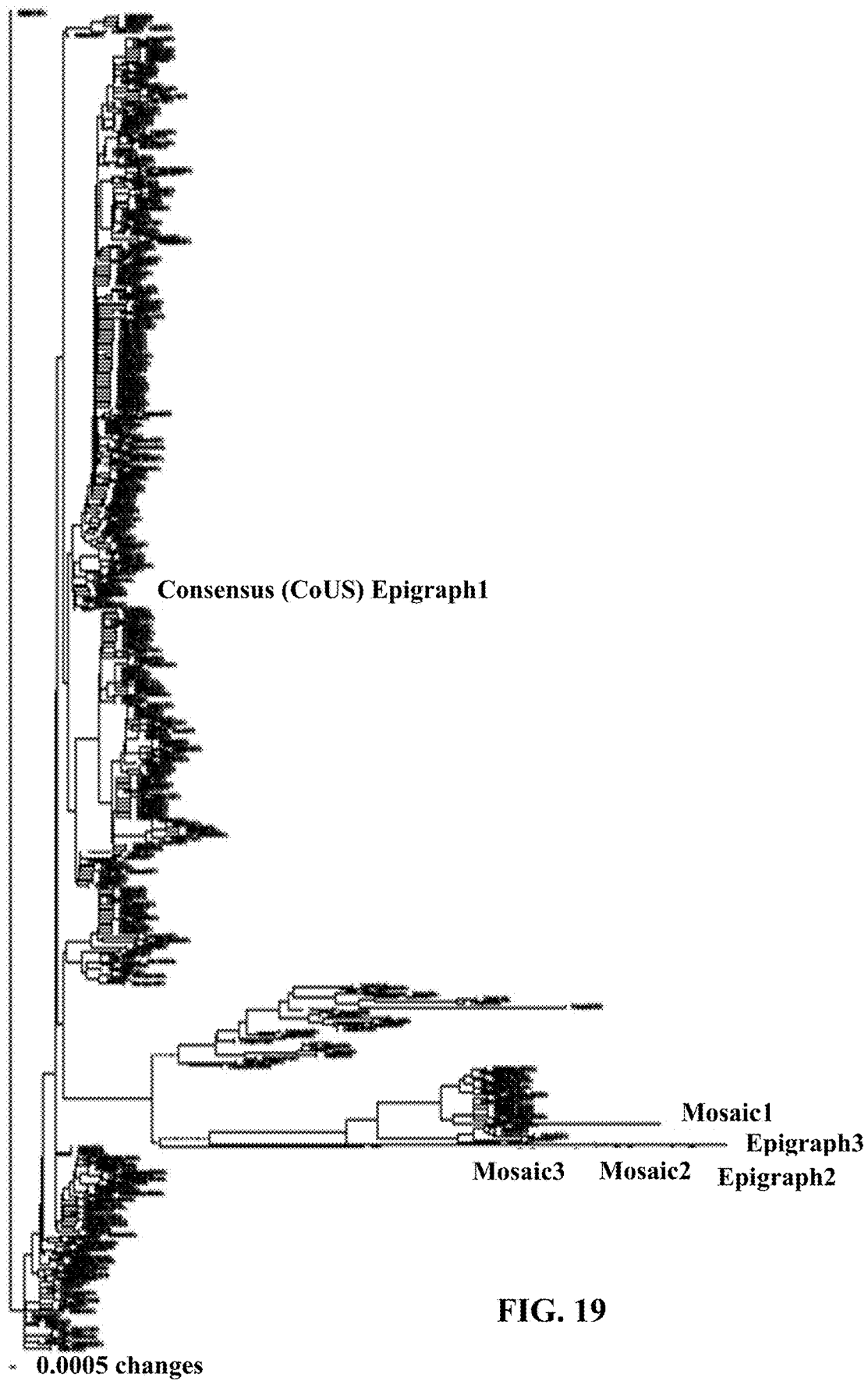
FIG. 19 shows the phylogenetic relationship between the vaccine genes described herein and various strains of human influenza B NA Yamagata.
Figure 20:
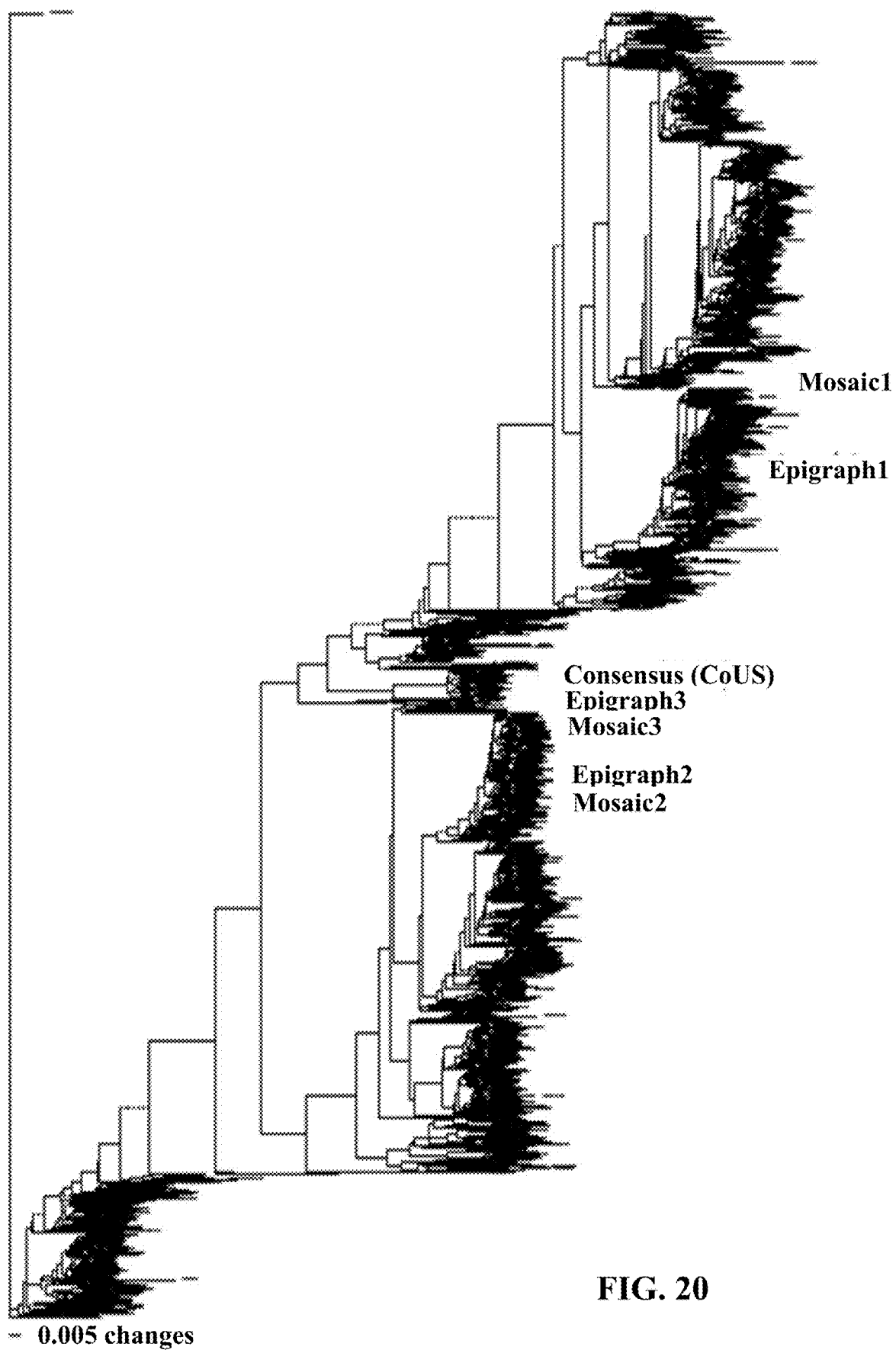
FIG. 20 shows the phylogenetic relationship between the vaccine genes described herein and various strains of swine influenza A H1.
Figure 21:
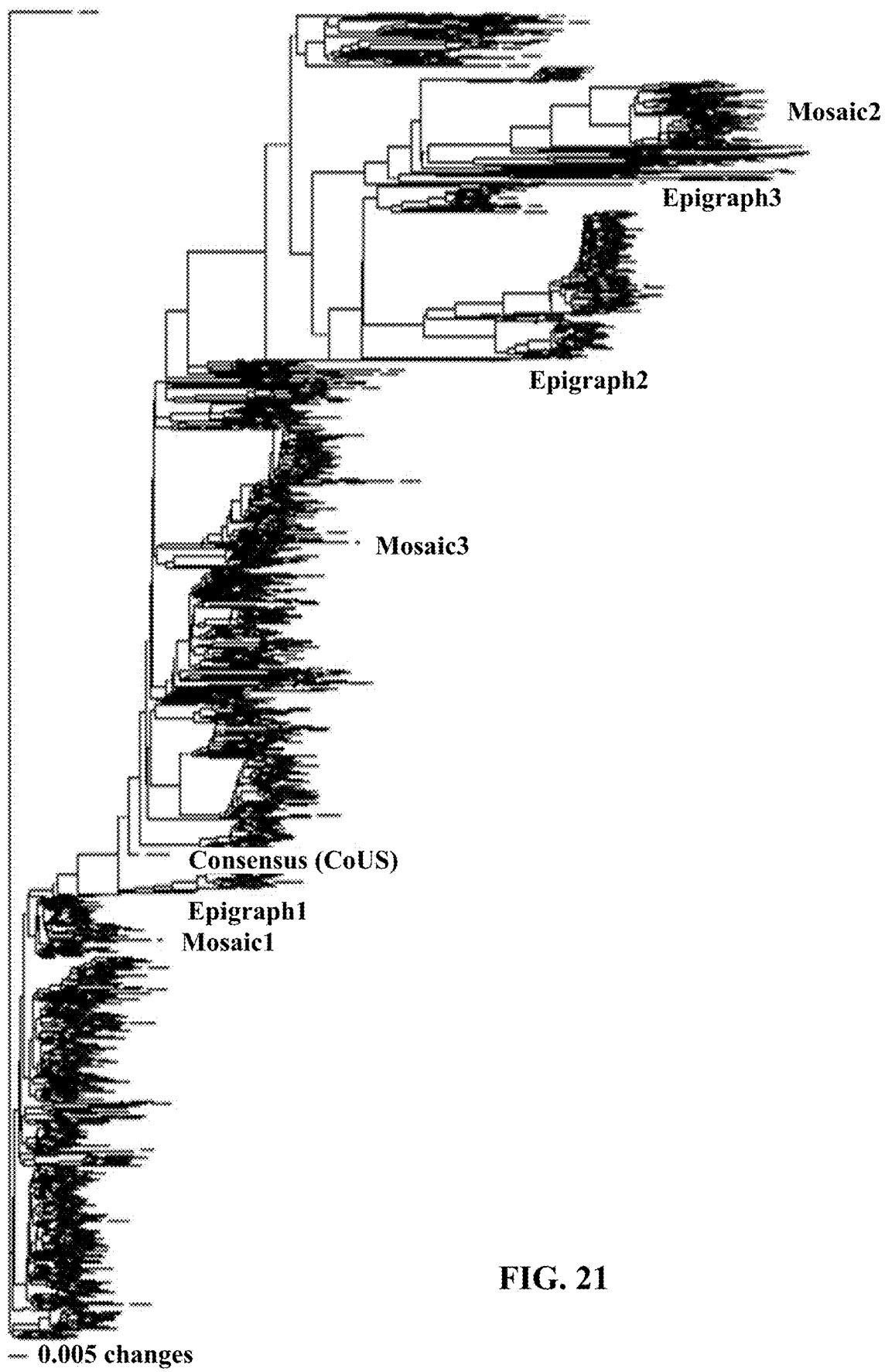
FIG. 21 shows the phylogenetic relationship between the vaccine genes described herein and various strains of swine influenza A H3.
Figure 22:
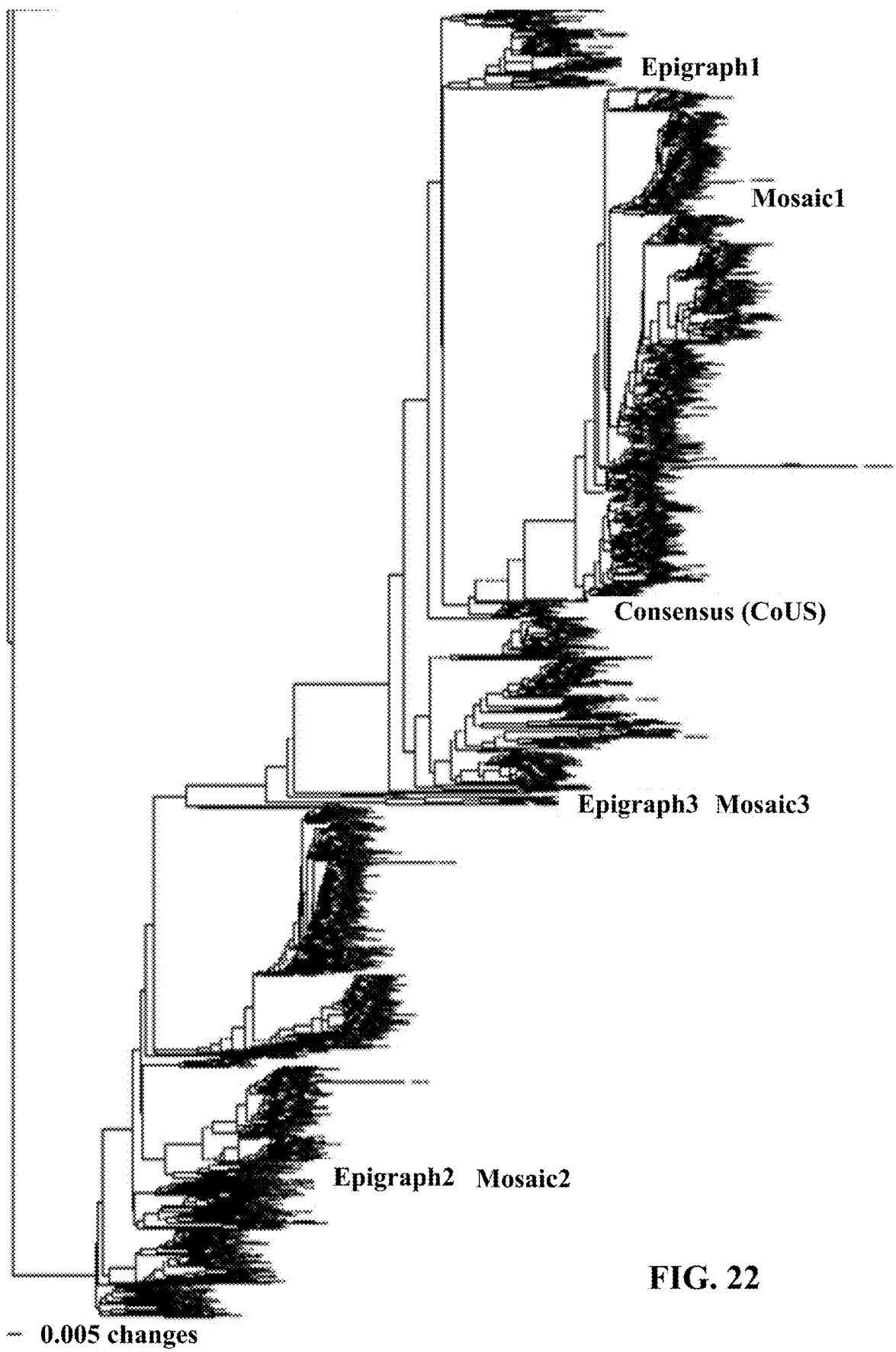
FIG. 22 shows the phylogenetic relationship between the vaccine genes described herein and various strains of swine influenza A N1.
Figure 23:
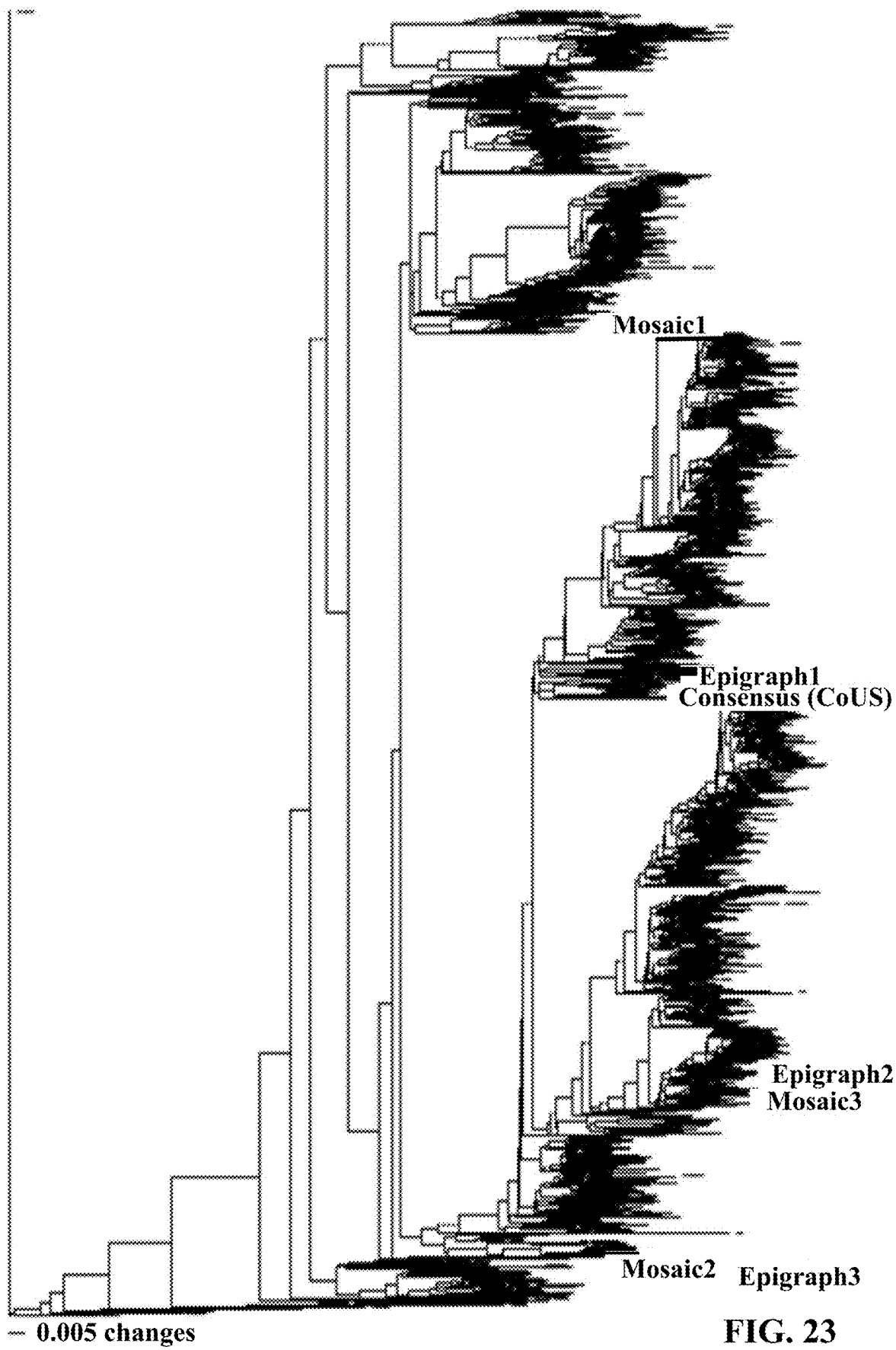
FIG. 23 shows the phylogenetic relationship between the vaccine genes described herein and various strains of swine influenza A N2.
Figure 24:
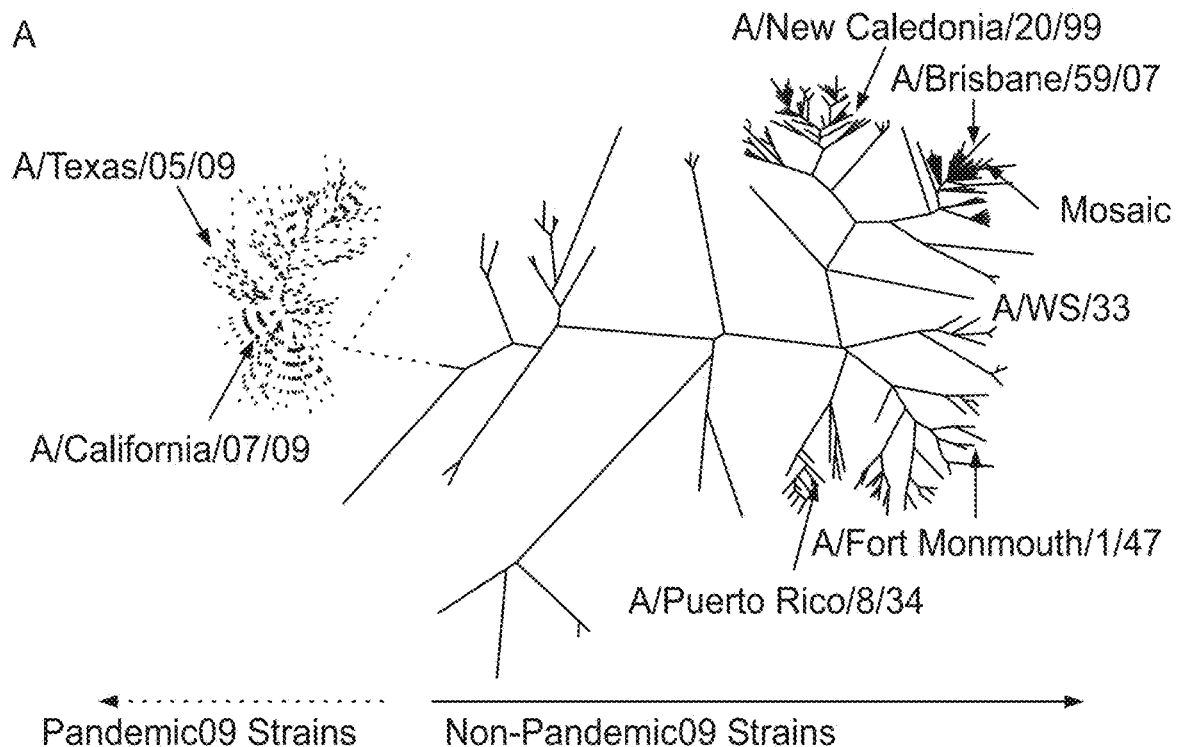
FIG. 24A shows a neighbor-joining phylogenetic tree of all unique H1 HA protein sequences with representative strains labelled. Pandemic 2009 (pdm09) strains are shown in dark blue.
FIG. 24B is a schematic of HA amino acid sequences submitted to SWISS-MODEL server and visualized with PyMOL software to predict the protein folding of each immunogen. The predicted structures of the mosaic (blue) and wild type comparator HA (grey and purple) for both the head (dark) and stalk (light) regions are shown along with a merged image superimposing all three HA structures.
FIG. 24C is a Western blot showing expression of the Mosaic and the two wild type comparator HA sequences (A/PR/8/34 and A/TX/05/09) in recombinant Adenovirus type 5.
Figure 24:
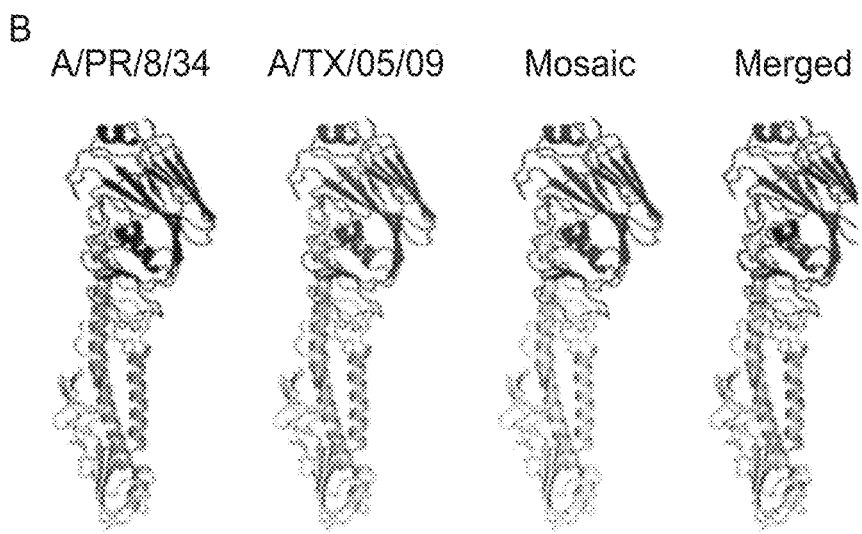
Figure 24:
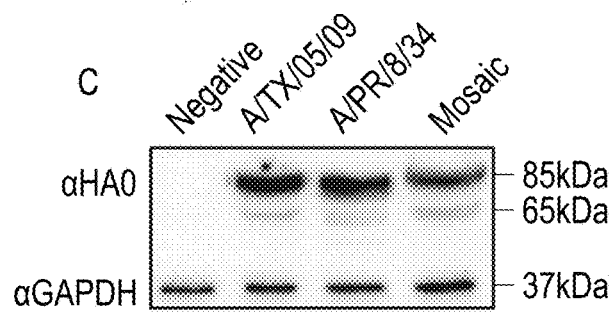
Figure 25:
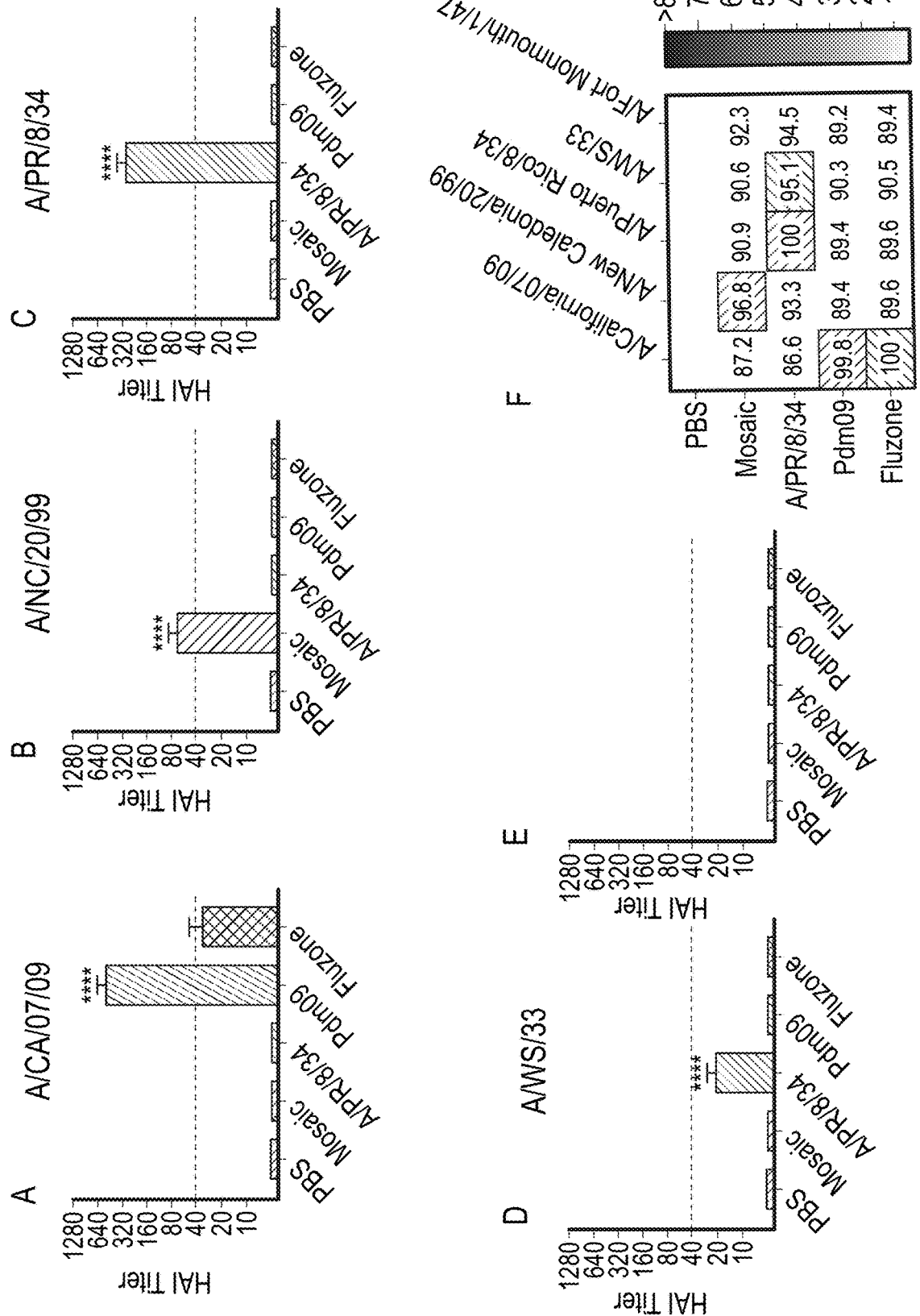
FIG. 25A-25E are graphs showing hemmaglutination inhibition (HI) titers after single shot vaccination of mice with Influenza strains A/CA/07/09 (25A), A/NC/20/99 (25B), A/PR/8/34 (25C), A/WS/33 (25D), and A/FM/1/47 (25E). Data is expressed as the mean with standard error (SEM).
FIG. 25F is a heat map of the HI titer responses, which reports the corresponding percent similarity between the vaccine group and virus (**$p<0.0001$, *$p<0.001$; one-way ANOVA with Bonferroni multiple comparisons).
Figure 26:
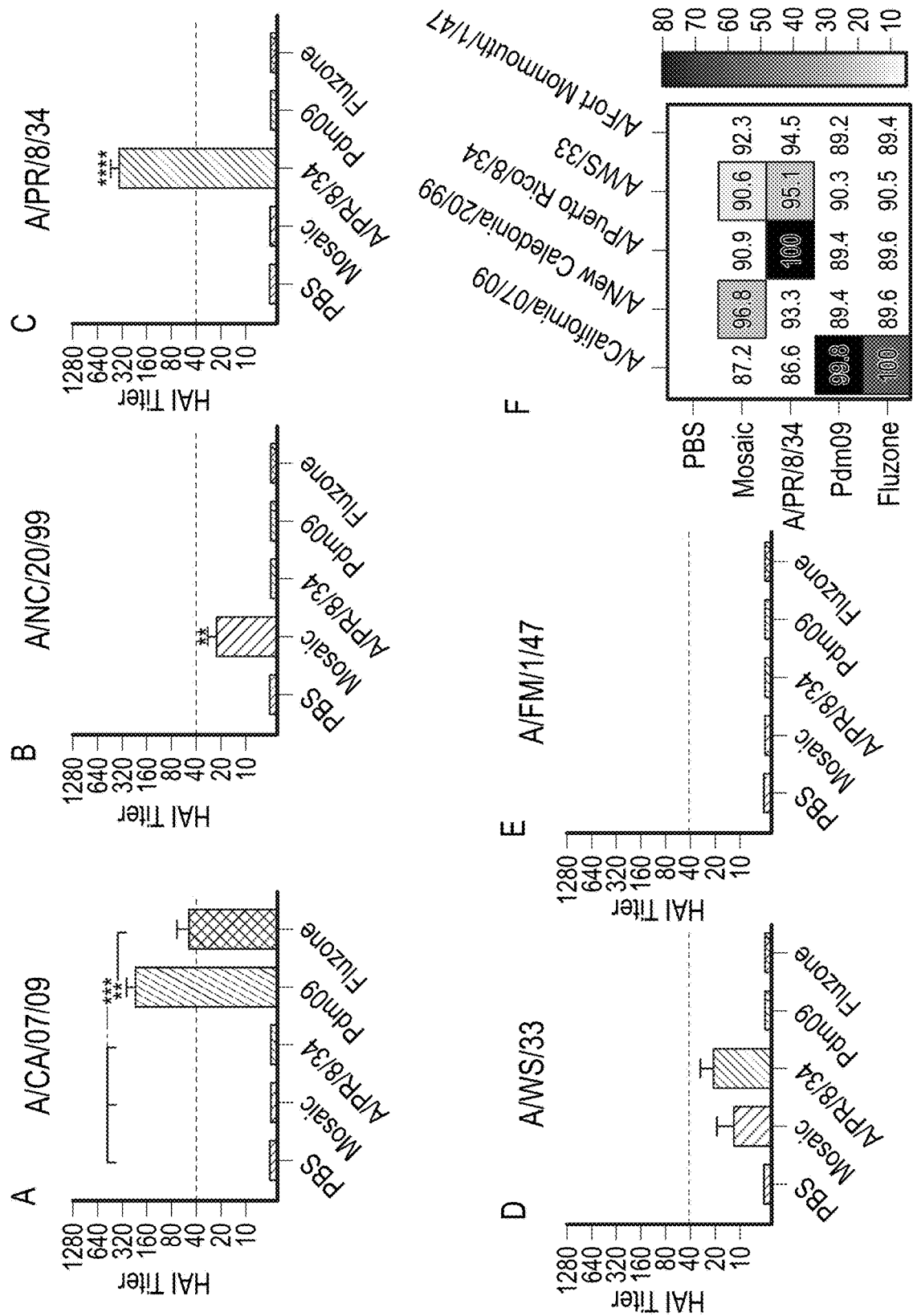
FIG. 26A-26E are graphs showing HI titers after vaccination of mice and boost with Influenza strains A/CA/07/09 (26A), A/NC/20/99 (26B), A/PR/8/34 (26C), A/WS/33 (26D), and A/FM/1/47 (26E).
FIG. 26F is a heat map of the HI titer responses reports the corresponding percent similarity between the vaccine group and virus. Data is expressed as the mean with standard error (SEM). (**$p<0.0001$, *$p<0.001$, **$p<0.01$; one-way ANOVA with Bonferroni multiple comparisons).
Figure 27:
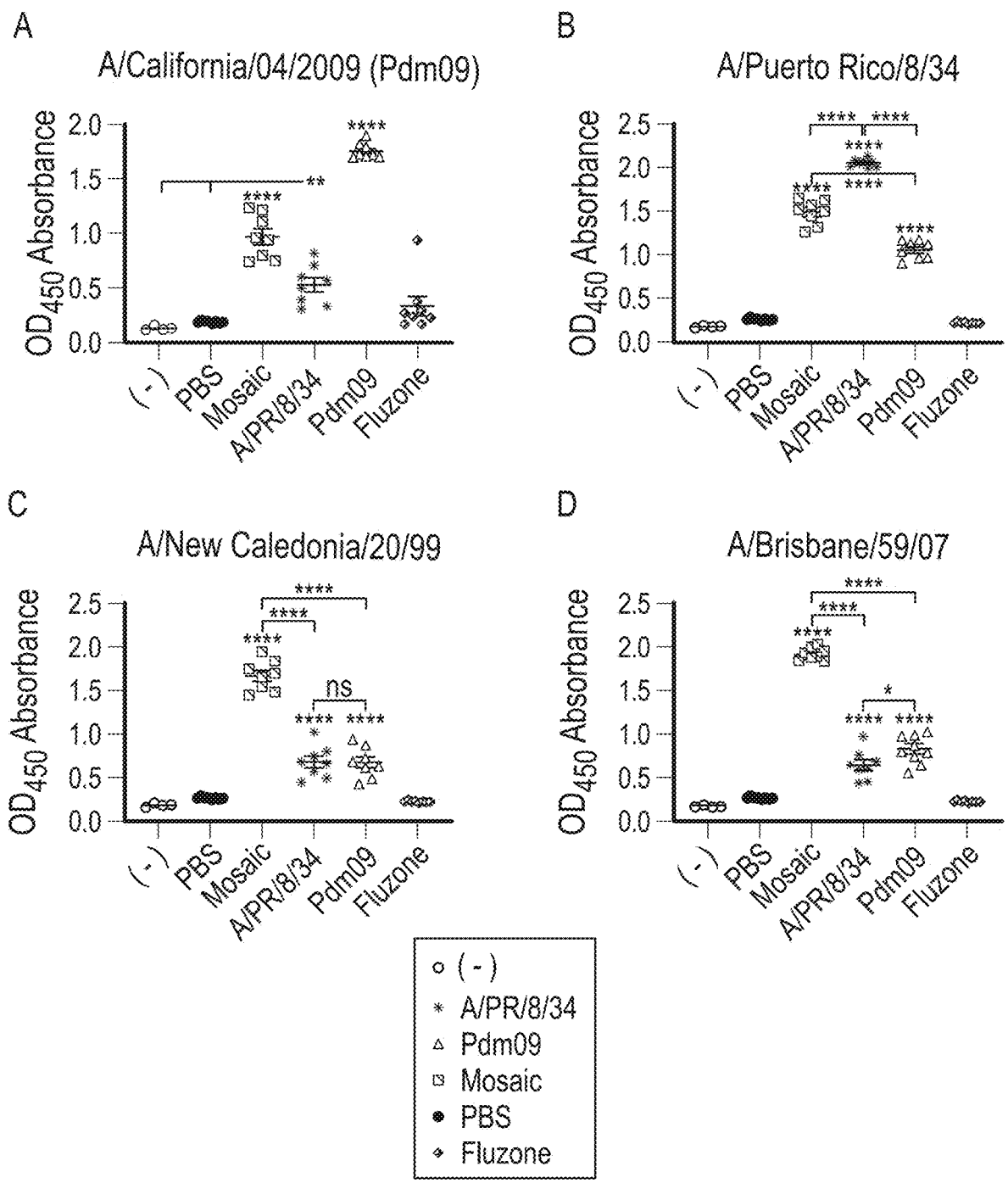
FIG. 27A-27D are graphs showing the antibody response after single shot vaccination with influenza strains A/CA/04/09 (27A), A/PR/8/34 (27B), A/NC/20/99 (27C), and A/Brisbane/59/07 (27D). The mean absorbance at OD450 is shown with standard error (SEM) (****$p<0.0001$.
Figure 28:
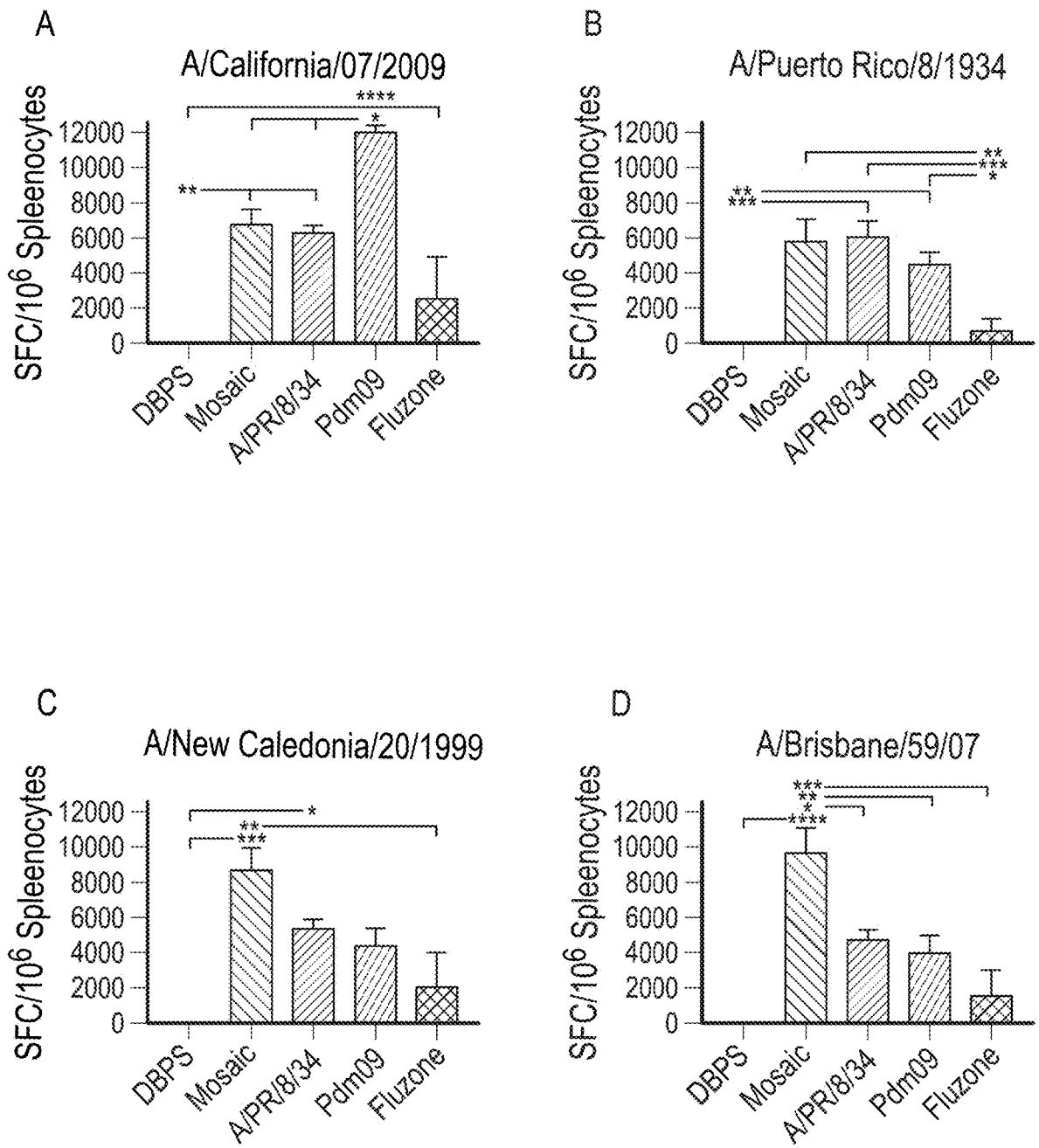

To determine if the unique immunogen design described herein would be better at inducing antibodies than wild type immunogens, cells were infected with equivalent infectious units of Ad-HA expressing viruses. The proteins were harvested and screened by Western blot. It was observed that all of the novel centralized and optimized vaccine immunogens were recognized more easily by serum from goats immunized with divergent A/swine/Indiana/0392/2011 virus as compared to the wild type TX98 HA protein. Since the novel vaccine immunogens were detected more readily as compared to the wild type TX/98 HA, this could indicate that these HA vaccines may be much better at presenting B cell epitopes and stimulating humoral immunity (FIG. 8).

Synthesis and cloning of wild type, COT, CoUS, Mosaic and Epigraph genes. The human HA Consensus COT, CoUS, Mosaic and Epigraph immunogens were computationally designed and analyzed. The genes were codon-optimized for humans since the target vaccines are human. The current 2018-19 Advisory Committee on Immunization Practices (ACIP) recommended wild type representative HA genes for both H1 and H3 be included. The wild type strain for use as the H1 comparator is A/Michigan/45/2015 (H1N1)pdm09-like. The wild type strain used as the H3 comparator was A/Singapore/INFIMH-16-0019/2016 (H3N2)-like virus. All of the codon-optimized HA genes were synthesized and cloned into pcDNA3.1 for T7 in vitro transcription (IVT). All of the vaccine genes are constructed synthetically by Genscript Corporation.

Production and quality control of mRNA and Lipid Nanoparticle (LNP) Vaccines. When comparing vaccine immunogens, it is essential that the quality of the vaccines are equivalent. Therefore, quality control of all mRNA-LNP vaccines were performed by analyzing the quality of mRNA by electrophoresis and densitometry analyses as well as quantitative protein expression by Western blot assays. All mRNA were produced using the HiScribe™ T7 ARCA mRNA Kit (with tailing).

Briefly, pcDNA3.1 plasmids containing the wild type and optimized vaccine immunogens were linearized using HindIII or XmaI, purified and used as template. RNA was transcribed from the template using the T7 RNA polymerase and incorporation of 5mCTP and pseudo-UTP for reduced innate immunity signaling. The RNA was capped using the ARCA capping enzyme and polyadenylated using the *E. coli* Poly(A) polymerase. The mRNA quality was confirmed by electrophoresis, quantitated by UV spectroscopy, aliquoted and stored at $-80°$ C. The lipids DSPC, cholesterol (Sigma-Aldrich), DMAP-BLP, PEG-DMG2K and PEG-DSG2K (NOF America Corporation) were dissolved at a molar ratio of 50:10:39.5:0.5 in ethanol using microfluidic mixing. The mRNA was mixed with the lipid:ethanol solution at a 3:1 ratio in 50 mM Citrate (pH-4.0). The mRNA-LNP was dialyzed using 100K MWCO dialysis cartridges against PBS (pH—7.4) overnight and concentrated using Amicon Ultra Centrifuge filters. The final mRNA-LNP products were stored at $4°$ C. The mRNA-LNPs size and quality were confirmed by electron microscopy.

Dose titration of representative vaccine candidate in order to determine vaccine doses. Previous studies have shown that as little as 2 µg of mRNA-LNP can protect against a lethal Zika virus challenge. However, since we are using highly lethal influenza challenge models, we may need to immunize with higher doses of mRNA-LNP vaccine doses or use a prime boost strategy in order to achieve protective levels. We confirmed this protection by immunizing groups of 5 mice with a range of doses vaccine doses (2, 10 and 20 µg/mouse) and challenging at 5 weeks post-vaccination with homologous A/PR/8/34 virus. If complete protection was not observed at the highest dose, then a third group was primed and boosted with 20 µg/mouse. The mice were challenged 3 weeks post-boost with a lethal influenza challenge. If the prime/boost immunization failed to provide complete protection, then a prime/boost/boost vaccine strategy was explored in order to determine the optimal vaccine dose capable of providing complete protection.

Animals were anesthetized using ketamine/xylazine for all vaccinations and viral challenges. Intramuscular immunizations consisted of a 50 µl vaccine diluted in PBS and injected using a 27 gauge needle into both quadriceps in two 25 µl injections. Initially, all immunizations were done by the intramuscular route. All initial studies were done as single dose vaccine agents. Mice were challenged with 10-100 MLD50 of mouse-adapted influenza virus, and disease and death were monitored.

Immune correlates such as HI titers and T cell ELISpot assays. Immune correlates were analyzed against at least 5-H1 and 5-H3 influenza strains. This data allowed us to extrapolate the true breadth and strength of the anti-influenza immunity induced by the various vaccines. Both cellular and humoral immunity were analyzed, as both play critical roles in protection and clearance. All candidate vaccine responses were compared to the commercial inactivated FluSure vaccine per manufacturer recommendations.

Hemagglutination Inhibition (HI) Assay. The primary determining factor for vaccine efficacy has always been the HI assay. Since all influenza viruses cannot be evaluated in mice, the HI assay allows the full evaluation of the cross-protective immune responses induced by the immunogens. Therefore, the HI assay was used to determine the induced cross-reactive antibodies.

Neutralization Assay. In order to determine the functional neutralization of the sera against homologous and heterologous sera, neutralization assays were performed.

Cellular Immunity (ELISpot). In order to determine the breadth and magnitude of the cellular immunity induced by the various vaccine immunogens, we epitope mapped and quantitated the absolute number of interferon secreting cells by IFN-γ ELISpot as previously described (REF 60) and shown in FIGS. 6 and 7.

Challenge study to determine most effective vaccine strategy. The most effective method of determining vaccine efficacy is the actual influenza challenge study. The H1 and H3 vaccines were tested separately in order to eliminate any potential interference between the vaccine immunogens. The vaccine groups consisted of single wild type, COT, CoUS or Mosaic HA immunogens. The epigraph immunogens were delivered as a cocktail. The HA-Epi vaccine consisted of the same final dose of mRNA-LNP as compared to the individual HA vaccines. Since the Epigraph vaccine was composed of a cocktail of 3 epigraph immunogens, each Epi mRNA was included in the vaccine at ⅓ of the final dose. For example, if the vaccine dose was 10 μg/mouse, the Epigraph vaccine consisted of 3.33 μg of each Epi mRNA-LNP vaccine. Groups of 5 control mice for each challenge virus were included. All of the vaccines were compared to a group that received the commercial quadrivalent FluZone at the mouse equivalent dose.

Determine if the vaccine candidates from the H1 and H3 vaccine challenge studies can be combined into one universal vaccine against both subtypes. An ideal vaccine requires as few immunizations as possible and protects against all viral variants. Therefore, we determined if a single immunization comprised of the most effective approach for vaccinating against each influenza subtype could be combined to make a universal vaccine that induces immunity against H1N1 and H3N2 influenza virus. This assumes that one vaccine immunogen approach is superior for both H1 and H3 influenza subtypes. However, it is very likely that one approach is more effective than the other, so multivalent vaccines that are comprised of two different vaccine immunogens can be tested. For example, the epigraph approach may be more effective against H1N1 influenza, whereas the Mosaic approach may be more effective against H3N2 influenza. Therefore, the Ad-H1-Epi+Ad-H3-Mos multivalent vaccine were tested for efficacy against all six influenza viruses. Groups of 5 control mice for each challenge virus were included.

Immunization in the presence of prior immunity due to previous vaccination. These experiments simulate an immune system that has been primed by a seasonal inactivated vaccine and not a natural infection. These conditions more accurately resemble the immune systems of vaccinated children. Groups of five mice were immunized with a seasonal inactivated FluZone vaccine. The mice were re-immunized six months later with either wild type or the universal multivalent optimized vaccine. The mice were challenged with a panel of influenza viruses to determine the degree of cross-protective immunity. All mice studies were repeated.

Immunization in the presence of prior immunity due to natural infection. In order to simulate immunity derived from a natural infection, mice were infected with a low dose of wild type influenza virus. These conditions more accurately resemble the immune systems of adults. The strain-specific wild type and universal vaccines were tested for their ability to induce cross-protective immunity in the context of this immune repertoire in the same manner as previously described for animals with prior immunity due to vaccination. All mice studies were repeated.

Influenza animal model. The ferret model closely mimics influenza infection in humans. Ferrets have similar clinical symptoms and are equally sensitive to influenza infection. The ferret model is considered the best animal model to evaluate influenza pathogenicity, virulence, infectivity, and vaccine efficacy (Herlocher et al., 2001, J. Infect. Dis., 184:542-6; Maassab et al., 1982, J. Infect. Dis., 146:780-90; Sweet & Smith, 1980, Microbiol. Rev., 44:303-30). Also, since the preliminary evaluation of cross-protective immune responses is done using BALB/c mice, it is important to determine the immune responses in an outbred genetic background. Therefore, the ferret model was used for a final evaluation of the most efficacious vaccines. All ferret studies were repeated.

Ferrets were used in the final analysis of the most promising broadly protective vaccines. Groups of five ferrets were immunized with the wild type, universal, and FluZone vaccines. Sera and nasal washes were obtained three weeks post-immunization. These samples were assayed against a large panel of influenza viruses using HI and micro-neutralization assays for a broader analysis of cross-protective immune responses. The immunized ferrets were challenged with at least four representative viruses from each subtype. The ferrets were monitored daily for temperature and dehydration. Fever in ferrets rarely approaches dangerous levels and there is some indication that reducing fever actually increases viremia. If the animals were dehydrated, they were treated daily by subcutaneous injection of 10 ml of sterile saline. Moribund animals were sacrificed. Disease as measured by weight loss, clinical score and nasal virus shedding was used to evaluate the protective responses of each vaccine.

Example 3—Representative Sequence Comparisons

The sequences of select vaccine polypeptides described herein were compared to one another as shown in Table 1.

TABLE 1

| Comparison of Select Influenza H1 HA Protein Sequences | | | | | | | | | |
|---|---|---|---|---|---|---|---|---|---|
| Strain Names | A/Brisbane/ 59/07 | A/NC/ 20/99 | A/PR/ 8/34 | A/FM/ 1/47 | A/WS/33 | A/CA/ 07/09 | A/TX/ 05/09 | A/Nanachang/ 1/99 | HuH1 Mosaic |
| | Identity Scores (%) | | | | | | | | |
| A/Brisbane/ 59/07 | 100.0 | 97.5 | 86.5 | 89.6 | 86.0 | 79.7 | 79.3 | | 97.2 |
| A/NC/20/99 | 98.4 | 100.0 | 88.1 | 91.3 | 87.8 | 80.0 | 79.7 | | 95.1 |
| A/PR/8/34 | 92.0 | 93.3 | 100.0 | 90.8 | 92.2 | 81.6 | 81.3 | | 84.8 |
| A/FM/1/47 | 93.8 | 95.2 | 94.5 | 100.0 | 90.8 | 81.1 | 80.7 | | 87.2 |
| A/WS/33 | 91.7 | 93.1 | 95.1 | 94.7 | 100.0 | 82.2 | 81.8 | | 84.3 |
| A/CA/07/09 | 88.7 | 89.6 | 89.6 | 89.4 | 90.5 | 100.0 | 99.6 | | 77.3 |
| A/TX/05/09 | 88.5 | 89.4 | 89.4 | 89.2 | 90.3 | 99.8 | 100.0 | | 76.9 |
| A/Nanachang/ 1/99 | | | | | | | | 100 | |
| HuH1 Mosaic | 98.4 | 96.8 | 90.9 | 92.3 | 90.6 | 87.2 | 87.1 | | 100 |
| | Similarity Scores (%) | | | | | | | | |

Example 4—Western Blot for the Detection of Vaccine Immunogens 293 cells were infected with 500 virus particles per cell and harvested 48 hours later. The Western blot was probed with anti-HA0 antibody (NR-3148) from the A/PR/8/34 strain and anti-HA1 antibody as the primary antibodies. Both the HA0 (85 kDa) and HA1 (65 kDa) bands were observed for all three recombinant adenoviruses and were expressed at similar levels (FIG. 24C).

Female Balb/c mice were immunized with 10e10 virus particles of recombinant Ad5-H1-Mosaic-HA, Ad5-A/PR/8/34-HA, Ad5-A/TX/05/09-HA (pdm09), 150 ng of Fluzone HA, or PBS and sera was harvested 3 weeks later (n=8). Sera was treated with RDE and measured for antibodies using HI titers starting at a 1:10 dilution. Influenza strains A/CA/07/09 (FIG. 25A), A/NC/20/99 (FIG. 25B), A/PR/8/34 (FIG. 25C), A/WS/33 (FIG. 25D), and A/FM/1/47 (FIG. 25E) were measured for antibodies by hemagglutination inhibition assay. Results are shown as the reciprocal of the highest dilution that prevented agglutination, and negative results are shown as half the limit of detection.

Female Balb/c mice were immunized with 10e10 virus particles, 150 ng of Fluzone HA, or PBS and boosted with the same dose 3 weeks later (n=5). Sera was harvested 10 days post-boost and treated with RDE to be measured for antibodies using HI titers starting at a 1:10 dilution. Influenza strains A/CA/07/09 (FIG. 26A), A/NC/20/99 (FIG. 26B), A/PR/8/34 (FIG. 26C), A/WS/33 (FIG. 26D), and A/FM/1/47 (FIG. 26E) were measured for antibodies by hemagglutination inhibition assay. Results are shown as the reciprocal of the highest dilution that prevented agglutination, and negative results are shown as half the limit of detection.

Female Balb/c mice were immunized with 10e10 virus particles of recombinant Ad5-H1-Mosaic-HA, Ad5-A/PR/8/34-HA, Ad5-A/TX/05/09-HA (pdm09), 150 ng of Fluzone HA, or PBS, and sera was harvested 3 weeks later (n=8). Sera was diluted 1:100 and measured for antibodies using ELISA assays. Plates were coated with 200 ng per well of recombinant HA protein from influenza strains A/CA/04/09 (FIG. 27A), A/PR/8/34 (FIG. 27B), A/NC/20/99 (FIG. 27C), and A/Brisbane/59/07 (FIG. 27D) and the absorbance at OD450 measured.

Female Balb/c mice were immunized with 10e10 virus particles of recombinant Ad5-H1-Mosaic-HA, Ad5-A/PR/8/34-HA, Ad5-A/TX/05/09-HA (pdm09), 150 ng of Fluzone HA, or PBS, and splenocytes were harvested 3 weeks later (n=8). Total T cell responses were measured by IFNgamma ELISpot assay using peptide arrays spanning the entire HA gene of A/California/07/09 (FIG. 28A), A/Puerto Rico/8/34 (FIG. 28B), A/New Caledonia/20/99 (FIG. 28C), or A/Brisbane/59/07 (FIG. 28D) strains and expressed as the mean number of spot forming cells (SFC) per million splenocytes.

Female Balb/c mice were immunized with 10e10 virus particles of recombinant Ad5-H1-Mosaic-HA, Ad5-A/PR/8/34-HA, Ad5-A/TX/05/09-HA (pdm09), 150 ng of Fluzone HA, or PBS and splenocytes were harvested 3 weeks later (n=8). T cell epitopes were mapped using overlapping peptide libraries spanning the entire HA gene. Responses greater than 50 spot forming cells (SFC) per million splenocytes were considered positive and are shown in relation to the HA gene location (FIG. 29A). Positive peptides for A/Brisbane/59/07 (FIG. 29B), A/New Caledonia/20/99 (FIG. 29C), and A/California/07/09 (FIG. 29D) are quantified. An alignment of the peptide strain (grey), mosaic (green), A/PR/8/34 (dark blue), and A/TX/05/09 pdm09 (light blue) HA sequences are shown directly under the positive peptide indicating the possible epitope locations.

Female Balb/c mice were immunized with either 10e8 or 10e10 virus particles of recombinant Ad5-H1-Mosaic-HA, Ad5-A/PR/8/34-HA, Ad5-A/TX/05/09-HA (pdm09), 150 ng of Fluzone HA, or PBS and challenged with 100MLD50 3 weeks later (n=5). Mice were monitored 14 days post challenge and humanely euthanized if 25% weight loss was recorded. Individual mice were monitored for weight loss (FIG. 30A, 30B), average weight loss (FIG. 30C, 30D), and percent survival (FIG. 30E, 30F).

Female Balb/c mice were immunized with either 10e8 or 10e10 virus particles of recombinant Ad5-H1-Mosaic-HA, Ad5-A/PR/8/34-HA, Ad5-A/TX/05/09-HA (pdm09), 150 ng of Fluzone HA, or PBS and challenged with 100 mouse lethal dose $(MLD)_{50}$ 3 weeks later (n=5). Mice were monitored 14 days post challenge and humanely euthanized if 25% weight loss was recorded. Weight loss for individual mice (FIG. 31A, 31B), average weight loss (FIG. 31C, 31D), and percent survival (FIG. 31E, 31F) were determined.

Female Balb/c mice were immunized with either 10e8 or 10e10 virus particles of recombinant Ad5-H1-Mosaic-HA, Ad5-A/PR/8/34-HA, Ad5-A/TX/05/09-HA (pdm09), 150 ng of Fluzone HA, or PBS and challenged with 100MLD50 3 weeks later (n=5). Mice were monitored 14 days post challenge and humanely euthanized if 25% weight loss was recorded. Weight loss for individual mice (FIG. 32A, 32B), average weight loss (FIG. 32C, 32D), and percent survival (FIG. 32E, 32F) were determined.

Female Balb/c mice were immunized with either 10e8 or 10e10 virus particles of recombinant Ad5-H1-Mosaic-HA, Ad5-A/PR/8/34-HA, Ad5-A/TX/05/09-HA (pdm09), 150 ng of Fluzone HA, or PBS and challenged with 100MLD50 3 weeks later (n=5). Mice were monitored 14 days post-challenge and humanely euthanized if 25% weight loss was recorded. Weight loss for individual mice (FIG. 33A, 33B), average weight loss (FIG. 33C, 33D), and percent survival (FIG. 33E, 33F) were determined.

Example 5—Phylogenetic Tree of Swine Influenza and Universal Vaccine Hemagglutinins All 1,561 unique swine H3 Influenza virus HA proteins (excluding laboratory strains and duplicate strains) were downloaded from the Influenza Research Database. The Mosaic Vaccine Design and Epigraph programs available through the HIV database tools suite were used to create the Mosaic and Epigraph candidate vaccine proteins, respectively. The Mosaic and three Epigraph immunogens were then aligned with the original sequence population using ClustalW and a Jukes-Cantor neighbor joining tree was constructed (FIG. 34A). These universal immunogens were synthesized and cloned into a replication-defective Adenovirus 5 vector. 293 cells were infected with equivalent infectious units, using a wild type comparator HA gene (A/swine/Texas/4199-2/1998 [TX98]) as a control, and Hemagglutinin protein expression was detected by probing the Western blots with polyclonal Goat anti A/swine/Indiana/0392/2011 serum (FIG. 34B).

Groups of 5 to 10 mice were immunized with $10^{10}$ viral particles (vp) of Ad5-vectored vaccines expressing the Mosaic, Epigraph, or wild type TX98 HA immunogens (FIG. 35A). Additionally, mice were immunized with commercial FluSure at a dose equivalent to a 10× dose as compared to a 3 week old piglet. A submandibular bleed was performed at week 3 for evaluation of antibodies after a single immunization. Mice were then boosted and sera was harvested 14 days post-boost (FIG. 35A).

Representative divergent H3 swine influenza viruses were chosen for analysis of antibody development (FIG. 35B), and hemmaglutination inhibition (HI) were performed as described by the World Health Organization standard protocols (FIG. 35C). The dotted line represents the standard titer or 40 considered to confer protection against challenge.

Balb/c mice (n=5) were vaccinated with Ad vectored vaccines expressing the Mosaic, Epigraph, and wild type TX98 HA immunogens as previously described in FIG. 35. Overlapping peptide libraries of 17-mers overlapping by 10 amino acids were used to determine the T cell epitopes induced by the vaccine immunogens to four representative divergent swH3 viruses. Interferon-γ inducing T cells were measured by ELISpot assay. A peptide was considered positive if the spot-forming cells (SFC) per million was greater than 50 (FIG. 36A). Individual responses to positive peptides (FIG. 36B) and total T-cell responses (FIG. 36C) were also measured.

Balb/c mice (n=5) were immunized as previously described for FIG. 35. Sera from vaccinated mice was incubated with representative human H3N2 virus isolates and the geometric mean HI titer was determined ±standard error (FIG. 37A). Splenocytes were evaluated for cross-reactive T-cell immune responses against four representative human influenza strains using overlapping peptide libraries and an IFN-γ ELISpot assay. A peptide was considered positive if the spot-forming cells (SFC) per million was greater than 50 (FIG. 37B). Individual responses to positive peptides (FIG. 37C) and total T-cell responses (FIG. 37D) were also measured.

Balb/c mice (n=5) were vaccinated with a single dose of 10e10 vp of Ad5 vectored vaccines expressing the Mosaic, Epigraph, or TX98 immunogens and compared to FluSure vaccinated animals or sham vaccinated animals. Three weeks later mice were infected intranasally with 10e5 TCID50 of Manitoba/2005 (FIG. 38A) or 10e3.5 TCID50 of Colorado/1977 (FIG. 38B) and monitored for weight loss. In addition, group of mice (n=5) was vaccinated and infected as previously described but sacrificed on day 3 post infection for analysis of lung viral titer by qPCR (on the right).

It is to be understood that, while the methods and compositions of matter have been described herein in conjunction with a number of different aspects, the foregoing description of the various aspects is intended to illustrate and not limit the scope of the methods and compositions of matter. Other aspects, advantages, and modifications are within the scope of the following claims.

Disclosed are methods and compositions that can be used for, can be used in conjunction with, can be used in preparation for, or are products of the disclosed methods and compositions. These and other materials are disclosed herein, and it is understood that combinations, subsets, interactions, groups, etc. of these methods and compositions are disclosed. That is, while specific reference to each various individual and collective combinations and permutations of these compositions and methods may not be explicitly disclosed, each is specifically contemplated and described herein. For example, if a particular composition of matter or a particular method is disclosed and discussed and a number of compositions or methods are discussed, each and every combination and permutation of the compositions and the methods are specifically contemplated unless specifically indicated to the contrary. Likewise, any subset or combination of these is also specifically contemplated and disclosed.

What is claimed is:

1. A vaccine polypeptide having at least 90% sequence identity to an amino acid sequence selected from the group consisting of any of SEQ ID NOs: 21, 22, 87 and 88, wherein the polypeptide is encoded by a nucleic acid sequence having at least 90% sequence identity to a nucleic acid sequence selected from the group consisting of SEQ ID NOs: 111, 112, 121 and 122, respectively.

2. The vaccine polypeptide of claim 1, wherein the polypeptide has at least 95% sequence identity to an amino acid sequence selected from the group consisting of any of SEQ ID NOs: 21, 22, 87 and 88.

3. The vaccine polypeptide of claim 1, wherein the polypeptide has at least 99% sequence identity to an amino acid sequence selected from the group consisting of any of SEQ ID NOs: 21, 22, 87 and 88.

4. The vaccine polypeptide of claim 1, wherein the polypeptide has 100% sequence identity to an amino acid sequence selected from the group consisting of any of SEQ ID NOs: 21, 22, 87 and 88.

5. The vaccine polypeptide of claim 1, wherein the polypeptide is encoded by a nucleic acid sequence having at least 95% sequence identity to a nucleic acid sequence selected from the group consisting of SEQ ID NOs: 111, 112, 121 and 122.

6. The vaccine polypeptide of claim 1, wherein the polypeptide is encoded by a nucleic acid sequence having at least 99% sequence identity to a nucleic acid sequence selected from the group consisting of SEQ ID NOs: 111, 112, 121 and 122.

7. The vaccine polypeptide of claim 1, wherein the polypeptide is encoded by a nucleic acid sequence having at least 100% sequence identity to a nucleic acid sequence selected from the group consisting of SEQ ID NOs: 111, 112, 121 and 122.

8. A vaccine composition comprising at least one of the vaccine polypeptides of claim 1 and a delivery vehicle.

9. The vaccine composition of claim 8, wherein the delivery vehicle is a virus.

10. The vaccine composition of claim 9, wherein the delivery vehicle virus is selected from the group consisting of an adenovirus, an adeno-associated virus, a retrovirus, an alphavirus, a paramyxovirus, and a rhabdovirus.

11. The vaccine composition of claim 8, wherein the delivery vehicle is a nanoparticle.

12. A method of vaccinating a subject, the method comprising:
administering the vaccine polypeptide of claim 1 to a subject in need of vaccination.

13. The method of claim 12, wherein the subject is selected from the group consisting of a human and a swine.

14. The method of claim 12, wherein the administering step is repeated more than once.

* * * * *